US012186388B2

(12) United States Patent
Kok

(10) Patent No.: US 12,186,388 B2
(45) Date of Patent: Jan. 7, 2025

(54) INTERFERON-PRODUCING UNIVERSAL SARBECOVIRUS VACCINES, AND USES THEREOF

(71) Applicant: Centre for Virology, Vaccinology and Therapeutics Limited, Hong Kong (HK)

(72) Inventor: Kin Hang Kok, Hong Kong (HK)

(73) Assignee: CENTRE FOR VIROLOGY, VACCINOLOGY AND THERAPEUTICS LIMITED, Hong Kong (HK)

( * ) Notice: Subject to any disclaimer, the term of this patent is extended or adjusted under 35 U.S.C. 154(b) by 0 days.

(21) Appl. No.: 18/165,286

(22) Filed: Feb. 6, 2023

(65) Prior Publication Data

US 2024/0139307 A1 May 2, 2024

Related U.S. Application Data

(60) Provisional application No. 63/382,009, filed on Nov. 2, 2022.

(51) Int. Cl.

*A61K 39/215* (2006.01)
*A61P 31/14* (2006.01)
*C12N 7/00* (2006.01)
*A61K 39/00* (2006.01)

(52) U.S. Cl.

CPC ............ *A61K 39/215* (2013.01); *A61P 31/14* (2018.01); *C12N 7/00* (2013.01); *A61K 2039/543* (2013.01); *C12N 2770/20022* (2013.01); *C12N 2770/20034* (2013.01); *C12N 2770/20071* (2013.01)

(58) Field of Classification Search

None

See application file for complete search history.

(56) References Cited

U.S. PATENT DOCUMENTS

| | | | | |
|---|---|---|---|---|
| 7,429,481 | B2 * | 9/2008 | Bergman | C07K 14/005 435/320.1 |
| 2008/0063664 | A1 * | 3/2008 | Hsiao | C07K 14/005 435/235.1 |
| 2021/0290756 | A1 * | 9/2021 | Sullivan | C07K 16/2818 |
| 2022/0325279 | A1 * | 10/2022 | Ellis | C07K 14/005 |
| 2024/0024461 | A1 | 1/2024 | Kok | |

FOREIGN PATENT DOCUMENTS

| | | | |
|---|---|---|---|
| WO | 2006136448 | A2 | 12/2006 |
| WO | 2017049266 | A2 | 3/2017 |
| WO | 2017223538 | A1 | 12/2017 |
| WO | WO-2022184287 | A1 * | 9/2022 |
| WO | 2023168880 | A1 | 9/2023 |
| WO | 2024094050 | A1 | 5/2024 |

OTHER PUBLICATIONS

Zhang, et al., Expression of Interferon-g by a Coronavirus Defective-Interfering RNA Vector and Its Effect on Viral Replication, Spread, and Pathogenicity, Virology, Jul. 7, 1997; vol. 233, No. (2):327-38. doi: 10.1006/viro.1997.8598. PMID: 9217056. (Year: 1997).*

Kumar, et al., Deletion in the C-terminal region of the envelope glycoprotein in some of the Indian SARS-COV-2 genome, Virus Research, Jan. 2, 2021;291:198222. doi: 10.1016/j.virusres.2020.198222. Epub Nov. 6, 2020. PMID: 33166565. (Year: 2021).*

Konishi K, Yamaji T, Sakuma C, Kasai F, Endo T, Kohara A, Hanada K, Osada N. Whole-Genome Sequencing of Vero E6 (Vero C1008) and Comparative Analysis of Four Vero Cell Sublines. Front Genet. Mar. 22, 2022;13:801382. doi: 10.3389/fgene.2022.801382. PMID: 35391802; PMCID: PMC8981525. (Year: 2022).*

Channappanavar, R. et al. (Feb. 10, 2016). "Dysregulated Type I Interferon and Inflammatory Monocyte-Macrophage Responses Cause Lethal Pneumonia in SARS-COV-Infected Mice," Cell Host Microbe. 19(2):181-193.

Channappanavar, R. et al. (Jul. 29, 2019). "IFN-I Response Timing Relative to Virus Replication Determines MERS Coronavirus Infection Outcomes," J Clin Invest. 129(9):3625-3639.

Chu, H. et al. (Sep. 15, 2020). "Comparative Replication and Immune Activation Profiles of SARS-COV-2 and SARS-COV in Human Lungs: An Ex Vivo Study with Implications for the Pathogenesis of COVID-19," Clin Infect Dis. 71:1400-1409.

Crouse, J. et al. (Jun. 19, 2014). "Type I Interferons Protect T Cells Against NK Cell Attack Mediated by the Activating Receptor NCR1," Immunity 40:961-973.

Doench, J. G. et al. (Feb. 2016). "Optimized SgRNA Design to Maximize Activity and Minimize Off-target Effects of CRISPR-Cas9," Nat Biotechnol. 34(2):184-191, 35 pages.

Fehr, A. R. et al. (2020). "Bacterial Artificial Chromosome-Based Lambda Red Recombination with the I-Scel Homing Endonuclease for Genetic Alteration of MERS-COV," Methods Mol Biol. 2099:53-68.

Gangaplara, A. et al. (Apr. 19, 2018). "Type I Interferon Signaling Attenuates Regulatory T Cell Function in Viral Infection and in the Tumor Microenvironment," PLOS Pathogens 14(4): e1006985, 27 pages.

GenBank Accession No. NC045512.2 last updated Jul. 18, 2020, located at a href="https://www.nobi.nim.nih.gov/nuccore/NC_045512.2/" target="_blank"https://www.nobl.nim.nih.gov/nuccore/NC_045512.2//a, last visited on Jan. 25, 2023, 16 pages.

(Continued)

*Primary Examiner* — Benjamin P Blumel
*Assistant Examiner* — Jeffrey Mark Sifford
(74) *Attorney, Agent, or Firm* — MORRISON & FOERSTER LLP

(57) ABSTRACT

The present invention relates to universal sarbecovirus vaccines that specifically express an interferon. This live universal sarbecovirus vaccine elicits mucosal immunity and heterotypic immunity against various sarbecoviruses, including SARS-CoV-1, SARS-CoV-2, and its variants. Interferon directly encoded from the genome of the live universal sarbecovirus overrides the virus-induced "delayed type-I interferon", resulting in enhancement of mucosal T cell responses. The present invention further relates to uses of the vaccines for the preparation of pharmaceutical compositions, methods of treating or preventing viral infections, and kits comprising the vaccines.

20 Claims, 27 Drawing Sheets

Specification includes a Sequence Listing.

(56) References Cited

OTHER PUBLICATIONS

GenBank Accession No. NM002176.4, last updated Jan. 22, 2023, located at a href="https://www.ncbi.nlm.nih.gov/nuccore/NM_002176.4/" target="_blank"https://www.ncbi.nim.nih.gov/nuccore/NM_002176.4/a, last visited on Jan. 26, 2023, 4 pages.
GenBank Accession No. NM010510.2, last updated Jan. 1, 2023, located at a href="https://www.ncbi.nim.nih.gov/nuccore/NM_010510.2/" target="_blank"https://www.nobl.nim.nih.gov/nuccore/NM_010510.2//a, last visited on Jan. 26, 2023, 3 pages.
GenBank Accession No. YP009725299.1, last updated Jul. 18, 2020, located at a href="https://www.ncbi.nim.nih.gov/protein/YP_009725299.1/" target="_blank"https://www.ncbi.nim.nih.gov/protein/YP_009725299.1//a, last visited on Jan. 25, 2023, 3 pages.
GenBank Accession No. YP009725300.1, last updated Jul. 18, 2020, located at a href="https://www.ncbi.nim.nih.gov/protein/YP_009725300.1/" target="_blank"https://www.ncbi.nim.nih.gov/protein/YP_009725300.1//a, last visited on Jan. 25, 2023, 2 pages.
GenBank Accession No. YP009725305.1, last updated Jul. 18, 2020, located at a href="https://www.ncbi.nim.nih.gov/protein/YP_009725305.1/" target="_blank"https://www.ncbi.nim.nih.gov/protein/YP_009725305.1//a, last visited on Oct. 9, 2002, 2 pages.
GISAID Sequence No. EPL_ISL_13777658, last updated Jul. 12, 2022, located at a href="https://gisaid.org/" target="_blank"https://gisaid.org//a, last visited on Jan. 26, 2023, 1 page.
GISAID Sequence No. EPI_ISL_9845731, last updated Feb. 14, 2022, located at a href="https://gisaid.org/" target="_blank"https://gisaid.org//a, last visited on Jan. 26, 2023, 1 page.
Gomez, C. E. et al.(Mar. 11, 2021). "Emerging SARS-COV-2 Variants and Impact in Global Vaccination Programs against SARS-COV-2/COVID-19," Vaccines 9(3):243, 13 pages.
Hatton, C. F. et al. (Dec. 7, 2021). "Delayed Induction of Type I and III Interferons Mediates Nasal Epithelial Cell Permissiveness to SARS-COV-2," Nat Commun. 12:7092, 17 pages.
Havenar-Daughton, C. et al. (Mar. 15, 2006). "Cutting Edge: The Direct Action of Type I IFN on CD4 T Cells Is Critical for Sustaining Clonal Expansion in Response to a Viral but Not a Bacterial Infection," J Immunol 176(6): 3315- 3319.
Huber, J. P. et al.(Apr. 2011, e-pub Mar. 10, 2011). "Regulation of Effector and Memory T-cell Functions by Type I Interferon," Immunology 132(4):466-474.
Lee, J. H. et al. (e-pub Apr. 2, 2022). "Interferon Antagonists Encoded by SARS-COV-2 at a Glance," Med Microbiol Immunol. 1-7.
O'Brien, T. R. et al. (Nov. 1, 2014). "IFN-Lambda4: The Paradoxical New Member of the Interferon Lambda Family," J Interferon Cytokine Res. 34(11):829-838.
Pestka, S. et al. (Dec. 2004). "Interferons, Interferon-like Cytokines, and Their Receptors," Immunol Rev. 202:8-32.
Public Health England (Apr. 1, 2021). "SARS-COV-2 Variants of Concern and Variants Under Investigation in England: Technical Briefing 8," Briefing, 50 pages.
Ramvikas, M. et al. (e-pub Oct. 7, 2016). "Nasal Vaccine Delivery," Micro and Nanotechnology in Vaccine Development 2017:279-301.
Reid, E. et al. (e-pub Sep. 2, 2014). "Type I and III Interferon Production in Response to RNA Viruses," J Interferon Cytokine Res 34(9):649-658.
Srivastava, S. et al. (May 5, 2014). "Type | Interferons Directly Inhibit Regulatory T Cells to Allow Optimal Antiviral T Cell Responses During Acute LCMV Infection," J Exp Med. 211(5):961-974.
Starr, T. N. et al. (Feb. 3, 2022). "ACE2 Binding is an Ancestral and Evolvable Trait of Sarbecoviruses," Nature 603:913-918.
Tang, J.W. et al. (Apr. 2021). "Emergence of a New SARS-COV-2 variant in the UK,"Journal of Infection 82(4):e27-e28.
Trimpert, J. et al. (Aug. 3, 2021). "Development of Safe and Highly Protective Live-Attenuated SARS-COV-2 Vaccine Candidates by Genome Recoding," Cell Rep 36(5):109493, 20 pages.
Xu, H. C. et al. (Jun. 19, 2014). "Type I Interferon Protects Antiviral CD8 T Cells from NK Cell Cytotoxicity," Immunity 40:949-960.
Ye, Z. W. et al. (Mar. 29, 2022). "Intranasal Administration of a Single Dose of a Candidate Live Attenuated Vaccine Derived from an NSP16-deficient SARS-COV-2 Strain Confers Sterilizing Immunity in Animals," Cell Mol Immunol 19:588-601.
Yuan, S. et al. (Jun. 23, 2022). "Pathogenicity, Transmissibility, and Fitness of SARS-COV-2 Omicron in Syrian Hamsters," Science 377(6604):428-433, 5 pages.
Yuen, C. K. et al. (2020, e-pub Jun. 20, 2020). "SARS-COV-2 nsp13, nsp14, nsp15 and orf6 Function as Potent Interferon Antagonists," Emerging Microbes and Infections 9(1):1418-1428.
Zhang, X. et al. (Apr. 15, 2021). "A Trans-Complementation System for SARS-COV-2 Recapitulates Authentic Viral Replication without Virulence," Cell 184(8): 2229-2238.
Qu, L. et al. (Sep. 30, 2019, e-pub. Jul. 15, 2019). "Programmable RNA Editing By Recruiting Endogenous ADAR Using Engineered RNAs," Nature Biotechnology 37:1059-1069.
U.S. Appl. No. 18/542,741, filed Aug. 21, 2023, for Kin Hang Kok et al. (U.S. Patent Application is not submitted herewith pursuant to the waiver of 37 C.F.R. §1.98(a)(2)(iii) issued by the Office on Sep. 21, 2004.).
Hoffmann, M. et al. (Apr. 16, 2020). "SARS-COV-2 Cell Entry Depends on ACE2 and TMPRSS2 and Is Blocked by a Clinically Proven Protease Inhibitor," Cell 181(2):271-280.
Li, F. et al. (Sep. 16, 2005). "Structure of SARS Coronavirus Spike Receptor-Binding Domain Complexed with Receptor," Science 309(5742):1864-1868.
Millet, J. K. et al. (Apr. 16, 2015). "Host Cell Proteases: Critical Determinants of Coronavirus Tropism and Pathogenesis," Virus Res. 202:120-134.
Walls, A. C. et al. (Apr. 16, 2020). "Structure, Function, and Antigenicity of the SARS-COV-2 Spike Glycoprotein," Cell 180(2):281-292, 38 pages.
Wang, Q. et al. (May 14, 2020). "Structural and Functional Basis of SARS-COV-2 Entry by Using Human ACE2," Cell 181(4):894-904.
Zhou, P. et al. (Mar. 12, 2020, e-pub. Feb. 3, 2020). "A Pneumonia Outbreak Associated With A New Coronavirus Of Probable Bat Origin," Nature 579:270-273.
U.S. Appl. No. 63/382,009, filed Nov. 2, 2022, for Kin Hang Kok et al. (U.S. Patent Application is not submitted herewith pursuant to the waiver of 37 C.F.R. §1.98(a)(2)(iii) issued by the Office on Sep. 21, 2004.).
Bracci, L. et al. (2005, e-pub. Dec. 31, 2004). "Type I IFN is a Powerful Mucosal Adjuvant for a Selective Intranasal Vaccination Against Influenza Virus in Mice and Affects Antigen Capture at Mucosal Level," Vaccine 23:2994-3004.
Faul, E. J. et al. (Dec. 20, 2008, e-pub. Oct. 21, 2008). "Interferon-beta Expressed by a Rabies Virus-based HIV-1 Vaccine Vector Serves as a Molecular Adjuvant and Decreases Pathogenicity," Virology 382(2): 226-238, 22 pages.
International Search Report and Written Opinion, mailed Feb. 16, 2024, for PCT Application No. PCT/CN2023/129016, filed Nov. 1, 2023, 12 pages.
Jimenez-Guardeno, J. M. et al. (Oct. 2015, e-pub.Oct. 29, 2015). "Identification of the Mechanisms Causing Reversion to Virulence in an Attenuated SARS-COV for the Design of a Genetically Stable Vaccine," PLoS Pathog. 11(10):e10055215, 36 pages.
Proietti, E. et al. (Jul. 1, 2002). "Type I IFN as a Natural Adjuvant for a Protective Immune Response: Lessons from the Influenza Vaccine Model," 169(1):375-383.
Regla-Nava, J. A. et al. (Apr. 1, 2015). "Severe Acute Respiratory Syndrome Coronaviruses with Mutations in the E Protein Are Attenuated and Promising Vaccine Candidates," J Virol. 89(7):3870-3887.
Sosa, J. P. et al. (Jun. 2021, e-pub. Jun. 17, 2021). "Effects of Interferon Beta in COVID-19 Adult Patients: Systematic Review," Infect Chemother. 53(2):247-260.

* cited by examiner

Modified Envelope gene in lentiviral vector mouse lethal infection setup
1st IBIS /BNT
2nd IBIS /BNT
SARS-CoV-2 infection
-28
-14
0
7
14 neutralization (FRNT50)
days post vaccination
14
28 anti-RBD IgG anti-N IgG anti-RBD IgM anti-N IgM
OD450
mock
IBIS
BNT

FIG. 6G
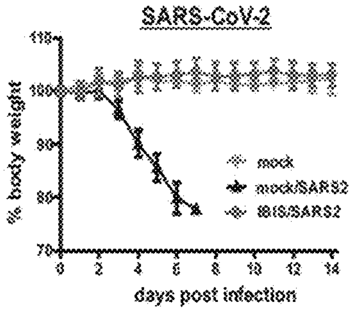
FIG. 6H
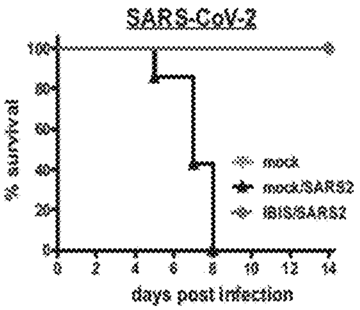
FIG. 6I
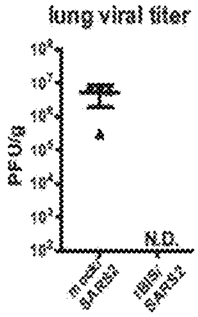
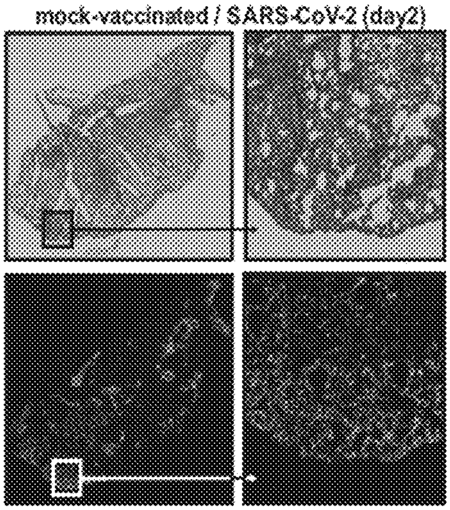
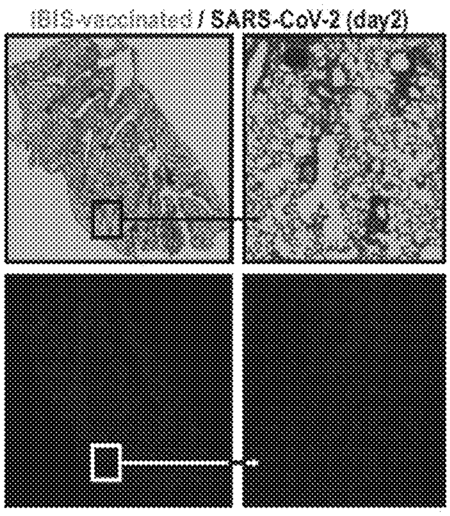
FIG. 6J
FIG. 6K FIG. 8A
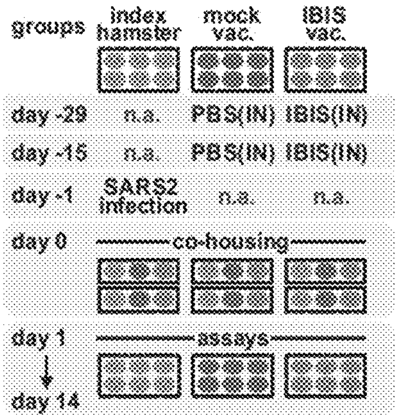
FIG. 8E
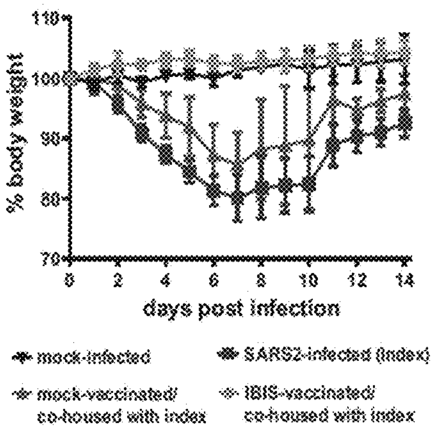
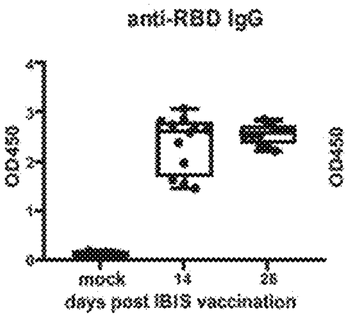
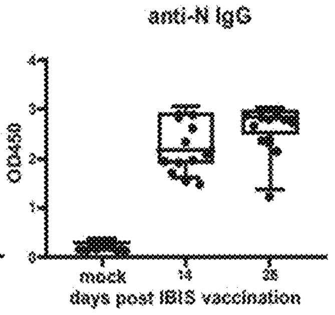
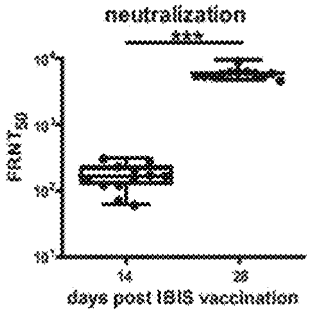
FIG. 8B FIG. 8C FIG. 8D FIG. 8F
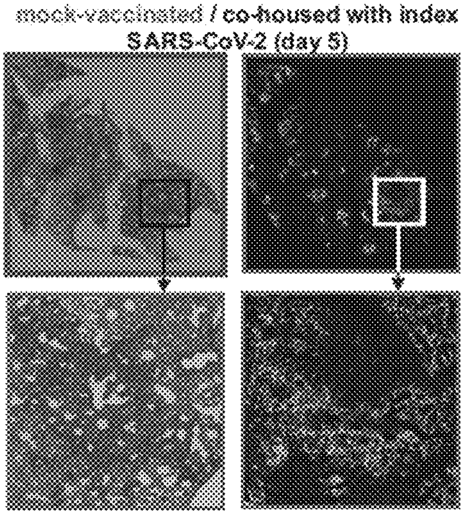
FIG. 8G
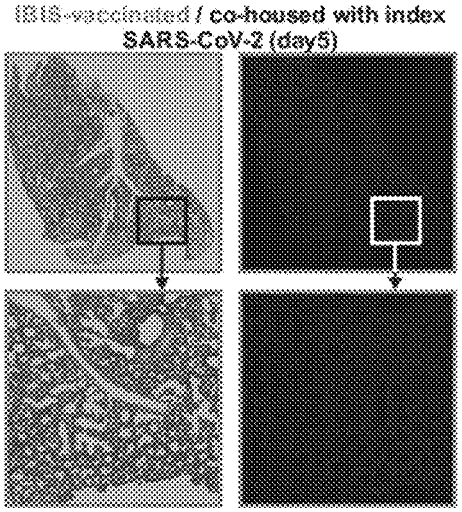
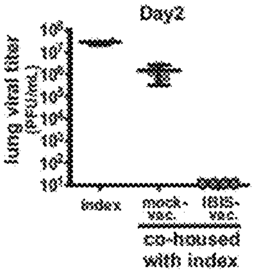
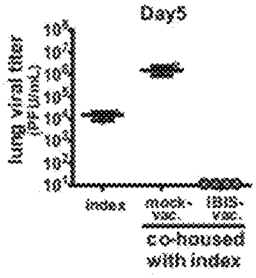
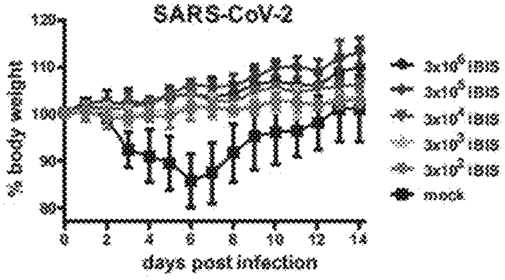
FIG. 8H FIG. 8I FIG. 8J FIG. 9A
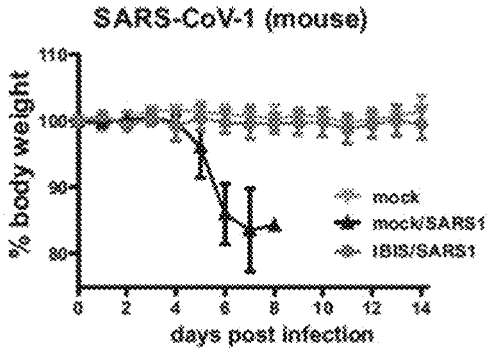
FIG. 9B
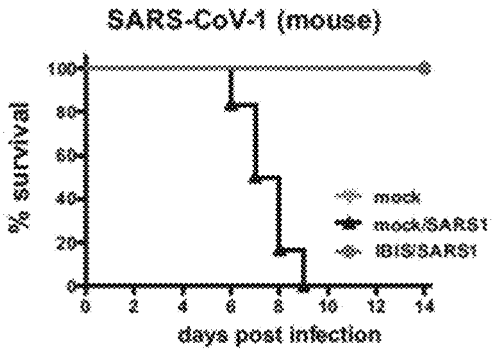
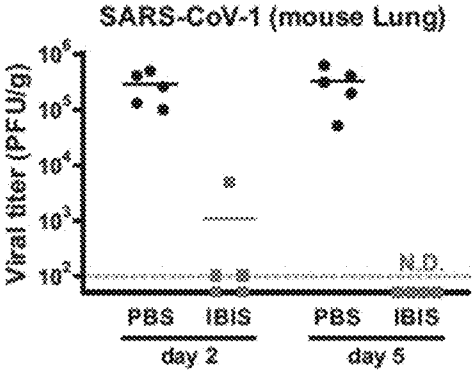
FIG. 9C
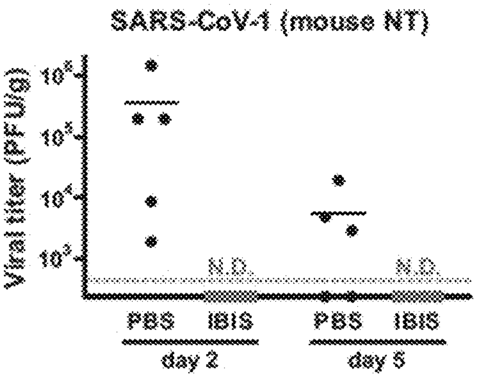
FIG. 9D FIG. 9E
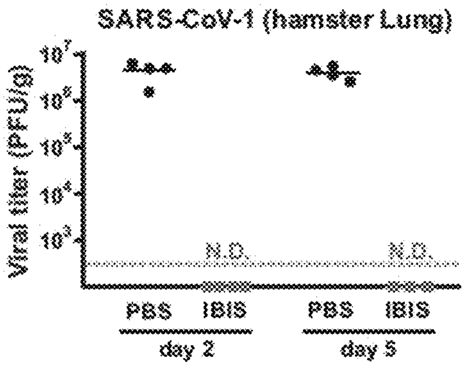
FIG. 9F
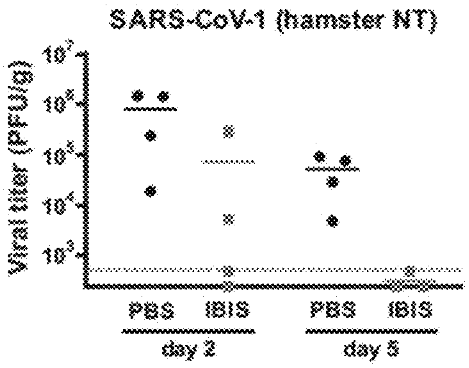
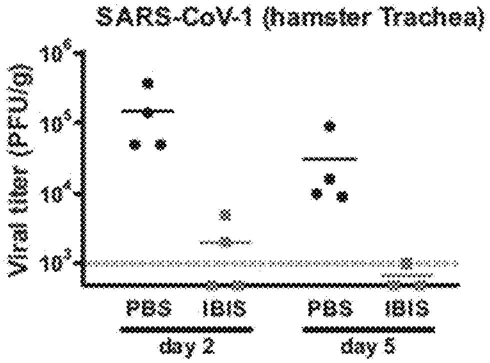
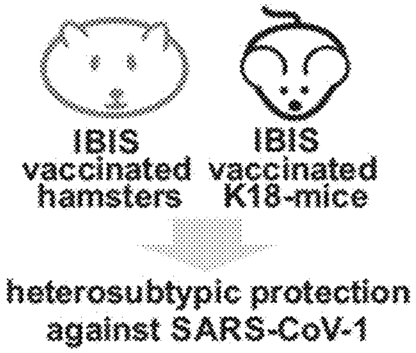
FIG. 9G FIG. 10A SARS-CoV-2 Omicron (hamster)

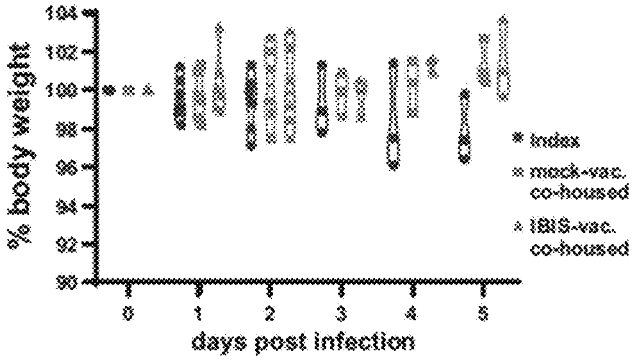

FIG. 10B SARS-CoV-2 Omicron (hamster)

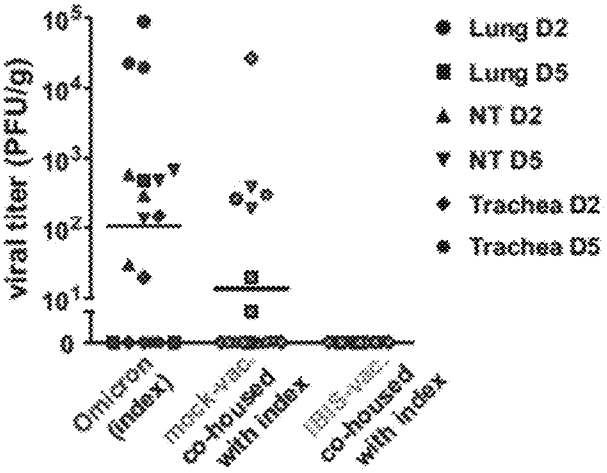

FIG. 10C SARS-CoV-2 Omicron (hamster)

Expression level of viral RNA

| | Day 2 | | | Day 5 | | |
|---|---|---|---|---|---|---|
| | Lung | Tra | NT | Lung | Tra | NT |
| Omicon (index) | ++++++ | +++++ | ++++++ | + | +++ | ++++++ |
| | +++++ | ++++++ | ++++++ | - | ++++ | ++++++ |
| | +++++ | +++++ | ++++++ | + | ++++ | ++++++ |
| mock-vac. co-housed with index | - | - | + | ++ | +++++ | ++++++ |
| | - | + | ++ | ++ | +++ | ++++++ |
| | ++++ | ++++++ | ++++ | - | ++ | +++ |
| IBIS-vac. co-housed with index | - | + | +++ | + | + | ++ |
| | - | + | ++ | + | + | ++ |
| | + | ++ | +++ | - | - | ++ |

FIG. 10D

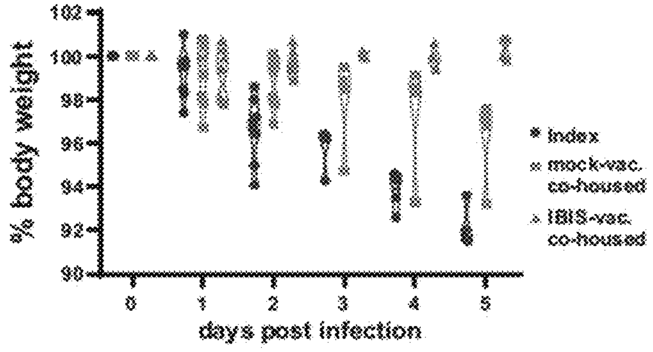

FIG. 10E

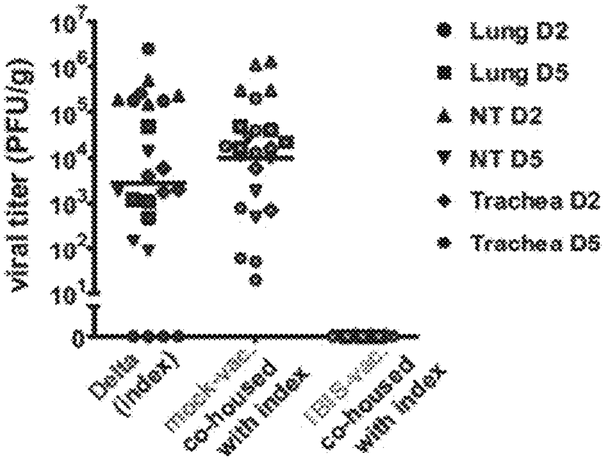

FIG. 10F SARS-CoV-2 Delta (hamster)

Expression level of viral RNA

| | Day 2 | | | Day 5 | | |
|---|---|---|---|---|---|---|
| | Lung | Tra | NT | Lung | Tra | NT |
| Delta (index) | ++++++ | ++++++ | ++++++ | - | ++++++ | ++++++ |
| | ++++++ | ++++++ | ++++++ | - | +++++ | ++++++ |
| | ++++++ | ++++++ | ++++++ | + | ++++ | ++++++ |
| | ++++++ | ++++++ | ++++++ | - | ++++ | ++++++ |
| mock-vac. co-housed with index | ++++++ | ++++++ | ++++++ | + | ++++++ | ++++++ |
| | +++++ | ++++++ | ++++++ | ++ | ++++++ | ++++++ |
| | ++++++ | ++++++ | ++++++ | +++ | ++++++ | ++++++ |
| | ++++++ | ++++++ | ++++++ | ++ | ++++++ | ++++++ |
| IBIS-vac. co-housed with index | - | + | ++++ | - | +++ | ++++ |
| | - | +++ | ++++++ | + | + | + |
| | + | +++ | +++ | - | + | ++ |
| | + | +++ | ++++ | - | + | ++ |

human A549-hACE2

| | -14 | 0 | +6 | +48 hours |
|---|---|---|---|---|
| mock | - | BA.2 | - | PFU |
| Pre- | IBIS | BA.2 | - | PFU |
| co- | - | IBIS/BA.2 | - | PFU |
| Post- | - | BA.2 | IBIS | PFU |
| +ve ctl | hIFNβ | BA.2 | - | PFU |

SEQUENCE LISTING

```
Sequence total quantity: 16
SEQ ID NO: 1            moltype = DNA  length = 29903
FEATURE                 Location/Qualifiers
source                  1..29903
                        mol_type = unassigned DNA
                        organism = SARS-CoV-2
SEQUENCE: 1
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
```

-continued gggtttaaat ggttacactg tagaggaggc aaagacagtg cttaaaaagt gtaaaagtgc 4320
cttttacatt ctaccatcta ttatctctaa tgagaagcaa gaaattcttg gaactgtttc 4380
ttggaatttg cgagaaatgc ttgcacatgc agaagaaaca cgcaaattaa tgcctgtctg 4440
tgtggaaact aaagccatag tttcaactat acagcgtaaa tataagggta ttaaaataca 4500
agagggtgtg gttgattatg gtgctagatt ttacttttac accagtaaaa caactgtagc 4560
gtcacttatc aacacactta acgatctaaa tgaaactctt gttacaatgc cacttggcta 4620
tgtaacacat ggcttaaatt tggaagaagc tgctcggtat atgagatctc tcaaagtgcc 4680
agctacagtt tctgtttctt cacctgatgc tgttacagcg tataatggtt atcttacttc 4740
ttcttctaaa acacctgaag aacattttat tgaaaccatc tcacttgctg gttcctataa 4800
agattggtcc tattctggac aatctacaca actaggtata gaatttctta agagaggtga 4860
taaaagtgta tattacacta gtaatcctac cacattccac ctagatggtg aagttatcac 4920
ctttgacaat cttaagacac ttctttcttt gagagaagtg aggactatta aggtgtttac 4980
aacagtagac aacattaacc tccacacgca agttgtggac atgtcaatga catatggaca 5040
acagtttggt ccaacttatt tggatggagc tgatgttact aaaataaaac ctcataattc 5100
acatgaaggt aaaacatttt atgttttacc taatgatgac actctacgtg ttgaggcttt 5160
tgagtactac cacacaactg atcctagttt tctgggtagg tacatgtcag cattaaatca 5220
cactaaaaag tggaaatacc cacaagttaa tggtttaact tctattaaat gggcagataa 5280
caactgttat cttgccactg cattgttaac actccaacaa atagagttga agtttaatcc 5340
acctgctcta caagatgctt attacagagc aagggctggt gaagctgcta actttgtgc 5400
acttatctta gcctactgta ataagacagt aggtgagtta ggtgatgtta gagaaacaat 5460
gagttacttg tttcaacatg ccaatttaga ttcttgcaaa agagtcttga acgtggtgtg 5520
taaaacttgt ggacaacagc agacaaccct taagggtgta gaagctgtta tgtacatggg 5580
cacactttct tatgaacaat ttaagaaagg tgttcagata ccttgtacgt gtggtaaaca 5640
agctacaaaa tatctagtac aacaggagtc accttttgtt atgatgtcag caccacctgc 5700
tcagtatgaa cttaagcatg gtacatttac ttgtgctagt gagtacactg gtaattacca 5760
gtgtggtcac tataaacata taacttctaa agaaactttg tattgcatag acggtgcttt 5820
acttacaaag tcctcagaat acaaaggtcc tattacggat gttttctaca aagaaaacag 5880
ttacacaaca accataaaac cagttactta taaattggat ggtgttgttt gtacagaaat 5940
tgaccctaag ttggacaatt attataagaa agacaattct tatttcacag agcaaccaat 6000
tgatcttgta ccaaaccaac catatccaaa cgcaagcttc gataatttta agtttgtatg 6060
tgataatatc aaatttgctg atgatttaaa ccagttaact ggttataaga aacctgcttc 6120
aagagagctt aaagttacat ttttccctga cttaaatggt gatgtggtgg ctattgatta 6180
taaacactac acaccctctt ttaagaaagg agctaaattg ttacataaac ctattgtttg 6240
gcatgttaac aatgcaacta ataaagccac gtataaacca aatacctggt gtatacgttg 6300
tctttggagc acaaaaccag ttgaaacatc aaattcgttt gatgtactga agtcagagga 6360
cgcgcaggga atggataatc ttgcctgcga agatctaaaa ccagtctctg aagaagtagt 6420
ggaaaatcct accatacaga aagacgttct tgagtgtaat gtgaaaacta ccgaagttgt 6480
aggagacatt atacttaaac cagcaaataa tagtttaaaa attacagaag aggttggcca 6540
cacagatcta atggctgctt atgtagacaa ttctagtctt actattaaga aacctaatga 6600
attatctaga gtattaggtt tgaaaaccct tgctactcat ggtttagctg ctgttaatag 6660
tgtcccttgg gatactatag ctaattatgc taagcctttt cttaacaaag ttgttagtac 6720
aactactaac atagttacac ggtgtttaaa ccgtgtttgt actaattata tgccttattt 6780
ctttacttta ttgctacaat tgtgtacttt tactagaagt acaaattcta gaattaaagc 6840
atctatgccg actactatag caaagaatac tgttaagagt gtcggtaaat tttgtctaga 6900
ggcttcattt aattatttga agtcacctaa tttttctaaa ctgataaata ttataatttg 6960
gtttttacta ttaagtgttt gcctaggttc tttaatctac tcaaccgctg ctttaggtgt 7020
tttaatgtct aatttaggca tgccttctta ctgtactggt tacagagaag gctatttgaa 7080
ctctactaat gtcactattg caacctactg tactggttct ataccttgta gtgtttgtct 7140
tagtggttta gattctttag acacctatcc ttctttagaa actatacaaa ttaccatttc 7200
atcttttaaa tgggatttaa ctgcttttgg cttagttgca gagtggtttt tggcatatat 7260
tcttttcact aggtttttct atgtacttgg attggctgca atcatgcaat tgtttttcag 7320
ctattttgca gtacatttta ttagtaattc ttggcttatg tggttaataa ttaatcttgt 7380
acaaatggcc ccgatttcag ctatggttag aatgtacatc ttctttgcat cattttatta 7440
tgtatggaaa agttatgtgc atgttgtaga cggttgtaat tcatcaactt gtatgatgtg 7500
ttacaaacgt aatagagcaa caagagtcga atgtacaact attgttaatg gtgttagaag 7560
gtccttttat gtctatgcta atggaggtaa aggcttttgc aaactacaca attggaattg 7620
tgttaattgt gatacattct gtgctggtag tacatttatt agtgatgaag ttgcgagaga 7680
cttgtcacta cagtttaaaa gaccaataaa tcctactgac cagtcttctt acatcgttga 7740
tagtgttaca gtgaagaatg gttccatcca tctttacttt gataaagctg gtcaaaagac 7800
ttatgaaaga cattctctct ctcattttgt taacttagac aacctgagag ctaataacac 7860
taaaggttca ttgcctatta atgttatagt tttgatggt aaatcaaaat gtgaagaatc 7920
atctgcaaaa tcagcgtctg tttactacag tcagcttatg tgtcaaccta tactgttact 7980
agatcaggca ttagtgtctg atgttggtga tagtgcggaa gttgcagtta aaatgtttga 8040
tgcttacgtt aatacgtttt catcaacttt taacgtacca atggaaaaac tcaaaacact 8100
agttgcaact gcagaagctg aacttgcaaa gaatgtgtcc ttagacaatg tcttatctac 8160
ttttatttca gcagctcggc aagggtttgt tgattcagat gtagaaacta aagatgttgt 8220
tgaatgtctt aaattgtcac atcaatctga catagaagtt actggcgata gttgtaataa 8280
ctatatgctc acctataaca aagttgaaaa catgacaccc cgtgaccttg gtgcttgtat 8340
tgactgtagt gcgcgtcata ttaatgcgca ggtagcaaaa agtcacaaca ttgctttgat 8400
atggaacgtt aaagatttca tgtcattgtc tgaacaacta cgaaaacaaa tacgtagtgc 8460
tgctaaaaag aataacttac cttttaagtt gacatgtgca actactagac aagttgttaa 8520
tgttgtaaca acaaagatag cacttaaggg tggtaaaatt gttaataatt ggttgaagca 8580
gttaattaaa gttacacttg tgttcctttt tgttgctgct attttctatt taataacacc 8640
tgttcatgtc atgtctaaac atactgactt ttcaagtgaa atcataggat acaaggctat 8700
tgatggtggt gtcactcgtg acatagcatc tacagatact tgttttgcta acaaacatgc 8760
tgattttgac acatggttta gccagcgtgg tggtagttat actaatgaca aagcttgccc 8820
attgattgct gcagtcataa caagagaagt gggttttgtc gtgcctggtt tgcctggcac 8880
gatattacgc acaactaatg gtgacttttt gcatttctta cctagagttt ttagtgcagt 8940
tggtaacatc tgttacacac catcaaaact tatagagtac actgactttg caacatcagc 9000

-continued

```
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtaccttttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
```

-continued

```
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat caccccgcaa gaagctataa gacatgtacg tgcatggatt  18300
ggcttcgatg tcgagggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
```

-continued

```
caccctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attaccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
```

-continued

```
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct tttcttgctt ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
```

-continued

```
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
acagtgaaca atgctaggga gagctgccta tatggaagag ccctaatgtg taaaattaat  29820
tttagtagtg ctatccccat gtgattttaa tagcttctta ggagaatgac aaaaaaaaaa  29880
aaaaaaaaaa aaaaaaaaaa aaa                                          29903
```

```
SEQ ID NO: 2             moltype = DNA  length = 30119
FEATURE                  Location/Qualifiers
source                   1..30119
                         mol_type = other DNA
                         organism = synthetic construct
SEQUENCE: 2
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
```

-continued

```
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat tttccctgaa cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
```

```
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt tttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtaccttttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggacctttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
```

-continued

```
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
```

-continued

```
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
```

-continued

```
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attaccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaattttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
```

```
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtaa  26280
atagttaata gctgacttct ttttcttgct ttcgtgtgat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgacca  27900
acaagtgtct cctccaaatt gctctcctgt tgtgcttctc cactacagct ctttccatga  27960
gctacaactt gcttggattc ctacaaagaa gcagcaattt tcagtgtcag aagctcctgt  28020
ggcaattgaa tgggaggctt gaatactgcc tcaaggacag gatgaacttt gacatccctg  28080
aggagattaa gcagctgcag cagttccaga aggaggacgc cgcattgacc atctatgaga  28140
tgctccagaa catctttgct attttcagac aagattcatc tagcactggc tggaatgaga  28200
ctattgttga gaacctcctg gctaatgtct atcatcagat aaaccatctg aagacagtcc  28260
tggaagaaaa actggagaaa gaagatttca ccaggggaaa actcatgagc agtctgcacc  28320
tgaaaagata ttatgggagg attctgcatt acctgaaggc caaggagtac agtcactgtg  28380
cctggaccat agtcagagtg gaaatcctaa ggaactttta cttcattaac agacttacag  28440
gttacctccg aaactgagac gttcgtgttg ttttagattt catctaaacg aacaaactaa  28500
aatgtctgat aatggacccc aaaatcagcg aaatgcaccc cgcattacgt ttggtggacc  28560
ctcagattca actggcagta accagaatgg agaacgcagt ggggcgcgat caaaacaacg  28620
tcggccccaa ggtttaccca ataatactgc gtcttggttc accgctctca ctcaacatgg  28680
caaggaagac cttaaattcc ctcgaggaca aggcgttcca attaacacca atagcagtcc  28740
agatgaccaa attggctact accgaagagc taccagacga attcgtggtg gtgacggtaa  28800
aatgaaagat ctcagtccaa gatggtattt ctactaccta ggaactgggc cagaagctgg  28860
acttccctat ggtgctaaca aagacggcat catatgggtt gcaactgagg gagccttgaa  28920
tacaccaaaa gatcacattg gcacccgcaa tcctgctaac aatgctgcaa tcgtgctaca  28980
acttcctcaa ggaacaacat tgccaaaagg cttctacgca gaagggagca gaggcggcag  29040
tcaagcctct tctcgttcct catcacgtag tcgcaacagt tcaagaaatt caactccagg  29100
cagcagtagg ggaacttctc ctgctagaat ggctggcaat ggcggtgatg ctgctcttgc  29160
tttgctgctg cttgacagat tgaaccagct tgagagcaaa atgtctggta aaggccaaca  29220
acaacaaggc caaactgtca ctaagaaatc tgctgctgag gcttctaaga agcctcggca  29280
aaaacgtact gccactaaag catacaatgt aacacaagct ttcggcagac gtggtccaga  29340
acaaacccaa ggaaattttg gggaccagga actaatcaga caaggaactg attacaaaca  29400
ttggccgcaa attgcacaat ttgcccccag cgcttcagcg ttcttcggaa tgtcgcgcat  29460
tggcatggaa gtcacacctt cgggaacgtg gttgacctac acaggtgcca tcaaattgga  29520
tgacaaagat ccaaatttca aagatcaagt cattttgctg aataagcata ttgacgcata  29580
caaaacattc ccaccaacag agcctaaaaa ggacaaaaag aagaaggctg atgaaactca  29640
agccttaccg cagagacaga agaaacagca aactgtgact cttcttcctg ctgcagattt  29700
ggatgatttc tccaaacaat tgcaacaatc catgagcagt gctgactcaa ctcaggccta  29760
aactcatgca gaccacacaa ggcagatggg ctatataaac gttttcgctt ttccgtttac  29820
gatatatagt ctactcttgt gcagaatgaa ttctcgtaac tacatagcac aagtagatgt  29880
agttaacttt aatctcacat agcaatcttt aatcagtgtg taacattagg gaggacttga  29940
aagagccacc acattttcac cgaggccacg cggagtacga tcgagtgtac agtgaacaat  30000
gctagggaga gctgcctata tggaagagcc ctaatgtgta aaattaattt tagtagtgct  30060
atccccatgt gattttaata gcttcttagg agaatgacaa aaaaaaaaaa aaaaaaaaa   30119
```

```
SEQ ID NO: 3            moltype = DNA  length = 30110
FEATURE                 Location/Qualifiers
source                  1..30110
                        mol_type = other DNA
                        organism = synthetic construct
SEQUENCE: 3
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
```

-continued

```
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gcttttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
```

-continued

```
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt ttttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtacctttct ggataacaat tgcttatatc atttgtattt ccacaaagca  9720
```

-continued

```
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
```

-continued

```
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
```

-continued

```
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttataa ccagaactca atcatacact aattctttca cacgtggtgt  21660
ttattaccct gacaaagttt tcagatcctc agttttacat tcaactcagg acttgttctt  21720
acctttcttt tccaatgtta cttggttcca tgctatacat gtctctggga ccaatggtac  21780
taagaggttt gataaccctg tcctaccatt taatgatggt gtttattttg cttccactga  21840
gaagtctaac ataataagag gctggatttt tggtactact ttagattcga agacccagtc  21900
cctacttatt gttaataacg ctactaatgt tgttattaaa gtctgtgaat ttcaattttg  21960
taatgatcca tttttggatg tttattacca caaaaacaac aaaagttgga tggaaagtga  22020
gttcagagtt tattctagtg cgaataattg cacttttgaa tatgtctctc agccttttct  22080
tatggacctt gaaggaaaac agggtaattt caaaaatctt agggaatttg tgtttaagaa  22140
tattgatggt tattttaaaa tatattctaa gcacacgcct attaatttag ggcgtgatct  22200
ccctcagggt ttttcggctt tagaaccatt ggtagatttg ccaataggta ttaacatcac  22260
taggtttcaa actttacttg ctttacatag aagttatttg actcctggtg attcttcttc  22320
aggttggaca gctggtgctg cagcttatta tgtgggttat cttcaaccta ggacttttct  22380
attaaaatat aatgaaaatg gaaccattac agatgctgta gactgtgcac ttgaccctct  22440
ctcagaaaca aagtgtacgt tgaaatcctt cactgtagaa aaaggaatct atcaaacttc  22500
taactttaga gtccaaccaa cagaatctat tgttagattt cctaatatta caaacttgtg  22560
ccctttttgat gaagttttta acgccaccag atttgcatct gtttatgctt ggaacaggaa  22620
gagaatcagc aactgtgttg ctgattattc tgtcctatat aatttcgcac catttttcgc  22680
ttttaagtgt tatggagtgt ctcctactaa attaaatgat ctctgcttta ctaatgtcta  22740
tgcagattca tttgtaatta gaggtaatga agtcagccaa atcgctccag ggcaaactgg  22800
aaatattgct gattataatt ataaattacc agatgatttt acaggctgcg ttatagcttg  22860
gaattctaac aagcttgatt ctaaggttgg tggtaattat aattacctgt atagattgtt  22920
taggaagtct aatctcaaac cttttgagag agatatttca actgaaatct atcaggccgg  22980
taacaaacct tgtaatggtg ttgcaggttt taattgttac tttcctttac gatcatatgg  23040
tttccgaccc acttatggtg ttggtcacca accatacaga gtagtagtac tttcttttga  23100
acttctacat gcaccagcaa ctgtttgtgg acctaaaaag tctactaatt tggttaaaaa  23160
caaatgtgtc aatttcaact tcaatggttt aacaggcaca ggtgttctta ctgagtctaa  23220
caaaaagttt ctgcctttcc aacaatttgg cagagacatt gctgacacta ctgatgctgt  23280
ccgtgatcca cagacacttg agattcttga cattacacca tgttcttttg gtggtgtcag  23340
tgttataaca ccaggaacaa atacttctaa ccaggttgct gttctttatc agggtgttaa  23400
ctgcacagaa gtccctgttg ctattcatgc agatcaactt actcctactt ggcgtgttta  23460
ttctacaggt tctaatgttt ttcaaacacg tgcaggctgt ttaatagggg ctgaatatgt  23520
caacaactca tatgagtgtg acatacccat tggtgcaggt atatgcgcta gttatcagac  23580
tcagactaag tctcatcggc gggcacgtag tgtagctagt caatccatca ttgcctacac  23640
tatgtcactt ggtgcagaaa attcagttgc ttactctaat aactctattg ccatacccac  23700
aaattttact attagtgtta ccacagaaat tctaccagtg tctatgacca agacatcagt  23760
agattgtaca atgtacattt gtggtgattc aactgaatgc agcaatcttt tgttgcaata  23820
tggcagtttt tgtacacaat taaaacgtgc tttaactgga atagctgttg aacaagacaa  23880
aaacacccaa gaagtttttg cacaagtcaa acaaatttac aaaacaccac caattaaata  23940
```

-continued

```
ttttggtggt tttaattttt cacaaatatt accagatcca tcaaaaccaa gcaagaggtc  24000
atttattgaa gatctacttt tcaacaaagt gacacttgca gatgctggct tcatcaaaca  24060
atatggtgat tgccttggtg atattgctgc tagagacctc atttgtgcac aaaagtttaa  24120
cggccttact gttttgccac ctttgctcac agatgaaatg attgctcaat acacttctgc  24180
actgttagcg ggtacaatca cttctggttg gacctttggt gcaggtgctg cattacaaat  24240
accatttgct atgcaaatgg cttataggtt taatggtatt ggagttacac agaatgttct  24300
ctatgagaac caaaaattga ttgccaacca atttaatagt gctattggca aaattcaaga  24360
ctcactttct tccacagcaa gtgcacttgg aaaacttcaa gatgtggtca accataatgc  24420
acaagcttta aacacgcttg ttaaacaact tagctccaaa tttggtgcaa tttcaagtgt  24480
tttaaatgat atcctttcac gtcttgacaa agttgaggct gaagtgcaaa ttgataggtt  24540
gatcacaggc agacttcaaa gtttgcagac atatgtgact caacaattaa ttagagctgc  24600
agaaatcaga gcttctgcta atcttgctgc tactaaaatg tcagagtgtg tacttggaca  24660
atcaaaaaga gttgattttt gtggaaaggg ctatcatctt atgtccttcc ctcagtcagc  24720
acctcatggt gtagtcttct tgcatgtgac ttatgtccct gcacaagaaa agaacttcac  24780
aactgctcct gccatttgtc atgatggaaa agcacacttt cctcgtgaag gtgtctttgt  24840
ttcaaatggc acacactggt ttgtaacaca aaggaatttt tatgaaccac aaatcattac  24900
tacagacaac acatttgtgt ctggtaactg tgatgttgta ataggaattg tcaacaacac  24960
agtttatgat cctttgcaac ctgaattaga ttcattcaag gaggagttag ataaatattt  25020
taagaatcat acatcaccag atgttgattt aggtgacatc tctggcatta atgcttcagt  25080
tgtaaacatt caaaaagaaa ttgaccgcct caatgaggtt gccaagaatt taaatgaatc  25140
tctcatcgat ctccaagaac ttggaaagta tgagcagtat ataaaatggc catggtacat  25200
ttggctaggt tttatagctg gcttgattgc catagtaatg gtgacaatta tgctttgctg  25260
tatgaccagt tgctgtagtt gtctcaaggg ctgttgttct tgtggatcct gctgcaaatt  25320
tgatgaagac gactctgagc cagtgctcaa aggagtcaaa ttacattaca cataaacgaa  25380
cttatggatt tgtttatgag aatcttcaca attggaactg taactttgaa gcaaggtgaa  25440
atcaaggatg ctactccttc agattttgtt cgcgctactg caacgatacc gatacaagcc  25500
tcactccctt tcggatggct tattgttggc gttgcacttc ttgctgtttt tcagagcgct  25560
tccaaaatca taaccctcaa aaagagatgg caactagcac tctccaaggg tgttcacttt  25620
gtttgcaact tgctgttgtt gtttgtaaca gtttactcac accttttgct cgttgctgct  25680
ggccttgaag ccccttttct ctatctttat gctttagtct acttcttgca gagtataaac  25740
tttgtaagaa taataatgag gctttggctt tgctggaaat gccgttccaa aaacccatta  25800
ctttatgatg ccaactattt tctttgctgg catactaatt gttacgacta ttgtatacct  25860
tacaatagtg taacttcttc aattgtcatt acttcaggtg atggcacaac aagtcctatt  25920
tctgaacatg actaccagat tggtggttat actgaaaaat gggaatctgg agtaaaagac  25980
tgtgttgtat tacacagtta cttcacttca gactattacc agctgtactc aactcaattg  26040
agtacagaca ctggtgttga acatgttacc ttcttcatct acaataaaat tgttgatgag  26100
cctgaagaac atgtccaaat tcacacaatc gacggttcat ccggagttgt taatccagta  26160
atggaaccaa tttatgatga accgacgacg actactagcg tgcctttgta agcacaagct  26220
gatgagtacg aacttatgta ctcattcgtt tcggaagaga caggtacgta aatagttaat  26280
agctgacttc tttttcttgc tttcgtggta ttcttgctag ttacactagc catccttact  26340
gcgcttcgat tgtgtgcgta ctgctgcaat attgttaacg tgagtcttgt aaaaccttct  26400
ttttacgttt actctcgtgt taaaaatctg aattcttcta gagttcctga tcttctggtc  26460
taaacgaact aaatattata ttagtttttc tgtttggaac tttaatttta gccatggcag  26520
attccaacgg tactattacc gttgaagagc ttaaaaagct ccttgaacaa tggaacctag  26580
taataggttt cctattcctt acatggattt gtcttctaca atttgcctat gccaacagga  26640
ataggttttt gtatataatt aagttaattt tcctctggct gttatggcca gtaactttag  26700
cttgttttgt gcttgctgct gtttacagaa taaattggat caccggtgga attgctatcg  26760
caatggcttg tcttgtaggc ttgatgtggc tcagctactt cattgcttct ttcagactgt  26820
ttgcgcgtac gcgttccatg tggtcattca atccagaaac taacattctt ctcaacgtgc  26880
cactccatgg cactattctg accagaccgc ttctagaaag tgaactcgta atcggagctg  26940
tgatccttcg tggacatctt cgtattgctg gacaccatct aggacgctgt gacatcaagg  27000
acctgcctaa agaaatcact gttgctacat cacgaacgct ttcttattac aaattgggag  27060
cttcgcagcg tgtagcaggt gactcaggtt ttgctgcata cagtcgctac aggattggca  27120
actataaatt aaacacagac cattccagta gcagtgacaa tattgctttg cttgtacagt  27180
aagtgacaac agatgtttca tctcgttgac tttcaggtta ctatagcaga gatattacta  27240
attattatga ggacttttaa agtttccatt tggaatcttg attacatcat aaacctcata  27300
attaaaaatt tatctaagtc actaactgag aataaatatt ctcaattaga tgaagagcaa  27360
ccaatggaga ttgattaaac gaacatgaaa attattcttt tcttggcact gataacactc  27420
gctacttgtg agctttatca ctaccaagag tgtgttagag gtacaacagt acttttaaaa  27480
gaaccttgct cttctggaac atacgagggc aattcaccat ttcatcctct agctgataac  27540
aaatttgcac tgacttgctt tagcactcaa tttgcttttg cttgtcctga cggcgtaaaa  27600
cacgtctatc agttacgtgc cagatcagtt tcacctaaac tgttcatcag acaagaggaa  27660
gttcaagaac tttactctcc aatttttctt attgttgcgg caatagtgtt tataacactt  27720
tgcttcacac tcaaaagaaa gacagaatga ttgaactttc attaattgac ttctatttgt  27780
gctttttagc ctttctgcta ttccttgttt taattatgct tattatcttt tggttctcac  27840
ttgaactgca agatcataat gaaacttgtc acgcctaaac gaacatgacc aacaagtgtc  27900
tcctccaaat tgctctcctg ttgtgcttct ccactacagc tctttccatg agctacaact  27960
tgcttggatt cctacaaaga agcagcaatt ttcagtgtca gaagctcctg tggcaattga  28020
atgggaggct tgaatactgc ctcaaggaca ggatgaactt tgacatccct gaggagatta  28080
agcagctgca gcagttccag aaggaggacg ccgcattgac catctatgag atgctccaga  28140
acatctttgc tattttcaga caagattcat ctagcactgg ctggaatgag actattgttg  28200
agaacctcct ggctaatgtc tatcatcaga taaaccatct gaagacagtc ctggaagaaa  28260
aactggagaa agaagatttc accaggggaa aactcatgag cagtctgcac ctgaaaagat  28320
attatgggag gattctgcat tacctgaagg ccaaggagta cagtcactgt gcctggacca  28380
tagtcagagt ggaaatccta aggaactttt acttcattaa cagacttaca ggttacctcc  28440
gaaactgaga cgttcgtgtt gttttagatt tcatctaaac gaacaaacta aaatgtctga  28500
taatggaccc caaaatcagc gaaatgcacc ccgcattacg tttggtggac cctcagattc  28560
aactggcagt aaccagaatg gagaacgcag tggggcgcga tcaaaacaac gtcggcccca  28620
aggtttaccc aataatactg cgtcttggtt caccgctctc actcaacatg gcaaggaaga  28680
```

```
ccttaaattc cctcgaggac aaggcgttcc aattaacacc aatagcagtc cagatgacca  28740
aattggctac taccgaagag ctaccagacg aattcgtggt ggtgacggta aaatgaaaga  28800
tctcagtcca agatggtatt tctactacct aggaactggg ccagaagctg gacttcccta  28860
tggtgctaac aaagacggca tcatatgggt tgcaactgag ggagccttga atacaccaaa  28920
agatcacatt ggcacccgca atcctgctaa caatgctgca atcgtgctac aacttcctca  28980
aggaacaaca ttgccaaaag gcttctacgc agaagggagc agaggcggca gtcaagcctc  29040
ttctcgttcc tcatcacgta gtcgcaacag ttcaagaaat tcaactccag gcagcagtag  29100
gggaacttct cctgctagaa tggctggcaa tggcggtgat gctgctcttg ctttgctgct  29160
gcttgacaga ttgaaccagc ttgagagcaa aatgtctggt aaaggccaac aacaacaagg  29220
ccaaactgtc actaagaaat ctgctgctga ggcttctaag aagcctcggc aaaaacgtac  29280
tgccactaaa gcatacaatg taacacaagc tttcggcaga cgtggtccag aacaaaccca  29340
aggaaatttt ggggaccagg aactaatcag acaaggaact gattacaaac attggccgca  29400
aattgcacaa tttgccccca gcgcttcagc gttcttcgga atgtcgcgca ttggcatgga  29460
agtcacacct tcgggaacgt ggttgaccta cacaggtgcc atcaaattgg atgacaaaga  29520
tccaaatttc aaagatcaag tcattttgct gaataagcat attgacgcat acaaaacatt  29580
cccaccaaca gagcctaaaa aggacaaaaa gaagaaggct gatgaaactc aagccttacc  29640
gcagagacag aagaaacagc aaactgtgac tcttcttcct gctgcagatt tggatgattt  29700
ctccaaacaa ttgcaacaat ccatgagcag tgctgactca actcaggcct aaactcatgc  29760
agaccacaca aggcagatgg gctatataaa cgttttcgct tttccgttta cgatatatag  29820
tctactcttg tgcagaatga attctcgtaa ctacatagca caagtagatg tagttaactt  29880
taatctcaca tagcaatctt taatcagtgt gtaacattag ggaggacttg aaagagccac  29940
cacattttca ccgaggccac gcggagtacg atcgagtgta cagtgaacaa tgctagggag  30000
agctgcctat atggaagagc cctaatgtgt aaaattaatt ttagtagtgc tatccccatg  30060
tgattttaat agcttcttag gagaatgaca aaaaaaaaaa aaaaaaaaaa            30110

SEQ ID NO: 4            moltype = DNA  length = 30104
FEATURE                 Location/Qualifiers
source                  1..30104
                        mol_type = other DNA
                        organism = synthetic construct
SEQUENCE: 4
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
```

-continued

```
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta actttgtgc   5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc acctttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
```

-continued

```
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt tttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtaccttttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
```

-continued

```
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
```

-continued

```
agtcattttg ctattggcct agctctctac taccettctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttataa ccagaactca atcatacact aattctttca cacgtggtgt  21660
ttattaccct gacaaagttt tcagatcctc agttttacat tcaactcagg acttgttctt  21720
acctttcttt tccaatgtta cttggttcca tgctatctct gggaccaatg gtactaagag  21780
gtttgataac cctgtcctac catttaatga tggtgtttat tttgcttcca ctgagaagtc  21840
```

```
taacataata agaggctgga tttttggtac tactttagat tcgaagaccc agtccctact  21900
tattgttaat aacgctacta atgttgttat taaagtctgt gaatttcaat tttgtaatga  21960
tccatttttg gatgtttatt accacaaaaa caacaaaagt tggatggaaa gtgagttcag  22020
agtttattct agtgcgaata attgcacttt tgaatatgtc tctcagcctt ttcttatgga  22080
ccttgaagga aaacagggta atttcaaaaa tcttagggaa tttgtgttta agaatattga  22140
tggttatttt aaaatatatt ctaagcacac gcctattaat ttagggcgtg atctccctca  22200
gggtttttcg gctttagaac cattggtaga tttgccaata ggtattaaca tcactaggtt  22260
tcaaacttta cttgctttac atagaagtta tttgactcct ggtgattctt cttcaggttg  22320
gacagctggt gctgcagctt attatgtggg ttatcttcaa cctaggactt ttctattaaa  22380
atataatgaa aatggaacca ttacagatgc tgtagactgt gcacttgacc ctctctcaga  22440
aacaaagtgt acgttgaaat ccttcactgt agaaaaagga atctatcaaa cttctaactt  22500
tagagtccaa ccaacagaat ctattgttag atttcctaat attacaaact tgtgcccttt  22560
tgatgaagtt tttaacgcca ccagatttgc atctgtttat gcttggaaca ggaagagaat  22620
cagcaactgt gttgctgatt attctgtcct atataatttc gcaccatttt tcgcttttaa  22680
gtgttatgga gtgtctccta ctaaattaaa tgatctctgc tttactaatg tctatgcaga  22740
ttcatttgta attagaggta atgaagtcag ccaaatcgct ccagggcaaa ctggaaatat  22800
tgctgattat aattataaat taccagatga ttttacaggc tgcgttatag cttggaattc  22860
taacaagctt gattctaagg ttggtggtaa ttataattac cggtatagat tgtttaggaa  22920
gtctaatctc aaaccttttg agagagatat ttcaactgaa atctatcagg ccggtaacaa  22980
accttgtaat ggtgttgcag gtgttaattg ttactttcct ttacaatcat atggtttccg  23040
acccacttat ggtgttggtc accaaccata cagagtagta gtactttctt ttgaacttct  23100
acatgcacca gcaactgttt gtggacctaa aaagtctact aatttggtta aaaacaaatg  23160
tgtcaatttc aacttcaatg gtttaacagg cacaggtgtt cttactgagt ctaacaaaaa  23220
gtttctgcct ttccaacaat ttggcagaga cattgctgac actactgatg ctgtccgtga  23280
tccacagaca cttgagattc ttgacattac accatgttct tttggtggtg tcagtgttat  23340
aacaccagga acaaatactt ctaaccaggt tgctgttctt tatcagggtg ttaactgcac  23400
agaagtccct gttgctattc atgcagatca acttactcct acttggcgtg tttattctac  23460
aggttctaat gtttttcaaa cacgtgcagg ctgtttaata ggggctgaat atgtcaacaa  23520
ctcatatgag tgtgacatac ccattggtgc aggtatatgc gctagttatc agactcagac  23580
taagtctcat cggcgggcac gtagtgtagc tagtcaatcc atcattgcct acactatgtc  23640
acttggtgca gaaaattcag ttgcttactc taataactct attgccatac ccacaaattt  23700
tactattagt gttaccacag aaattctacc agtgtctatg accaagacat cagtagattg  23760
tacaatgtac atttgtggtg attcaactga atgcagcaat cttttgttgc aatatggcag  23820
tttttgtaca caattaaaac gtgctttaac tggaatagct gttgaacaag acaaaaacac  23880
ccaagaagtt tttgcacaag tcaaacaaat ttacaaaaca ccaccaatta aatattttgg  23940
tggttttaat ttttcacaaa tattaccaga tccatcaaaa ccaagcaaga ggtcatttat  24000
tgaagatcta cttttcaaca aagtgacact tgcagatgct ggcttcatca aacaatatgg  24060
tgattgcctt ggtgatattg ctgctagaga cctcatttgt gcacaaaagt ttaacggcct  24120
tactgttttg ccacctttgc tcacagatga aatgattgct caatacactt ctgcactgtt  24180
agcgggtaca atcacttctg gttggacctt tggtgcaggt gctgcattac aaataccatt  24240
tgctatgcaa atggcttata ggtttaatgg tattggagtt acacagaatg ttctctatga  24300
gaaccaaaaa ttgattgcca accaatttaa tagtgctatt ggcaaaattc aagactcact  24360
ttcttccaca gcaagtgcac ttggaaaact tcaagatgtg gtcaaccata atgcacaagc  24420
tttaaacacg cttgttaaac aacttagctc caaatttggt gcaatttcaa gtgttttaaa  24480
tgatatcctt tcacgtcttg acaaagttga ggctgaagtg caaattgata ggttgatcac  24540
aggcagactt caaagtttgc agacatatgt gactcaacaa ttaattagag ctgcagaaat  24600
cagagcttct gctaatcttg ctgctactaa aatgtcagag tgtgtacttg gacaatcaaa  24660
aagagttgat ttttgtggaa agggctatca tcttatgtcc ttccctcagt cagcacctca  24720
tggtgtagtc ttcttgcatg tgacttatgt ccctgcacaa gaaaagaact tcacaactgc  24780
tcctgccatt tgtcatgatg gaaaagcaca ctttcctcgt gaaggtgtct ttgtttcaaa  24840
tggcacacac tggtttgtaa cacaaaggaa tttttatgaa ccacaaatca ttactacaga  24900
caacacattt gtgtctggta actgtgatgt tgtaatagga attgtcaaca acacagttta  24960
tgatcctttg caacctgaat tagattcatt caaggaggag ttagataaat attttaagaa  25020
tcatacatca ccagatgttg atttaggtga catctctggc attaatgctt cagttgtaaa  25080
cattcaaaaa gaaattgacc gcctcaatga ggttgccaag aatttaaatg aatctctcat  25140
cgatctccaa gaacttggaa agtatgagca gtatataaaa tggccatggt acatttggct  25200
aggttttata gctggcttga ttgccatagt aatggtgaca attatgcttt gctgtatgac  25260
cagttgctgt agttgtctca agggctgttg ttcttgtgga tcctgctgca aatttgatga  25320
agacgactct gagccagtgc tcaaaggagt caaattacat tacacataaa cgaacttatg  25380
gatttgttta tgagaatctt cacaattgga actgtaactt tgaagcaagg tgaaatcaag  25440
gatgctactc cttcagattt tgttcgcgct actgcaacga taccgataca agcctcactc  25500
cctttcggat ggcttattgt tggcgttgca cttcttgctg tttttcagag cgcttccaaa  25560
atcataaccc tcaaaaagag atggcaacta gcactctcca agggtgttca ctttgtttgc  25620
aacttgctgt tgttgtttgt aacagtttac tcacaccttt tgctcgttgc tgctggcctt  25680
gaagcccctt ttctctatct ttatgcttta gtctacttct tgcagagtat aaactttgta  25740
agaataataa tgaggctttg gctttgctgg aaatgccgtt ccaaaaaccc attactttat  25800
gatgccaact attttctttg ctggcatact aattgttacg actattgtat accttacaat  25860
agtgtaactt cttcaattgt cattacttca ggtgatggca caacaagtcc tatttctgaa  25920
catgactacc agattggtgg ttatactgaa aaatgggaat ctggagtaaa agactgtgtt  25980
gtattacaca gttacttcac ttcagactat taccagctgt actcaactca attgagtaca  26040
gacactggtg ttgaacatgt taccttcttc atctacaata aaattgttga tgagcctgaa  26100
gaacatgtcc aaattcacac aatcgacggt tcatccggag ttgttaatcc agtaatggaa  26160
ccaatttatg atgaaccgac gacgactact agcgtgcctt tgtaagcaca agctgatgag  26220
tacgaactta tgtactcatt cgtttcggaa gagacaggta cgtaaatagt taatagctga  26280
cttctttttc ttgctttcgt gtgattcttg ctagttacac tagccatcct tactgcgctt  26340
cgattgtgtg cgtactgctg caatattgtt aacgtgagtc ttgtaaaacc ttctttttac  26400
gtttactctc gtgttaaaaa tctgaattct tctagagttc ctgatcttct ggtctaaacg  26460
aactaaatat tatattagtt tttctgtttg gaactttaat tttagccatg gcagattcca  26520
acggtactat taccgttgaa gagcttaaaa agctccttga acaatggaac ctagtaatag  26580
```

-continued

```
gtttcctatt ccttacatgg atttgtcttc tacaatttgc ctatgccaac aggaataggt  26640
ttttgtatat aattaagtta attttcctct ggctgttatg gccagtaact ttagcttgtt  26700
ttgtgcttgc tgctgtttac agaataaatt ggatcaccgg tggaattgct atcgcaatgg  26760
cttgtcttgt aggcttgatg tggctcagct acttcattgc ttctttcaga ctgtttgcgc  26820
gtacgcgttc catgtggtca ttcaatccag aaactaacat tcttctcaac gtgccactcc  26880
atggcactat tctgaccaga ccgcttctag aaagtgaact cgtaatcgga gctgtgatcc  26940
ttcgtggaca tcttcgtatt gctggacacc atctaggacg ctgtgacatc aaggacctgc  27000
ctaaagaaat cactgttgct acatcacgaa cgctttctta ttacaaattg ggagcttcgc  27060
agcgtgtagc aggtgactca ggttttgctg catacagtcg ctacaggatt ggcaactata  27120
aattaaacac agaccattcc agtagcagtg acaatattgc tttgcttgta cagtaagtga  27180
caacagatgt ttcatctcgt tgactttcag gttactatag cagagatatt actaattatt  27240
atgaggactt ttaaagtttc catttggaat cttgattaca tcataaacct cataattaaa  27300
aatttatcta agtcactaac tgagaataaa tattctcaat tagatgaaga gcaaccaatg  27360
gagattgatt aaacgaacat gaaaattatt cttttcttgg cactgataac actcgctact  27420
tgtgagcttt atcactacca agagtgtgtt agaggtacaa cagtactttt aaaagaacct  27480
tgctcttctg gaacatacga gggcaattca ccatttcatc ctctagctga taacaaattt  27540
gcactgactt gctttagcac tcaatttgct tttgcttgtc ctgacggcgt aaaacacgtc  27600
tatcagttac gtgccagatc agtttcacct aaactgttca tcagacaaga ggaagttcaa  27660
gaactttact ctccaatttt tcttattgtt gcggcaatag tgtttataac actttgcttc  27720
acactcaaaa gaaagacaga atgattgaac tttcattaat tgacttctat ttgtgctttt  27780
tagcctttct gctattcctt gttttaatta tgcttattat cttttggttc tcacttgaac  27840
tgcaagatca taatgaaact tgtcacgcct aaacgaacat gaccaacaag tgtctcctcc  27900
aaattgctct cctgttgtgc ttctccacta cagctctttc catgagctac aacttgcttg  27960
gattcctaca aagaagcagc aattttcagt gtcagaagct cctgtggcaa ttgaatggga  28020
ggcttgaata ctgcctcaag gacaggatga actttgacat ccctgaggag attaagcagc  28080
tgcagcagtt ccagaaggag gacgccgcat tgaccatcta tgagatgctc cagaacatct  28140
ttgctatttt cagacaagat tcatctagca ctggctggaa tgagactatt gttgagaacc  28200
tcctggctaa tgtctatcat cagataaacc atctgaagac agtcctggaa gaaaaactgg  28260
agaaagaaga tttcaccagg ggaaaactca tgagcagtct gcacctgaaa agatattatg  28320
ggaggattct gcattacctg aaggccaagg agtacagtca ctgtgcctgg accatagtca  28380
gagtggaaat cctaaggaac ttttacttca ttaacagact tacaggttac ctccgaaact  28440
gagacgttcg tgttgtttta gatttcatct aaacgaacaa actaaaatgt ctgataatgg  28500
accccaaaat cagcgaaatg caccccgcat tacgtttggt ggaccctcag attcaactgg  28560
cagtaaccag aatggagaac gcagtggggc gcgatcaaaa caacgtcggc cccaaggttt  28620
acccaataat actgcgtctt ggttcaccgc tctcactcaa catggcaagg aagaccttaa  28680
attccctcga ggacaaggcg ttccaattaa caccaatagc agtccagatg accaaattgg  28740
ctactaccga agagctacca gacgaattcg tggtggtgac ggtaaaatga aagatctcag  28800
tccaagatgg tatttctact acctaggaac tgggccagaa gctggacttc cctatggtgc  28860
taacaaagac ggcatcatat gggttgcaac tgagggagcc ttgaatacac caaaagatca  28920
cattggcacc cgcaatcctg ctaacaatgc tgcaatcgtg ctacaacttc ctcaaggaac  28980
aacattgcca aaaggcttct acgcagaagg gagcagaggc ggcagtcaag cctcttctcg  29040
ttcctcatca cgtagtcgca acagttcaag aaattcaact ccaggcagca gtaggggaac  29100
ttctcctgct agaatggctg gcaatggcgg tgatgctgct cttgctttgc tgctgcttga  29160
cagattgaac cagcttgaga gcaaaatgtc tggtaaaggc caacaacaac aaggccaaac  29220
tgtcactaag aaatctgctg ctgaggcttc taagaagcct cggcaaaaac gtactgccac  29280
taaagcatac aatgtaacac aagctttcgg cagacgtggt ccagaacaaa cccaaggaaa  29340
ttttggggac caggaactaa tcagacaagg aactgattac aaacattggc cgcaaattgc  29400
acaatttgcc cccagcgctt cagcgttctt cggaatgtcg cgcattggca tggaagtcac  29460
accttcggga acgtggttga cctacacagg tgccatcaaa ttggatgaca aagatccaaa  29520
tttcaaagat caagtcattt tgctgaataa gcatattgac gcatacaaaa cattcccacc  29580
aacagagcct aaaaaggaca aaaagaagaa ggctgatgaa actcaagcct taccgcagag  29640
acagaagaaa cagcaaactg tgactcttct tcctgctgca gatttggatg atttctccaa  29700
acaattgcaa caatccatga gcagtgctga ctcaactcag gcctaaactc atgcagacca  29760
cacaaggcag atgggctata taaacgtttt cgcttttccg tttacgatat atagtctact  29820
cttgtgcaga atgaattctc gtaactacat agcacaagta gatgtagtta actttaatct  29880
cacatagcaa tctttaatca gtgtgtaaca ttagggagga cttgaaagag ccaccacatt  29940
ttcaccgagg ccacgcggag tacgatcgag tgtacagtga acaatgctag ggagagctgc  30000
ctatatggaa gagccctaat gtgtaaaatt aattttagta gtgctatccc catgtgattt  30060
taatagcttc ttaggagaat gacaaaaaaa aaaaaaaaaa aaaa                  30104
```

```
SEQ ID NO: 5           moltype = DNA  length = 29445
FEATURE                Location/Qualifiers
source                 1..29445
                       mol_type = other DNA
                       organism = synthetic construct
SEQUENCE: 5
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
```

-continued

```
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
```

-continued

```
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt ttttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtacctttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
```

-continued

```
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
```

-continued

```
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat caccccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagattttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
```

-continued

```
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga cataccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
```

-continued

```
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtaa  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacaatg ataatgaaac ttgtcacgcc taaacgaaca tgaccaacaa gtgtctcctc  27240
caaattgctc tcctgttgtg cttctccact acagctcttt ccatgagcta caacttgctt  27300
ggattcctac aaagaagcag caattttcag tgtcagaagc tcctgtggca attgaatggg  27360
aggcttgaat actgcctcaa ggacaggatg aactttgaca tccctgagga gattaagcag  27420
ctgcagcagt tccagaagga ggacgccgca ttgaccatct atgagatgct ccagaacatc  27480
tttgctattt tcagacaaga ttcatctagc actggctgga atgagactat tgttgagaac  27540
ctcctggcta atgtctatca tcagataaac catctgaaga cagtcctgga agaaaaactg  27600
gagaaagaag atttcaccag gggaaaactc atgagcagtc tgcacctgaa aagatattat  27660
gggaggattc tgcattacct gaaggccaag gagtacagtc actgtgcctg gaccatagtc  27720
agagtggaaa tcctaaggaa cttttacttc attaacagac ttacaggtta cctccgaaac  27780
tgagacgttc gtgttgtttt agatttcatc taaacgaaca aactaaaatg tctgataatg  27840
gaccccaaaa tcagcgaaat gcaccccgca ttacgtttgg tggaccctca gattcaactg  27900
gcagtaacca gaatggagaa cgcagtgggg cgcgatcaaa acaacgtcgg ccccaaggtt  27960
tacccaataa tactgcgtct tggttcaccg ctctcactca acatggcaag gaagacctta  28020
aattccctcg aggacaaggc gttccaatta acaccaatag cagtccagat gaccaaattg  28080
gctactaccg aagagctacc agacgaattc gtggtggtga cggtaaaatg aaagatctca  28140
gtccaagatg gtatttctac tacctaggaa ctgggccaga agctggactt ccctatggtg  28200
ctaacaaaga cggcatcata tgggttgcaa ctgagggagc cttgaataca ccaaaagatc  28260
acattggcac ccgcaatcct gctaacaatg ctgcaatcgt gctacaactt cctcaaggaa  28320
caacattgcc aaaaggcttc tacgcagaag ggagcagagg cggcagtcaa gcctcttctc  28380
gttcctcatc acgtagtcgc aacagttcaa gaaattcaac tccaggcagc agtaggggaa  28440
cttctcctgc tagaatggct ggcaatggcg gtgatgctgc tcttgctttg ctgctgcttg  28500
acagattgaa ccagcttgag agcaaaatgt ctggtaaagg ccaacaacaa caaggccaaa  28560
ctgtcactaa gaaatctgct gctgaggctt ctaagaagcc tcggcaaaaa cgtactgcca  28620
ctaaagcata caatgtaaca caagctttcg gcagacgtgg tccagaacaa acccaaggaa  28680
attttgggga ccaggaacta atcagacaag gaactgatta caaacattgg ccgcaaattg  28740
cacaatttgc ccccagcgct tcagcgttct tcggaatgtc gcgcattggc atggaagtca  28800
caccttcggg aacgtggttg acctacacag gtgccatcaa attggatgac aaagatccaa  28860
atttcaaaga tcaagtcatt ttgctgaata agcatattga cgcatacaaa acattcccac  28920
caacagagcc taaaaaggac aaaaagaaga aggctgatga aactcaagcc ttaccgcaga  28980
gacagaagaa acagcaaact gtgactcttc ttcctgctgc agatttggat gatttctcca  29040
aacaattgca acaatccatg agcagtgctg actcaactca ggcctaaact catgcagacc  29100
acacaaggca gatgggctat ataaacgttt tcgcttttcc gtttacgata tatagtctac  29160
tcttgtgcag aatgaattct cgtaactaca tagcacaagt agatgtagtt aactttaatc  29220
```

-continued

```
tcacatagca atctttaatc agtgtgtaac attagggagg acttgaaaga gccaccacat  29280
tttcaccgag gccacgcgga gtacgatcga gtgtacagtg aacaatgcta gggagagctg  29340
cctatatgga agagccctaa tgtgtaaaat taattttagt agtgctatcc ccatgtgatt  29400
ttaatagctt cttaggagaa tgacaaaaaa aaaaaaaaaa aaaaa                 29445

SEQ ID NO: 6           moltype = DNA  length = 29436
FEATURE                Location/Qualifiers
source                 1..29436
                       mol_type = other DNA
                       organism = synthetic construct
SEQUENCE: 6
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
```

-continued

```
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gtttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt ttttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgatttgac acatggttta gccagcgtgg tggtagttat actaatgaca aagcttgccc  8820
```

-continued

```
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtacctttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt tttaaacgg gtttgcggtg taagtgcagc ccgtcttaca  13500
ccgtgcggca caggcactag tactgatgtc gtatacaggg cttttgacat ctacaatgat  13560
```

-continued

```
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
```

-continued

```
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagattttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt tttttcttgtt ttattgccac tagtctctag  21600
tcagtgtgtt aatcttataa ccagaactca atcatacact aattctttca cacgtggtgt  21660
ttattaccct gacaaagttt tcagatcctc agttttacat tcaactcagg acttgttctt  21720
acctttcttt tccaatgtta cttggttcca tgctatacat gtctctggga ccaatggtac  21780
taagaggttt gataaccctg tcctaccatt taatgatggt gtttattttg cttccactga  21840
gaagtctaac ataataagag gctggatttt tggtactact ttagattcga agacccagtc  21900
cctacttatt gttaataacg ctactaatgt tgttattaaa gtctgtgaat ttcaattttg  21960
taatgatcca tttttggatg tttattacca caaaaacaac aaaagttgga tggaaagtga  22020
gttcagagtt tattctagtg cgaataattg cacttttgaa tatgtctctc agccttttct  22080
tatggacctt gaaggaaaac agggtaattt caaaaatctt agggaatttg tgtttaagaa  22140
tattgatggt tattttaaaa tatattctaa gcacacgcct attaatttag ggcgtgatct  22200
ccctcagggt ttttcggctt tagaaccatt ggtagatttg ccaataggta ttaacatcac  22260
taggtttcaa actttacttg ctttacatag aagttatttg actcctggtg attcttcttc  22320
aggttggaca gctggtgctg cagcttatta tgtgggttat cttcaaccta ggacttttct  22380
attaaaatat aatgaaaatg gaaccattac agatgctgta gactgtgcac ttgaccctct  22440
ctcagaaaca aagtgtacgt tgaaatcctt cactgtagaa aaaggaatct atcaaacttc  22500
taactttaga gtccaaccaa cagaatctat tgttagattt cctaatatta caaacttgtg  22560
cccttttgat gaagttttta acgccaccag atttgcatct gtttatgctt ggaacaggaa  22620
gagaatcagc aactgtgttg ctgattattc tgtcctatat aatttcgcac catttttcgc  22680
ttttaagtgt tatggagtgt ctcctactaa attaaatgat ctctgcttta ctaatgtcta  22740
tgcagattca tttgtaatta gaggtaatga agtcagccaa atcgctccag ggcaaactgg  22800
aaatattgct gattataatt ataaattacc agatgatttt acaggctgcg ttatagcttg  22860
gaattctaac aagcttgatt ctaaggttgg tggtaattat aattacctgt atagattgtt  22920
taggaagtct aatctcaaac cttttgagag agatatttca actgaaatct atcaggccgg  22980
taacaaacct tgtaatggtg ttgcaggttt taattgttac tttcctttac gatcatatgg  23040
```

-continued

```
tttccgaccc acttatggtg ttggtcacca accatacaga gtagtagtac tttcttttga  23100
acttctacat gcaccagcaa ctgtttgtgg acctaaaaag tctactaatt tggttaaaaa  23160
caaatgtgtc aatttcaact tcaatggttt aacaggcaca ggtgttctta ctgagtctaa  23220
caaaaagttt ctgcctttcc aacaatttgg cagagacatt gctgacacta ctgatgctgt  23280
ccgtgatcca cagacacttg agattcttga cattacacca tgttcttttg gtggtgtcag  23340
tgttataaca ccaggaacaa atacttctaa ccaggttgct gttctttatc agggtgttaa  23400
ctgcacagaa gtccctgttg ctattcatgc agatcaactt actcctactt ggcgtgttta  23460
ttctacaggt tctaatgttt ttcaaacacg tgcaggctgt ttaatagggg ctgaatatgt  23520
caacaactca tatgagtgtg acatacccat tggtgcaggt atatgcgcta gttatcagac  23580
tcagactaag tctcatcggc gggcacgtag tgtagctagt caatccatca ttgcctacac  23640
tatgtcactt ggtgcagaaa attcagttgc ttactctaat aactctattg ccatacccac  23700
aaattttact attagtgtta ccacagaaat tctaccagtg tctatgacca agacatcagt  23760
agattgtaca atgtacattt gtggtgattc aactgaatgc agcaatcttt tgttgcaata  23820
tggcagtttt tgtacacaat taaaacgtgc tttaactgga atagctgttg aacaagacaa  23880
aaacacccaa gaagtttttg cacaagtcaa acaaatttac aaaacaccac caattaaata  23940
ttttggtggt tttaattttt cacaaatatt accagatcca tcaaaaccaa gcaagaggtc  24000
atttattgaa gatctacttt tcaacaaagt gacacttgca gatgctggct tcatcaaaca  24060
atatggtgat tgccttggtg atattgctgc tagagacctc atttgtgcac aaaagtttaa  24120
cggccttact gttttgccac ctttgctcac agatgaaatg attgctcaat acacttctgc  24180
actgttagcg ggtacaatca cttctggttg gacctttggt gcaggtgctg cattacaaat  24240
accatttgct atgcaaatgg cttataggtt taatggtatt ggagttacac agaatgttct  24300
ctatgagaac caaaaattga ttgccaacca atttaatagt gctattggca aaattcaaga  24360
ctcactttct tccacagcaa gtgcacttgg aaaacttcaa gatgtggtca accataatgc  24420
acaagcttta aacacgcttg ttaaacaact tagctccaaa tttggtgcaa tttcaagtgt  24480
tttaaatgat atcctttcac gtcttgacaa agttgaggct gaagtgcaaa ttgataggtt  24540
gatcacaggc agacttcaaa gtttgcagac atatgtgact caacaattaa ttagagctgc  24600
agaaatcaga gcttctgcta atcttgctgc tactaaaatg tcagagtgtg tacttggaca  24660
atcaaaaaga gttgattttt gtggaaaggg ctatcatctt atgtccttcc ctcagtcagc  24720
acctcatggt gtagtcttct tgcatgtgac ttatgtccct gcacaagaaa agaacttcac  24780
aactgctcct gccatttgtc atgatggaaa agcacacttt cctcgtgaag gtgtctttgt  24840
ttcaaatggc acacactggt ttgtaacaca aaggaatttt tatgaaccac aaatcattac  24900
tacagacaac acatttgtgt ctggtaactg tgatgttgta ataggaattg tcaacaacac  24960
agtttatgat cctttgcaac ctgaattaga ttcattcaag gaggagttag ataaatattt  25020
taagaatcat acatcaccag atgttgattt aggtgacatc tctggcatta atgcttcagt  25080
tgtaaacatt caaaaagaaa ttgaccgcct caatgaggtt gccaagaatt taaatgaatc  25140
tctcatcgat ctccaagaac ttggaaagta tgagcagtat ataaaatggc catggtacat  25200
ttggctaggt tttatagctg gcttgattgc catagtaatg gtgacaatta tgctttgctg  25260
tatgaccagt tgctgtagtt gtctcaaggg ctgttgttct tgtggatcct gctgcaaatt  25320
tgatgaagac gactctgagc cagtgctcaa aggagtcaaa ttacattaca cataaacgaa  25380
cttatggatt tgtttatgag aatcttcaca attggaactg taactttgaa gcaaggtgaa  25440
atcaaggatg ctactccttc agattttgtt cgcgctactg caacgatacc gatacaagcc  25500
tcactccctt tcggatggct tattgttggc gttgcacttc ttgctgtttt tcagagcgct  25560
tccaaaatca taaccctcaa aaagagatgg caactagcac tctccaaggg tgttcacttt  25620
gtttgcaact tgctgttgtt gtttgtaaca gtttactcac acctttttgct cgttgctgct  25680
ggccttgaag ccccttttct ctatctttat gctttagtct acttcttgca gagtataaac  25740
tttgtaagaa taataatgag gctttggctt tgctggaaat gccgttccaa aaacccatta  25800
ctttatgatg ccaactattt tctttgctgg catactaatt gttacgacta ttgtatacct  25860
tacaatagtg taacttcttc aattgtcatt acttcaggtg atggcacaac aagtcctatt  25920
tctgaacatg actaccagat tggtggttat actgaaaaat gggaatctgg agtaaaagac  25980
tgtgttgtat tacacagtta cttcacttca gactattacc agctgtactc aactcaattg  26040
agtacagaca ctggtgttga acatgttacc ttcttcatct acaataaaat tgttgatgag  26100
cctgaagaac atgtccaaat tcacacaatc gacggttcat ccggagttgt taatccagta  26160
atggaaccaa tttatgatga accgacgacg actactagcg tgcctttgta agcacaagct  26220
gatgagtacg aacttatgta ctcattcgtt tcggaagaga caggtacgta aatagttaat  26280
agctgacttc tttttcttgc tttcgtgtga ttcttgctag ttacactagc catccttact  26340
gcgcttcgat tgtgtgcgta ctgctgcaat attgttaacg tgagtcttgt aaaaccttct  26400
ttttacgttt actctcgtgt taaaaatctg aattcttcta gagttcctga tcttctggtc  26460
taaacgaact aaatattata ttagtttttc tgtttggaac tttaatttta gccatggcag  26520
attccaacgg tactattacc gttgaagagc ttaaaaagct ccttgaacaa tggaacctag  26580
taataggttt cctattcctt acatggattt gtcttctaca atttgcctat gccaacagga  26640
ataggttttt gtatataatt aagttaattt tcctctggct gttatggcca gtaactttag  26700
cttgttttgt gcttgctgct gtttacagaa taaattggat caccggtgga attgctatcg  26760
caatggcttg tcttgtaggc ttgatgtggc tcagctactt cattgcttct ttcagactgt  26820
ttgcgcgtac gcgttccatg tggtcattca atccagaaac taacattctt ctcaacgtgc  26880
cactccatgg cactattctg accagaccgc ttctagaaag tgaactcgta atcggagctg  26940
tgatccttcg tggacatctt cgtattgctg gacaccatct aggacgctgt gacatcaagg  27000
acctgcctaa agaaatcact gttgctacat cacgaacgct ttcttattac aaattgggag  27060
cttcgcagcg tgtagcaggt gactcaggtt ttgctgcata cagtcgctac aggattggca  27120
actataaatt aaacacagac cattccagta gcagtgacaa tattgctttg cttgtacaat  27180
gataatgaaa cttgtcacgc ctaaacgaac atgaccaaca agtgtctcct ccaaattgct  27240
ctcctgttgt gcttctccac tacagctctt tccatgagct acaacttgct tggattccta  27300
caaagaagca gcaattttca gtgtcagaag ctcctgtggc aattgaatgg gaggcttgaa  27360
tactgcctca aggacaggat gaactttgac atccctgagg agattaagca gctgcagcag  27420
ttccagaagg aggacgccgc attgaccatc tatgagatgc tccagaacat ctttgctatt  27480
ttcagacaag attcatctag cactggctgg aatgagacta ttgttgagaa cctcctggct  27540
aatgtctatc atcagataaa ccatctgaag acagtcctgg aagaaaaact ggagaaagaa  27600
gatttcacca ggggaaaact catgagcagt ctgcacctga aaagatatta tgggaggatt  27660
ctgcattacc tgaaggccaa ggagtacagt cactgtgcct ggaccatagt cagagtggaa  27720
atcctaagga acttttactt cattaacaga cttacaggtt acctccgaaa ctgagacgtt  27780
```

```
cgtgttgttt tagatttcat ctaaacgaac aaactaaaat gtctgataat ggaccccaaa  27840
atcagcgaaa tgcaccccgc attacgtttg gtggaccctc agattcaact ggcagtaacc  27900
agaatggaga acgcagtggg gcgcgatcaa aacaacgtcg gccccaaggt ttacccaata  27960
atactgcgtc ttggttcacc gctctcactc aacatggcaa ggaagacctt aaattccctc  28020
gaggacaagg cgttccaatt aacaccaata gcagtccaga tgaccaaatt ggctactacc  28080
gaagagctac cagacgaatt cgtggtggtg acggtaaaat gaaagatctc agtccaagat  28140
ggtatttcta ctacctagga actgggccag aagctggact tccctatggt gctaacaaag  28200
acggcatcat atgggttgca actgagggag ccttgaatac accaaaagat cacattggca  28260
cccgcaatcc tgctaacaat gctgcaatcg tgctacaact tcctcaagga acaacattgc  28320
caaaaggctt ctacgcagaa gggagcagag gcggcagtca agcctcttct cgttcctcat  28380
cacgtagtcg caacagttca agaaattcaa ctccaggcag cagtagggga acttctcctg  28440
ctagaatggc tggcaatggc ggtgatgctg ctcttgcttt gctgctgctt gacagattga  28500
accagcttga gagcaaaatg tctggtaaag gccaacaaca acaaggccaa actgtcacta  28560
agaaatctgc tgctgaggct tctaagaagc ctcggcaaaa acgtactgcc actaaagcat  28620
acaatgtaac acaagctttc ggcagacgtg gtccagaaca aacccaagga aatttggggg  28680
accaggaact aatcagacaa ggaactgatt acaaacattg gccgcaaatt gcacaatttg  28740
cccccagcgc ttcagcgttc ttcggaatgt cgcgcattgg catggaagtc acaccttcgg  28800
gaacgtggtt gacctacaca ggtgccatca aattggatga caaagatcca aatttcaaag  28860
atcaagtcat tttgctgaat aagcatattg acgcatacaa aacattccca ccaacagagc  28920
ctaaaaagga caaaaagaag aaggctgatg aaactcaagc cttaccgcag agacagaaga  28980
aacagcaaac tgtgactctt cttcctgctg cagatttgga tgatttctcc aaacaattgc  29040
aacaatccat gagcagtgct gactcaactc aggcctaaac tcatgcagac cacacaaggc  29100
agatgggcta tataaacgtt ttcgcttttc cgtttacgat atatagtcta ctcttgtgca  29160
gaatgaattc tcgtaactac atagcacaag tagatgtagt taactttaat ctcacatagc  29220
aatctttaat cagtgtgtaa cattagggag gacttgaaag agccaccaca ttttcaccga  29280
ggccacgcgg agtacgatcg agtgtacagt gaacaatgct agggagagct gcctatatgg  29340
aagagcccta atgtgtaaaa ttaattttag tagtgctatc cccatgtgat tttaatagct  29400
tcttaggaga atgacaaaaa aaaaaaaaaa aaaaaa                            29436

SEQ ID NO: 7           moltype = DNA  length = 29430
FEATURE                Location/Qualifiers
source                 1..29430
                       mol_type = other DNA
                       organism = synthetic construct
SEQUENCE: 7
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
```

-continued

```
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc acctttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
```

-continued

```
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt tttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtacctttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
```

```
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgtttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
```

-continued

```
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
```

-continued

```
tcagtgtgtt aatcttataa ccagaactca atcatacact aattctttca cacgtggtgt  21660
ttattaccct gacaaagttt tcagatcctc agttttacat tcaactcagg acttgttctt  21720
acctttcttt tccaatgtta cttggttcca tgctatctct gggaccaatg gtactaagag  21780
gtttgataac cctgtcctac catttaatga tggtgtttat tttgcttcca ctgagaagtc  21840
taacataata agaggctgga tttttggtac tactttagat tcgaagaccc agtccctact  21900
tattgttaat aacgctacta atgttgttat taaagtctgt gaatttcaat tttgtaatga  21960
tccatttttg gatgtttatt accacaaaaa caacaaaagt tggatggaaa gtgagttcag  22020
agtttattct agtgcgaata attgcacttt tgaatatgtc tctcagcctt ttcttatgga  22080
ccttgaagga aaacagggta atttcaaaaa tcttagggaa tttgtgttta agaatattga  22140
tggttatttt aaaatatatt ctaagcacac gcctattaat ttagggcgtg atctccctca  22200
gggtttttcg gctttagaac cattggtaga tttgccaata ggtattaaca tcactaggtt  22260
tcaaacttta cttgctttac atagaagtta tttgactcct ggtgattctt cttcaggttg  22320
gacagctggt gctgcagctt attatgtggg ttatcttcaa cctaggactt ttctattaaa  22380
atataatgaa aatggaacca ttacagatgc tgtagactgt gcacttgacc ctctctcaga  22440
aacaaagtgt acgttgaaat ccttcactgt agaaaaagga atctatcaaa cttctaactt  22500
tagagtccaa ccaacagaat ctattgttag atttcctaat attacaaact tgtgcccttt  22560
tgatgaagtt tttaacgcca ccagatttgc atctgtttat gcttggaaca ggaagagaat  22620
cagcaactgt gttgctgatt attctgtcct atataatttc gcaccatttt tcgcttttaa  22680
gtgttatgga gtgtctccta ctaaattaaa tgatctctgc tttactaatg tctatgcaga  22740
ttcatttgta attagaggta atgaagtcag ccaaatcgct ccagggcaaa ctggaaatat  22800
tgctgattat aattataaat taccagatga ttttacaggc tgcgttatag cttggaattc  22860
taacaagctt gattctaagg ttggtggtaa ttataattac cggtatagat tgtttaggaa  22920
gtctaatctc aaacctttg agagagatat ttcaactgaa atctatcagg ccggtaacaa  22980
accttgtaat ggtgttgcag gtgttaattg ttactttcct ttacaatcat atggtttccg  23040
acccacttat ggtgttggtc accaaccata cagagtagta gtactttctt ttgaacttct  23100
acatgcacca gcaactgttt gtggacctaa aaagtctact aatttggtta aaaacaaatg  23160
tgtcaatttc aacttcaatg gtttaacagg cacaggtgtt cttactgagt ctaacaaaaa  23220
gtttctgcct ttccaacaat ttggcagaga cattgctgac actactgatg ctgtccgtga  23280
tccacagaca cttgagattc ttgacattac accatgttct tttggtggtg tcagtgttat  23340
aacaccagga acaaatactt ctaaccaggt tgctgttctt tatcagggtg ttaactgcac  23400
agaagtccct gttgctattc atgcagatca acttactcct acttggcgtg tttattctac  23460
aggttctaat gtttttcaaa cacgtgcagg ctgtttaata ggggctgaat atgtcaacaa  23520
ctcatatgag tgtgacatac ccattggtgc aggtatatgc gctagttatc agactcagac  23580
taagtctcat cggcgggcac gtagtgtagc tagtcaatcc atcattgcct acactatgtc  23640
acttggtgca gaaaattcag ttgcttactc taataactct attgccatac ccacaaattt  23700
tactattagt gttaccacag aaattctacc agtgtctatg accaagacat cagtagattg  23760
tacaatgtac atttgtggtg attcaactga atgcagcaat cttttgttgc aatatggcag  23820
tttttgtaca caattaaaac gtgctttaac tggaatagct gttgaacaag acaaaaacac  23880
ccaagaagtt tttgcacaag tcaaacaaat ttacaaaaca ccaccaatta aatattttgg  23940
tggttttaat ttttcacaaa tattaccaga tccatcaaaa ccaagcaaga ggtcatttat  24000
tgaagatcta cttttcaaca aagtgacact tgcagatgct ggcttcatca aacaatatgg  24060
tgattgcctt ggtgatattg ctgctagaga cctcatttgt gcacaaaagt ttaacggcct  24120
tactgttttg ccacctttgc tcacagatga aatgattgct caatacactt ctgcactgtt  24180
agcgggtaca atcacttctg gttggacctt tggtgcaggt gctgcattac aaataccatt  24240
tgctatgcaa atggcttata ggtttaatgg tattggagtt acacagaatg ttctctatga  24300
gaaccaaaaa ttgattgcca accaatttaa tagtgctatt ggcaaaattc aagactcact  24360
ttcttccaca gcaagtgcac ttggaaaact tcaagatgtg gtcaaccata atgcacaagc  24420
tttaaacacg cttgttaaac aacttagctc caaatttggt gcaatttcaa gtgttttaaa  24480
tgatatcctt tcacgtcttg acaaagttga ggctgaagtg caaattgata ggttgatcac  24540
aggcagactt caaagtttgc agacatatgt gactcaacaa ttaattagag ctgcagaaat  24600
cagagcttct gctaatcttg ctgctactaa aatgtcagag tgtgtacttg gacaatcaaa  24660
aagagttgat ttttgtggaa agggctatca tcttatgtcc ttccctcagt cagcacctca  24720
tggtgtagtc ttcttgcatg tgacttatgt ccctgcacaa gaaaagaact tcacaactgc  24780
tcctgccatt tgtcatgatg gaaaagcaca ctttcctcgt gaaggtgtct ttgtttcaaa  24840
tggcacacac tggtttgtaa cacaaaggaa tttttatgaa ccacaaatca ttactacaga  24900
caacacattt gtgtctggta actgtgatgt tgtaatagga attgtcaaca acacagttta  24960
tgatcctttg caacctgaat tagattcatt caaggaggag ttagataaat attttaagaa  25020
tcatacatca ccagatgttg atttaggtga catctctggc attaatgctt cagttgtaaa  25080
cattcaaaaa gaaattgacc gcctcaatga ggttgccaag aatttaaatg aatctctcat  25140
cgatctccaa gaacttggaa agtatgagca gtatataaaa tggccatggt acatttggct  25200
aggttttata gctggcttga ttgccatagt aatggtgaca attatgcttt gctgtatgac  25260
cagttgctgt agttgtctca agggctgttg ttcttgtgga tcctgctgca aatttgatga  25320
agacgactct gagccagtgc tcaaaggagt caaattacat tacacataaa cgaacttatg  25380
gatttgttta tgagaatctt cacaattgga actgtaactt tgaagcaagg tgaaatcaag  25440
gatgctactc cttcagattt tgttcgcgct actgcaacga taccgataca agcctcactc  25500
cctttcggat ggcttattgt tggcgttgca cttcttgctg tttttcagag cgcttccaaa  25560
atcataaccc tcaaaaagag atggcaacta gcactctcca agggtgttca ctttgtttgc  25620
aacttgctgt tgttgtttgt aacagtttac tcacaccttt tgctcgttgc tgctggcctt  25680
gaagcccctt ttctctatct ttatgcttta gtctacttct tgcagagtat aaactttgta  25740
agaataataa tgaggctttg gctttgctgg aaatgccgtt ccaaaaaccc attactttat  25800
gatgccaact attttctttg ctggcatact aattgttacg actattgtat accttacaat  25860
agtgtaactt cttcaattgt cattacttca ggtgatggca caacaagtcc tatttctgaa  25920
catgactacc agattggtgg ttatactgaa aaatgggaat ctggagtaaa agactgtgtt  25980
gtattacaca gttacttcac ttcagactat taccagctgt actcaactca attgagtaca  26040
gacactggtg ttgaacatgt taccttcttc atctacaata aaattgttga tgagcctgaa  26100
gaacatgtcc aaattcacac aatcgacggt tcatccggag ttgttaatcc agtaatggaa  26160
ccaatttatg atgaaccgac gacgactact agcgtgcctt tgtaagcaca agctgatgag  26220
tacgaactta tgtactcatt cgtttcggaa gagacaggta cgtaaatagt taatagctga  26280
cttctttttc ttgctttcgt gtgattcttg ctagttacac tagccatcct tactgcgctt  26340
```

-continued

```
cgattgtgtg cgtactgctg caatattgtt aacgtgagtc ttgtaaaacc ttctttttac  26400
gtttactctc gtgttaaaaa tctgaattct tctagagttc ctgatcttct ggtctaaacg  26460
aactaaatat tatattagtt tttctgtttg gaactttaat tttagccatg gcagattcca  26520
acggtactat taccgttgaa gagcttaaaa agctccttga acaatggaac ctagtaatag  26580
gtttcctatt ccttacatgg atttgtcttc tacaatttgc ctatgccaac aggaataggt  26640
ttttgtatat aattaagtta attttcctct ggctgttatg gccagtaact ttagcttgtt  26700
ttgtgcttgc tgctgtttac agaataaatt ggatcaccgg tggaattgct atcgcaatgg  26760
cttgtcttgt aggcttgatg tggctcagct acttcattgc ttctttcaga ctgtttgcgc  26820
gtacgcgttc catgtggtca ttcaatccag aaactaacat tcttctcaac gtgccactcc  26880
atggcactat tctgaccaga ccgcttctag aaagtgaact cgtaatcgga gctgtgatcc  26940
ttcgtggaca tcttcgtatt gctggacacc atctaggacg ctgtgacatc aaggacctgc  27000
ctaaagaaat cactgttgct acatcacgaa cgctttctta ttacaaattg ggagcttcgc  27060
agcgtgtagc aggtgactca ggttttgctg catacagtcg ctacaggatt ggcaactata  27120
aattaaacac agaccattcc agtagcagtg acaatattgc tttgcttgta caatgataat  27180
gaaacttgtc acgcctaaac gaacatgacc aacaagtgtc tcctccaaat tgctctcctg  27240
ttgtgcttct ccactacagc tctttccatg agctacaact tgcttggatt cctacaaaga  27300
agcagcaatt ttcagtgtca gaagctcctg tggcaattga atgggaggct tgaatactgc  27360
ctcaaggaca ggatgaactt tgacatccct gaggagatta agcagctgca gcagttccag  27420
aaggaggacg ccgcattgac catctatgag atgctccaga acatctttgc tattttcaga  27480
caagattcat ctagcactgg ctggaatgag actattgttg agaacctcct ggctaatgtc  27540
tatcatcaga taaaccatct gaagacagtc ctggaagaaa aactggagaa agaagatttc  27600
accaggggaa aactcatgag cagtctgcac ctgaaaagat attatgggag gattctgcat  27660
tacctgaagg ccaaggagta cagtcactgt gcctggacca tagtcagagt ggaaatccta  27720
aggaactttt acttcattaa cagacttaca ggttacctcc gaaactgaga cgttcgtgtt  27780
gttttagatt tcatctaaac gaacaaacta aaatgtctga taatggaccc caaaatcagc  27840
gaaatgcacc ccgcattacg tttggtggac cctcagattc aactggcagt aaccagaatg  27900
gagaacgcag tggggcgcga tcaaaacaac gtcggcccca aggtttaccc aataatactg  27960
cgtcttggtt caccgctctc actcaacatg gcaaggaaga ccttaaattc cctcgaggac  28020
aaggcgttcc aattaacacc aatagcagtc cagatgacca aattggctac taccgaagag  28080
ctaccagacg aattcgtggt ggtgacggta aaatgaaaga tctcagtcca agatggtatt  28140
tctactacct aggaactggg ccagaagctg gacttcccta tggtgctaac aaagacggca  28200
tcatatgggt tgcaactgag ggagccttga atacaccaaa agatcacatt ggcacccgca  28260
atcctgctaa caatgctgca atcgtgctac aacttcctca aggaacaaca ttgccaaaag  28320
gcttctacgc agaagggagc agaggcggca gtcaagcctc ttctcgttcc tcatcacgta  28380
gtcgcaacag ttcaagaaat tcaactccag gcagcagtag gggaacttct cctgctagaa  28440
tggctggcaa tggcggtgat gctgctcttg ctttgctgct gcttgacaga ttgaaccagc  28500
ttgagagcaa aatgtctggt aaaggccaac aacaacaagg ccaaactgtc actaagaaat  28560
ctgctgctga ggcttctaag aagcctcggc aaaaacgtac tgccactaaa gcatacaatg  28620
taacacaagc tttcggcaga cgtggtccag aacaaaccca aggaaatttt ggggaccagg  28680
aactaatcag acaaggaact gattacaaac attggccgca aattgcacaa tttgccccca  28740
gcgcttcagc gttcttcgga atgtcgcgca ttggcatgga agtcacacct tcgggaacgt  28800
ggttgaccta cacaggtgcc atcaaattgg atgacaaaga tccaaatttc aaagatcaag  28860
tcattttgct gaataagcat attgacgcat acaaaacatt cccaccaaca gagcctaaaa  28920
aggacaaaaa gaagaaggct gatgaaactc aagccttacc gcagagacag aagaaacagc  28980
aaactgtgac tcttcttcct gctgcagatt tggatgattt ctccaaacaa ttgcaacaat  29040
ccatgagcag tgctgactca actcaggcct aaactcatgc agaccacaca aggcagatgg  29100
gctatataaa cgttttcgct tttccgttta cgatatatag tctactcttg tgcagaatga  29160
attctcgtaa ctacatagca caagtagatg tagttaactt taatctcaca tagcaatctt  29220
taatcagtgt gtaacattag ggaggacttg aaagagccac cacattttca ccgaggccac  29280
gcggagtacg atcgagtgta cagtgaacaa tgctagggag agctgcctat atggaagagc  29340
cctaatgtgt aaaattaatt ttagtagtgc tatccccatg tgattttaat agcttcttag  29400
gagaatgaca aaaaaaaaaa aaaaaaaaaa                                   29430
```

```
SEQ ID NO: 8            moltype = DNA  length = 30104
FEATURE                 Location/Qualifiers
source                  1..30104
                        mol_type = other DNA
                        organism = synthetic construct
SEQUENCE: 8
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
```

-continued

```
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagcttgt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
aatgaagagt gaaaagcaag ttgaacaaaa gatcgctgag attcctaaag aggaagttaa  3900
gccatttata actgaaagta aaccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttacttttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gtttctaca aagaaaacag  5880
ttacacaaca accataaaac cagttactta taaattggat ggtgttgttt gtacagaaat  5940
```

-continued tgaccctaag ttggacaatt attataagaa agacaattct tatttcacag agcaaccaat 6000
tgatcttgta ccaaaccaac catatccaaa cgcaagcttc gataatttta agtttgtatg 6060
tgataatatc aaatttgctg atgatttaaa ccagttaact ggttataaga aacctgcttc 6120
aagagagctt aaagttacat ttttccctga cttaaatggt gatgtggtgg ctattgatta 6180
taaacactac acaccctctt ttaagaaagg agctaaattg ttacataaac ctattgtttg 6240
gcatgttaac aatgcaacta ataaagccac gtataaacca aatacctggt gtatacgttg 6300
tctttggagc acaaaaccag ttgaaacatc aaattcgttt gatgtactga agtcagagga 6360
cgcgcaggga atggataatc ttgcctgcga agatctaaaa ccagtctctg aagaagtagt 6420
ggaaaatcct accatacaga aagacgttct tgagtgtaat gtgaaaacta ccgaagttgt 6480
aggagacatt atacttaaac cagcaaataa tagtttaaaa attacagaag aggttggcca 6540
cacagatcta atggctgctt atgtagacaa ttctagtctt actattaaga aacctaatga 6600
attatctaga gtattaggtt tgaaaaccct tgctactcat ggtttagctg ctgttaatag 6660
tgtcccttgg gatactatag ctaattatgc taagcctttt cttaacaaag ttgttagtac 6720
aactactaac atagttacac ggtgtttaaa ccgtgtttgt actaattata tgccttattt 6780
ctttacttta ttgctacaat tgtgtacttt tactagaagt acaaattcta gaattaaagc 6840
atctatgccg actactatag caaagaatac tgttaagagt gtcggtaaat tttgtctaga 6900
ggcttcattt aattatttga agtcacctaa tttttctaaa ctgataaata ttataatttg 6960
gtttttacta ttaagtgttt gcctaggttc tttaatctac tcaaccgctg ctttaggtgt 7020
tttaatgtct aatttaggca tgccttctta ctgtactggt tacagagaag gctatttgaa 7080
ctctactaat gtcactattg caacctactg tactggttct ataccttgta gtgtttgtct 7140
tagtggttta gattctttag acacctatcc ttctttagaa actatacaaa ttaccatttc 7200
atcttttaaa tgggatttaa ctgcttttgg cttagttgca gagtggtttt tggcatatat 7260
tcttttcact aggtttttct atgtacttgg attggctgca atcatgcaat tgtttttcag 7320
ctattttgca gtacatttta ttagtaattc ttggcttatg tggttaataa ttaatcttgt 7380
acaaatggcc ccgatttcag ctatggttag aatgtacatc ttctttgcat catttatta 7440
tgtatggaaa agttatgtgc atgttgtaga cggttgtaat tcatcaactt gtatgatgtg 7500
ttacaaacgt aatagagcaa caagagtcga atgtacaact attgttaatg gtgttagaag 7560
gtccttttat gtctatgcta atggaggtaa aggcttttgc aaactacaca attggaattg 7620
tgttaattgt gatacattct gtgctggtag tacatttatt agtgatgaag ttgcgagaga 7680
cttgtcacta cagtttaaaa gaccaataaa tcctactgac cagtcttctt acatcgttga 7740
tagtgttaca gtgaagaatg gttccatcca tctttacttt gataaagctg gtcaaaagac 7800
ttatgaaaga cattctctct ctcattttgt taacttagac aacctgagag ctaataacac 7860
taaaggttca ttgcctatta atgttatagt tttgatggt aaatcaaaat gtgaagaatc 7920
atctgcaaaa tcagcgtctg tttactacag tcagcttatg tgtcaaccta tactgttact 7980
agatcaggca ttagtgtctg atgttggtga tagtgcggaa gttgcagtta aaatgtttga 8040
tgcttacgtt aatacgtttt catcaacttt taacgtacca atggaaaaac tcaaaacact 8100
agttgcaact gcagaagctg aacttgcaaa gaatgtgtcc ttagacaatg tcttatctac 8160
ttttatttca gcagctcggc aagggtttgt tgattcagat gtagaaacta aagatgttgt 8220
tgaatgtctt aaattgtcac atcaatctga catagaagtt actggcgata gttgtaataa 8280
ctatatgctc acctataaca aagttgaaaa catgacaccc cgtgaccttg gtgcttgtat 8340
tgactgtagt gcgcgtcata ttaatgcgca ggtagcaaaa agtcacaaca ttgctttgat 8400
atggaacgtt aaagatttca tgtcattgtc tgaacaacta cgaaaacaaa tacgtagtgc 8460
tgctaaaaag aataacttac cttttaagtt gacatgtgca actactagac aagttgttaa 8520
tgttgtaaca acaaagatag cacttaaggg tggtaaaatt gttaataatt ggttgaagca 8580
gttaattaaa gttacacttg tgttcctttt tgttgctgct attttctatt taataacacc 8640
tgttcatgtc atgtctaaac atactgactt ttcaagtgaa atcataggat acaaggctat 8700
tgatggtggt gtcactcgtg acatagcatc tacagatact tgttttgcta acaaacatgc 8760
tgattttgac acatggttta gccagcgtgg tggtagttat actaatgaca aagcttgccc 8820
attgattgct gcagtcataa caagagaagt gggttttgtc gtgcctggtt tgcctggcac 8880
gatattacgc acaactaatg gtgacttttt gcatttctta cctagagttt ttagtgcagt 8940
tggtaacatc tgttacacac catcaaaact tatagagtac actgactttg caacatcagc 9000
ttgtgttttg gctgctgaat gtacaatttt taaagatgct tctggtaagc cagtaccata 9060
ttgttatgat accaatgtac tagaaggttc tgttgcttat gaaagtttac gccctgacac 9120
acgttatgtg ctcatggatg gctctattat tcaatttcct aacacctacc ttgaaggttc 9180
tgttagagtg gtaacaactt ttgattctga gtactgtagg cacggcactt gtgaaagatc 9240
agaagctggt gtttgtgtat ctactagtgg tagatgggta cttaacaatg attattacag 9300
atctttacca ggagttttct gtggtgtaga tgctgtaaat ttacttacta atatgtttac 9360
accactaatt caacctattg gtgctttgga catatcagca tctatagtag ctggtggtat 9420
tgtagctatc gtagtaacat gccttgccta ctattttatg aggtttagaa gagcttttgg 9480
tgaatacagt catgtagttg cctttaatac tttactattc cttatgtcat tcactgtact 9540
ctgtttaaca ccagtttact cattcttacc tggtgtttat tctgttattt acttgtactt 9600
gacattttat cttactaatg atgtttcttt tttagcacat attcagtgga tggttatgtt 9660
cacaccttta gtacctttct ggataacaat tgcttatatc atttgtattt ccacaaagca 9720
tttctattgg ttctttagta attacctaaa gagacgtgta gtctttaatg gtgtttcctt 9780
tagtactttt gaagaagctg cgctgtgcac ctttttgtta aataaagaaa tgtatctaaa 9840
gttgcgtagt gatgtgctat tacctcttac gcaatataat agatacttag ctctttataa 9900
taagtacaag tattttagtg gagcaatgga tacaactagc tacagagaag ctgcttgttg 9960
tcatctcgca aaggctctca atgacttcag taactcaggt tctgatgttc tttaccaacc 10020
accacaaacc tctatcacct cagctgtttt gcagagtggt tttagaaaaa tggcattccc 10080
atctggtaaa gttgagggtt gtatggtaca agtaacttgt ggtacaacta cacttaacgg 10140
tctttggctt gatgacgtag tttactgtcc aagacatgtg atctgcacct ctgaagacat 10200
gcttaaccct aattatgaag atttactcat tcgtaagtct aatcataatt tcttggtaca 10260
ggctggtaat gttcaactca gggttattgg acattctatg caaaattgtg tacttaagct 10320
taaggttgat acagccaatc ctaagacacc taagtataag tttgttcgca ttcaaccagg 10380
acagactttt tcagtgttag cttgttacaa tggttcacca tctggtgttt accaatgtgc 10440
tatgaggccc aatttcacta ttaagggttc attccttaat ggttcatgtg gtagtgttgg 10500
ttttaacata gattatgact gtgtctcttt ttgttacatg caccatatgg aattaccaac 10560
tggagttcat gctggcacag acttagaagg taactttat ggaccttttg ttgacaggca 10620
aacagcacaa gcagctggta cggacacaac tattacagtt aatgttttag cttggttgta 10680

-continued

```
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
```

-continued

```
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagattttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt tgttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
```

-continued

```
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcacctttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gcctttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
```

-continued

```
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtaa  26280
atagttaata gctgacttct ttttcttgct ttcgtgtgat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaca  27900
acaggtggat cctccacgct gcgttcctgc tgtgcttctc caccacagcc ctctccatca  27960
actataagca gctccagctc caagaaagga cgaacattcg gaaatgtcag gagctcctgg  28020
agcagctgaa tggaaagatc aacctcacct acagggcgga cttcaagatc cctatggaga  28080
tgacggagaa gatgcagaag agttacactg cctttgccat ccaagagatg ctccagaatg  28140
tctttcttgt cttcagaaac aatttctcca gcactgggtg gaatgagact attgttgtac  28200
gtctcctgga tgaactccac cagcagacag tgtttctgaa gacagtacta gaggaaaagc  28260
aagaggaaag attgacgtgg gagatgtcct caactgctct ccacttgaag agctattact  28320
ggagggtgca aaggtacctt aaactcatga agtacaacag ctacgcctgg atggtggtcc  28380
gagcagagat cttcaggaac tttctcatca ttcgaagact taccagaaac ttccaaaact  28440
gagacgttcg tgttgtttta gatttcatct aaacgaacaa actaaaatgt ctgataatgg  28500
accccaaaat cagcgaaatg caccccgcat tacgtttggt ggaccctcag attcaactgg  28560
cagtaaccag aatggagaac gcagtggggc gcgatcaaaa caacgtcggc cccaaggttt  28620
acccaataat actgcgtctt ggttcaccgc tctcactcaa catggcaagg aagaccttaa  28680
attccctcga ggacaaggcg ttccaattaa caccaatagc agtccagatg accaaattgg  28740
ctactaccga agagctacca gacgaattcg tggtggtgac ggtaaaatga aagatctcag  28800
tccaagatgg tatttctact acctaggaac tgggccagaa gctggacttc cctatggtgc  28860
taacaaagac ggcatcatat gggttgcaac tgagggagcc ttgaatacac caaaagatca  28920
cattggcacc cgcaatcctg ctaacaatgc tgcaatcgtg ctacaacttc ctcaaggaac  28980
aacattgcca aaaggcttct acgcagaagg gagcagaggc ggcagtcaag cctcttctcg  29040
ttcctcatca cgtagtcgca acagttcaag aaattcaact ccaggcagca gtaggggaac  29100
ttctcctgct agaatggctg gcaatggcgg tgatgctgct cttgctttgc tgctgcttga  29160
cagattgaac cagcttgaga gcaaaatgtc tggtaaaggc caacaacaac aaggccaaac  29220
tgtcactaag aaatctgctg ctgaggcttc taagaagcct cggcaaaaac gtactgccac  29280
taaagcatac aatgtaacac aagctttcgg cagacgtggt ccagaacaaa cccaaggaaa  29340
ttttggggac caggaactaa tcagacaagg aactgattac aaacattggc cgcaaattgc  29400
acaatttgcc cccagcgctt cagcgttctt cggaatgtcg cgcattggca tggaagtcac  29460
accttcggga acgtggttga cctacacagg tgccatcaaa ttggatgaca aagatccaaa  29520
tttcaaagat caagtcattt tgctgaataa gcatattgac gcatacaaaa cattcccacc  29580
aacagagcct aaaaaggaca aaaagaagaa ggctgatgaa actcaagcct taccgcagag  29640
```

-continued

```
acagaagaaa cagcaaactg tgactcttct tcctgctgca gatttggatg atttctccaa  29700
acaattgcaa caatccatga gcagtgctga ctcaactcag gcctaaactc atgcagacca  29760
cacaaggcag atgggctata taaacgtttt cgcttttccg tttacgatat atagtctact  29820
cttgtgcaga atgaattctc gtaactacat agcacaagta gatgtagtta actttaatct  29880
cacatagcaa tctttaatca gtgtgtaaca ttagggagga cttgaaagag ccaccacatt  29940
ttcaccgagg ccacgcggag tacgatcgag tgtacagtga acaatgctag ggagagctgc  30000
ctatatggaa gagccctaat gtgtaaaatt aattttagta gtgctatccc catgtgattt  30060
taatagcttc ttaggagaat gacaaaaaaa aaaaaaaaaa aaaa                  30104

SEQ ID NO: 9            moltype = DNA  length = 29430
FEATURE                 Location/Qualifiers
source                  1..29430
                        mol_type = other DNA
                        organism = synthetic construct
SEQUENCE: 9
attaaaggtt tataccttcc caggtaacaa accaaccaac tttcgatctc ttgtagatct  60
gttctctaaa cgaactttaa aatctgtgtg gctgtcactc ggctgcatgc ttagtgcact  120
cacgcagtat aattaataac taattactgt cgttgacagg acacgagtaa ctcgtctatc  180
ttctgcaggc tgcttacggt ttcgtccgtg ttgcagccga tcatcagcac atctaggttt  240
cgtccgggtg tgaccgaaag gtaagatgga gagccttgtc cctggtttca acgagaaaac  300
acacgtccaa ctcagtttgc ctgttttaca ggttcgcgac gtgctcgtac gtggctttgg  360
agactccgtg gaggaggtct tatcagaggc acgtcaacat cttaaagatg gcacttgtgg  420
cttagtagaa gttgaaaaag gcgttttgcc tcaacttgaa cagccctatg tgttcatcaa  480
acgttcggat gctcgaactg cacctcatgg tcatgttatg gttgagctgg tagcagaact  540
cgaaggcatt cagtacggtc gtagtggtga gacacttggt gtccttgtcc ctcatgtggg  600
cgaaatacca gtggcttacc gcaaggttct tcttcgtaag aacggtaata aaggagctgg  660
tggccatagt tacggcgccg atctaaagtc atttgactta ggcgacgagc ttggcactga  720
tccttatgaa gattttcaag aaaactggaa cactaaacat agcagtggtg ttacccgtga  780
actcatgcgt gagcttaacg gaggggcata cactcgctat gtcgataaca acttctgtgg  840
ccctgatggc taccctcttg agtgcattaa agaccttcta gcacgtgctg gtaaagcttc  900
atgcactttg tccgaacaac tggactttat tgacactaag aggggtgtat actgctgccg  960
tgaacatgag catgaaattg cttggtacac ggaacgttct gaaaagagct atgaattgca  1020
gacacctttt gaaattaaat tggcaaagaa atttgacacc ttcaatgggg aatgtccaaa  1080
ttttgtattt cccttaaatt ccataatcaa gactattcaa ccaagggttg aaaagaaaaa  1140
gcttgatggc tttatgggta gaattcgatc tgtctatcca gttgcgtcac caaatgaatg  1200
caaccaaatg tgcctttcaa ctctcatgaa gtgtgatcat tgtggtgaaa cttcatggca  1260
gacgggcgat tttgttaaag ccacttgcga attttgtggc actgagaatt tgactaaaga  1320
aggtgccact acttgtggtt acttacccca aaatgctgtt gttaaaattt attgtccagc  1380
atgtcacaat tcagaagtag gacctgagca tagtcttgcc gaataccata atgaatctgg  1440
cttgaaaacc attcttcgta agggtggtcg cactattgcc tttggaggct gtgtgttctc  1500
ttatgttggt tgccataaca agtgtgccta ttgggttcca cgtgctagcg ctaacatagg  1560
ttgtaaccat acaggtgttg ttggagaagg ttccgaaggt cttaatgaca accttcttga  1620
aatactccaa aaagagaaag tcaacatcaa tattgttggt gactttaaac ttaatgaaga  1680
gatcgccatt attttggcat ctttttctgc ttccacaagt gcttttgtgg aaactgtgaa  1740
aggtttggat tataaagcat tcaaacaaat tgttgaatcc tgtggtaatt ttaaagttac  1800
aaaaggaaaa gctaaaaaag gtgcctggaa tattggtgaa cagaaatcaa tactgagtcc  1860
tctttatgca tttgcatcag aggctgctcg tgttgtacga tcaattttct cccgcactct  1920
tgaaactgct caaaattctg tgcgtgtttt acagaaggcc gctataacaa tactagatgg  1980
aatttcacag tattcactga gactcattga tgctatgatg ttcacatctg atttggctac  2040
taacaatcta gttgtaatgg cctacattac aggtggtgtt gttcagttga cttcgcagtg  2100
gctaactaac atctttggca ctgtttatga aaaactcaaa cccgtccttg attggcttga  2160
agagaagttt aaggaaggtg tagagtttct tagagacggt tgggaaattg ttaaatttat  2220
ctcaacctgt gcttgtgaaa ttgtcggtgg acaaattgtc acctgtgcaa aggaaattaa  2280
ggagagtgtt cagacattct ttaagctttt aaataaattt ttggctttgt gtgctgactc  2340
tatcattatt ggtggagcta aacttaaagc cttgaattta ggtgaaacat ttgtcacgca  2400
ctcaaaggga ttgtacagaa agtgtgttaa atccagagaa gaaactggcc tactcatgcc  2460
tctaaaagcc ccaaaagaaa ttatcttctt agagggagaa acacttccca cagaagtgtt  2520
aacagaggaa gttgtcttga aaactggtga tttacaacca ttagaacaac ctactagtga  2580
agctgttgaa gctccattgg ttggtacacc agtttgtatt aacgggctta tgttgctcga  2640
aatcaaagac acagaaaagt actgtgccct tgcacctaat atgatggtaa caaacaatac  2700
cttcacactc aaaggcggtg caccaacaaa ggttactttt ggtgatgaca ctgtgataga  2760
agtgcaaggt tacaagagtg tgaatatcac ttttgaactt gatgaaagga ttgataaagt  2820
acttaatgag aagtgctctg cctatacagt tgaactcggt acagaagtaa atgagttcgc  2880
ctgtgttgtg gcagatgctg tcataaaaac tttgcaacca gtatctgaat tacttacacc  2940
actgggcatt gatttagatg agtggagtat ggctacatac tacttatttg atgagtctgg  3000
tgagtttaaa ttggcttcac atatgtattg ttctttctac cctccagatg aggatgaaga  3060
agaaggtgat tgtgaagaag aagagtttga gccatcaact caatatgagt atggtactga  3120
agatgattac caaggtaaac ctttggaatt tggtgccact tctgctgctc ttcaacctga  3180
agaagagcaa gaagaagatt ggttagatga tgatagtcaa caaactgttg gtcaacaaga  3240
cggcagtgag gacaatcaga caactactat tcaaacaatt gttgaggttc aacctcaatt  3300
agagatggaa cttacaccag ttgttcagac tattgaagtg aatagtttta gtggttattt  3360
aaaacttact gacaatgtat acattaaaaa tgcagacatt gtggaagaag ctaaaaaggt  3420
aaaaccaaca gtggttgtta atgcagccaa tgtttacctt aaacatggag gaggtgttgc  3480
aggagcctta aataaggcta ctaacaatgc catgcaagtt gaatctgatg attacatagc  3540
tactaatgga ccacttaaag tgggtggtag ttgtgtttta agcggacaca atcttgctaa  3600
acactgtctt catgttgtcg gcccaaatgt taacaaaggt gaagacattc aacttcttaa  3660
gagtgcttat gaaaatttta atcagcacga agttctactt gcaccattat tatcagctgg  3720
tatttttggt gctgacccta tacattcttt aagagtttgt gtagatactg ttcgcacaaa  3780
tgtctactta gctgtctttg ataaaaatct ctatgacaaa cttgtttcaa gctttttgga  3840
```

```
aatgaagagt gaaaagcaag ttgaacaaaa gatcgctgag attcctaaag aggaagttaa  3900
gccatttata actgaaagta aacccttcagt tgaacagaga aaacaagatg ataagaaaat  3960
caaagcttgt gttgaagaag ttacaacaac tctggaagaa actaagttcc tcacagaaaa  4020
cttgttactt tatattgaca ttaatggcaa tcttcatcca gattctgcca ctcttgttag  4080
tgacattgac atcactttct taaagaaaga tgctccatat atagtgggtg atgttgttca  4140
agagggtgtt ttaactgctg tggttatacc tactaaaaag gctggtggca ctactgaaat  4200
gctagcgaaa gctttgagaa aagtgccaac agacaattat ataaccactt acccgggtca  4260
gggtttaaat ggttacactg tagaggaggc aaagacagtg cttaaaaagt gtaaaagtgc  4320
cttttacatt ctaccatcta ttatctctaa tgagaagcaa gaaattcttg gaactgtttc  4380
ttggaatttg cgagaaatgc ttgcacatgc agaagaaaca cgcaaattaa tgcctgtctg  4440
tgtggaaact aaagccatag tttcaactat acagcgtaaa tataagggta ttaaaataca  4500
agagggtgtg gttgattatg gtgctagatt ttactttac accagtaaaa caactgtagc  4560
gtcacttatc aacacactta acgatctaaa tgaaactctt gttacaatgc cacttggcta  4620
tgtaacacat ggcttaaatt tggaagaagc tgctcggtat atgagatctc tcaaagtgcc  4680
agctacagtt tctgtttctt cacctgatgc tgttacagcg tataatggtt atcttacttc  4740
ttcttctaaa acacctgaag aacattttat tgaaaccatc tcacttgctg gttcctataa  4800
agattggtcc tattctggac aatctacaca actaggtata gaatttctta agagaggtga  4860
taaaagtgta tattacacta gtaatcctac cacattccac ctagatggtg aagttatcac  4920
ctttgacaat cttaagacac ttctttcttt gagagaagtg aggactatta aggtgtttac  4980
aacagtagac aacattaacc tccacacgca agttgtggac atgtcaatga catatggaca  5040
acagtttggt ccaacttatt tggatggagc tgatgttact aaaataaaac ctcataattc  5100
acatgaaggt aaaacatttt atgttttacc taatgatgac actctacgtg ttgaggcttt  5160
tgagtactac cacacaactg atcctagttt tctgggtagg tacatgtcag cattaaatca  5220
cactaaaaag tggaaatacc cacaagttaa tggtttaact tctattaaat gggcagataa  5280
caactgttat cttgccactg cattgttaac actccaacaa atagagttga agtttaatcc  5340
acctgctcta caagatgctt attacagagc aagggctggt gaagctgcta acttttgtgc  5400
acttatctta gcctactgta ataagacagt aggtgagtta ggtgatgtta gagaaacaat  5460
gagttacttg tttcaacatg ccaatttaga ttcttgcaaa agagtcttga acgtggtgtg  5520
taaaacttgt ggacaacagc agacaaccct taagggtgta gaagctgtta tgtacatggg  5580
cacactttct tatgaacaat ttaagaaagg tgttcagata ccttgtacgt gtggtaaaca  5640
agctacaaaa tatctagtac aacaggagtc accttttgtt atgatgtcag caccacctgc  5700
tcagtatgaa cttaagcatg gtacatttac ttgtgctagt gagtacactg gtaattacca  5760
gtgtggtcac tataaacata taacttctaa agaaactttg tattgcatag acggtgcttt  5820
acttacaaag tcctcagaat acaaaggtcc tattacggat gttttctaca aagaaaacag  5880
ttacacaaca accataaaac cagttactta taaattggat ggtgttgttt gtacagaaat  5940
tgaccctaag ttggacaatt attataagaa agacaattct tatttcacag agcaaccaat  6000
tgatcttgta ccaaaccaac catatccaaa cgcaagcttc gataatttta agtttgtatg  6060
tgataatatc aaatttgctg atgatttaaa ccagttaact ggttataaga aacctgcttc  6120
aagagagctt aaagttacat ttttccctga cttaaatggt gatgtggtgg ctattgatta  6180
taaacactac acaccctctt ttaagaaagg agctaaattg ttacataaac ctattgtttg  6240
gcatgttaac aatgcaacta ataaagccac gtataaacca aatacctggt gtatacgttg  6300
tctttggagc acaaaaaccag ttgaaacatc aaattcgttt gatgtactga agtcagagga  6360
cgcgcaggga atggataatc ttgcctgcga agatctaaaa ccagtctctg aagaagtagt  6420
ggaaaatcct accatacaga aagacgttct tgagtgtaat gtgaaaacta ccgaagttgt  6480
aggagacatt atacttaaac cagcaaataa tagtttaaaa attacagaag aggttggcca  6540
cacagatcta atggctgctt atgtagacaa ttctagtctt actattaaga aacctaatga  6600
attatctaga gtattaggtt tgaaaaccct tgctactcat ggtttagctg ctgttaatag  6660
tgtcccttgg gatactatag ctaattatgc taagcctttt cttaacaaag ttgttagtac  6720
aactactaac atagttacac ggtgtttaaa ccgtgtttgt actaattata tgccttattt  6780
ctttacttta ttgctacaat tgtgtacttt tactagaagt acaaattcta gaattaaagc  6840
atctatgccg actactatag caaagaatac tgttaagagt gtcggtaaat tttgtctaga  6900
ggcttcattt aattatttga agtcacctaa tttttctaaa ctgataaata ttataatttg  6960
gtttttacta ttaagtgttt gcctaggttc tttaatctac tcaaccgctg ctttaggtgt  7020
tttaatgtct aatttaggca tgccttctta ctgtactggt tacagagaag gctatttgaa  7080
ctctactaat gtcactattg caacctactg tactggttct ataccttgta gtgtttgtct  7140
tagtggttta gattctttag acacctatcc ttctttagaa actatacaaa ttaccatttc  7200
atcttttaaa tgggatttaa ctgcttttgg cttagttgca gagtggtttt tggcatatat  7260
tcttttcact aggtttttct atgtacttgg attggctgca atcatgcaat tgtttttcag  7320
ctattttgca gtacatttta ttagtaattc ttggcttatg tggttaataa ttaatcttgt  7380
acaaatggcc ccgatttcag ctatggttag aatgtacatc ttctttgcat cattttatta  7440
tgtatggaaa agttatgtgc atgttgtaga cggttgtaat tcatcaactt gtatgatgtg  7500
ttacaaacgt aatagagcaa caagagtcga atgtacaact attgttaatg gtgttagaag  7560
gtccttttat gtctatgcta atggaggtaa aggcttttgc aaactacaca attggaattg  7620
tgttaattgt gatacattct gtgctggtag tacatttatt agtgatgaag ttgcgagaga  7680
cttgtcacta cagtttaaaa gaccaataaa tcctactgac cagtcttctt acatcgttga  7740
tagtgttaca gtgaagaatg gttccatcca tctttacttt gataaagctg gtcaaaagac  7800
ttatgaaaga cattctctct ctcattttgt taacttagac aacctgagag ctaataacac  7860
taaaggttca ttgcctatta atgttatagt tttgatggt aaatcaaaat gtgaagaatc  7920
atctgcaaaa tcagcgtctg tttactacag tcagcttatg tgtcaaccta tactgttact  7980
agatcaggca ttagtgtctg atgttggtga tagtgcggaa gttgcagtta aaatgtttga  8040
tgcttacgtt aatacgtttt catcaacttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta aagatgttgt  8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
```

-continued

```
gttaattaaa gttacacttg tgttcctttt tgttgctgct attttctatt taataacacc  8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgacttttt gcatttctta cctagagttt ttagtgcagt  8940
tggtaacatc tgttacacac catcaaaact tatagagtac actgactttg caacatcagc  9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggtttagaa gagcttttgg  9480
tgaatacagt catgtagttg cctttaatac tttactattc cttatgtcat tcactgtact  9540
ctgtttaaca ccagtttact cattcttacc tggtgtttat tctgttattt acttgtactt  9600
gacattttat cttactaatg atgtttcttt tttagcacat attcagtgga tggttatgtt  9660
cacaccttta gtacctttct ggataacaat tgcttatatc atttgtattt ccacaaagca  9720
tttctattgg ttctttagta attacctaaa gagacgtgta gtctttaatg gtgtttcctt  9780
tagtactttt gaagaagctg cgctgtgcac ctttttgtta aataaagaaa tgtatctaaa  9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
acctttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
```

-continued

```
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac taccettctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
```

-continued

```
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagattttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
```

-continued

```
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtaa  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacaatg ataatgaaac ttgtcacgcc taaacgaaca tgaacaacag gtggatcctc  27240
cacgctgcgt tcctgctgtg cttctccacc acagccctct ccatcaacta taagcagctc  27300
cagctccaag aaaggacgaa cattcggaaa tgtcaggagc tcctggagca gctgaatgga  27360
aagatcaacc tcacctacag ggcggacttc aagatcccta tggagatgac ggagaagatg  27420
cagaagagtt acactgcctt tgccatccaa gagatgctcc agaatgtctt tcttgtcttc  27480
agaaacaatt tctccagcac tgggtggaat gagactattg ttgtacgtct cctggatgaa  27540
```

-continued

```
ctccaccagc agacagtgtt tctgaagaca gtactagagg aaaagcaaga ggaaagattg  27600
acgtgggaga tgtcctcaac tgctctccac ttgaagagct attactggag ggtgcaaagg  27660
taccttaaac tcatgaagta caacagctac gcctggatgg tggtccgagc agagatcttc  27720
aggaactttc tcatcattcg aagacttacc agaaacttcc aaaactgaga cgttcgtgtt  27780
gttttagatt tcatctaaac gaacaaacta aaatgtctga taatggaccc caaaatcagc  27840
gaaatgcacc ccgcattacg tttggtggac cctcagattc aactggcagt aaccagaatg  27900
gagaacgcag tggggcgcga tcaaaacaac gtcggcccca aggtttaccc aataatactg  27960
cgtcttggtt caccgctctc actcaacatg gcaaggaaga ccttaaattc cctcgaggac  28020
aaggcgttcc aattaacacc aatagcagtc cagatgacca aattggctac taccgaagag  28080
ctaccagacg aattcgtggt ggtgacggta aaatgaaaga tctcagtcca agatggtatt  28140
tctactacct aggaactggg ccagaagctg gacttcccta tggtgctaac aaagacggca  28200
tcatatgggt tgcaactgag ggagccttga atacaccaaa agatcacatt ggcacccgca  28260
atcctgctaa caatgctgca atcgtgctac aacttcctca aggaacaaca ttgccaaaag  28320
gcttctacgc agaagggagc agaggcggca gtcaagcctc ttctcgttcc tcatcacgta  28380
gtcgcaacag ttcaagaaat tcaactccag gcagcagtag gggaacttct cctgctagaa  28440
tggctggcaa tggcggtgat gctgctcttg ctttgctgct gcttgacaga ttgaaccagc  28500
ttgagagcaa aatgtctggt aaaggccaac aacaacaagg ccaaactgtc actaagaaat  28560
ctgctgctga ggcttctaag aagcctcggc aaaaacgtac tgccactaaa gcatacaatg  28620
taacacaagc tttcggcaga cgtggtccag aacaaaccca aggaaatttt ggggaccagg  28680
aactaatcag acaaggaact gattacaaac attggccgca aattgcacaa tttgccccca  28740
gcgcttcagc gttcttcgga atgtcgcgca ttggcatgga agtcacacct tcgggaacgt  28800
ggttgaccta cacaggtgcc atcaaattgg atgacaaaga tccaaatttc aaagatcaag  28860
tcattttgct gaataagcat attgacgcat acaaaacatt cccaccaaca gagcctaaaa  28920
aggacaaaaa gaagaaggct gatgaaactc aagccttacc gcagagacag aagaaacagc  28980
aaactgtgac tcttcttcct gctgcagatt tggatgattt ctccaaacaa ttgcaacaat  29040
ccatgagcag tgctgactca actcaggcct aaactcatgc agaccacaca aggcagatgg  29100
gctatataaa cgttttcgct tttccgttta cgatatatag tctactcttg tgcagaatga  29160
attctcgtaa ctacatagca caagtagatg tagttaactt taatctcaca tagcaatctt  29220
taatcagtgt gtaacattag ggaggacttg aaagagccac cacattttca ccgaggccac  29280
gcggagtacg atcgagtgta cagtgaacaa tgctagggag agctgcctat atggaagagc  29340
cctaatgtgt aaaattaatt ttagtagtgc tatccccatg tgattttaat agcttcttag  29400
gagaatgaca aaaaaaaaaa aaaaaaaaaa                                   29430

SEQ ID NO: 10          moltype = DNA  length = 564
FEATURE                Location/Qualifiers
source                 1..564
                       mol_type = unassigned DNA
                       organism = Homo sapiens
SEQUENCE: 10
atgaccaaca agtgtctcct ccaaattgct ctcctgttgt gcttctccac tacagctctt  60
tccatgagct acaacttgct tggattccta caaagaagca gcaattttca gtgtcagaag  120
ctcctgtggc aattgaatgg gaggcttgaa tactgcctca aggacaggat gaactttgac  180
atccctgagg agattaagca gctgcagcag ttccagaagg aggacgccgc attgaccatc  240
tatgagatgc tccagaacat ctttgctatt ttcagacaag attcatctag cactggctgg  300
aatgagacta ttgttgagaa cctcctggct aatgtctatc atcagataaa ccatctgaag  360
acagtcctgg aagaaaaact ggagaaagaa gatttcacca ggggaaaact catgagcagt  420
ctgcacctga aaagatatta tgggaggatt ctgcattacc tgaaggccaa ggagtacagt  480
cactgtgcct ggaccatagt cagagtggaa atcctaagga acttttactt cattaacaga  540
cttacaggtt acctccgaaa ctga                                         564

SEQ ID NO: 11          moltype = DNA  length = 549
FEATURE                Location/Qualifiers
source                 1..549
                       mol_type = unassigned DNA
                       organism = Mus musculus
SEQUENCE: 11
atgaacaaca ggtggatcct ccacgctgcg ttcctgctgt gcttctccac cacagccctc  60
tccatcaact ataagcagct ccagctccaa gaaaggacga acattcggaa atgtcaggag  120
ctcctggagc agctgaatgg aaagatcaac ctcacctaca gggcggactt caagatccct  180
atggagatga cggagaagat gcagaagagt tacactgcct ttgccatcca agagatgctc  240
cagaatgtct ttcttgtctt cagaaacaat ttctccagca ctgggtggaa tgagactatt  300
gttgtacgtc tcctggatga actccaccag cagacagtgt ttctgaagac agtactagag  360
gaaaagcaag aggaaagatt gacgtgggag atgtcctcaa ctgctctcca cttgaagagc  420
tattactgga gggtgcaaag gtaccttaaa ctcatgaagt acaacagcta cgcctggatg  480
gtggtccgag cagagatctt caggaacttt ctcatcattc gaagacttac cagaaacttc  540
caaaactga                                                          549

SEQ ID NO: 12          moltype = DNA  length = 228
FEATURE                Location/Qualifiers
source                 1..228
                       mol_type = unassigned DNA
                       organism = SARS-CoV-2
SEQUENCE: 12
atgtactcat tcgtttcgga agagacaggt acgttaatag ttaatagcgt acttcttttt  60
cttgctttcg tggtattctt gctagttaca ctagccatcc ttactgcgct tcgattgtgt  120
gcgtactgct gcaatattgt taacgtgagt cttgtaaaac cttcttttta cgtttactct  180
cgtgttaaaa atctgaattc ttctagagtt cctgatcttc tggtctaa               228

SEQ ID NO: 13          moltype = AA  length = 72
```

-continued

```
FEATURE              Location/Qualifiers
source               1..72
                     mol_type = protein
                     organism = SARS-CoV-2
SEQUENCE: 13
MYSFVSEETG TIVNSLLFLA FVFLLVTLAI LTALRLCAYC CNIVNVSLVK PSFYVYSRVK  60
NLNSSRVPDL LV                                                      72

SEQ ID NO: 14        moltype = DNA  length = 228
FEATURE              Location/Qualifiers
source               1..228
                     mol_type = unassigned DNA
                     organism = SARS-CoV-2
SEQUENCE: 14
atgtactcat tcgtttcgga agagacaggt acgtaaatag ttaatagctg acttcttttt  60
cttgctttcg tgtgattctt gctagttaca ctagccatcc ttactgcgct tcgattgtgt  120
gcgtactgct gcaatattgt taacgtgagt cttgtaaaac cttcttttta cgtttactct  180
cgtgttaaaa atctgaattc ttctagagtt cctgatcttc tggtctaa              228

SEQ ID NO: 15        moltype = DNA  length = 228
FEATURE              Location/Qualifiers
source               1..228
                     mol_type = unassigned DNA
                     organism = SARS-CoV-2
SEQUENCE: 15
atgtatagct ttgtgagcga ggaaaccggc accctgatcg tgaactccgt gctgctgttc  60
ctggcctttg tcgtgtttct gctggtgacc ctggctattc tgaccgccct gagactctgc  120
gcctattgct gtaacatcgt gaatgtctcc ctggtgaagc ccagcttcta tgtgtatagc  180
agggtgaaga acctcaacag cagcagagtg cccgacctgc tcgtgtaa              228

SEQ ID NO: 16        moltype = AA  length = 75
FEATURE              Location/Qualifiers
source               1..75
                     mol_type = protein
                     organism = SARS-CoV-2
SEQUENCE: 16
MYSFVSEETG TLIVNSVLLF LAFVVFLLVT LAILTALRLC AYCCNIVNVS LVKPSFYVYS  60
RVKNLNSSRV PDLLV                                                   75
```

INTERFERON-PRODUCING UNIVERSAL SARBECOVIRUS VACCINES, AND USES THEREOF

CROSS-REFERENCE TO RELATED APPLICATIONS

This application claims the benefit of, and priority to, U.S. Provisional Application No. 63/382,009, filed on Nov. 2, 2022, the content of which is incorporated herein by reference in its entirety.

REFERENCE TO AN ELECTRONIC SEQUENCE LISTING

The content of the electronic sequence listing (253322000200SEQLIST.xml; Size: 284,897 bytes; and Date of Creation: Jan. 17, 2023) is herein incorporated by reference in its entirety.

FIELD OF THE INVENTION

The present invention relates to interferon (IFN)-producing universal sarbecovirus vaccines, such as IFN-producing universal SARS-CoV-2 vaccines. Further provided herein are pharmaceutical compositions comprising the vaccines, methods of preventing or ameliorating viral infection using the vaccines, and kits comprising the vaccines.

BACKGROUND OF THE INVENTION

Since the first human case of COVID-19 was reported in late 2019, SARS-CoV-2 has caused more than 0.6 billion infections and 6.5 million deaths globally as of 27 Sep. 2022. Three major categories of COVID-19 vaccines (lipid nanoparticle-based mRNA vaccines, adenoviral vector-based vaccines, and inactivated whole virion vaccines) are currently available. Both mRNA and adenoviral vector-based vaccines encode the SARS-CoV-2 surface spike protein as the immunogen, while the inactivated vaccine was made of inactivated whole virions. All these first-generation vaccines were designed based on the original SARS-CoV-2 strain circulating during the early pandemic. However, SARS-CoV-2 has evolved significantly during the first two years of worldwide spread and several variants of concern, such as alpha (lineage B.1.1.7), beta (B.1.351), delta (B.1.617.2), and the most recent omicron (B.1.1.529) variants have emerged. Unfortunately, the omicron variant and its various subvariants, unlike other SARS-CoV-2 variants, carry more than thirty non-synonymous mutations in the spike protein, largely evading the antibodies generated from current vaccinations, which lost the ability to neutralize omicron and subvariants, resulting in a high incidence of breakthrough infections worldwide, thereby necessitating next-generation vaccination designs to overcome viral immune evasion.

BRIEF SUMMARY OF THE INVENTION

The present invention provides a novel next-generation vaccine that elicits heterotypic immunity against sarbecoviruses via the enhancement of protective B and T cell immunity.

In one aspect of the present invention, there is provided a construct comprising a modified genome of a sarbecovirus, wherein the modified genome comprises a modified envelope gene and a nucleic acid encoding an interferon integrated into the genome. In some embodiments, the construct comprises a nucleic acid fragment inserted into the viral genome that encodes an interferon. In some embodiments, the nucleic acid encodes an interferon that replaces viral open reading frame 8 (ORF8). In some embodiments, the interferon is type I interferon. In some embodiments, the interferon is interferon-beta (IFNβ).

In some embodiments according to any of the constructs described above, the modified envelope gene comprises one or more stop codons. In some embodiments, the modified envelope gene comprises at least three stop codons. In some embodiments, at least one stop codon is present at the 5'-terminal 100 nucleic acids of the modified envelope gene. In some embodiments, the construct further comprises at least a functional portion of ORF6, ORF7a, ORF7b, and/or ORF8 in the modified genome to be deleted and/or inactivated by introducing a stop codon.

In some embodiments according to any of the constructs described above, the sarbecovirus is selected from the group consisting of SARS-CoV, SARS-CoV-2, SARS-CoV-2 B.1.1.7, SARS-CoV-2 B.1.351, SARS-CoV-2 B1.617.2, SAR-CoV-2 B.1.1.529, SC2r-CoV, RaTG13, SC2r-CoV GX-PSL, and SARS-CoV combined variants of concern (VOC). In some embodiments, the sarbecovirus is SARS-CoV-2.

In some embodiments according to any of the constructs described above, the modified genome comprises a wild-type spike gene. In some embodiments, the modified genome comprises a variant spike gene. In some embodiments, the variant spike gene is BA.2, BA.5, BA.2.75.2, BQ.1, BQ.1.1, or XBB.

In one aspect, there is provided a recombinant sarbecovirus comprising any of the constructs described herein.

In one aspect, there is provided a sarbecovirus vaccine comprising any of the recombinant sarbecovirus described herein.

In some embodiments according to any of the sarbecovirus vaccines described above, the sarbecovirus vaccine is formulated for mucosal administration. In some embodiments, the sarbecovirus vaccine is formulated as a nasal spray. In some embodiments, the sarbecovirus vaccine is formulated for parenteral administration, such as for intradermal or intramuscular administration.

In one aspect, there is provided a host cell (such as for producing any of the recombinant sarbecovirus described herein) comprising any of the constructs described herein. In some embodiments, the host cell is defective in interferon signaling. In some embodiments, the host cell comprises a mutation (e.g., knockout) in a gene selected from the group consisting of STAT1, IRF9, STAT2, IFNAR1, IFNAR2, type I interferon, and type III interferon. In some embodiments, the host cell comprises a mutation (e.g., knockout) in the STAT1 gene. Defective interferon signaling can also be accomplished, for example, by inhibiting the expression of any proteins involved in the interferon signaling pathway, which include, for example, STAT1, IRF9, STAT2, IFNAR1, IFNAR2, type I interferon, and type III interferons.

In some embodiments according to any of the host cells described above, the host cell further comprises a heterologous nucleic acid encoding a viral envelope protein. In some embodiments, the nucleic acid sequence of the heterologous nucleic acid encoding the viral envelope protein has less than about 60% sequence identity to the sequence of the modified or naturally existing viral envelope gene. In some embodiments, the nucleic acid sequence of the heterologous nucleic acid encoding the envelope protein has less than about 80% sequence identity to the sequence of the naturally existing viral envelope gene.

In one aspect, there is provided a method of making a recombinant sarbecovirus, comprising culturing any of the host cells described herein and isolating the recombinant sarbecovirus.

In one aspect, there is provided a method of vaccinating an individual (e.g., human) against a sarbecovirus, comprising administering any of the sarbecovirus vaccines described herein to the individual. In some embodiments, the method of vaccinating an individual comprises a method of prophylactically immunizing an individual. In some embodiments, the method of vaccinating an individual comprises a method of preventing an individual from contracting a sarbecovirus infection. In some embodiments, the method of vaccinating an individual comprises a method of reducing the severity of a sarbecovirus infection in an individual. In some embodiments, the method of vaccinating an individual further comprises a method of treating an individual having a sarbecovirus infection. In some embodiments, the method of vaccinating an individual comprises a method of eliciting an immune response in an individual.

In some embodiments according to any of the vaccinating methods described above, the sarbecovirus vaccine is administered intranasally.

In some embodiments according to any of the vaccinating methods described above, the sarbecovirus vaccine is administered once. In some embodiments, the sarbecovirus vaccine is administered more than once, optionally with an interval of about two weeks to about one year.

In some embodiments according to any of the vaccinating methods described above, the sarbecovirus vaccine is administered at a dose of about $10^5$ PFU to about $10^{10}$ PFU.

In some embodiments according to any of the vaccinating methods described above, the individual is a human individual.

These and other aspects and advantages of the present invention will become apparent from the subsequent detailed description and the appended claims. It is to be understood that one, some, or all of the properties of the various embodiments described herein may be combined to form other embodiments of the present invention.

The disclosures of all publications, patents, patent applications and published patent applications referred to herein are hereby incorporated herein by reference in their entirety.

BRIEF DESCRIPTION OF THE DRAWINGS

FIGS. 6G and 6H show IBIS protected mice from lethal SARS-CoV-2 infection. Mice were either PBS-vaccinated or vaccinated with two doses of IBIS. 28 days post-vaccination, the mice were lethally challenged by intranasal inoculation of SARS-CoV-2 (WT) ($1\times10^3$ PFU). Body weight change (FIG. 6G) and survival (FIG. 6H) of the infected mice were monitored for 14 days. Mock-infected (n=3). PBS-vaccinated/SARS-CoV-2 infected (n=7). IBIS-vaccinated/SARS-CoV-2 infected (n=7).

FIG. 6I shows the viral titer in infected mouse lungs. Lungs of the infected mice were harvested at day 2 post-infection and homogenized for viral titer quantitation by plaque assay. PBS-vaccinated (n=4). IBIS-vaccinated (n=5). Error bar=S.D. N.D., not detected.

FIGS. 6J and 6K show the histology of infected mouse lungs. IBIS-vaccinated mice showed potent immune cell infiltration post-infection. PBS-(J) or IBIS-vaccinated mice (K) were lethally challenged with $1\times10^3$ PFU of SARS-CoV-2 (WT) virus. 2-days post-infection, the lungs of the infected mice were harvested and PFA-fixed for histological examination by H&E staining (upper panels) and IHC staining for SARS-CoV-2 nucleoprotein (lower panels). Punctate haematoxylin staining pattern implicating immune cell infiltration was observed in the IBIS-vaccinated group. PBS-vaccinated (n=4). IBIS-vaccinated (n=5).

FIG. 8A depicts a schematic timeline of vaccination and viral challenge. Golden Syrian hamsters were intranasally vaccinated with 2 doses of IBIS ($3\times10^6$ PFU) on day-28 and day-14, respectively (similar to FIG. 6A). On day −1, index hamsters were infected by intranasal inoculation of SARS-CoV-2 (WT) ($1\times10^3$ PFU). 1-day after infection (day 0), the index hamsters were co-housed with one PBS- and one IBIS-vaccinated hamsters for 24 hr, and then separated.

FIGS. 8B and 8C show that IBIS vaccination induced production of IgG against SARS-CoV-2 RBD, and N. Hamster sera were collected 14- and 28-days post-IBIS vaccination. IgG antibodies against SARS-CoV-2 RBD (FIG. 8B) and N (FIG. 8C) were detected by ELISA.

FIG. 8D shows that IBIS vaccination potently induced production of neutralizing antibodies against SARS-CoV-2. Hamster sera were collected 14- and 28-days post-IBIS vaccination and were evaluated for the presence of neutralizing antibodies against SARS-CoV-2 (WT) virus by $FRNT_{50}$.

FIG. 8E shows the body weight change of SARS-CoV-2-infected or co-housed vaccinated hamsters. Mock (n=4). Index, PBS-vaccinated and IBIS-vaccinated (n=6). Error bar=S.D.

FIGS. 8F and 8G show lung histology of co-housed hamsters. Lungs of PBS-(F) and IBIS-vaccinated hamsters (G) were harvested 5-days post-co-housing. Left lobe of each hamster was fixed in 4% PFA for H&E (left panels) and IHC staining against SARS-CoV-2 NP protein (right panels). Areas in black or white squares were enlarged and shown in the lower panels. N=4 for all groups.

FIGS. 8H and 8I show that IBIS completely prevents SARS-CoV-2 viral transmission to vaccinated hamsters. Lungs of hamsters were harvested 2- and 5-days post-infection (Index) or post-co-housing (PBS- and IBIS-vaccinated). Viral titer of the lung homogenates was determined by plaque assay. Error bar=S.D.

FIG. 8J shows that single low-dose IBIS vaccination is enough to protect hamsters from SARS-CoV-2 infection. Hamsters were vaccinated with single dose of IBIS in 10-fold serial dilution. 14-days post-vaccination, the hamsters were intranasally challenged with $1\times10^3$ PFU of SARS-CoV-2 (WT) virus. Body weight change was monitored for 14 days. N=3 for all groups. Error bar=S.D.

FIGS. 9A and 9B show that IBIS vaccination protects K18-hACE2 transgenic mice from lethal SARS-CoV-1 infection. K18-hACE2 transgenic mice were vaccinated with 2 doses of IBIS (as in FIG. 6A). 28-days after vaccination, mice were infected by intranasal inoculation of SARS-CoV-1 (GZ/50) ($2\times10^3$ PFU). Body weight change (FIG. 9A) and survival (FIG. 9B) were monitored for 14 days post-infection. Mock infected (n=3). PBS-vaccinated and IBIS-vaccinated (n=6).

FIGS. 9C and 9D show that IBIS vaccination quells SARS-CoV-1 viral replication in mice. Lungs (FIG. 9C) and nasal turbinates (FIG. 9D) of the vaccinated SARS-CoV-1 infected mice were harvested day2 and day5 post-infection for viral titer quantitation. N=5 for all group, except IBIS-day5 (n=4). N.D., not detected. Grey dotted line=detection limit.

FIGS. 9E-9G show that IBIS vaccination protects hamsters from SARS-CoV-1 infection. Hamsters were vaccinated (as in FIG. 6A), followed by intranasal inoculation of SARS-CoV-1 (GZ/50) ($2\times10^3$ PFU) at 28-day post-vaccination. Lungs (FIG. 9E), nasal turbinates (FIG. 9F), and trachea (FIG. 9G) were harvested at day2 and day5 post-infection for viral titer quantitation. N=4 for all group, except IBIS-day5 (n=3). N.D., not detected. Grey dotted line=detection limit.

FIGS. 10A-10F show results from hamsters that were vaccinated and infected with either delta ($2\times10^3$ PFU) or Omicron-B A.1 ($1\times10^4$ PFU) SARS-CoV-2 variants following the scheme described in FIG. 8A. Body weight (FIGS. 10A and 10D) of the infected/co-housed hamsters were monitored for 5 days till the day of tissue harvest. Hamster lungs, nasal turbinates and trachea were harvested day2 and day5 post-infection/co-housing for viral titer (FIGS. 10B and 10E) and RNA transcript level (FIGS. 10C and 10F) quantitation. N=4 for all groups infected with delta variant. N=3 for all groups infected with Omicron-BA.1 variant.

DETAILED DESCRIPTION OF THE INVENTION

Figure 1A:
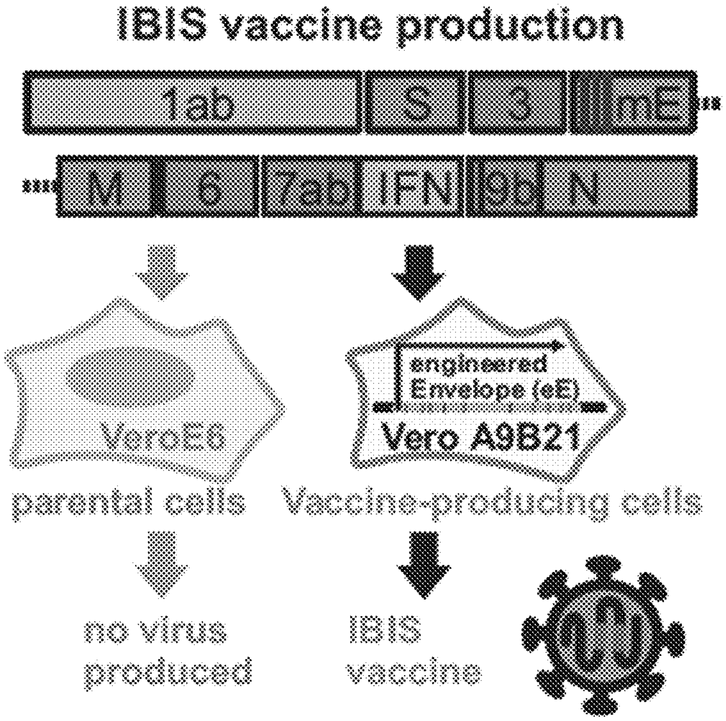
FIG. 1A depicts the design and production of IBIS, a live but defective SARS-CoV-2 virus that contains a modified envelope (mE) gene harboring three stop codons (gray lines) introduced to abrogate envelope protein expression. An open-reading frame coding for interferon-beta (IFNβ) was also inserted in the place of ORF8 (gray box around "IFN"). A version of IBIS having mouse IFNβ (mIFNβ) was produced for mouse and hamster experiments. The virus was rescued and propagated in VeroE6 cells stably expressing an engineered Envelope transgene (VeroE6-eE). A STAT1 knock-out clone A9B21 was further produced to support optimal virus production. The virus could only be propagated in VeroE6-eE or -A9B21 cells but not in wild-type VeroE6 cells. IBIS, Interferon-Beta-Integrated SARS-CoV-2.

The rapid mutation rate of sarbecoviruses, such as SARS-CoV-2, presents a unique challenge to standard vaccination development models. For example, in the past year, SARS-CoV-2 has significantly evolved such that the omicron variant and its various subvariants largely evade the antibodies generated from current vaccinations, which have demonstrated reduced ability to neutralize omicron and its subvariants. Although the very recent introduction of the newly bivalent SARS-CoV-2 vaccine aims to overcome this problem for the omicron variant, invariably this approach requires continued production, testing, and approval of new vaccines that lag behind the speed of the evolution of new variants.

The present invention provides a novel universal sarbecovirus and universal sarbecovirus construct that comprises a nucleic acid encoding an interferon integrated into the viral genome in conjunction with the modification of the sarbecovirus envelope gene that inactivates the virus and makes it suitable to use safely for vaccination. This universal sarbecovirus vaccine acts to vaccinate, prophylactically immunize, prevent contraction, prevent transmission, reduce infection severity, ameliorate infection symptoms, treat infection, or elicit an immune response in an individual having or being exposed to a sarbecovirus infection of one or more heterotypic sarbecovirus species.

After extensive investigation, inventors of the present application discovered that the universal sarbecovirus construct encoding an interferon integrated into the viral genome and a modified envelope protein has several unexpected advantages compared to other vaccine constructs. Vaccination with the universal sarbecovirus construct described herein reduced SARS-CoV1 and SARS-CoV-2 infection and transmission. When provided after infection, vaccination reduced SARS-CoV-2 infection severity across multiple variants (i.e., alpha, delta, omicron). As well, integration of IFNβ in the universal vaccine construct preferentially enhanced mucosal immune response. This novel next-generation vaccine elicits heterotypic immunity against various species of sarbecoviruses via generation of protective B and T cell immunity (e.g., CD4+ T cells).

Also provided herein are host cells that comprise the novel universal sarbecovirus and/or universal sarbecovirus construct. These host cells optionally further comprise a sarbecovirus envelope gene and defective in interferon signaling for the generation and packaging of universal sarbecovirus vaccine, making them particularly suitable for packing recombinant sarbecovirus described herein.

Accordingly, in one aspect, the present invention provides a construct that comprises a modified genome of a sarbecovirus, wherein the modified genome comprises a modified envelope gene and a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the construct comprises a nucleic acid that encodes an interferon that is inserted into the viral genome. In some embodiments, the nucleic acid encodes an interferon that replaces viral open reading frame 8 (ORF8). In some embodiments, the interferon is type I interferon, such as interferon β. In some embodiments, the modified envelope gene comprises one or more stop codons, such as at least three stop codons, which is present at the 5'-terminal 100 nucleic acids of the modified envelope gene. In some embodiments, the construct further comprises at least a functional portion of ORF6, ORF7a, ORF7b, and/or ORF8 in the modified genome to be deleted and/or inactivated by introducing a stop codon.

Thus, in one aspect, there is provided a recombinant sarbecovirus comprising the construct described herein. In another aspect, there is provided a sarbecovirus vaccine comprising the recombinant sarbecovirus.

Also provided are pharmaceutical compositions and kits comprising any of the IFN-producing sarbecovirus vaccines described herein, methods of preparing any of the IFN-producing sarbecovirus vaccines and the accompanying host cells described herein, and methods of use thereof for preventing or ameliorating viral infection, particularly SARS-CoV-2 viral infection.

I. Definitions

The practice of the present invention will employ, unless indicated specifically to the contrary, conventional methods of virology, immunology, microbiology, molecular biology, and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al., Short Protocols in Molecular Biology, 3rd ed., John Wiley & Sons, 1995; Sambrook and Russell, Molecular Cloning: A Laboratory Manual (3rd Edition, 2001); Maniatis et al., Molecular Cloning: A Laboratory Manual (1982); DNA Cloning: A Practical Approach, vol. I&II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

It will be understood by one of ordinary skill in the art that uracil and thymine can both be represented by 't', instead of 'u' for uracil and T for thymine; in the context of a ribonucleic acid, it will be understood that T is used to represent uracil unless otherwise indicated.

The term "genomic RNA" as used herein refers to the heritable genetic information of an RNA virus. However, in the context of the present invention the term "genome" typically also refers to the genome of an RNA virus and hence an RNA genome having a ribonucleic acid sequence. The person skilled in the art will understand that the genome of an RNA virus may also be provided as a DNA sequence in a vector, such as a plasmid (or referred to as "DNA construct"). The RNA genome is then generated in a host cell following transfection of the host cell via transcription. Hence it will be understood that when referring to nucleic acid sequences of a positive-sense RNA virus, sequences in the "Sequence Listing" section can refer to RNA sequence (replacing "T" with "U") or DNA sequence.

The term "gene" as used herein refers to a DNA or RNA locus of heritable genomic sequence which affects an organism's (e.g., RNA virus) traits by being expressed as a functional product or by regulation of gene expression. Genes and polynucleotides may include introns and exons as in genomic sequence, or just the coding sequences as in cDNAs, such as an open reading frame (ORF), comprising a start codon (methionine codon) and a translation stop codon. Genes and polynucleotides can also include regions that regulate their expression, such as transcription initiation, translation, and transcription termination. Thus, also included are regulatory elements such as a promoter.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA, negative-sense and positive-sense), double stranded RNA (dsRNA), genomic DNA, cDNA, cRNA, recombinant DNA, or recombinant RNA and derivatives thereof, such as those containing modified backbones.

The term "ribonucleic acid", "RNA" or "RNA oligonucleotide" as used herein describes a molecule consisting of a sequence of nucleotides, which are built of a nucleobase a ribose sugar, and a phosphate group. RNAs are usually single stranded molecules and can exert various functions.

The terms "upstream" and "downstream" refer to a relative position in DNA or RNA. Each strand of DNA or RNA possesses a 5' end and a 3' end, relating to the terminal carbon position of the deoxyribose or ribose units. By convention, "upstream" means towards the 5' end of a polynucleotide, whereas "downstream" means towards the 3' end of a polynucleotide. In the case of double stranded DNA, e.g., genomic DNA, the term "upstream" means towards the 5' end of the coding strand, whereas "downstream" means towards the 3' end of the coding strand.

The term "coding strand" or "positive-sense strand" refers to an RNA strand encoding for proteins.

The term "non-coding strand" "anti-sense strand" or "negative-sense strand" or "negative-strand" refers to an RNA strand that needs to be transcribed by an RNA-dependent RNA polymerase into a positive strand RNA prior to translation.

The term "encodes" and "codes for" refers broadly to any process whereby the information in a polymeric macromolecule is used to direct the production of a second molecule that is different from the first. The second molecule may have a chemical structure that is different from the chemical nature of the first molecule. For example, the term "encode" describes the process of semiconservative DNA replication, where one strand of a double-stranded DNA molecule is used as a template to encode a newly synthesized complementary sister strand by a DNA-dependent DNA polymerase. Further, a DNA molecule can encode an RNA molecule (e.g., by use of a DNA-dependent RNA polymerase) or an RNA molecule (negative stranded) can encode an RNA molecule (positive-stranded) (e.g., by use of an RNA-dependent RNA polymerase). Also, an RNA molecule (positive-stranded) can encode a polypeptide, as in the process of translation. When used to describe the process of translation, the term "encode" also extends to the triplet codon that encodes an amino acid. An RNA molecule can also encode a DNA molecule, e.g., by the process of reverse transcription using an RNA-dependent DNA polymerase. When referring to a DNA molecule encoding a polypeptide, a process of transcription and translation is referred to.

The term "heterologous polypeptide" or "heterologous protein" as used herein refers to a protein derived from a different organism or a different species from the recipient, e.g., the RNA virus or the host cell. In the context of the present invention the skilled person would understand that it refers to a protein not naturally expressed by the virus or the host cell. The term "heterologous" when used with reference to portions of a protein may also indicate that the protein comprises two or more amino acid sequences that are not found in the same relationship to each other in nature.

The term "expression" as used herein refers to transcription and/or translation of a heterologous nucleic acid sequence within a host cell. The level of expression of a gene product of interest in a host cell may be determined on the basis of either the amount of the corresponding mRNA (or positive-stranded RNA) that is present in the cell, or the amount of the polypeptide encoded by the selected sequence. For example, RNA transcribed from a selected sequence can be quantified by Northern blot hybridization, ribonuclease RNA protection, in situ hybridization to cellular RNA, or by PCR, such as qPCR. Proteins encoded by a selected sequence can be quantitated by various methods, e.g., by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

A "reference strain" of a virus is a strain that does not comprise any of the human made mutations as described herein and is the viral strain on which all other versions thereof are compared. For example, the reference SARS-CoV-2 virus is the originally isolated strain from Wuhan, China (see SEQ ID NO: 1) and described by NIH GenBank Locus NC_045512 and as the hCoV-19 reference sequence by the Global Initiative on Sharing Avian Influenza Data (GISAID).

As used herein, the term "treatment" refers to clinical intervention designed to alter the natural course of the infection in an individual or cell being treated prophylactically or during the course of clinical pathology. Desirable effects of treatment include ameliorating or reducing the sarbecovirus infection and symptoms thereof and eliciting an immune response to induce the amelioration or reduction of the infection and symptoms thereof. For example, an individual is successfully "treated" if one or more symptoms associated with sarbecovirus infection are prevented, mitigated, or eliminated, including, but not limited to, increasing the quality of life of those suffering from the infection, decreasing the dose of other medications required to treat the infection, and/or prolonging survival of individuals.

As used herein, an "effective amount" refers to an amount of an agent or drug effective to vaccinate or treat a sarbecovirus infection in a subject. The "therapeutically effective amount" can vary depending on the compound or the cell, the disease and its severity and the age, weight, etc., of the subject to be treated.

As used herein, an "individual" or a "subject" refers to a mammal, including, but not limited to, human, bovine, horse, feline, canine, rodent, or primate. In some embodiments, the individual is a human.

The term "vaccine" is used in the broadest sense and specifically covers any biological preparation that provides active acquired immunity to a particular infectious disease.

As used herein, the term "vaccinate" refers to clinical intervention designed to administer a therapeutically effective amount of a vaccine to an individual in need thereof in order to prevent infection, prophylactically immunize, prevent transmission, reduce severity, elicit an immune response, or treat an infection in an individual who has been or may be exposed to a pathogen such as viruses. For example, an individual who is effectively vaccinated may not contract or may contract only mild illness caused by an infection compared to an individual who is not vaccinated.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

As used herein, "percent (%) nucleic acid sequence identity" and "homology" with respect to a nucleic acid, DNA, or RNA sequence are defined as the percentage of nucleic acid nucleotides in a candidate sequence that are identical with the nucleic acid nucleotides in the specific DNA or RNA sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, ALIGN, or MEGALIGN™ (DNASTAR) software. Those skilled in the art can determine appropriate parameters for measuring alignment, including any algorithms needed to achieve maximal alignment over the full length of the sequences being compared.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "cell" includes the primary subject cell and its progeny.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Universal Sarbecovirus Vaccine Constructs

Sarbecovirus Vaccine Constructs

Sarbecovirus is a subgenus of the Betacoronavirus genus within the Coronaviridae family of viruses. Examples of sarbecoviruses include, but are not limited to, SARS-CoV/SARS-CoV-1, SARS-CoV-2, SC2r-CoV, SC2r-CoV GX-PSL, Bat CoV BtKY72, Bat CoV BM48-31, 16BO133, JTMC15, Bat SARS CoV Rf1, BtCoV HKU3, LYRa11, Bat SARS-CoV/Rp3, Bat SL-CoV YNLF_31C, Bat SL-CoV YNLF_34C, SHC014-CoV, WIV1, WIV16, Civet SARS-CoV, (Bat) Rc-o319, Bat SL-ZXC21, Bat SL-ZC45, Pangolin SARSr-CoV-GX, Pangolin SARSr-CoV-GD, Rs7327, Rs4231, Rs4084, Rf4092, JL2012, 273-2005, HeB2013, HuB2013, Rs4247, Longquan-140, HKU3-1, GX2013, Shaanxi2011, 279-2005, As6526, Yunnan2011, Rs4237, Rs4081, Bat RshSTT182, Bat RshSTT200, (Bat) RacCS203, (Bat) RmYN02, (Bat) RpYN06, YN2013, (Bat) RaTG13, (Bat) BANAL-52, and SARS-CoV-2 combined variants of concern (VOC) (for example, see Nature (2022) 603:913-918, hereby incorporated by reference in its entirety). A SARS-CoV-2 variant is defined as being a "variant of concern" (VOC) upon demonstration of the following: (i) an increase in transmissibility or other detrimental change in epidemiology, (ii) an increase in virulence or change in clinical disease presentation, (iii) escape from immunity derived from natural infection, and/or (iv) a decrease in effectiveness of public health or clinical countermeasures, such as vaccination, treatment in current clinical use, testing if the impact is such that it is not easily mitigated by standard, and laboratory quality and regulatory measures. Sarbecoviruses are generally understood to be enveloped, positive-sense single-stranded RNA viruses that enter host cells by binding to the angiotensin-converting enzyme 2 (ACE2) receptor. For example, SARS-CoV-2 binds both ACE2 and TMPRSS2, both of which are expressed by epithelial cells that can be found in various tissues, such as prostate, testis, ovary, uterus, breast, lung, oral, cardiac, nasal passageway, ileum, intestine, colon, stomach, thyroid, liver, gallbladder, pancreas, kidney, bladder, cornea, neural, placental, etc. Receptor expression levels are increased in various inflammatory disease states, including but not limited to, in hypertension, COPD, asthma, cardiovascular disease, diabetes, Crohn's disease (CD), inflammatory bowel disease (IBD), etc. As a result, individuals with any of these or similar diseases or with immunodeficiency diseases are at an increased risk for sarbecovirus infection and complications thereof.

The present invention provides a construct that comprises a modified genome of a sarbecovirus, wherein the modified genome comprises a modified envelope gene (e.g., viral RNA gene, including an RNA sequence or a reverse-transcribed DNA sequence thereof) and a nucleic acid encoding an interferon integrated (e.g., inserted) into the genome. In some embodiments, the construct comprising a modified genome of a sarbecovirus is a viral RNA construct. In some embodiments, the construct is an RNA viral vector. In some embodiments, the construct is an RNA molecule. In some embodiments, the construct is a DNA vector, such as Bacterial artificial chromosome (BAC) construct. In some embodiments, the construct comprising a modified genome of a sarbecovirus is a DNA polynucleotide encoding the modified viral RNA genome, such as in a DNA plasmid. In some embodiments, the nucleic acid encoding the interferon is inserted in the viral genome. In some embodiments, the nucleic acid encoding the interferon replaces a portion of the viral genome. In some embodiments, the modified envelope gene does not produce any functional envelope protein. This can be accomplished, for example, by incorporating one or more stop codons into the envelope protein coding sequence, or by introducing mutations into the envelope protein coding sequence that makes the protein expressed therefrom non-functional. In some embodiments, the modified envelope gene comprises one or more stop codons. In some embodiments, the modified envelope gene comprises at least three, such as at least any of 4, 5, 6, 7, 8, 9, 10, or more stop codons. In some embodiments, at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments when the modified envelope gene comprises two or more stop codons, the stop codons are clustered together or spread out (e.g., evenly or unevenly) over the entire gene sequence (e.g., viral RNA gene sequence, including an RNA sequence or a reverse-transcribed DNA sequence thereof). In some embodiments, at least a functional portion of ORF6, ORF7a, ORF7b, and/or ORF8 in the modified viral genome is deleted and/or inactivated, for example by introducing one or more stop codons. In some embodiments, at least a functional portion of (e.g., the entirety of) ORF6 in the modified viral genome is deleted and/or inactivated, for example by introducing one or more stop codons. In some embodiments, at least a functional portion of (e.g., the entirety of) ORF7a in the modified viral genome is deleted and/or inactivated, for example by introducing one or more stop codons. In some embodiments, at least a functional portion of (e.g., the entirety of) ORF7b in the modified viral genome is deleted and/or inactivated, for example by introducing one or more stop codons. In some embodiments, at least a functional portion of (e.g., the entirety of) ORF8 in the modified viral genome is deleted and/or inactivated, for example by introducing one or more stop codons. In some embodiments, a functional portion of (e.g., the entirety of) each of 2, 3, or 4 of ORF6, ORF7a, ORF7b, and ORF8 in the modified viral genome is deleted and/or inactivated, for example by introducing one or more stop codons.

In some embodiments, the wildtype envelope gene (e.g., SARS-CoV-2 wildtype envelope gene, e.g., viral RNA gene, including an RNA sequence or a reverse-transcribed DNA sequence thereof) comprises a nucleic acid sequence of SEQ ID NO: 12. In some embodiments, the modified envelope gene comprises one or more mutations (e.g., frameshift, non-sense, missense, insertion, deletion, and/or substitution), such as in reference to SEQ ID NO: 12. In some embodiments, the modified envelope gene comprises a nucleic acid sequence of SEQ ID NO: 14. In some embodiments, the nucleic acid encoding the modified envelope gene has at least about 80% (such as at least about any of 85%, 90%, 95%, 96%, 97%, 98%, 99%, or higher) nucleic acid sequence identity to the nucleic acid sequence of SEQ ID NO: 14. In some embodiments, the modified envelope gene encodes a modified envelope protein comprising the sequence of SEQ ID NO: 13.

In some embodiments, the interferon is Type I interferon. In some embodiments, the interferon is Type III interferon. In some embodiments, the interferon is interferon (3 (IFNβ). In some embodiments, the IFNβ is encoded by a nucleic acid having the sequence of SEQ ID NO: 10 or 11, or a variant thereof having at least about 80% (such as at least about any of 85%, 90%, 95%, 96%, 97%, 98%, 99%, or higher) amino acid sequence identity to that of an interferon encoded by the nucleic acid having the sequence of SEQ ID NO: 10 or 11.

In some embodiments, the nucleic acid encoding the interferon has at least about 80% (such as at least about any of 85%, 90%, 95%, 96%, 97%, 98%, 99%, or higher) nucleic acid sequence identity to the nucleic acid sequence of SEQ ID NO: 10 or 11. In some embodiments, the human IFNβ nucleic acid comprises the nucleic acid sequence of SEQ ID NO: 10. In some embodiments, the mouse IFNβ nucleic acid comprises the nucleic acid sequence of SEQ ID NO: 11.

In some embodiments, the nucleic acid encoding the interferon is inserted at a location between ORF6 and ORF9b of the sarbecovirus genome, such as at ORF6, ORF7a, ORF7b, or ORF8, or anywhere between these ORFs. In some embodiments, the nucleic acid encoding the interferon replaces any one of ORF6, ORF7a, ORF7b, or ORF8 (or functional portion thereof), or any sequences between these ORFs, in the modified viral genome. In some embodiments, the nucleic acid encoding the interferon replaces ORF8 (or functional portion thereof) in the modified viral genome.

Thus, in some embodiments, there is provided a construct comprising a modified genome of a sarbecovirus (such as SARS-CoV-2), wherein the modified genome comprises a modified envelope gene (e.g., viral RNA gene, including an RNA sequence or a reverse-transcribed DNA sequence thereof) and a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a construct comprising a modified genome of a sarbecovirus (such as SARS-CoV-2), wherein the modified genome comprises a modified envelope gene (e.g., viral RNA gene, including an RNA sequence or a reverse-transcribed DNA sequence thereof), wherein the modified envelope gene does not produce any functional envelope protein, and a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a construct comprising a modified genome of a sarbecovirus (such as SARS-CoV-2), wherein the modified genome comprises i) a modified envelope gene (e.g., viral RNA gene, including an RNA sequence or a reverse-transcribed DNA sequence thereof), wherein the modified envelope gene comprises one or more stop codons (such as at least any of 3, 4, 5, 6, 7, 8, 9, 10, or more stop codons), and ii) a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a construct comprising a modified genome of a sarbecovirus (such as SARS-CoV-2), wherein the modified genome comprises a modified envelope gene (e.g., viral RNA gene, including an RNA sequence or a reverse-transcribed DNA sequence thereof) and a nucleic acid encoding an interferon inserted between ORF6 and ORF9b. In some embodiments, the nucleic acid encoding the interferon replaces a portion of the virus genome. In some embodiments, the nucleic acid encoding the interferon replaces ORF8 in the modified viral genome. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a construct comprising a modified genome of a sarbecovirus (such as SARS-CoV-2), wherein the modified genome comprises i) a modified envelope gene (e.g., viral RNA gene, including an RNA sequence or a reverse-transcribed DNA sequence thereof), wherein the modified envelope gene does not produce any functional envelope protein, and ii) a nucleic acid encoding an interferon inserted between ORF6 and ORF9b. In some embodiments, the nucleic acid encoding the interferon replaces a portion of the virus genome. In some embodiments, the nucleic acid encoding the interferon replaces ORF8. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a construct comprising a modified genome of a sarbecovirus (such as SARS-CoV-2), wherein the modified genome comprises i) a modified envelope gene (e.g., viral RNA gene, including an RNA sequence or a reverse-transcribed DNA sequence thereof), wherein the modified envelope gene comprises one or more stop codons (such as at least any of 3, 4, 5, 6, 7, 8, 9, 10, or more stop codons), and ii) a nucleic acid encoding an interferon inserted between ORF6 and ORF9b. In some embodiments, the nucleic acid encoding the interferon replaces a portion of the virus genome. In some embodiments, the nucleic acid encoding the interferon replaces ORF8 in the modified viral genome. In some embodiments, the at least one (e.g., 2, 3, 4, 5, 6, 7, 8, 9, or 10) stop codon is present at the 5'-terminal 100 nucleic acids of the modified envelope gene, for example at the 5'-terminal 10, 20, 30, 40, 50, 60, 70, 80, 90 nucleic acids of the modified envelope gene. In some embodiments, the interferon is Type I interferon. In some embodiments, the interferon is interferon β.

In some embodiments, at least a functional portion of ORF6, ORF7a, ORF7b, and/or ORF8 in the modified viral genome is deleted.

In some embodiments, the modified genome comprises a wild-type spike gene. In some embodiments, the modified genome comprises a variant spike gene.

In some embodiments, the construct comprises a nucleic acid sequence of any one of SEQ ID NOs: 2-9. In some embodiments, the construct comprises a nucleic acid sequence of any one of SEQ ID NOs: 2-7. In some embodiments, the construct comprises a nucleic acid sequence of SEQ ID NO: 8 or 9.

The present invention also provides a recombinant sarbecovirus comprising any of the constructs described herein. Because the genome of the sarbecoviruses comprises a defective envelope gene (e.g., viral RNA gene), they can be packaged in a host cell supplementing a functional envelope gene but cannot replicate themselves. In some embodiments, the recombinant sarbecovirus comprising any of the constructs described herein are packaged in a host cell as a viral RNA construct. In some embodiments, the recombinant sarbecovirus comprising any of the constructs described herein are packaged in a host cell as a DNA polynucleotide encoding the modified viral RNA genome, such as in a DNA plasmid. In some embodiments, the recombinant sarbecovirus comprises a viral RNA construct.

In another aspect, there is provided a sarbecovirus vaccine comprising any of the recombinant sarbecovirus described herein. The vaccine can further comprise, for example, adjuvants or excipients suitable for vaccination. In some embodiments, the sarbecovirus vaccine is formulated for mucosal administration, including for example as a nasal spray or nasal drops.

Thus, for example, in some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises a modified envelope gene (e.g., viral RNA gene, including an RNA sequence or a reverse-transcribed DNA sequence thereof) and a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the vaccine is formulated for mucosal administration, such as intranasal administration. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises i) a modified envelope gene (e.g., viral RNA gene, including an RNA sequence or a reverse-transcribed DNA sequence thereof), wherein the modified envelope gene does not produce any functional envelope protein, and ii) a nucleic acid encoding an interferon integrated into the genome. In some embodiments, the nucleic acid encoding the interferon is inserted in the viral genome. In some embodiments, the nucleic acid encoding the interferon replaces a portion of the viral genome. In some embodiments, the vaccine is formulated for mucosal administration, such as intranasal administration. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises i) a modified envelope gene (e.g., viral RNA gene, including an RNA sequence or a reverse-transcribed DNA sequence thereof), wherein the modified envelope gene comprises one or more stop codons (such as at least any of 3, 4, 5, 6, 7, 8, 9, 10, or more stop codons), and ii) a nucleic acid encoding an interferon integrated into the genome. In some embodiments, the vaccine is formulated for mucosal administration, such as intranasal administration. In some embodiments, the at least one (e.g., 2, 3, 4, 5, 6, 7, 8, 9, or 10) stop codon is present at the 5'-terminal 100 nucleic acids of the modified envelope gene, for example at the 5'-terminal 10, 20, 30, 40, 50, 60, 70, 80, 90 nucleic acids of the modified envelope gene. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises a modified envelope gene (e.g., viral RNA gene, including an RNA sequence or a reverse-transcribed DNA sequence thereof) and a nucleic acid encoding an interferon inserted between ORF6 and ORF9b. In some embodiments, the vaccine is formulated for mucosal administration, such as intranasal administration. In some embodiments, the nucleic acid encoding the interferon replaces a portion of the virus genome. In some embodiments, the nucleic acid encoding the interferon replaces ORF8 in the modified viral genome. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises i) a modified envelope gene (e.g., viral RNA gene, including an RNA sequence or a reverse-transcribed DNA sequence thereof), wherein the modified envelope gene does not produce any functional envelope protein, and ii) a nucleic acid encoding an interferon inserted between ORF6 and ORF9b. In some embodiments, the vaccine is formulated for mucosal administration, such as intranasal administration. In some embodiments, the nucleic acid encoding the interferon replaces a portion of the virus genome. In some embodiments, the nucleic acid encoding the interferon replaces ORF8 in the modified viral genome. In some embodiments, the interferon is Type I interferon. In some embodiments, the interferon is interferon β. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a recombinant sarbecovirus (such as SARS-CoV-2) or a vaccine comprising the recombinant sarbecovirus, wherein the sarbecovirus comprises a construct comprising a modified genome of a sarbecovirus, wherein the modified genome comprises i) a modified envelope gene (e.g., viral RNA gene, including an RNA sequence or a reverse-transcribed DNA sequence thereof), wherein the modified envelope gene comprises one or more stop codons (such as at least any of 3, 4, 5, 6, 7, 8, 9, 10, or more stop codons), and ii) a nucleic acid encoding an interferon inserted between ORF6 and ORF9b. In some embodiments, the vaccine is formulated for mucosal administration, such as intranasal administration. In some embodiments, the nucleic acid encoding the interferon replaces a portion of the virus genome. In some embodiments, the nucleic acid encoding the interferon replaces ORF8 in the modified viral genome. In some embodiments, the at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments, the interferon is Type I interferon. In some embodiments, the interferon is interferon R. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, the recombinant sarbecovirus or the vaccine comprising the recombinant sarbecovirus comprises a construct that comprises a nucleic acid sequence of any of SEQ ID NOs: 2-9. In some embodiments, the construct comprises a nucleic acid sequence of any of SEQ ID NOs: 2-7. In some embodiments, the construct comprises a nucleic acid sequence of SEQ ID NO: 8 or 9.

Sarbecovirus

In some embodiments, the sarbecovirus is selected from the group consisting of SARS-CoV, SARS-CoV-2, SARS-CoV-2 B.1.1.7, SARS-CoV-2 B.1.351, SARS-CoV-2 B1.617.2, SAR-CoV-2 B.1.1.529, SC2r-CoV, RaTG13, SC2r-CoV GX-PSL, and SARS-CoV combined VOC. In some embodiments, the sarbecovirus is SARS-CoV-2. In some embodiments, the modified genome comprises a wild-type spike gene. In some embodiments, the modified genome comprises a variant spike gene. In some embodiments, the variant spike gene is BA.2, BA.5, BA.2.75.2, BQ.1, BQ.1.1, or XBB.

The SARS-CoV-2 virus has a single-stranded RNA genome with about 29891 nucleotides that encode about 9860 amino acids. A SARS-CoV-2 selected RNA genome can be copied and made into a DNA by reverse transcription and formation of a cDNA. A linear SARS-CoV-2 DNA can be circularized by ligation of SARS-CoV-2 DNA ends.

As used herein, a "SARS-CoV-2 genome" refers to the 29903 nucleotide sequence described by NIH GenBank Locus NC_045512, or the hCoV-19 reference sequence described by the Global Initiative on Sharing Avian Influenza Data (GISAID). A DNA sequence for the SARS-CoV-2 genome, with coding regions, is available as accession number NC_045512.2 from the NCBI website (provided as SEQ ID NO: 1 herein). In some embodiments, the recombinant SARS-CoV-2 construct comprises SEQ ID NO: 1 or its encoded RNA sequence (i.e., substituting T with U), or a sequence comprising at least about 90% sequence identity (such as at least about any of 91%, 92%, 93%, 94%, 95%, 96%, 97%, 98%, 99%, or higher sequence identity) to the sequence of SEQ ID NO: 1 or its encoded RNA sequence.

Viral genomes comprise subunits known as open reading frames (ORFs) that may encode for viral proteins. Within the SARS-CoV-2 genome, these subunits may include ORF 1ab, RNA-dependent RNA polymerase, helicase, gene S, nsp3, nsp4B, nsp9, ORF3a, gene E, gene M/ORF5, ORF6, ORF7a, ORF7b, ORF8, gene N/ORF9, and ORF10. Each of these subunits corresponds to sections of SEQ ID NO:1 as described in Table 1 below.

ORF1ab encodes a large polyprotein that encompasses multiple of the proteins encoded by other ORFs described herein, as indicated in Table 1 below. Nsp3 encodes a protein that includes a transmembrane domain 1 (TM1), which has NCBI accession no. YP_009725299.1. The nsp3 protein has additional conserved domains including an N-terminal acidic (Ac), a predicted phosphoesterase, a papain-like proteinase, Y-domain, transmembrane domain 1 (TM1), and an adenosine diphosphate-ribose 1"-phosphatase (ADRP). Nsp4b encodes a protein that includes transmembrane domain 2 (TM2), which has NCBI accession no. YP_009725300. Nsp9 encodes a ssRNA-binding protein with NCBI accession number YP_009725305.1. Genes E, M, S, and N encode the envelope, membrane, spike, and nucleocapsid proteins, respectively. The viral envelope protein is a membrane protein that is involved in viral assembly, budding, and envelope formation. Viral membrane proteins attach the virus to the host cell and promote fusion between viral and host cell membranes for viral entry. The viral spike protein binds to specific receptors on the host cell to engage in viral entry of host cells and initiation of host cell infection. The viral nucleocapsid protein binds to and encapsulates the viral RNA. Together, these four proteins make up the integral structural proteins found in sarbecoviruses, e.g., in SARS-CoV-2.

TABLE 1

Locations of nucleotide sequences that encode SARS-CoV-2 viral proteins and ORFs

| SARS-CoV-2 Subunit/Open Reading Frame | Nucleotide Location within SEQ ID NO: 1 |
|---|---|
| Leader sequence/5' UTR | Position 1-265 |
| 3' UTR | Position 29,675-29,870 |
| Poly-A tail | Position 29,871-29,903 |
| ORF1ab | Position 266-21,552 |
| nsp3 | Position 2,720-8,554 |
| nsp4B | Position 8,555-10,054 |
| nsp9 | Position 12,686-13,024 |
| RNA-dependent RNA polymerase | Positions 13,442-13,468 and 13,468-16,236 |
| Helicase | Position 16,237-18,039 |
| Spike (S) | Position 21,563-25,384 |
| ORF3a | Position 25,393-26,220 |
| Envelope (E)/ORF4 | Position 26,245-26,472 |
| Membrane (M)/ORF5 | Position 26,523-27,191 |
| ORF6 | Position 27,202-27,387 |
| ORF7a | Position 27,394-27,759 |
| ORF7b | Position 27,756-27,887 |
| ORF8 | Position 27,894-28,259 |
| Nucleocapsid (N)/ORF9 | Position 28,274-29,553 |
| ORF10 | Position 29,558-29,674 |

In some embodiments, the recombinant SARS-CoV-2 construct does not comprise any portion of the nucleotide sequences for any one or more of ORF 1ab, RNA-dependent RNA polymerase, helicase, gene S, nsp3, nsp4B, nsp9, ORF3a, gene E, ORF5, ORF6, ORF7a, ORF7b, ORF8, ORF9, and ORF10. In some embodiments, the recombinant SARS-CoV-2 construct comprises a portion (e.g., no more than about any of 90%, 80%, 70%, 60%, 50%, 40%, 30%, 20%, 10%, or 5%) of the nucleotide sequence for any one or more of ORF 1ab, RNA-dependent RNA polymerase, helicase, gene S, nsp3, nsp4B, nsp9, ORF3a, gene E, ORF5, ORF6, ORF7a, ORF7b, ORF8, ORF9, and ORF10. In some embodiments, the recombinant SARS-CoV-2 construct comprises a full length or a portion (e.g., at least about any of 90%, 80%, 70%, 60%, 50%, 40%, 30%, 20%, 10%, or 5%) of the nucleotide sequence for any one or more of ORF 1ab, RNA-dependent RNA polymerase, helicase, gene S, nsp3, nsp4B, nsp9, ORF3a, gene E, ORF5, ORF6, ORF7a, ORF7b, ORF8, ORF9, and ORF10. In some embodiments, the recombinant SARS-CoV-2 construct comprises a full length or a portion (e.g., at least about any of 90%, 80%, 70%, 60%, 50%, 40%, 30%, 20%, 10%, or 5%) of the nucleotide sequence for any one or more of ORF 1ab, RNA-dependent RNA polymerase, helicase, gene S, nsp3, nsp4B, nsp9, ORF3a, gene E, ORF5, ORF6, ORF7a, ORF7b, ORF8, ORF9, and ORF10, wherein the full length or a portion of the nucleotide sequence comprises a frameshift mutation, a deletion, an insertion, a non-sense mutation, or a missense mutation, which may further render no protein translation at all or no translation of a functional viral protein.

In some embodiments, the foregoing nucleotide sequences are DNA sequences. In some embodiments, the foregoing nucleotide sequences are RNA sequences (e.g., replacing the "T" in DNA sequence with "U". In some embodiments, the SARS-CoV-2 nucleic acids used in the recombinant SARS-CoV-2 constructs described herein are DNA sequences. In some embodiments, the SARS-CoV-2 nucleic acids used in the recombinant SARS-CoV-2 constructs described herein are RNA sequences. In some embodiments, the recombinant SARS-CoV-2 constructs described herein comprise both DNA and RNA sequences (e.g., SARS-CoV-2 DNA sequences and SARS-CoV-2 RNA sequences). It is to be understood that, when the SARS-CoV-2 construct is RNA, the nucleotide sequence of the construct would be the RNA sequence corresponding to the DNA sequences provided herein, e.g., replacing "T" with "U".

In addition, the sarbecovirus genome, e.g., SARS-CoV-2 genome, can naturally have structural variations that are reflections of sequence variations that arise as the sarbecovirus genome mutates over time in response to evolutionary pressures. Thus, the sarbecovirus can be a variant sarbecovirus that has one or more mutations in the genomic sequence compared to the reference sarbecovirus (e.g., the SARS-CoV-2 virus of SEQ ID NO: 1), wherein the one or more mutations contribute to phenotypic differences, such as increased viral fitness, including for example, infectivity, virulence, and/or drug resistance. For example, the genomes of widespread variant SARS-CoV-2 viruses have shown an increase in transmissibility and infectiousness as well as a decrease in mortality. As a result, currently available vaccines and treatments have become less effective at vaccinating or treating individuals against the variants that are increasingly divergent in nucleic acid sequence identity from the reference SARS-CoV-2. A variant further can be termed a variant of interest, a variant of concern, or a variant of high consequence. In some embodiments, the sarbecovirus is a SARS-CoV-2 virus that further is a variant selected from the group consisting of a B.1.1.7 variant, a B.1.351 variant, a B.1.526 variant, a B1.526.1 variant, a B1.617 variant, a B.1.617.1 variant, a B.1.617.2 variant, a B1.617.3 variant, a P.2 variant, a P.1 (also known as B.1.1.28.1) variant, an A.23.1 variant, a CAL.20C variant, a B.1.427 variant, a B.1.429 variant, a B.1.525 variant, a BA.2, BA.5 variant, a BA.2.75.2 variant, a BQ.1 variant, a BQ.1.1 variant, an XBB variant, and a P.1.351 variant. Other variants of SARS-CoV-2 are known in the art. For example, see Gomez et al., Vaccines 9(3): 243, 2021 and Tang et al., Journal of Infection 82: e27-e28, 2021, which are incorporated herein by reference in their entirety.

Hence, the sarbecovirus used in the recombinant sarbecovirus vaccine or constructs described herein can, for example for SARS-CoV-2, have one or more nucleotide or amino acid differences from the sequences as indicated in Table 1 above. In some cases, the SARS-CoV-2 nucleic acids used in the recombinant sarbecovirus vaccine or constructs described herein can, for example, have two, three, four, five, six, seven, eight, nine, ten, fifteen, twenty, twenty-five, thirty, or more nucleotide differences from the sequences as signified in reference to SEQ ID NO: 1 as shown in Table 1. In some embodiments, the recombinant SARS-CoV-2 construct can comprise a sequence that is at least about any of 10%, 20%, 25%, 30%, 35%, 40%, 45%, 50%, 55%, 60%, 65%, 70%, 75%, 80%, 85%, 90%, 95%, 96%, 97%, 98%, 99%, or higher homologous to a nucleotide sequence discussed above for one or more of ORF1ab, RNA-dependent RNA polymerase, helicase, gene S, nsp3, nsp4B, nsp9, ORF3a, gene E, ORF5, ORF6, ORF7a, ORF7b, ORF8, ORF9, ORF10, or a portion thereof. In some embodiments, the at least one (e.g., 2, 3, 4, 5, 6, 7, 8, 9, or 10) stop codon is present at the 5'-terminal 100 nucleotides of the modified envelope gene (e.g., viral RNA gene), for example at the 5'-terminal 10, 20, 30, 40, 50, 60, 70, 80, 90 nucleotides of the modified envelope gene. In some embodiments, at least a functional portion of ORF6, ORF7a, ORF7b, and/or ORF8 in the modified genome is deleted. In some embodiments, the modified genome comprises a wild-type spike gene. In some embodiments, the modified genome comprises a variant spike gene. In some embodiments, the recombinant sarbecovirus construct comprises a variant spike gene selected from any one of: BA.2, BA.5, BA.2.75.2, BQ.1, BQ.1.1, and XBB. In some embodiments, the recombinant sarbecovirus or recombinant sarbecovirus vaccine comprises a variant spike gene selected from any one of: BA.2, BA.5, BA.2.75.2, BQ.1, BQ.1.1, and XBB.

The recombinant SARS-CoV-2 constructs described herein can have portions of the SARS-CoV-2 genome, for example, the deletions of the genome can include at least about any of 5, 10, 20, 50, 100, 500, 1000, 1500, 2000, 2500, 3000, 4000, 5000 or more nucleotides of the SARS-CoV-2 genome. In some embodiments, at least a functional portion of ORF6, ORF7a, ORF7b, and/or ORF8 in the modified genome is deleted. In some embodiments, the modified genome comprises a wild-type spike gene. In some embodiments, the modified genome comprises a variant spike gene. In some embodiments, the recombinant sarbecovirus construct comprises a variant spike gene selected from any one of: BA.2, BA.5, BA.2.75.2, BQ.1, BQ.1.1, and XBB. In some embodiments, the recombinant sarbecovirus or recombinant sarbecovirus vaccine comprises a variant spike gene selected from any one of: BA.2, BA.5, BA.2.75.2, BQ.1, BQ.1.1, and XBB.

Exemplary SARS-CoV-2 variants and their properties are shown in the Table 2 below. The SARS-CoV-2 variants described herein are named according to the Phylogenetic Assignment of Named Global Outbreak (PANGO) Lineages software. It is understood that the same variants may be referred to using different naming systems and algorithms in the art. SARS-CoV-2 variant classifications and definitions, as well as a list of known SARS-CoV-2 variants can be found at worldwide web.cdc.gov/coronavirus/2019-ncov/variants/variant-info.html.

TABLE 2

SARS-CoV-2 variants and properties.

| Name | Spike Protein Substitutions | Phenotypes |
|---|---|---|
| B.1.525 | Spike: A67V, 69del, 70del, 144del, E484K, D614G, Q677H, F888L | Potential reduction in neutralization by some Emergency Use Authorization (EUA) monoclonal antibody treatments<br>Potential reduction in neutralization by convalescent and post-vaccination sera |
| B.1.526 | Spike: (L5F*), T95I, D253G, (S477N*), (E484K*), D614G, (A701V*) | Reduced susceptibility to the combination of bamlanivimab and etesevimab monoclonal antibody treatment; however, the clinical implications of this are not known. Alternative monoclonal antibody treatments are available.<br>Reduced neutralization by convalescent and post- vaccination sera |
| B.1.526.1 | Spike: D80G, 144del, F157S, L452R, D614G, (T791I*), (T859N*), D950H | Potential reduction in neutralization by some EUA monoclonal antibody treatments<br>Potential reduction in neutralization by convalescent and post-vaccination sera |
| B.1.617 | Spike: L452R, E484Q, D614G | Potential reduction in neutralization by some EUA monoclonal antibody treatments<br>Slightly reduced neutralization by post-vaccination sera |
| B.1.617.1 | Spike: (T95I), G142D, E154K, L452R, E484Q, D614G, P681R, Q1071H | Potential reduction in neutralization by some EUA monoclonal antibody treatments<br>Potential reduction in neutralization by post-vaccination sera |
| B.1.617.2 | Spike: T19R, (G142D), 156del, 157del, R158G, L452R, T478K, D614G, P681R, D950N | Potential reduction in neutralization by some EUA monoclonal antibody treatments<br>Potential reduction in neutralization by post-vaccination sera |
| B.1.617.3 | Spike: T19R, G142D, L452R, E484Q, D614G, P681R, D950N | Potential reduction in neutralization by some EUA monoclonal antibody treatments<br>Potential reduction in neutralization by post-vaccination sera |
| P.2 | Spike: E484K, (F565L*), D614G, V1176F | Potential reduction in neutralization by some EUA monoclonal antibody treatments<br>Reduced neutralization by post-vaccination sera |
| B.1.1.7 | 69del, 70del, 144del, (E484K*), (S494P*), N501Y, A570D, D614G, P681H, T716I, S982A, D1118H (K1191N*) | ~50% increased transmission<br>Potential increased severity based on hospitalizations and case fatality rates<br>No impact on susceptibility to EUA monoclonal antibody treatments<br>Minimal impact on neutralization by convalescent and post-vaccination sera |
| B.1.351 | D80A, D215G, 241del, 242del, 243del, K417N, E484K, N501Y, D614G, A701V | ~50% increased transmission<br>Significant decrease in susceptibility to the combination of bamlanivimab and etesevimab monoclonal antibody treatment, but other EUA monoclonal antibody treatments are available<br>Reduced neutralization by convalescent and post- vaccination sera |
| B.1.427 | L452R, D614G | ~20% increased transmissibility<br>Modest decrease in susceptibility to the combination of bamlanivimab and etesevimab; however, the clinical implications of this decrease are not known. Alternative monoclonal antibody treatments are available.<br>Reduced neutralization by convalescent and post- vaccination sera |
| B.1.429 | S13I, W152C, L452R, D614G | ~20% increased transmissibility<br>Modest decrease in susceptibility to the combination of bamlanivimab and etesevimab; however, the clinical implications of this decrease are not known. Alternative monoclonal antibody treatments are available.<br>Reduced neutralization by convalescent and post- vaccination sera |
| P.1 | L18F, T20N, P26S, D138Y, R190S, K417T, E484K, N501Y, D614G, H655Y, T1027I | Significant decrease in susceptibility to the combination of bamlanivimab and etesevimab monoclonal antibody treatment, but other EUA monoclonal antibody treatments are available<br>Reduced neutralization by convalescent and post- vaccination sera |

Interferons

Any suitable interferon can be used herein. Type-I and III interferon signaling provide key innate antiviral mechanisms against RNA virus infections (J Interferon Cytokine Res (2014) 34:649-58, hereby incorporated by reference in its entirety). Viral RNAs can be recognized by host pattern recognition receptors, such as RIG-I-like receptors and Toll-like receptors, which activate adaptors, kinases, and transcriptional factors, leading to induction of endogenous type-I/III interferons. Type-I interferons include 13 partially homologous IFNα subtypes in humans, IFNβ, IFNε, IFNτ, IFNκ, IFNω, IFNδ, and IFNζ (see, e.g., Immunol. Rev. (2004) 202, 8-32, hereby incorporated by reference in its entirety). The type III IFN family comprises IFNλ1, IFNλ2 and IFNλ3 (also called IL-29, IL-28A and IL-28B, respectively) and the recently identified IFNλ4 (see, e.g., J. Interferon Cytokine Res. (2014) 34, 829-838, hereby incorporated by reference in its entirety). The secreted interferons function as both paracrine and autocrine signals, protecting the neighboring uninfected cells and restricting virus replication in infected cells respectively. In addition, timely production of type-I interferons, such as IFNβ, by infected cells could optimally activate adaptive immune responses, shaping the effector and memory T cells (Immunology (2011) 132: 466-474, hereby incorporated by reference in its entirety). However, delayed type-I interferon signaling is the hallmark of coronavirus infections, including but not limited to SARS-CoV-1, MERS-CoV, and SARS-CoV-2 (Cell Host Microbe (2016) 19:181-193; J Clin Invest (2019) 129:3625-3639; Nat Commun (2021) 12:7092, hereby all incorporated by reference in their entirety). When compared to SARS-CoV-1, SARS-CoV-2 almost fully suppresses both type-I and type-III interferons in vitro (Clin Infect Dis (2020) 71:1400-1409, hereby incorporated by reference in its entirety). A handful of SARS-CoV-2 viral proteins function as potent interferon antagonists (Med Microbiol Immunol (2022) 1-7; Emerg Microbes Infect (2020) 9:1418-1428, hereby both incorporated by reference in their entirety). Thus, it is suggested that coronaviruses, especially SARS-CoV-2, can manipulate cellular induction of interferon signaling not only to escape the host antiviral response, but also to dampen host innate immunity and in turn lead to sub-optimal adaptive immunity. In some embodiments, the interferon is type I interferon, such as IFNβ.

SARS-CoV-2 encodes more than ten viral interferon antagonists for the inhibition of interferon signaling during early infection (see, e.g., Med Microbiol Immunol 2022 1-7; Emerg Microbes Infect. 2020 9:1418-1428, hereby both incorporated by reference in their entirety). The functional redundance of different antagonists suggests the importance of suppressing interferon signaling for successful infection. This is also supported by the evident that infection of SARS-CoV-2, as well as SARS-CoV-1, in ex vivo human lung tissues did not induce production of endogenous interferons (see, e.g., Clin Infect Dis 2020 71:1400-1409, hereby incorporated by reference in its entirety). In addition, early studies of SARS-CoV-1 have demonstrated that delayed type-I interferon is one of the key features contributing to viral pathogenesis in mouse models (see, e.g., Cell Host Microbe 2016 19:181-193, hereby incorporated by reference in its entirety), while blockade of interferon signaling impairs MERS-CoV-specific T cell responses and delays viral clearance (see, e.g., J Clin Invest. 2019 129:3625-3639, hereby incorporated by reference in its entirety).

In some embodiments, the IFNβ nucleic acid comprises the nucleic acid sequence of SEQ ID NO: 10 or 11. In some embodiments, the human IFNβ nucleic acid comprises the nucleic acid sequence of SEQ ID NO: 10. In some embodiments, the mouse IFNβ nucleic acid comprises the nucleic acid sequence of SEQ ID NO: 11. In some embodiments, the production of integrated IFNβ depends on the sarbecovirus Transcriptional Regulatory Sequence (TRS).

III. Host Cells for Production of Recombinant Sarbecoviruses

Also provided herein are host cells for packaging and producing the recombinant sarbecoviruses described herein.

Suitable host cells can include, without limitation, higher eukaryotic cells such as mammalian cells. Suitable higher eukaryotic cells include, without limitation, invertebrate cells and insect cells, and vertebrate cells. In some embodiments, the present application provides methods of making the host cell, wherein the host cell is modified using standard genome or RNA editing techniques including, but not limited to, CRISPR/Cas (e.g., paired with homologous recombination-mediated repair), Bacterial Artificial Chromosome (BAC) recombineering, viral transduction, TALENS, zinc finger nuclease system (ZFN), or LEAPER (leveraging endogenous ADAR for programmable editing of RNA leveraging endogenous ADAR for programmable editing of RNA; see, e.g., Qu et al., *Nat Biotechnol.* 2019 September; 37(9):1059-1069, the content of which is incorporated herein by reference in its entirety), to generate host cells that express engineered sarbecovirus envelope protein and are deficient in IFN signaling. Standard methods for genome editing of host cells for expression of a viral envelope protein and deletion of STAT1 or other modulators of IFN signaling are well known in the art.

The host cell can be transfected as part of the standard methods of genome editing using any suitable methods known in the art, including, but not limited to, DEAE-dextran mediated delivery, calcium phosphate precipitate method, cationic lipids mediated delivery, liposome mediated transfection, electroporation, lentiviral transduction, microprojectile bombardment, receptor-mediated gene delivery, delivery mediated by polylysine, histone, chitosan, and peptides. Standard methods for transfection and transformation of cells for expression of a vector of interest are well known in the art.

In some embodiments, the host cell is deficient in IFN signaling. In some embodiments, the host cell comprises a mutation (such as a deletion) in a gene (e.g., host cell DNA gene) selected from the group consisting of STAT1, IRF9, STAT2, IFNAR1, IFNAR2, and type I and III interferons, which expresses no corresponding protein or renders the encoded protein non-functional. In some embodiments, the host cell is knocked out for any of IRF9, STAT2, IFNAR1, IFNAR2, and type I and III interferons. In some embodiments, the host cell is knocked out for STAT1. In some embodiments, the host cell is knocked out for STAT1 using the CRISPR/Cas genome editing technique. In some embodiments, the host cell is knocked out for STAT1 using CRISPR/Cas9.

"CRISPR" or "CRISPR gene editing" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas, which can be used to silence, knock out, or mutate a target gene. The CRISPR system further comprises Cas proteins, including but not limited to, Cas9, Cas3, Csn2, Cas4, Cas12, Cas12a (Cpfl), Cas12b (C2c1), Cas12c (C2c3), Cas12d (CasY), Cas12e (CasX), Cas12f, Cas12 g, Cas12h, Cas12i, Cas12k (C2c5), Cas13, Cas13a (C2c2), Cas13b, Cas13c, and Cas13d.

The CRISPR/Cas system is based on two elements. The first element is an endonuclease, or Cas, (e.g., Cas9 and MAD7) that has a binding site for the second element, which is the guide polynucleotide (e.g., guide RNA or gRNA). The guide polynucleotide (e.g., guide RNA) directs the Cas protein to double stranded DNA templates based on sequence homology. The Cas protein then cleaves that DNA template. By delivering the Cas protein and appropriate guide polynucleotides (e.g., guide RNAs) into a cell, the organism's genome is cut at a desired location. Following cleavage of a targeted genomic sequence by a Cas/gRNA complex, one of two alternative DNA repair mechanisms can restore chromosomal integrity: 1) non-homologous end joining (NHEJ), which generates insertions and/or deletions of a few base-pairs (bp) of DNA at the gRNA cut site, or 2) homology-directed repair (HDR), which can correct the lesion via an additional "bridging" DNA template that spans the gRNA cut site. CRISPR/Cas systems are classified by class and by type. Class 2 systems currently represent a single interference protein that is categorized into three distinct types (types II, V, and VI). Any class 2 CRISPR/Cas system suitable for gene editing, for example a type II, a type V, or a type VI system, is envisaged as within the scope of the instant disclosure. Exemplary Class 2 type II CRISPR systems include Cas9, Csn2, and Cas4. Exemplary Class 2, type V CRISPR systems include Cas12, Cas12a (Cpfl), Cas12b (C2c1), Cas12c (C2c3), Cas12d (CasY), Cas12e (CasX), Cas12f, Cas12 g, Cas12h, Cas12i, and Cas12k (C2c5). Exemplary Class 2 Type VI systems include Cas13, Cas13a (C2c2), Cas13b, Cas13c, and Cas13d.

The CRISPR sequence, sometimes called a CRISPR locus, comprises alternating repeats and spacers. In a naturally-occurring CRISPR, the spacers usually comprise sequences foreign to the bacterium such as a plasmid or phage sequence. As described herein, spacer sequences may also be referred to as "targeting sequences." In CRISPR/Cas systems for genetic engineering, the spacers are derived from the target gene sequence (the gRNA).

The targeting sequence can be designed or chosen using computer programs known to persons of ordinary skill in the art. The computer program can use variables, such as predicted melting temperature, secondary structure formation, predicted annealing temperature, sequence identity, genomic context, chromatin accessibility, % GC content, frequency of genomic occurrence (e.g., of sequences that are identical or are similar but vary in one or more spots as a result of mismatch, insertion, or deletion), methylation status, presence of single nucleotide polymorphisms (SNPs), and the like. Available computer programs can take as input NCBI gene IDs, official gene symbols, Ensembl Gene IDs, genomic coordinates, or DNA sequences, and create an output file containing sgRNAs targeting the appropriate genomic regions designated as input. The computer program may also provide a summary of statistics and scores indicating on- and off-target binding of the sgRNA for the target gene (Doench et al. (2016) Nat Biotechnol. 34: 184-191, hereby incorporated by reference in its entirety).

The target sequence is complementary to, and hybridizes with, the targeting sequence of the gRNA. The target nucleic acid sequence can comprise 20 nucleotides. The target nucleic acid can comprise less than 20 nucleotides. The target nucleic acid can comprise more than 20 nucleotides. The target nucleic acid can comprise at least about any of: 5, 10, 15, 16, 17, 18, 19, 20, 21, 22, 23, 24, 25, 30 or more nucleotides. The target nucleic acid can comprise at most about any of: 5, 10, 15, 16, 17, 18, 19, 20, 21, 22, 23, 24, 25, 30 or more nucleotides.

The CRISPR/Cas system can thus be used to edit a target gene, such as a gene targeted for editing in the cells described herein, by adding or deleting a base pair, introducing a premature stop codon, or introducing a frame-shift mutation which thus decreases expression of the target, in part or completely. The CRISPR/Cas system can alternatively be used like RNA interference, turning off a target gene in a reversible fashion. In a mammalian cell, for example, the RNA can guide the Cas protein to a target gene promoter, sterically blocking RNA polymerases. Further aspects of the CRISPR/Cas system known to those of ordinary skill are described in PCT Publication Nos. WO 2017/049266 and WO 2017/223538, the entire contents of which are hereby incorporated by reference.

Defective interferon signaling can also be accomplished, for example, by inhibiting the expression of any proteins involved in the interferon signaling pathway, which include, for example, STAT1, IRF9, STAT2, IFNAR1, IFNAR2, and type I interferon, type II interferon, and type III interferons. Examples of technologies to prevent or inhibit protein expression include, but are not limited to, antisense oligonucleotides (ASO), short hairpin RNA (shRNA), small interfering RNA (siRNA), and microRNA (miRNA). Antisense oligonucleotides are short, synthetic, chemically modified chains of nucleotides that have the potential to target any gene product of interest. These ASOs act by binding to specific RNA molecules, which prevents protein translation from occurring for those bound RNA molecules. Short hairpin RNAs (shRNA) are short sequences of RNA that make tight hairpin turns and can be used to silence gene expression by RNA interference (RNAi), which targets the corresponding complementary RNA molecule for degradation. shRNAs can be stably integrated into a host cell via virus-mediated transduction. Small interfering RNAs are short double stranded RNAs (dsRNAs) or short duplexes of about 20-24 base pairs (bps) with two-nucleotide 3' end overhangs that are transiently expressed in cells, such as host cells, following standard transfection methods (e.g., chemical transfection, electroporation, lipid-mediated cell membrane diffusion). These siRNA molecules activate the RNAi pathway, leading to the degradation of mRNAs in a sequence-specific manner dependent upon complementary binding of the target mRNA. miRNAs are small, single-stranded RNA molecules of about 18-25 bps. Similarly to RNAi, cells, such as host cells, use miRNAs to negatively regulate gene expression by repressing protein translation or directing sequence-specific degradation of target mRNAs.

In some embodiments, the host cell (e.g., VeroE6 cell or BHK21 cell) comprises a heterologous nucleic acid encoding a viral envelope protein. To avoid integration of the heterologous nucleic acid into the viral genome, in some embodiments, the nucleic acid sequence of the heterologous nucleic acid encoding the envelope protein has less than about 80% (such as less than about any of 75%, 70%, 65%, 60%, 55%, 50%, 45%, or 40%) sequence identity to the sequence of the modified envelope gene (e.g., viral RNA gene, including an RNA sequence or a reverse-transcribed DNA sequence thereof) described herein (e.g., SEQ ID NO: 14). In some embodiments, the nucleic acid sequence of the heterologous nucleic acid encoding the envelope protein has less than about 80% (such as less than about any of 75%, 70%, 65%, 60%, 55%, 50%, 45%, 40%, 30%, 20%, 10%, or less) sequence identity to the sequence of the naturally existing viral envelope gene (e.g., SEQ ID NO: 12). In some embodiments, the heterologous nucleic acid encoding the envelope protein comprises the nucleic acid sequence of SEQ ID NO: 15. In some embodiments, the amino acid sequence translated from the heterologous nucleic acid comprises the amino acid sequence of SEQ ID NO: 16. In some embodiments, the heterologous nucleic acid encoding the envelope protein comprises at least about 30 (e.g., at least about any of 40, 50, 60, 70, 80, 90, or more) synonymous nucleotide substitutions to minimize the chance of recombination between the envelope transgene and viral genome. In some embodiments, the heterologous nucleic acid is cloned into a lentivirus vector cassette and transduced into the host cell. In some embodiments, the lentivirus vector cassette with the heterologous nucleic acid further comprises a human elongation factor-1 alpha (EF1α) promoter with the first EF1α intron, a puromycin resistance gene (PuroR) driven by an internal ribosomal entry site (IRES), and a woodchuck hepatitis virus posttranscriptional regulatory element (WPRE). In some embodiments, the expression of the heterologous nucleic acid is driven by the human EF1α promoter. In some embodiments, the expression of the heterologous nucleic acid is enhanced by the WPRE element that is located at the 3' end of the heterologous nucleic acid. In some embodiments, the transfected host cell expresses the heterologous nucleic acid. In some embodiments, the transfected host cell produces the protein translated from the heterologous nucleic acid.

Thus, in some embodiments, there is provided a host cell (e.g., VeroE6 cell or BHK21 cell) comprising a construct, wherein the construct comprises a modified genome of a sarbecovirus (such as SARS-Cov-2), wherein the modified genome comprises a modified envelope gene (e.g., viral RNA gene, including an RNA sequence or a reverse-transcribed DNA sequence thereof) and a nucleic acid encoding an interferon (such as Type I interferon, for example interferon β) integrated into the viral genome. In some embodiments, the nucleic acid encoding the interferon is inserted in the viral genome. In some embodiments, the nucleic acid encoding the interferon replaces a portion of the viral genome. In some embodiments, the modified envelope gene does not produce any functional envelope protein. In some embodiments, the modified envelope gene comprises one or more stop codons (such as at least any of 3, 4, 5, 6, 7, 8, 9, 10, or more stop codons). In some embodiments, the at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments, the nucleic acid encoding the interferon is inserted between ORF6 and ORF9b of the viral genome. In some embodiments, the nucleic acid encoding the interferon replaces a portion of the virus genome, such as ORF8. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene, (e.g., BA.2, BA.5, BA.2.75.2, BQ.1, BQ.1.1, or XBB). In some embodiments, the host cell is knocked out for STAT1.

In some embodiments, there is provided a host cell (e.g., VeroE6 cell or BHK21 cell) comprising a construct, wherein the construct comprises a modified genome of a sarbecovirus (such as SARS-CoV-2), wherein the modified genome comprises a modified envelope gene (e.g., viral RNA gene, including an RNA sequence or a reverse-transcribed DNA sequence thereof) and a nucleic acid encoding an interferon (such as Type I interferon, for example interferon β) integrated into the viral genome, and wherein the host cell is defective in interferon signaling. In some embodiments, the nucleic acid encoding the interferon is inserted in the viral genome. In some embodiments, the nucleic acid encoding the interferon replaces a portion of the viral genome. In some embodiments, the host cell is knocked out for STAT1. In some embodiments, the modified envelope gene does not produce any functional envelope protein. In some embodiments, the modified envelope gene comprises one or more stop codons (such as at least any of 3, 4, 5, 6, 7, 8, 9, 10, or more stop codons). In some embodiments, the at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments, the nucleic acid encoding the interferon is inserted between ORF6 and ORF9b of the viral genome. In some embodiments, the nucleic acid encoding the interferon replaces a portion of the virus genome, such as ORF8. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene.

In some embodiments, there is provided a host cell (e.g., VeroE6 cell or BHK21 cell) comprising a construct, wherein the construct comprises a modified genome of a sarbecovirus (such as SARS-CoV-2), wherein the modified genome comprises a modified envelope gene (e.g., viral RNA gene, including an RNA sequence or a reverse-transcribed DNA sequence thereof) and a nucleic acid encoding an interferon (such as Type I interferon, for example interferon β) integrated into the viral genome, and wherein the host cell further comprises a heterologous nucleic acid encoding a viral envelope protein. In some embodiments, the nucleic acid encoding the interferon is inserted in the viral genome. In some embodiments, the nucleic acid encoding the interferon replaces a portion of the viral genome. In some embodiments, the nucleic acid sequence of the heterologous nucleic acid encoding the envelope protein has less than about 80% (such as less than about any of 75%, 70%, 65%, 60%, 55%, 50%, 45%, 40%, 30%, 20%, 10%, or less) sequence identity to the sequence of the modified envelope gene (e.g., SEQ ID NO: 14). In some embodiments, the nucleic acid sequence of the heterologous nucleic acid encoding the envelope protein has less than about 80% sequence identity to the naturally occurring envelope gene, (e.g., SEQ ID NO: 12). In some embodiments, the modified envelope gene does not produce any functional envelope protein. In some embodiments, the modified envelope gene comprises one or more stop codons (such as at least any of 3, 4, 5, 6, 7, 8, 9, 10, or more stop codons). In some embodiments, the at least one (e.g., 2, 3, 4, 5, 6, 7, 8, 9, or 10) stop codon is present at the 5'-terminal 100 nucleotides of the modified envelope gene, for example at the 5'-terminal 10, 20, 30, 40, 50, 60, 70, 80, 90 nucleotides of the modified envelope gene. In some embodiments, the nucleic acid encoding the interferon is inserted between ORF6 and ORF9b of the viral genome. In some embodiments, the nucleic acid encoding the interferon replaces a portion of the virus genome, such as ORF8. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene. In some embodiments, the host cell is knocked out for STAT1.

In some embodiments, there is provided a host cell (e.g., VeroE6 cell or BHK21 cell) comprising a construct, wherein the construct comprises a modified genome of a sarbecovirus (such as SARS-CoV-2), wherein the modified genome comprises a modified envelope gene (e.g., viral RNA gene, including an RNA sequence or a reverse-transcribed DNA sequence thereof) and a nucleic acid encoding an interferon (such as Type I interferon, for example interferon β) integrated into the viral genome, wherein the host cell is defective in interferon signaling, and wherein the host cell further comprises a heterologous nucleic acid encoding a viral envelope protein. In some embodiments, the host cell is knocked out for STAT1. In some embodiments, the nucleic acid encoding the interferon is inserted in the viral genome. In some embodiments, the nucleic acid encoding the interferon replaces a portion of the viral genome. In some embodiments, the nucleic acid sequence of the heterologous nucleic acid encoding the envelope protein has less than about 80% (such as less than about any of 75%, 70%, 65%, 60%, 55%, 50%, 45%, 40%, 30%, 20%, 10%, or less) sequence identity to the sequence of the modified envelope gene (e.g., SEQ ID NO: 14). In some embodiments, the nucleic acid sequence of the heterologous nucleic acid encoding the envelope protein has less than about 80% (such as less than about any of 75%, 70%, 65%, 60%, 55%, 50%, 45%, 40%, 30%, 20%, 10%, or less) sequence identity to the naturally occurring envelope gene, (e.g., SEQ ID NO: 12). In some embodiments, the modified envelope gene does not produce any functional envelope protein. In some embodiments, the modified envelope gene comprises one or more stop codons (such as at least any of 3, 4, 5, 6, 7, 8, 9, 10, or more stop codons). In some embodiments, the at least one (e.g., 2, 3, 4, 5, 6, 7, 8, 9, or 10) stop codon is present at the 5'-terminal 100 nucleic acids of the modified envelope gene, for example at the 5'-terminal 10, 20, 30, 40, 50, 60, 70, 80, 90 nucleic acids of the modified envelope gene. In some embodiments, the nucleic acid encoding the interferon is inserted between ORF6 and ORF9b of the viral genome. In some embodiments, the nucleic acid encoding the interferon replaces a portion of the virus genome, such as ORF8. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene. In some embodiments, the modified envelope gene comprises the sequence of SEQ ID NO: 13. In some embodiments, the heterologous nucleic acid encoding the viral envelope protein comprises the sequence of SEQ ID NO: 15.

In some embodiments, there is provided a host cell (e.g., VeroE6 cell or BHK21 cell) comprising a construct, wherein the construct comprises a modified genome of a sarbecovirus (such as SARS-CoV-2), wherein the modified genome comprises i) a modified envelope gene (e.g., viral RNA gene, including an RNA sequence or a reverse-transcribed DNA sequence thereof) comprising the sequence of SEQ ID NO: 13, and ii) a nucleic acid encoding an interferon (such as Type I interferon, for example interferon β) integrated (e.g., inserted) into the viral genome, wherein the host cell is defective in interferon signaling, and wherein the host cell further comprises a heterologous nucleic acid (e.g., SEQ ID NO: 15) encoding a viral envelope protein. In some embodiments, the nucleic acid encoding the interferon comprises the sequence of SEQ ID NO: 10 or 11. In some embodiments, the host cell is knocked out for any of STAT1, IRF9, STAT2, IFNAR1, IFNAR2, and type I and III interferons, such as STAT1. In some embodiments, the nucleic acid encoding the interferon is inserted between ORF6 and ORF9b of the viral genome. In some embodiments, the nucleic acid encoding the interferon replaces a portion of the virus genome, such as ORF8. In some embodiments, at least a functional portion of ORF6, ORF7a, ORF7b, and/or ORF8 in the modified viral genome is deleted. In some embodiments, the modified genome comprises a wild-type spike gene. In some embodiments, the modified genome comprises a variant spike gene (e.g., BA.2, BA.5, BA.2.75.2, BQ.1, BQ.1.1, or XBB).

Any suitable host cells for viral packaging or virus production can be used here. Host cells can include but are not limited to, BHK21 cells, VeroE6 cells, L929 cells, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRCS cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, NS0 cells, PerC6 cells, Sp2/0 cells, BHK cells, C127 cells, 211 A cells, and any host cells derived from any of these cells. In some embodiments, the suitable host cell is genetically modified to delete or inactivate STAT1. In some embodiments, the suitable host cell is genetically modified to express an engineered sarbecovirus envelope protein. In some embodiments, the suitable host cell is genetically modified both to delete STAT1 and to express an engineered sarbecovirus envelope protein (e.g., SEQ ID NO: 16).

In some embodiments, the host cell is a VeroE6 cell. In some embodiments, the VeroE6 cell is genetically modified to delete or inactivate STAT1. In some embodiments, the VeroE6 cell is genetically modified to express an engineered sarbecovirus envelope protein. In some embodiments, the VeroE6 cell is genetically modified both to delete STAT1 and to express an engineered sarbecovirus envelope protein (e.g., SEQ ID NO: 16), thereby generating Vero-A9B21 cells.

In some embodiments, the host cell is a BHK21 cell. In some embodiments, the BHK21 cell is genetically modified to express an engineered sarbecovirus envelope protein (e.g., SEQ ID NO: 16), thereby generating BHK21-eE cells. In some embodiments, the BHK21 cell is further genetically modified to delete or inactivate STAT1.

IV. Methods of Preparation

The IFN-producing (e.g., IFNβ-producing) universal sarbecovirus vaccine described herein may be prepared by any of the known nucleic acid expression and virion purification methods in the art. For example, see Example 1. DNA sequences encoding the modified sarbecovirus can be fully synthesized. After obtaining such sequence, it is transfected into a suitable host cell (for example, into BHK21 cells expressing an engineered sarbecovirus envelope transgene). The transfected host cells are cultured (for example, co-cultured with Vero-A9B21 cells), and the virus is plaque-purified and further expanded in suitable host cells (for example, in Vero-A9B21 cells). Once viral titers reach a threshold level for plaque forming units (PFU; for example, $4.4\times10^7$ PFU), then the IFN-producing universal sarbecovirus of the present invention is obtained and prepared into vaccine for vaccination administration.

In some embodiments, the present application provides isolated nucleic acids encoding one or more of the constructs comprising a modified genome of a sarbecovirus described herein, the recombinant sarbecovirus described herein, or the IFN-producing (e.g., IFNβ-producing) universal sarbecovirus vaccines described herein. In some embodiments, the isolated nucleic acid comprises the nucleic acid sequence of any of SEQ ID NOs: 2-9. In some embodiments, the isolated nucleic acid for vaccinating a human individual comprises the nucleic acid sequence of any of SEQ ID NOs: 2-7. In some embodiments, the isolated nucleic acid for vaccinating a mouse or a hamster comprises the nucleic acid sequence of SEQ ID NO: 8 or 9. The isolated nucleic acids may be DNA or RNA.

In some embodiments, the recombinant sarbecovirus construct as described herein may be introduced into a host cell to allow expression of the nucleic acid within the host cell. The recombinant sarbecovirus construct may contain a variety of elements for controlling gene expression, including without limitation, promoter sequences, transcription initiation sequences, enhancer sequences, selectable markers, and signal sequences. These elements may be native to the virus or may be further selected as appropriate by a person of ordinary skill in the art. For example, the promoter sequences for the inserted IFNβ gene may be selected to promote the transcription of the polynucleotide. Suitable promoter sequences include, without limitation, T7 promoter, T3 promoter, SP6 promoter, beta-actin promoter, EF1α promoter, CMV promoter, SV40 promoter, or any Transcriptional Regulatory Sequence (TRS) of sarbecoviruses. Enhancer sequences may be selected to enhance the transcription of the nucleic acids. Selectable markers may be chosen to allow selection of the host cells inserted with the recombinant sarbecovirus or construct thereof from those not, for example, the selectable markers may be genes that confer antibiotic resistance. Signal sequences may be selected to allow the expressed IFNβ polypeptide to be transported outside of the host cell.

The recombinant sarbecovirus construct can be introduced to the host cell using any suitable methods known in the art, including, but not limited to, DEAE-dextran mediated delivery, calcium phosphate precipitate method, cationic lipids mediated delivery, liposome mediated transfection, electroporation, lentiviral transduction, microprojectile bombardment, receptor-mediated gene delivery, delivery mediated by polylysine, histone, chitosan, and peptides. Standard methods for transfection and transformation of cells for expression of a vector of interest are well known in the art.

In some embodiments, the present application provides methods of making any of the IFN-producing recombinant sarbecovirus or the IFN-producing universal sarbecovirus vaccines described herein, comprising culturing an isolated host cell comprising any of the isolated nucleic acid constructs described herein, under a condition suitable for the expression of any of the vaccines described herein, and obtaining the expressed recombinant sarbecovirus or vaccines from said host cell (e.g., from the cell culture). The isolated host cells are cultured under conditions that allow expression of the recombinant sarbecovirus nucleic acids transfected into the host cell. Suitable conditions for expression may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

V. Pharmaceutical Compositions, Unit Dosages, Articles of Manufacture, and Kits Further provided by the present application are pharmaceutical compositions comprising any one of the IFN-producing universal sarbecovirus vaccines described herein, and optionally a pharmaceutically acceptable carrier.

The pharmaceutical compositions may be suitable for a variety of modes of administration described herein, including for example systemic or localized administration. In some embodiments, the pharmaceutical composition is formulated for mucosal administration. In some embodiments, the pharmaceutical composition is formulated for administration by nasal spray. In some embodiments, the pharmaceutical composition is formulated for administration by nasal drops. In some embodiments, the pharmaceutical composition is administered parenterally, such as by intramuscular or intradermal administration. In some embodiments, the pharmaceutical composition is administered as a single dose. In some embodiments, the pharmaceutical composition is administered as multiple doses. In some embodiments, the individual (such as a human) is 65 years of age or older, for example any of 65, 70, 75, 80, 85, 86, 87, 88, 89, 90 years or older. In some embodiments, the individual (such as a human) has a medical condition, a pre-existing condition, or a condition that reduces heart, lung, brain, or immune system function. In some embodiments, the individual (such as a human) is immunocompromised.

Micro- and nanocarrier-based delivery systems as nasal vaccines induce humoral, cellular, and mucosal immunity. The nasal route of vaccination could also offer immunity at several distant mucosal sites (e.g., oral, rectal, vaginal, and pulmonary). Nasal vaccine delivery blocks pathogen entry at the mucosal site by inducing local immunity, displays increased bioavailability to other administration routes, demonstrates swift uptake to the blood circulatory system via mucosal absorption, and encourages better patient compliance that other administration routes, e.g., parenteral (see, e.g., Ramvikas et al. (2016) Micro and Nanotechnology in Vaccine Development 2017: 279-301, hereby incorporated by reference in its entirety). Nasal vaccine delivery formulations can include, but are not limited to, form of microparticulates, nanoparticulates, and liposomes. Therefore, in some embodiments, the pharmaceutical composition is formulated for mucosal administration. In some embodiments, the pharmaceutical composition is formulated for administration by nasal spray or nasal drops. In some embodiments, the pharmaceutical composition is administered as a single dose. In some embodiments, the pharmaceutical composition is administered as multiple doses. In some embodiments, the individual (such as a human) is 65 years of age or older, for example any of 65, 70, 75, 80, 85, 86, 87, 88, 89, 90 years or older. In some embodiments, the individual (such as a human) has a medical condition, a pre-existing condition, or a condition that reduces heart, lung, brain, or immune system function. In some embodiments, the individual (such as a human) is immunocompromised.

In some cases, a subject method involves administering to an individual in need thereof an effective amount of a recombinant sarbecovirus vaccine or construct (or pharmaceutical composition thereof). In some embodiments, an "effective amount" of a subject vaccine is an amount that, when administered to an individual in one or more doses, in monotherapy or in combination therapy, is effective to prevent sarbecovirus infection or transmission or to reduce symptoms of a sarbecovirus infection in the individual by at least about 10%, at least about 20%, at least about 25%, at least about 30%, at least about 40%, at least about 50%, at least about 60%, at least about 70%, at least about 80%, at least about 2-fold, at least about 2.5-fold, at least about 3-fold, at least about 5-fold, at least about 10-fold, or greater than 10-fold, compared to the individual in the absence of treatment with the vaccine.

"Carriers" as used herein include pharmaceutically acceptable carriers, excipients, or stabilizers which are nontoxic to the cell or individual being exposed thereto at the dosages and concentrations employed. Often the physiologically acceptable carrier is an aqueous pH buffered solution. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition is formulated to have a pH in the range of about 4.5 to about 6.5. In some embodiments, the pharmaceutical composition can also be made to be isotonic with blood by the addition of a suitable tonicity modifier.

The pharmaceutical compositions to be used for in vivo administration are generally formulated as sterile, substantially isotonic, and in full compliance with all Good Manufacturing Practice (GMP) regulations of the U.S. Food and Drug Administration. Sterility is readily accomplished by filtration through sterile filtration membranes. In some embodiments, the composition is free of pathogens. For parenteral administration, the pharmaceutical composition can be in the form of liquid solutions, for example in physiologically compatible buffers such as Hank's solution or Ringer's solution. In addition, the pharmaceutical composition can be in a solid form and re-dissolved or suspended, e.g., in water, immediately prior to use. Lyophilized compositions are also included. Injectable solutions and suspensions can be prepared from sterile powders, granules, and tablets, as described herein.

An aerosol formulation suitable for administration via inhalation also can be made. The aerosol formulation can be placed into a pressurized acceptable propellant, such as dichlorodifluoromethane, propane, nitrogen, and the like.

In some embodiments, the pharmaceutical composition is formulated in accordance with routine procedures as a pharmaceutical composition adapted for mucosal administration, in particular for intranasal administration. In some embodiments, the pharmaceutical composition is formulated in accordance with routine procedures as a pharmaceutical composition adapted for parenteral administration, such as for intramuscular or intradermal administration.

In some embodiments, the pharmaceutical composition is formulated in accordance with routine procedures as a pharmaceutical composition adapted for injection intravenously, intraperitoneally, subcutaneously, intramuscularly, or intravitreally. In some embodiments, a subject delivery system comprises a device for delivery to nasal passages or lungs. For example, the compositions described herein can be formulated for delivery by a nebulizer, an inhaler device, or the like.

In some embodiments, the pharmaceutical composition is formulated in accordance with routine procedures as a pharmaceutical composition adapted for mucosal administration, such as intranasal administration. Intranasal administration can be achieved via nasal powders, nasal drops, nasal aerosols, nasal gels, etc. In some embodiments, the pharmaceutical composition is formulated in accordance with routine procedures as a pharmaceutical composition adapted for injection intravenously, intraperitoneally, subcutaneously, intramuscularly, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered, it can be reconstituted as needed accordingly.

In some embodiments, the pharmaceutical composition is suitable for administration to a human. In some embodiments, the pharmaceutical composition is suitable for administration to a rodent (e.g., mice, rats) or non-human primates (e.g., Cynomolgus monkey). In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

Also provided are unit dosage forms of any of the vaccines described herein, or compositions (such as pharmaceutical compositions) thereof. For example, in some embodiments, the sarbecovirus vaccine is administered at a dose of about $10^5$ PFU to about $10^{10}$ PFU. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

The present application further provides articles of manufacture comprising the compositions (such as pharmaceutical compositions) described herein in suitable packaging. Suitable packaging for compositions (such as pharmaceutical compositions) described herein are known in the art, and include, for example, vials (such as sealed vials), nasal spray or nasal drop bottles, vessels, ampules, bottles, jars, flexible packaging (e.g., sealed Mylar or plastic bags), and the like. These articles of manufacture may further be sterilized and/or sealed.

The present application also provides kits comprising compositions (such as pharmaceutical compositions) described herein and may further comprise instruction(s) on methods of using the composition, such as uses described herein. The kits described herein may further include other materials desirable from a commercial and user standpoint, including other buffers, diluents, filters, spray bottles, nebulizers, inhaler devices, needles, syringes, and package inserts with instructions for performing any methods described herein.

VI. Methods of Vaccinating

One aspect of the present application provides a method of vaccinating against a viral infection (e.g., sarbecovirus infection, such as SARS-CoV-2 infection) in an individual (such as a human), comprising administering to the individual an effective amount of any of the IFN-producing universal sarbecovirus vaccines described herein, or a composition (such as pharmaceutical composition) thereof. In some embodiments, the method of vaccinating an individual comprises a method of prophylactically immunizing an individual. In some embodiments, the method of vaccinating an individual comprises a method of preventing an individual from contracting a sarbecovirus infection. In some embodiments, the method of vaccinating an individual comprises a method of preventing sarbecovirus transmission from a vaccinated individual to an unvaccinated individual. In some embodiments, the method of vaccinating an individual comprises a method of reducing the severity of a sarbecovirus infection in an individual. In some embodiments, the method of vaccinating an individual further comprises a method of treating an individual having a sarbecovirus infection. In some embodiments, the method of vaccinating an individual comprises a method of eliciting an immune response in an individual. In some embodiments, the method of vaccinating an individual comprises a method of enhancing the T cell response in an individual. In some embodiments, the method of eliciting an immune response, such as enhancing the T cell response, in an individual further comprises a method of activating CD4+ T cells. In some embodiments, the method of vaccination comprises administering the sarbecovirus vaccine described herein wherein the vaccine further provides heterosubtypic protection against different sarbecovirus species. In some embodiments, the individual is a mammal, for example, a human, bovine, horse, feline, canine, rodent, or primate. In some embodiments, the individual is a human. In some embodiments, the individual is at risk of contracting or has contracted a sarbecovirus infection. In some embodiments, the individual is at elevated risk of mortality upon contraction of a sarbecovirus infection. In some embodiments, the individual (such as a human) is 65 years of age or older, for example any of 65, 70, 75, 80, 85, 86, 87, 88, 89, 90 years or older. In some embodiments, the individual (such as a human) has a medical condition, a pre-existing condition, or a condition that reduces heart, lung, brain, or immune system function. In some embodiments, the individual (such as a human) is immunocompromised. In some embodiments, the individual has a compromised adaptive immune system and/or a compromised innate immune system. In some embodiments, the individual has a weakened immune system. In some embodiments, the individual has a weakened adaptive immune system and/or a weakened innate immune system. In some embodiments, the individual is administered one or more courses of immunosuppresants. In some embodiments, the individual had been administered one or more courses of immunosuppresants.

In some embodiments, symptoms of a sarbecovirus infection, e.g., a SARS-CoV-2 infection, include any one of fever, cough, sore throat, nasal congestion, malaise, headache, muscle pain, malaise, shortness of breath, mild pneumonia, severe pneumonia, acute pneumonia, sepsis, septic shock, or any combination thereof. Signs of infection include altered mental status, difficult or fast breathing, low oxygen saturation, reduced urine output, fast heart rate, weak pulse, cold extremities or low blood pressure, skin mottling, or laboratory evidence of coagulopathy, thrombocytopenia, acidosis, high lactate, or hyperbilirubinemia. In some embodiments, sarbecovirus infection, e.g., SARS-CoV-2 infection, significantly elevates levels of inflammatory cytokines in an infected individual. In some embodiments, elevated levels of inflammatory cytokines, i.e., cytokine storm, triggers excessive, uncontrolled systemic inflammation. In some instances, uncontrolled systemic inflammation leads to pneumonitis, respiratory failure, shock, organ failure, secondary bacterial pneumonia, and potentially death in an individual infected with a sarbecovirus.

In some embodiments, the severity of a sarbecovirus infection in an individual is reduced following vaccination with any one of the IFN-producing universal sarbecovirus vaccines described herein. In some embodiments, an immune response in an individual is elicited following vaccination with any one of the IFN-producing universal sarbecovirus vaccines described herein. In some embodiments the elicited immune response comprises a T cell response, such as T cell activation, in an individual. In some embodiments, the enhanced the T cell response in an individual further comprises a method of activating CD4+ T cells. In some embodiments, progression of a sarbecovirus infection in an individual is delayed by vaccination with any one of the IFN-producing universal sarbecovirus vaccines described herein. In some embodiments, mortality caused by infection with a sarbecovirus infection in an individual is prevented by vaccination with any one of the IFN-producing universal sarbecovirus vaccines described herein. In some embodiments, an individual vaccinated with any one of the IFN-producing universal sarbecovirus vaccines described herein who becomes or already is infected with a sarbecovirus infection is prevented from transmitting the sarbecovirus infection to an unvaccinated individual.

Efficacy of the treatments described herein can be evaluated, for example, by measuring viral load (e.g., via detection of viral DNA), duration of individual's survival, quality of life, viral protein expression and/or activity, detection of serological antibodies against the coronavirus, assessment of respiratory functions, and/or Computerized Tomography (CT) imaging.

Efficacy of the IFN-producing universal sarbecovirus vaccine can be evaluated, for example, by levels of neutralizing antibodies against one or more proteins of the sarbecovirus (such as SARS-CoV-2) in serum or other bodily fluid (such as but not limited to bronchoalveolar lavage fluids), or by the neutralizing activity of serum or other bodily fluid against one or more strains of the sarbecovirus (such as SARS-CoV-2).

In some embodiments, wherein the method comprises administrating to the individual an effective amount of any one of the IFN-producing universal sarbecovirus vaccines described herein, the individual displays increased neutralizing antibody level in serum against SARS-CoV-2 spike RBD (receptor binding domain of spike protein) as compared to before administration of the IFN-producing universal sarbecovirus vaccine. In some embodiments, the individual displays increased neutralizing antibody level in serum against a SARS-CoV-2 variant spike RBD as compared to before administration of the IFN-producing universal sarbecovirus vaccine. In some embodiments according to any one of the methods described herein, the individual displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to before administration of the IFN-producing universal sarbecovirus vaccine. In some embodiments, the neutralizing antibody level is determined at about any one of 1, 7, 14, 21, 30, 45, 60, 90, 120, 180, 240, 360, 480, or 720 days after administration of the IFN-producing universal sarbecovirus vaccine.

In some embodiments, wherein the method comprises administrating to the mucosa of the individual an effective amount of any one of the IFN-producing universal sarbecovirus vaccines described herein, the individual displays increased mucosal immunity against SARS-CoV-2 as compared to before administration of the chimeric protein. In some embodiments, the individual displays induction of lung resident memory B cells subsequent to administration of the IFN-producing universal sarbecovirus vaccine. In some embodiments, the individual displays induction of follicular helper T cells subsequent to administration of the IFN-producing universal sarbecovirus vaccine. In some embodiments, the individual displays increased neutralizing antibody level in bronchoalveolar lavage (BAL) fluids against SARS-CoV-2 as compared to before administration of the IFN-producing universal sarbecovirus vaccine. In some embodiments, the individual displays increased neutralizing antibody level in BAL fluids against a SARS- CoV-2 variant spike RBD as compared to before administration of the IFN-producing universal sarbecovirus vaccine. In some embodiments, the neutralizing antibody comprises IgA. In some embodiments according to any one of the methods described herein, the individual displays an increase in the neutralizing antibody level by about any one of 10%, 20%, 50%, 75%, 100%, 2-fold, 5-fold, 10-fold, 25-fold, 50-fold, 100-fold, 500-fold, or 1000-fold or more, as compared to before administration of the IFN-producing universal sarbecovirus vaccine. In some embodiments, the neutralizing antibody level is determined at about any one of 1, 7, 14, 21, 30, 45, 60, 90, 120, 180, 240, 360, 480, or 720 days after administration of the IFN-producing universal sarbecovirus vaccine.

In some embodiments, wherein the method comprises administrating to the individual an effective amount of any one of the IFN-producing universal sarbecovirus vaccine described herein, the individual displays increased neutralizing activity in serum against SARS-CoV-2 as compared to before administration of the IFN-producing universal sarbecovirus vaccine. In some embodiments, the individual displays increased neutralizing activity in serum against a SARS-CoV-2 variant as compared to before administration of the IFN-producing universal sarbecovirus vaccine. In some embodiments, the neutralizing activity is quantitatively determined by focus reduction neutralization assay against the virus strain. In some embodiments according to any one of the methods described herein, the individual displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to before administration of the IFN-producing universal sarbecovirus vaccine. In some embodiments, the neutralizing activity is determined at about any one of 1, 7, 14, 21, 30, 45, 60, 90, 120, 180, 240, 360, 480, or 720 days after administration of the IFN-producing universal sarbecovirus vaccine.

In some embodiments, wherein the method comprises administrating to the mucosa of the individual an effective amount of any one of the IFN-producing universal sarbecovirus vaccine described herein, the individual displays increased mucosal immunity against SARS-CoV-2 as compared to before administration of the chimeric protein. In some embodiments, the individual displays increased neutralizing activity in bronchoalveolar lavage fluids (BAL) fluids against SARS-CoV-2 as compared to before administration of the IFN-producing universal sarbecovirus vaccine. In some embodiments, the individual displays increased neutralizing activity in BAL fluids against a SARS-CoV-2 variant as compared to before administration of the IFN-producing universal sarbecovirus vaccine. In some embodiments, the neutralizing activity is quantitatively determined by focus reduction neutralization assay against the authentic live virus. In some embodiments according to any one of the methods described herein, the individual displays an increase in the neutralizing activity by about any one of 10%, 20%, 50%, 75%, 100%, 2-fold, 5-fold, 10-fold, 25-fold, 50-fold, 100-fold, 500-fold, or 1000-fold or more, as compared to before administration of the IFN-producing universal sarbecovirus vaccine. In some embodiments, the neutralizing activity is determined at about any one of 1, 7, 14, 21, 30, 45, 60, 90, 120, 180, 240, 360, 480, or 720 days after administration of the IFN-producing universal sarbecovirus vaccine.

In some embodiments, there is provided a method of vaccinating against a viral infection (e.g., sarbecovirus infection, such as SARS-CoV-2 infection) in an individual (such as a human), comprising administering to the individual an effective amount of the IFN-producing universal sarbecovirus vaccine (or a pharmaceutical composition thereof), wherein the sarbecovirus vaccine or pharmaceutical composition thereof is administered at a dose of about $10^5$ PFU to about $10^{10}$ PFU. For example, in some embodiments, the sarbecovirus vaccine or pharmaceutical composition thereof is administered at a dose of any of about $10^5$ PFU to about $10^6$ PFU, about $10^5$ PFU to about $10^7$ PFU, about $10^5$ PFU to about $10^8$ PFU, about $10^5$ PFU to about $10^9$ PFU, about $10^5$ PFU to about $10^{10}$ PFU, about $10^6$ PFU to about $10^7$ PFU, about $10^6$ PFU to about $10^8$ PFU, about $10^6$ PFU to about $10^9$ PFU, about $10^6$ PFU to about $10^{10}$ PFU, about $10^7$ PFU to about $10^8$ PFU, about $10^7$ PFU to about $10^9$ PFU, about $10^7$ PFU to about $10^{10}$ PFU, about $10^8$ PFU to about $10^9$ PFU, about $10^8$ PFU to about $10^{10}$ PFU, or about $10^9$ PFU to about $10^{10}$ PFU. The doses described herein may refer to a suitable dose for mice, a human equivalent dose thereof, a human dose, or an equivalent dose for the specific species of the individual.

In some embodiments, the sarbecovirus vaccine or the composition (such as pharmaceutical composition) thereof is administered intranasally. In some embodiments, the sarbecovirus vaccine or the composition (such as pharmaceutical composition) thereof is administered parenterally, such as by intramuscular or intradermal administration. In some embodiments, the sarbecovirus vaccine or the composition (such as pharmaceutical composition) thereof is administered once. In some embodiments, the sarbecovirus vaccine or the composition (such as pharmaceutical composition) thereof is administered more than once, for example with an interval of about 2 weeks to about 1 year. In some embodiments, the sarbecovirus vaccine or the composition (such as pharmaceutical composition) thereof is administered with an interval of about any of every 2 weeks, 3 weeks, 4 weeks, 5 weeks, 6 weeks, 7 weeks, 8 weeks, 1 month, 2 months, 3 months, 4 months, 5 months, 6 months, 7 months, 8 months, 9 months, 10 months, 11 months, 12 months, 13 months, 14 months, 15 months, 16 months, or 1 year.

In some embodiments, the method is used to vaccinate an individual (such as human) who has previously been vaccinated. Any of the methods of vaccination provided herein may be used to vaccinate an individual (such as a human) who has not previously been vaccinated. In some embodiments, the method is used to prophylactically immunize an individual (such as a human). In some embodiments, the method is used to prevent sarbecovirus transmission from a vaccinated individual (such as a human) to an unvaccinated individual. In some embodiments, the method is used to treat a sarbecovirus infection in an individual (such as a human). In some embodiments, the method further ameliorates or reduces the infection and associated symptoms in an infected individual (such as a human). In some embodiments, the method is used to elicit an immune response (such as activation of lymphocytes, such as B cells or T cells, including CD4+ T cells and/or CD8+ T cells; and myeloid cells, including but not limited to monocytes, macrophages, neutrophils, granulocytes, mast cells, dendritic cells, and/or eosinophils) in an individual (such as a human). In some embodiments, the method is used as a prophylactic vaccine. In some embodiments, the method is used to enhance T cell response in an individual (such as a human). In some embodiments, the method is used as a first- or second-line therapy to ameliorate or otherwise reduce the sarbecovirus infection and associated symptoms thereof. In some embodiments, the individual (such as a human) is 65 years of age or older, for example any of 65, 70, 75, 80, 85, 86, 87, 88, 89, 90 years or older. In some embodiments, the individual (such as a human) has a medical condition, a pre-existing condition, or a condition that reduces heart, lung, brain, or immune system function. In some embodiments, the individual (such as a human) is immunocompromised.

The methods described herein are suitable for vaccinating against a variety of sarbecoviruses, and/or treating a disease associated with a variety of sarbecoviruses. The methods are applicable to all sarbecoviruses, including SARS-CoV/SARS-CoV-1, SARS-CoV-2, SC2r-CoV, SC2r-CoV GX-PSL, Bat CoV BtKY72, Bat CoV BM48-31, 16BO133, JTMC15, Bat SARS CoV Rf1, BtCoV HKU3, LYRa11, Bat SARS-CoV/Rp3, Bat SL-CoV YNLF_31C, Bat SL-CoV YNLF_34C, SHC014-CoV, WIV1, WIV16, Civet SARS-CoV, (Bat) Rc-o319, Bat SL-ZXC21, Bat SL-ZC45, Pangolin SARSr-CoV-GX, Pangolin SARSr-CoV-GD, Rs7327, Rs4231, Rs4084, Rf4092, JL2012, 273-2005, HeB2013, HuB2013, Rs4247, Longquan-140, HKU3-1, GX2013, Shaanxi2011, 279-2005, As6526, Yunnan2011, Rs4237, Rs4081, Bat RshSTT182, Bat RshSTT200, (Bat) RacCS203, (Bat) RmYN02, (Bat) RpYN06, YN2013, (Bat) RaTG13, (Bat) BANAL-52, and SARS-CoV combined variants of concern (VOC) (for example, see Nature (2022) 603:913-918, hereby incorporated by reference in its entirety). In one aspect, there is provided a recombinant sarbecovirus comprising the construct described herein. In one aspect is described a sarbecovirus vaccine comprising the recombinant sarbecovirus. In some embodiments, the sarbecovirus is selected from the group consisting of SARS-CoV, SARS-CoV-2, SARS-CoV-2 B.1.1.7, SARS-CoV-2 B.1.351, SARS-CoV-2 B1.617.2, SAR-CoV-2 B.1.1.529, SC2r-CoV, RaTG13, SC2r-CoV GX-PSL, and SARS-CoV combined variants of concern (VOC). In some embodiments, the sarbecovirus is SARS-CoV-2.

The methods described herein may be used as a vaccination, a viral transmission preventative, or a treatment to reduce disease, wherein the treatment may act as a first therapy, second therapy, third therapy, or combination therapy with other types of anti-viral therapies known in the art, such as therapeutic agents selected from the group consisting of a corticosteroid, an anti-inflammatory signal transduction modulator, a β2-adrenoreceptor agonist bronchodilator, an anticholinergic, a mucolytic agent, an antiviral agent, an anti-fibrotic agent, hypertonic saline, an antibody, a vaccine, and mixtures thereof or the like, in an adjuvant setting or a neoadjuvant setting. For example, the antiviral agent can be further selected from the group consisting of remdesivir, lopinavir/ritonavir, IFN-α, lopinavir, ritonavir, penciclovir, galidesivir, disulfiram, darunavir, cobicistat, ASC09F, disulfiram, nafamostat, griffithsin, alisporivir, chloroquine, nitazoxanide, baloxavir marboxil, oseltamivir, zanamivir, peramivir, amantadine, rimantadine, favipiravir, laninamivir, ribavirin, umifenovir, and any combinations thereof. In one aspect, there is provided a method of vaccinating an individual against a sarbecovirus, comprising administering a sarbecovirus vaccine to the individual. In some embodiments, the method of vaccinating an individual comprises a method of prophylactically immunizing an individual. In some embodiments, the method of vaccinating an individual comprises a method of preventing an individual from contracting a sarbecovirus infection. In some embodiments, the method of vaccinating an individual comprises a method of preventing transmission of a sarbecovirus from a vaccinated individual to an unvaccinated individual. In some embodiments, the method of vaccinating an individual comprises a method of reducing the severity of a sarbecovirus infection in an individual. In some embodiments, the method of vaccinating an individual further comprises a method of treating an individual having a sarbecovirus infection. In some embodiments, the method of vaccinating an individual comprises a method of eliciting an immune response in an individual. In some embodiments, the method of vaccinating an individual comprises a method of enhancing the T cell response in an individual. In some embodiments, the method of eliciting an immune response, such as enhancing the T cell response, in an individual further comprises a method of activating CD4+ T cells. In some embodiments, the method of vaccination comprises administering the sarbecovirus vaccine described herein wherein the vaccine further provides heterosubtypic protection against different sarbecovirus species. In some embodiments, the individual (such as a human) is 65 years of age or older, for example any of 65, 70, 75, 80, 85, 86, 87, 88, 89, 90 years or older. In some embodiments, the individual (such as a human) has a medical condition, a pre-existing condition, or a condition that reduces heart, lung, brain, or immune system function. In some embodiments, the individual (such as a human) is immunocompromised.

Exemplary routes of administration of any of the IFN-producing universal sarbecovirus vaccines described herein (or pharmaceutical composition thereof) include, but are not limited to, oral, intravenous, intracavitary, intratumoral, intraarterial, intramuscular, subcutaneous, parenteral, transmucosal, transdermal, ocular, topical, intraperitoneal, intracranial, intrapleural, and epidermal routes, or be delivered into lymph glands, body spaces, organs or tissues known to be virally infected cells. In some embodiments, the sarbecovirus vaccine (or pharmaceutical composition thereof) is administered mucosally, such as by nasal spray or nasal drops. In some embodiments, the sarbecovirus vaccine (or pharmaceutical composition thereof) is administered parenterally, such as by intramuscular or intradermal administration. In some embodiments, the sarbecovirus vaccine or pharmaceutical composition thereof is administered intranasally.

The dosing regimen of the vaccine (or pharmaceutical composition thereof) administered to the individual (such as human) may vary with the particular vaccine composition, the method of administration, and the particular type and stage of viral infection being treated. In some embodiments, that effective amount of the vaccine is below the level that induces a toxicological effect (i.e., an effect above a clinically acceptable level of toxicity) or is at a level where a potential side effect can be controlled or tolerated when the composition is administered to the individual.

EXEMPLARY EMBODIMENTS

Embodiment 1: A construct comprising a modified genome of a sarbecovirus, wherein the modified genome comprises a modified envelope gene and a nucleic acid encoding an interferon integrated into the genome.

Embodiment 2: The construct of embodiment 1, wherein the nucleic acid encoding an interferon is inserted into the viral genome.

Embodiment 3: The construct of embodiment 1, wherein the nucleic acid encoding an interferon replaces ORF8.

Embodiment 4: The construct of embodiment 1, wherein the modified envelope gene comprises one or more stop codons.

Embodiment 5: The construct of embodiment 4, wherein the modified envelope gene comprising at least three stop codons.

Embodiment 6: The construct of embodiment 4 or 5, wherein at least one stop codon is present at the 5'-terminal 100 nucleic acids of the modified envelope gene.

Embodiment 7: The construct of any one of embodiments 1-6, wherein at least a functional portion of ORF6, ORF7a, ORF7b, and/or ORF8 in the modified genome is deleted and/or inactivated by introducing stop codon.

Embodiment 8: The construct of any one of embodiments 1-7, wherein the sarbecovirus is selected from the group consisting of SARS-CoV, SARS-CoV-2, SARS-CoV-2 B.1.1.7, SARS-CoV-2 B.1.351, SARS-CoV-2 B1.617.2, SAR-CoV-2 B.1.1.529, SC2r-CoV, RaTG13, SC2r-CoV GX-PSL, and SARS-CoV combined variants of concern (VOC).

Embodiment 9: The construct of embodiment 8, wherein the sarbecovirus is SARS-CoV-2.

Embodiment 10: The construct of embodiment 9, wherein the modified genome comprises a wild-type spike gene.

Embodiment 11: The construct of embodiment 9, wherein the modified genome comprises a variant spike gene.

Embodiment 12: The construct of embodiment 11, wherein the variant spike gene is BA.2, BA.5, BA.2.75.2, BQ.1, BQ.1.1, or XBB.

Embodiment 13: The construct of any one of embodiments 1-12, wherein the interferon is type I interferon.

Embodiment 14: The construct of embodiment 13, wherein the interferon is interferon β.

Embodiment 15: A recombinant sarbecovirus comprising the construct of any one of embodiments 1-14.

Embodiment 16: A sarbecovirus vaccine comprising the recombinant sarbecovirus of embodiment 15.

Embodiment 17: The sarbecovirus vaccine of embodiment 16, wherein the sarbecovirus vaccine is formulated for mucosal administration.

Embodiment 18: The sarbecovirus vaccine of embodiment 16, wherein the sarbecovirus vaccine is formulated as a nasal spray.

Embodiment 19: The sarbecovirus vaccine of embodiment 16, wherein the sarbecovirus vaccine is formulated for parenteral administration.

Embodiment 20: The sarbecovirus vaccine of embodiment 19, wherein the sarbecovirus vaccine is formulated for intradermal or intramuscular administration.

Embodiment 21: A host cell for producing the recombinant sarbecovirus, comprising the construct of any one of embodiments 1-14.

Embodiment 22: The host cell of embodiment 21, wherein the host cell is defective in interferon signaling.

Embodiment 23: The host cell of embodiment 22, wherein the host cell comprises a mutation in a gene selected from the group consisting of STAT1, IRF9, STAT2, IFNAR1, IFNAR2, and type I and III interferons.

Embodiment 24: The host cell of embodiment 23, wherein the host cell is knocked out for STAT1.

Embodiment 25: The host cell of embodiment 24, further comprises a heterologous nucleic acid encoding a viral envelope protein.

Embodiment 26: The host cell of embodiment 25, wherein the nucleic acid sequence of the heterologous nucleic acid encoding the envelope protein has less than about 60% sequence identity to the sequence of the modified or naturally existing viral envelope gene.

Embodiment 27: The host cell of embodiment 26, wherein the nucleic acid sequence of the heterologous nucleic acid encoding the envelope protein has less than about 80% sequence identity to the sequence of the naturally existing viral envelope gene.

Embodiment 28: A method of making a recombinant sarbecovirus, comprising culturing the host cell of any one of embodiments 21-27 and isolating the recombinant sarbecovirus.

Embodiment 29: A method of vaccinating an individual against sarbecovirus, comprising administering a sarbecovirus vaccine of any one of embodiments 15-20 to the individual, wherein the method further comprises:

a) a method of prophylactically immunizing an individual;

b) a method of preventing an individual from contracting a sarbecovirus infection;

c) a method of reducing the severity of a sarbecovirus infection in an individual;

d) a method of eliciting heterosubtypic protection against one or more other sarbecovirus species;

e) a method of preventing transmission of a sarbecovirus from a vaccinated individual to an unvaccinated individual;

f) a method of treating an individual having a sarbecovirus infection;

g) a method of eliciting an immune response in an individual; and/or h) a method of enhancing T cell response in an individual.

Embodiment 30: The method of embodiments 29, wherein the sarbecovirus vaccine is administered intranasally.

Embodiment 31: The method of embodiments 30, wherein the sarbecovirus vaccine is administered once.

Embodiment 32: The method of embodiments 30, wherein the sarbecovirus vaccine is administered more than once, with an interval of about 2 weeks to about 1 year.

Embodiment 33: The method of any one of embodiments 29-32, wherein the sarbecovirus vaccine is administered at a dose of about 105 PFU to about 1010 PFU.

Embodiment 34: The method of any one of embodiments 29-33, wherein the individual is a human individual.

EXAMPLES

The examples below are intended to be purely exemplary of the invention and should therefore not be considered to limit the invention in any way. The following examples and detailed description are offered by way of illustration and not by way of limitation. For the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

Example 1: Design and High-Titer Generation of an Interferon-Integrated SARS-CoV-2 Vaccine The purpose of this Example is to demonstrate whether (i) the restoration of early interferon signaling would help promote optimal induction of adaptive immunity; (ii) the secretion of interferon directly produced by a vaccine could protect the neighboring epithelial cells from any natural upper respiratory tract infection; and (iii) minimization of the chance of viral co-infection upon interferon secretion.

Figure 1B:
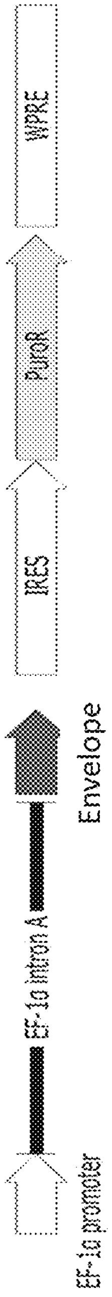
FIG. 1B shows the expression of an engineered SARS-CoV-2 envelope transgene that is driven by the human elongation factor-1 alpha (EF1α) promoter with the first EF1α intron included. Bicistronic expression of the puromycin resistance (PuroR) gene is driven by an internal ribosomal entry site (IRES). A woodchuck hepatitis virus posttranscriptional regulatory element (WPRE) was included at the 3' end to enhance transgene expression.
Figure 2A:
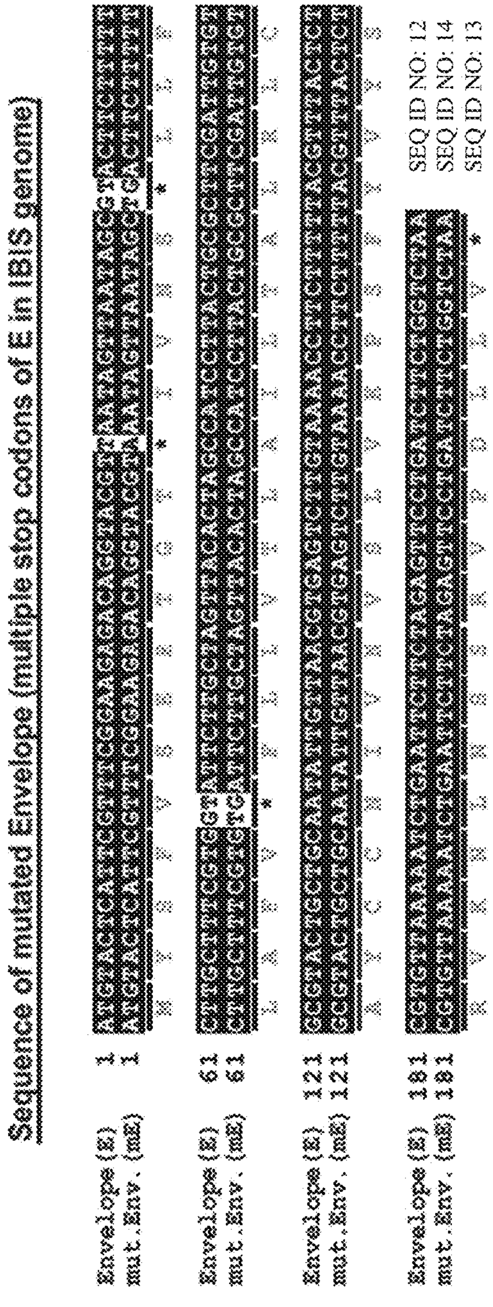
FIG. 2A provides the nucleotide sequences of the wild-type Envelope gene and modified Envelope in IBIS. Sequence alignment between wildtype Envelope sequence and modified Envelope (mE) in IBIS. Three early stop codons (indicated with *) were introduced to abrogate Envelope protein expression. Amino acids translated by mE were shown with gray lettering below the corresponding DNA sequence.
Figure 2B:
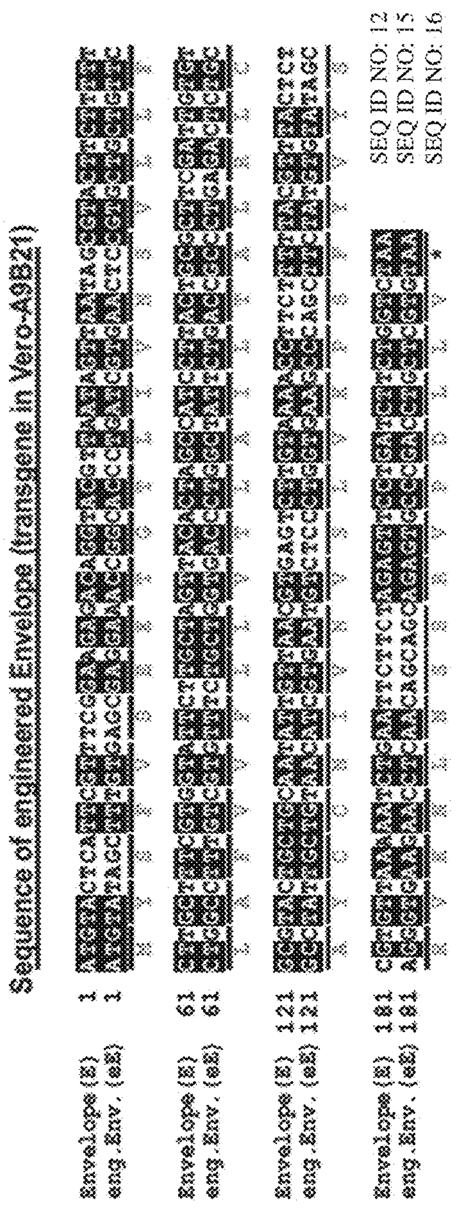
FIG. 2B shows the sequence alignment between wild-type Envelope and engineered Envelope (eE) transgene in Vero-A9B21 cells. eE was codon-optimized with significant nucleotide difference from the wildtype without introducing non-synonymous mutations. Black boxes represent the same nucleotide, while white boxes represent different nucleotides between the two sequences.

A novel mucosal vaccine was designed by integrating interferon-beta (IFNβ) into a defective SARS-CoV-2 genome, in which the envelope gene was inactivated by the insertion of three pre-mature stop codons using two-step red recombination into the Bacterial artificial chromosome (BAC) construct of the wildtype SARS-CoV-2 HKU-001a clone (FIG. 1A), thereby generating the Interferon-Beta-Integrated SARS-CoV-2 ("IBIS") vaccine. To support the replication of the defective virus, the VeroE6 parental cells were engineered to express a cassette of a modified SARS-CoV-2 envelope (eE) transgene (FIG. 1B). VeroE6-eE host cells were generated by transducing parental VeroE6 cells with lentivirus carrying an engineered SARS-CoV-2 E (eE) transgene followed by puromycin selection. Ninety synonymous nucleotide substitutions were introduced in the modified envelope transgene (eE) to minimize the chance of recombination between the mutated envelope (mE) in vaccine genome (FIG. 2A) and envelope transgene (eE) expressed in vaccine producing cells (FIG. 2B). The transduced VeroE6 parental cells were single-cell FACS sorted, and the VeroE6-eE clone VeroA9 was selected for further genetic modification.

To rescue the SARS-CoV-2 mutated envelope (SARS2-mE) and IBIS virus, the BACs were transfected with Lipofectamine 2000 into BHK21-eE (engineered Envelope) cells. Transfected BHK21-eE were trypsin-dissociated and co-cultured with VeroE6-eE or Vero-A9B21 cells 6-8 hr post-transfection. Recombinant viruses generated were plaque-purified, further propagated in Vero-A9B21 cells, and quantitated by plaque assay in VeroE6-eE or Vero-A9B21 stable cells. The recombinant viruses were then concentrated by ultra-centrifugation at 28000 rpm, 4° C. for 4 hr against a 25% sucrose bed on Optima XPN-100 ultracentrifuge. Absence of replicative virus in the SARS2-mE and IBIS virus stock was confirmed by plaque assay using parental VeroE6 cells, which showed complete absence of plaques and cytopathic effect (CPE).

Figure 2C:
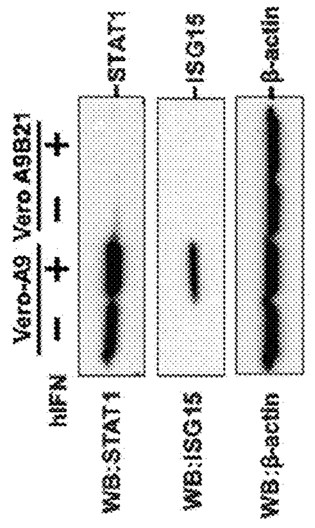
FIG. 2C provides validation of clonal Vero-A9B21 cells. Vero-A9 cells were used as the positive control showing the induction of STAT1 and ISG15 by interferon treatment. The absence of the induction of both STAT1 and ISG15 in Vero-A9B21 cells indicated the loss of interferon signaling.

The possibility for IFNβ to be produced by the vaccine in the host cell and thereby activated interferon signaling was a potential concern because it could lead to suppression of viral replication by the host cell. To prevent this possibility, the host cells VeroE6-eE were engineered to further knockout the STAT1 gene by CRISPR-Cas9 genome editing, which is a key signaling molecule essential for interferon signaling. Clonal STAT1 knockout (STAT1 KO) cells were selected and the VeroE6-eE STAT1-K0 clone Vero-A9B21 was chosen for vaccine production. The knockout of STAT1 and loss of interferon signaling were confirmed by the treatment of interferon and Western blotting (FIG. 2C).

Figure 1C:
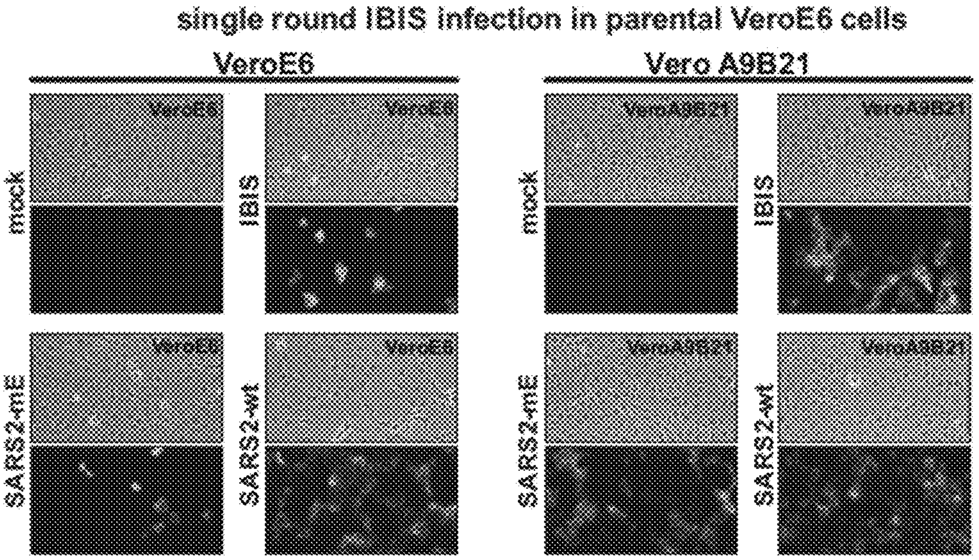
FIG. 1C shows single round infection of IBIS vaccine in parental VeroE6 cells. Parental VeroE6 (left panel) or Vero-A9B21 cells (right panel) were either mock infected or infected with IBIS, SARS-CoV-2 virus having mE but without mIFNβ transgene (SARS2-mE) or wildtype SARS-CoV-2 virus at MOI 0.1. 24 hr post-infection, cells were PFA-fixed and stained for SARS-CoV-2 NP protein.

As a result, the IBIS vaccine, as well as the defective SARS-CoV-2 virus with mutated envelope (SARS2-mE), could only replicate in Vero-A9B21 cells but not in parental VeroE6 cells (FIG. 1C). The viral titer of IBIS grown in a standard T-75 flask of Vero-A9B21 cells reached $4.4\times10^7$ plaque forming units (PFU), similar to the viral titer of SARS2-mE (FIG. 1D).

To test the efficacy of IBIS against SARS-CoV-2 infection, L929-hACE2 cells were generated in-house by stable transduction with lentivirus encoding a human ACE2 transgene, followed by puromycin selection. Prior to vaccination or infection, animals were anesthetized with intraperitoneal injection of ketamine and xylazine. For IBIS vaccination, $1\times10^6$ PFU/mouse in 20 μL PBS, or $3\times10^6$ PFU/hamster in 50 μL PBS was intranasally inoculated into the nostril of each anesthetized animal if not specified. For mRNA vaccination, 1 μg of BioNTech mRNA vaccine was intramuscularly injected into the hind-limb muscle of mice. 14-days after vaccination, a booster of the same strength was given in the same route as first vaccination. Blood was collected from the facial vein of mice or gingival vein of hamsters under anesthesia. Animals were infected by intranasal inoculation of SARS-CoV-1 or SARS-CoV-2 virus diluted in 20 μl (mouse) or 50 uL (hamster) PBS. Body weight and disease of infected animals were monitored for 14 days. Tissues were harvested at the indicated time points. For tissue homogenization, tissues were homogenized in 1 mL cold PBS using TissueRuptor II. Homogenate was then centrifuged at 3220 g, 4° C. for 10 min. Clear supernatant was aliquoted and stored at −80° C. in for future assays. For histology, tissues were fixed in 4% paraformaldehyde (PFA) in PBS for >24 hr, followed by paraffin embedding, sectioning, and H&E staining or IHC staining.

Figure 1E:
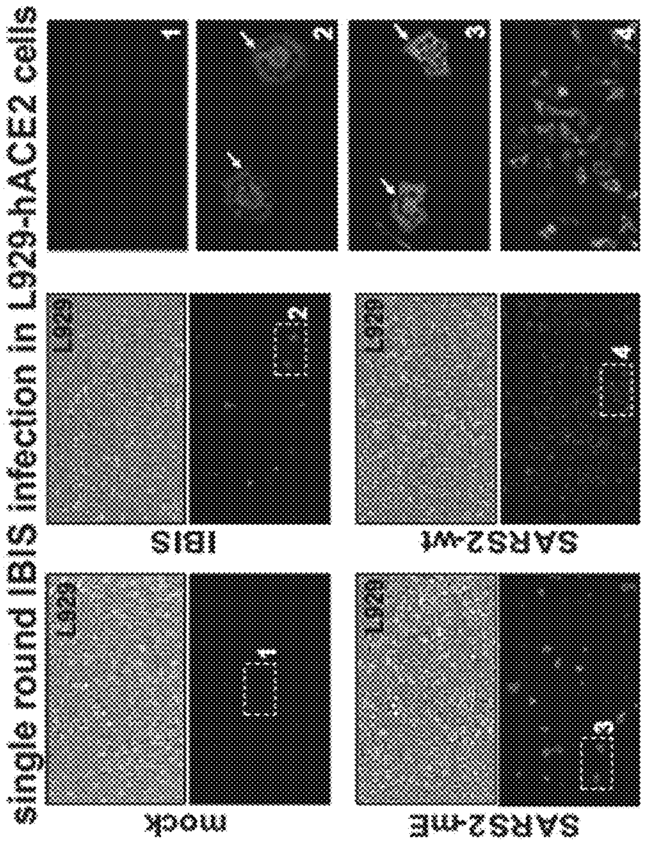
FIG. 1E shows single-round infection of IBIS in mIFNβ-responsive cells. Murine fibroblasts L929 stably expressing a human ACE2 (hACE2) transgene were either mock infected or infected with IBIS, SARS2-mE, or wildtype SARS-CoV-2 virus at MOI 0.1 (left and middle panels). Cells were PFA-fixed at 24 hr post-infection and stained for SARS-CoV-2 NP protein. Selected areas (boxes in white dotted line) were enlarged and shown on the right panels.
Figure 1D:
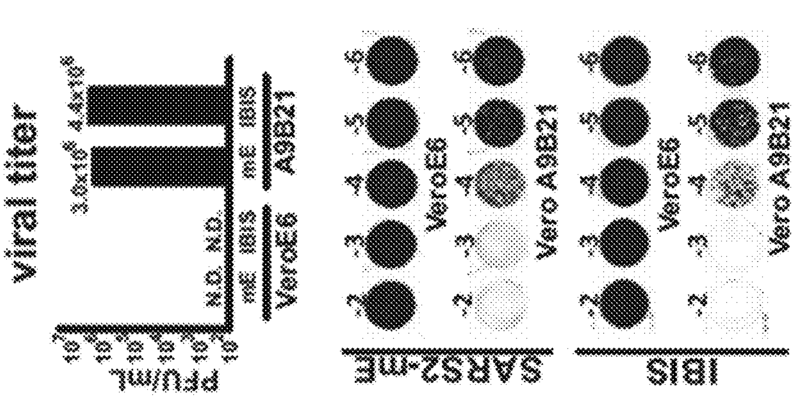
FIG. 1D shows plaque formation and quantitation of IBIS in Vero-A9B21 cells. SARS2-mE virus and IBIS were titered by plaque assay using wildtype VeroE6 or Vero-A9B21 cells (upper panel). Plaque formation and cytopathic effect could only be observed in VeroE6-A9B21 cells (middle and lower panel). PFU, plaque-forming unit.
Figure 3:
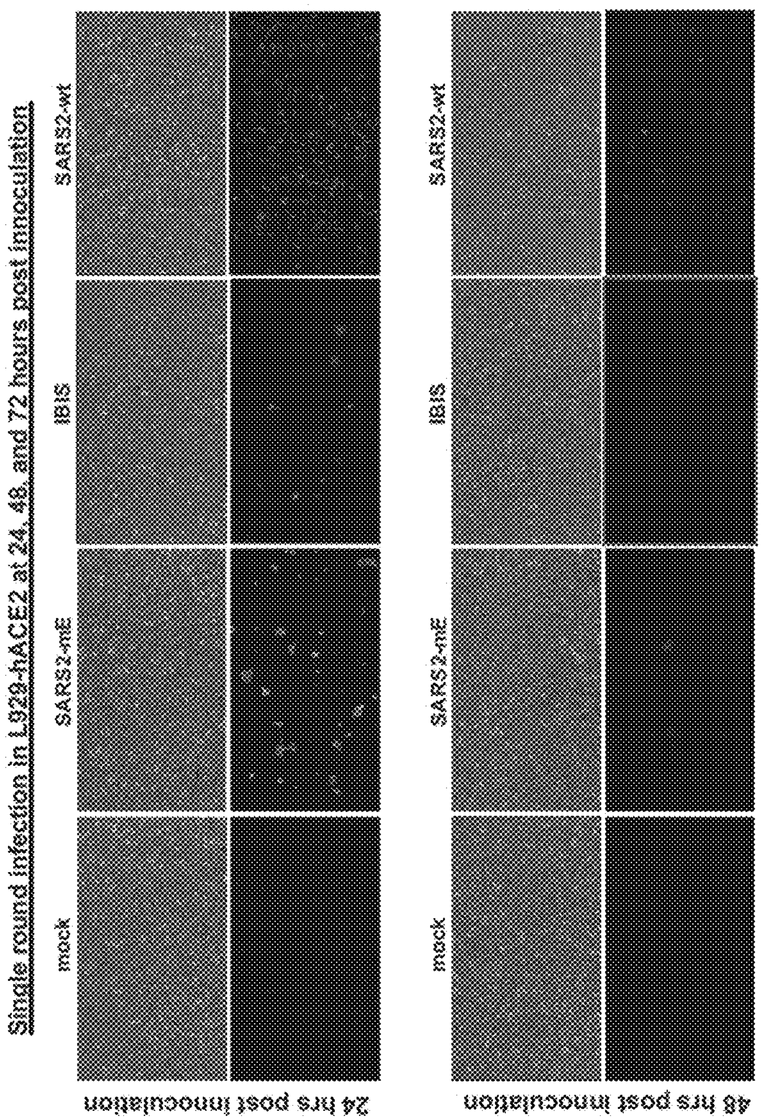
FIG. 3 shows immunostaining and plaque assay of infected L929-hACE2. L929-hACE2 cells were either mock infected, or infected with SARS2-mE, IBIS, or wildtype SARS-CoV-2 virus. Cells were PFA-fixed at 24, 48, and 72 hr post-infection, and stained with anti-SARS-CoV-2 NP antibody. The upper panel of each timepoint shows the brightfield images. CPE is only observed in wild-type SARS-CoV-2-infected cells. The lower panel shows the titer of the infectious progeny virus detected.
Figure 3:
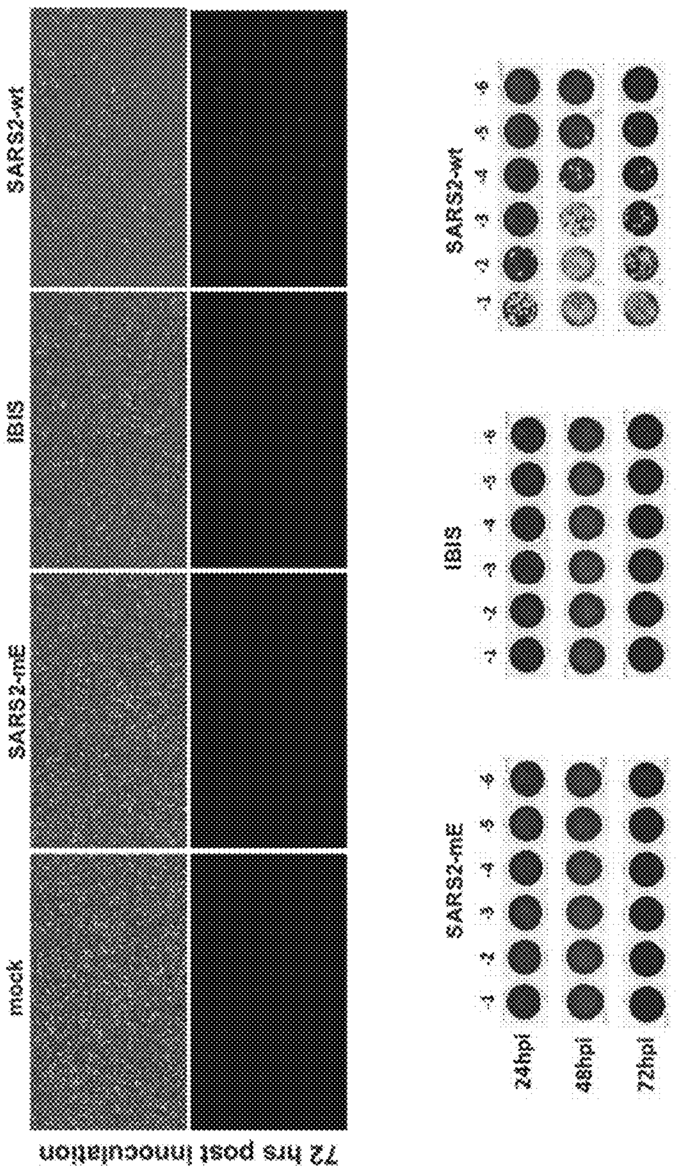

Examination of IBIS, SARS2-mE, and wild-type SARS-CoV-2 (SARS2-wt) infection in these hACE2-expressing mouse L929 (L929-hACE2) cells demonstrated that both IBIS and SARS2-mE, which lack functional envelope protein expression, could only establish single round infection, contrary to the multiple round infection of SARS2-wt that caused cytopathic effects (FIG. 1E). The single round infection of IBIS in L929-hACE2 lasted for at least 24 hours (FIG. 3). Taken together, the IBIS vaccine was only produced in the envelope-expressing STAT1-knockout Vero-A9B21 cells but not in VeroE6 nor L929-hACE2 cells.

Example 2: In Vitro and In Vivo Expression of Interferon-Beta by IBIS

The anti-viral function of interferon produced by IBIS was examined. Plaque-purified IBIS was inoculated into Vero-A9B21 cells, and culture supernatant was collected during serial passages and tested by ELISA: mouse IFNβ and TNFα protein were quantitated using mIFNβ and mTNFα Quantikine ELISA kits respectively according to manufacturer's instructions. Anti-RBD and anti-N antibodies were quantitated by in-house ELISA. Briefly, high-binding ELISA plates were coated with recombinant RBD or N protein, BSA-blocked and loaded with 1:100 diluted animal sera. After washing, biotin-conjugated anti-mouse IgG, anti-mouse IgM or anti-hamster IgG antibodies were added, followed by HRP-Streptavidin. After thorough washing, TMB-substrate was then added to allow color development and sulphuric acid for termination of reaction. Absorbance at 450 nm was measured using a Varioskan LUX multimode microplate reader.

Figure 4A:
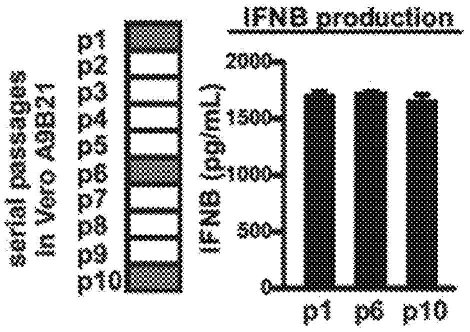
FIG. 4A shows the IFNβ production by serially passaged IBIS. IBIS was serially passaged ten times in Vero-A9B21 cells. IFNβ in the viral supernatant of passages 1, 6 and 10 were quantitated by ELISA.

IFNβ ELISA results showed that more than 1500 pg/mL of IFNβ was produced in supernatant obtained from passages 1, 6, and 10, indicating that a significant amount of IFNβ was secreted during the productive infection of IBIS in Vero-A9B21 cells (FIG. 4A). The expression of IFNβ from IBIS also was stable during passaging.

The function of IBIS-encoded IFNβ was then determined by a classical interferon bioassay. Briefly, samples were diluted in MEM with 10% FBS according to the indicated dilution. 1 ml of diluted sample was treated onto L929 cells in 12-well plate. 24 hr post-treatment, the inoculum was removed and the L929 cells were further infected with vesicular stomatitis virus containing a GFP reporter (VSV-GFP). Infected cells were fixed with 4% PFA and GFP was observed using fluorescence microscope. Absence of GFP indicates the presence of functional mouse IFNβ protein in a concentration high enough to protect treated cells from VSV-GFP infection.

Figure 4B:
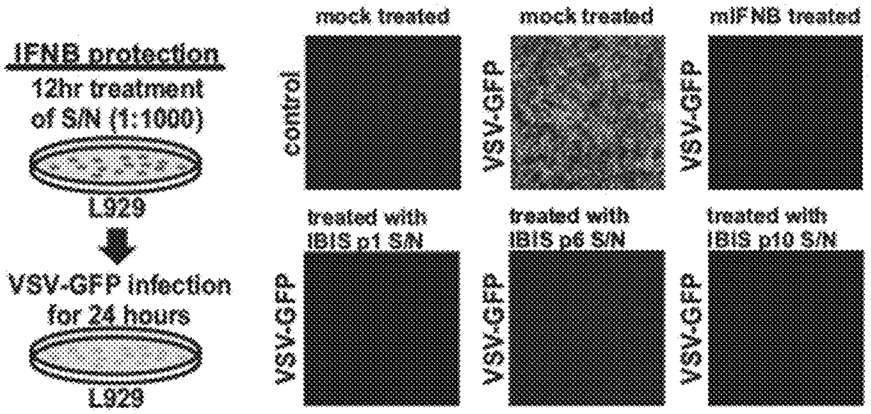
FIG. 4B shows that the IFNβ produced by IBIS inhibits viral infection in interferon bioassay. L929-hACE2 cells were either mock-treated, treated with 1000 IU/ml recombinant mouse IFNβ, or with 1:1000 diluted IBIS viral supernatant of passage 1, 6 and 10. At 24 hours post-treatment, cells were subjected to VSV-GFP infection. GFP signal was observed at 24 hours post-infection under a fluorescence microscope.
Figure 4C:
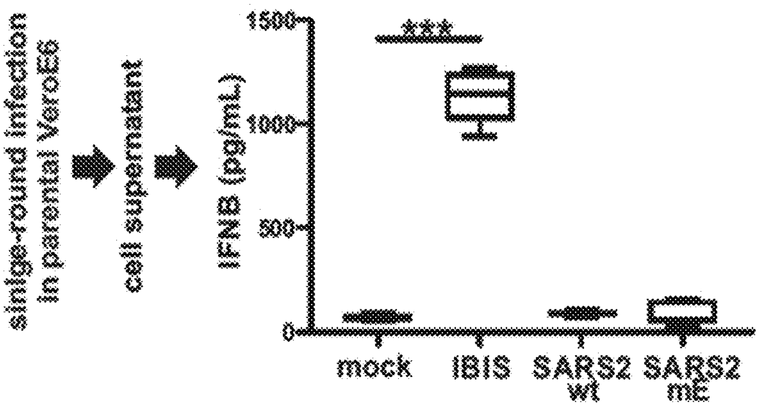
FIGS. 4C and 4D show that single-round IBIS infection in cultured cells produced a detectable amount of function IFNβ protein. Parental VeroE6 cells were either mock infected, or infected with IBIS, wildtype SARS-CoV-2 (SARS2-wt) or SARS2-mE at MOI 0.1. Culture supernatant was collected at 24 hours post-infection. The amount of IFNβ was quantitated by ELISA (FIG. 4C). L929-hACE2 cells were further treated with the undiluted supernatant for 24 hours, followed by VSV-GFP infection and GFP signal detection (FIG. 4D).
Figure 4D:
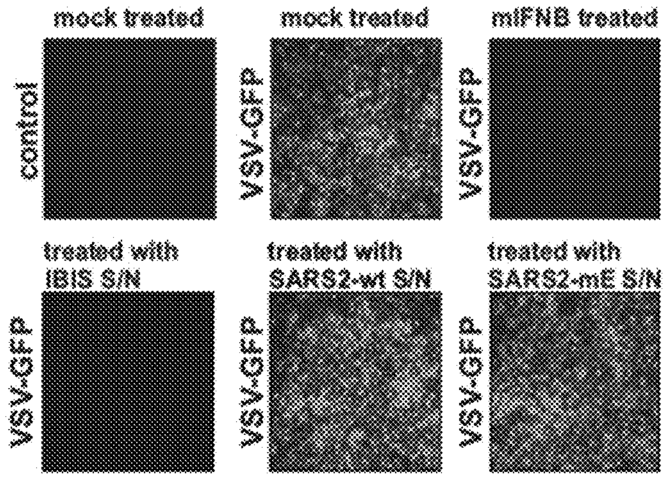

Treatment with 1:1000 diluted supernatant obtained from IBIS-infected Vero-A9B21 cells during passages 1, 6, and 10 was found to completely protect cells from VSV-GFP infection in L929-hACE2 cells (FIG. 4B). To mimic a vaccination during which cells could only be single-round infected by IBIS due to the lack of envelope protein expression, the IBIS infection was repeated in parental VeroE6 cells. Culture supernatants of IBIS-, SARS-mE- and SARS-wt-infected VeroE6 cells were harvested for the quantitation of secreted IFNβ and its antiviral activity. Single-round infection of IBIS produced more than 1000 pg/mL of IFNβ (FIG. 4C). Treatment with IBIS-supernatant completely blocked the VSV-GFP virus infection in L929-hACE2 cells (FIG. 4D). In contrast, neither SARS-mE nor SARS-wt supernatant prevented VSV-GFP infection.

Figure 4E:
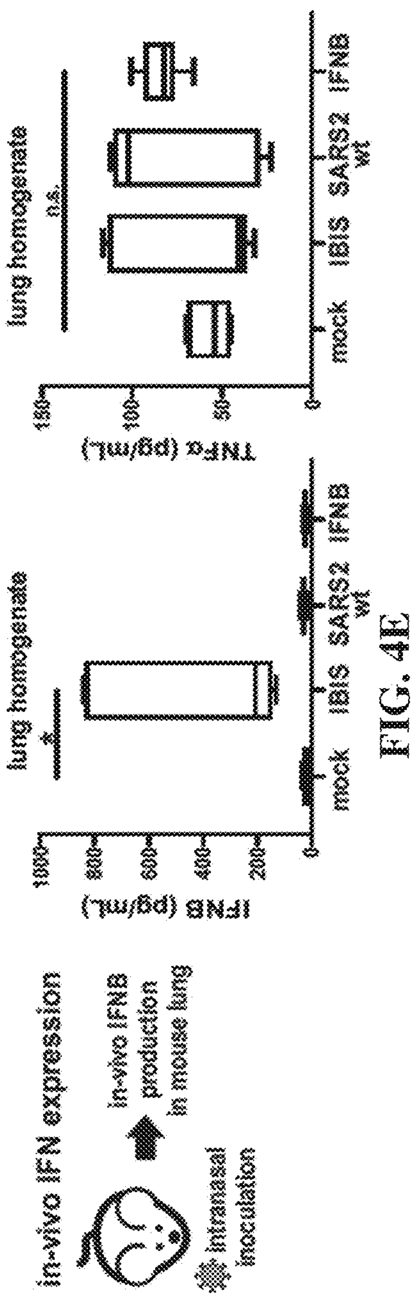
FIGS. 4E and 4F show that IBIS vaccination produced a detectable amount of IFNβ in vivo. K18-hACE2 transgenic mice were either intranasally inoculated with PBS, IBIS ($1\times10^6$ PFU), SARS2-wt ($1\times10^3$ PFU) or recombinant mouse IFNβ ($1\times10^5$ IU). At 24 hours post-infection/treatment, mouse lungs were harvested and homogenized in PBS. The amount of mouse IFNβ and TNFα in the lung homogenate was quantitated by ELISA (FIG. 4E). Mouse lungs were also PFA-fixed for sectioning and H&E staining (FIG. 4F).
Figure 4F:
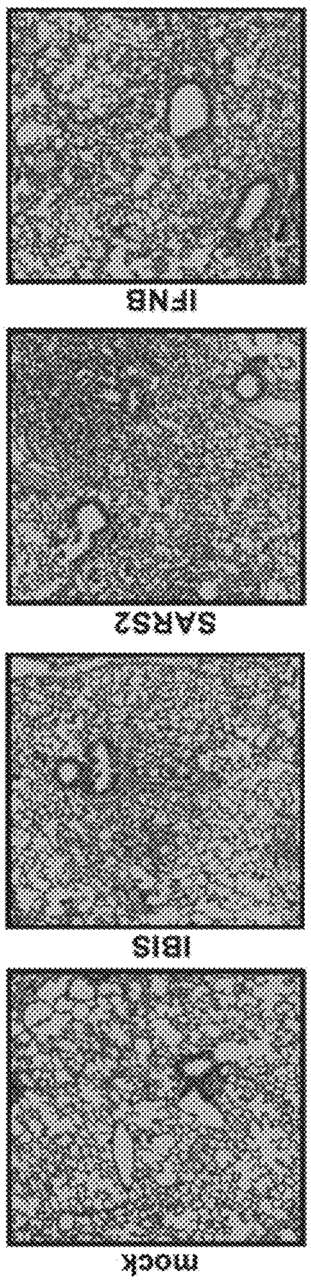
Figure 5:
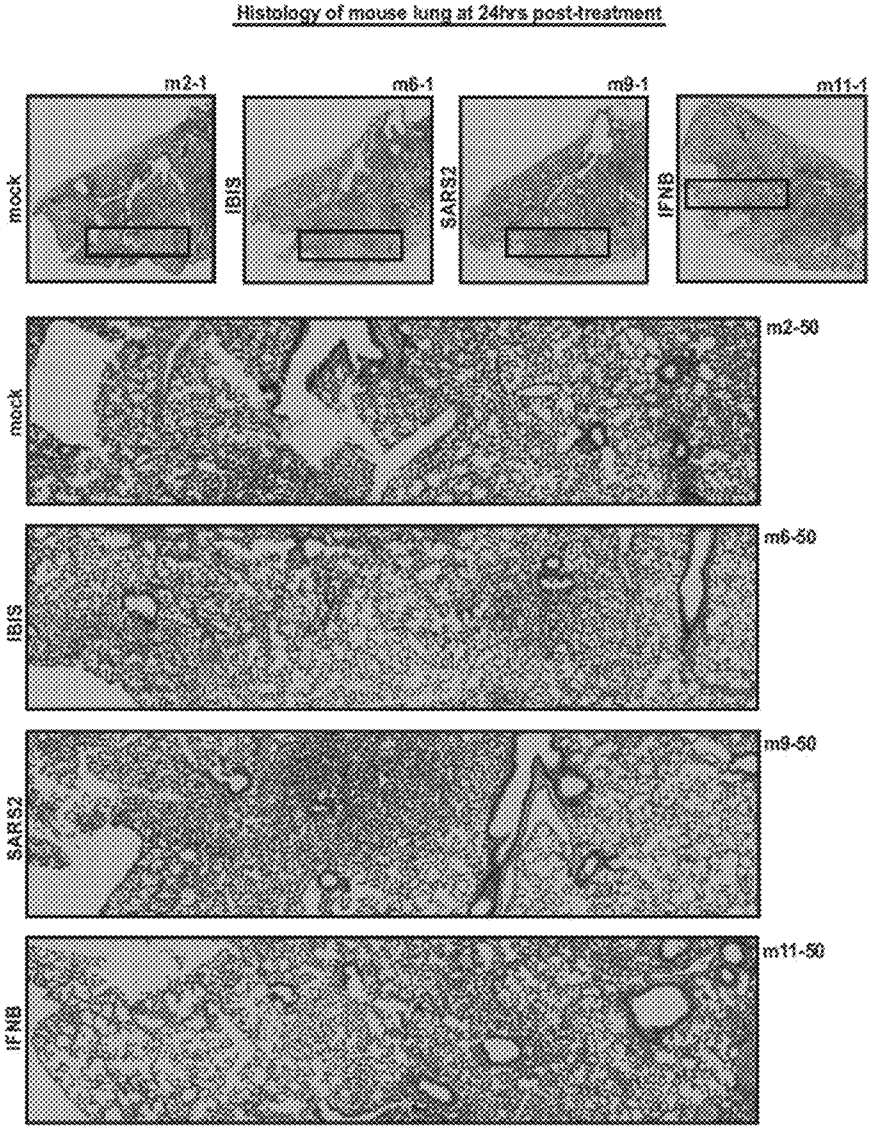
FIG. 5 provides images of H&E-stained mouse lungs that correspond to data in FIG. 4F. K18-hACE2 transgenic mice were either mock-infected or infected with IBIS ($1\times10^6$ PFU) or wildtype SARS-CoV-2 ($1\times10^3$ PFU) or treated with recombinant mouse IFNβ ($1\times10^5$ IU). 24 hr post-infection/treatment, the left lobe of the lungs was harvested and PFA-fixed for H&E staining. The upper panels show images of the whole lung section captured with an inverted light microscope. The areas in black boxes were enlarged and shown in the low panels.

The in vivo production of IFNβ by IBIS also was evaluated. A significant amount of IFNβ was detected in the lung homogenate of mice infected with IBIS, but not in the SARS2-wt-infected nor recombinant IFNβ-treated mouse lungs (FIG. 4E). At 24 hours post-infection of IBIS, SARS2-wt or post-treatment of IFNβ, no observable histological changes were identified in lung tissue of any mice (FIG. 4F and FIG. 5).

Figures 6A, 6B, 6C, 6D, 6E, 6F:
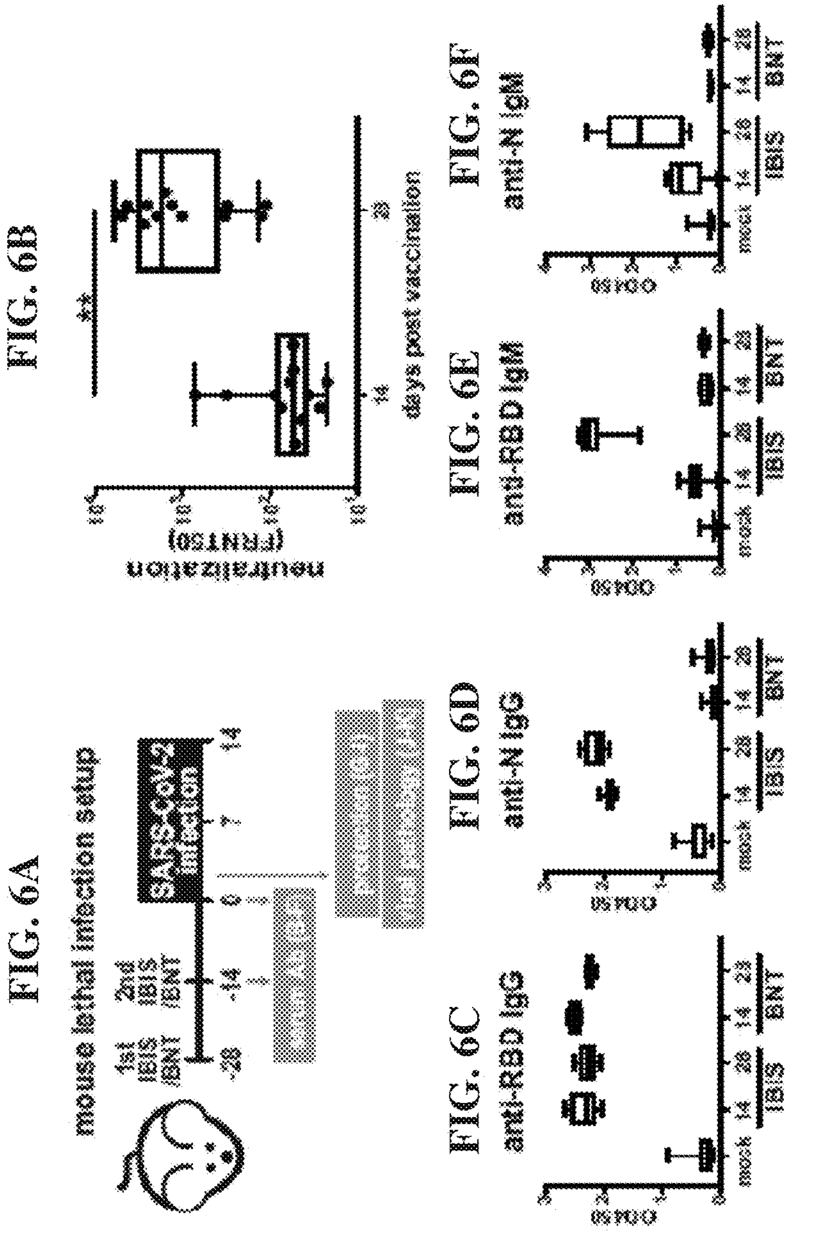
FIG. 6A depicts a schematic timeline of vaccination and viral challenge. K18-hACE2 transgenic mice were intranasally vaccinated with two doses of IBIS ($1\times10^6$ PFU per dose) on day−28 and day−14, respectively. Sera were collected 14 days after each vaccination (day−14 and day 0 respectively). On day 0, vaccinated mice were lethally challenged by intranasal inoculation of SARS-CoV-2 (WT) ($1\times10^3$ PFU). Body weight and survival were monitored for 14 days post-infection. Tissues were also harvested on day 2 post-infection.
FIG. 6B shows IBIS vaccination-induced production of neutralizing antibodies in mice. Sera collected 14-days or 28-days post-vaccination was evaluated for the presence of neutralizing antibodies against SARS-CoV-2 (WT) by focus-reduction neutralization test with 50% reduction cut-off ($FRNT_{50}$) quantitation. N=12 for each time point.
FIGS. 6C-6F show that IBIS potently induced IgG and IgM against both SARS-CoV-2 RBD and N. Mice were either vaccinated with two doses of intranasal IBIS or two doses of intramuscular COVID-19 mRNA vaccine (BNT). Sera collected 14-days after each dose were evaluated for IgG (FIGS. 6C and 6D) and IgM (FIGS. 6E and 6F) against SARS-CoV-2 (WT) Spike receptor-binding domain (RBD) or nucleoprotein (N) by ELISA. N=12 for IBIS groups. N=6 for BNT groups.

Example 3: Intranasal IBIS Vaccination Protects Mice Against Lethal SARS-CoV-2 Infection The protective efficacy and antibody response elicited by the IBIS vaccination were evaluated (FIG. 6A). Two doses of IBIS vaccine were given intranasally to K18-hACE2 transgenic mice over a 14-day interval. Serum samples were harvested at 14- and 28-days post-vaccination. Serum neutralization against authentic virus was determined by focus reduction neutralization test (FRNT) (FIG. 6B). Briefly, animal sera were serially diluted. The diluted serum was then mixed with an equal volume of 300 FFU of SARS-CoV-2 virus. The serum/virus mix was incubated at 37° C. for 1 hr, and then transferred to VeroE6 cells seeded in 96-well plates. After 1 hr adsorption, the inoculum was aspirated. Cells were then PBS-washed and replenished with fresh DMEM containing 1% FBS. 6 hr post-infection, cells were PFA-fixed for immunostaining against SARS-CoV-2 NP protein. Stained plates were scanned using Cytation 7 cell imaging multi-mode reader, and the number of foci in each well was counted with Gen5 software. The serum dilution at which half of the number of foci could be observed was calculated to represent the 50% reduction in FRNT (FRNT50).

On average, above 1000 $FRNT_{50}$ titer could be detected in mouse sera 28-days post-vaccination, suggesting that IBIS vaccination could induce high serum neutralizing antibody titers in mice. The anti-spike RBD-specific IgG and IgM, as well as anti-nucleoprotein IgG and IgM antibodies by ELISA were quantitated (FIGS. 6C-6F). In the IBIS-vaccinated group, the quantity of anti-RBD IgG was potently induced as high as the positive control group (with two doses of BioNTech mRNA vaccine). As expected, high-titer of anti-nucleoprotein IgG antibody was measured in serum of IBIS-vaccinated mice, but not in mice vaccinated with BioNTech mRNA vaccine not expressing nucleoprotein.

The protective efficacy of IBIS vaccination against homotypic SARS-CoV-2 infection was analyzed. All IBIS-vaccinated mice survived from lethal infection and no weight loss was observed (FIGS. 6G-6H). Moreover, no infectious virus could be detected in the lungs of IBIS-vaccinated mice contrary to the robust viral replication in mock vaccinated mice (FIG. 6I). Histological examination was performed to assess any damage to airway organ structures. Animal tissues were fixed in 4% PFA for >24 hr and paraffin-embedded. Tissue sections were mounted onto microscope slides and de-waxed in xylene. Antigen retrieval was performed by microwaving the slides in citrate-based antigen unmasking solution, followed by blocking in 5% normal goat serum. The slides were then stained with rabbit anti-SARS-CoV-2 NP antibody and then Alexa Fluor 488-conjugated goat anti-rabbit IgG antibody. Nuclei of cells were counter-stained with DAPI and autofluorescence was quenched by Suden Black B. Fluorescence images were captured with a Zeiss LSM900 confocal microscope.

Figure 7:
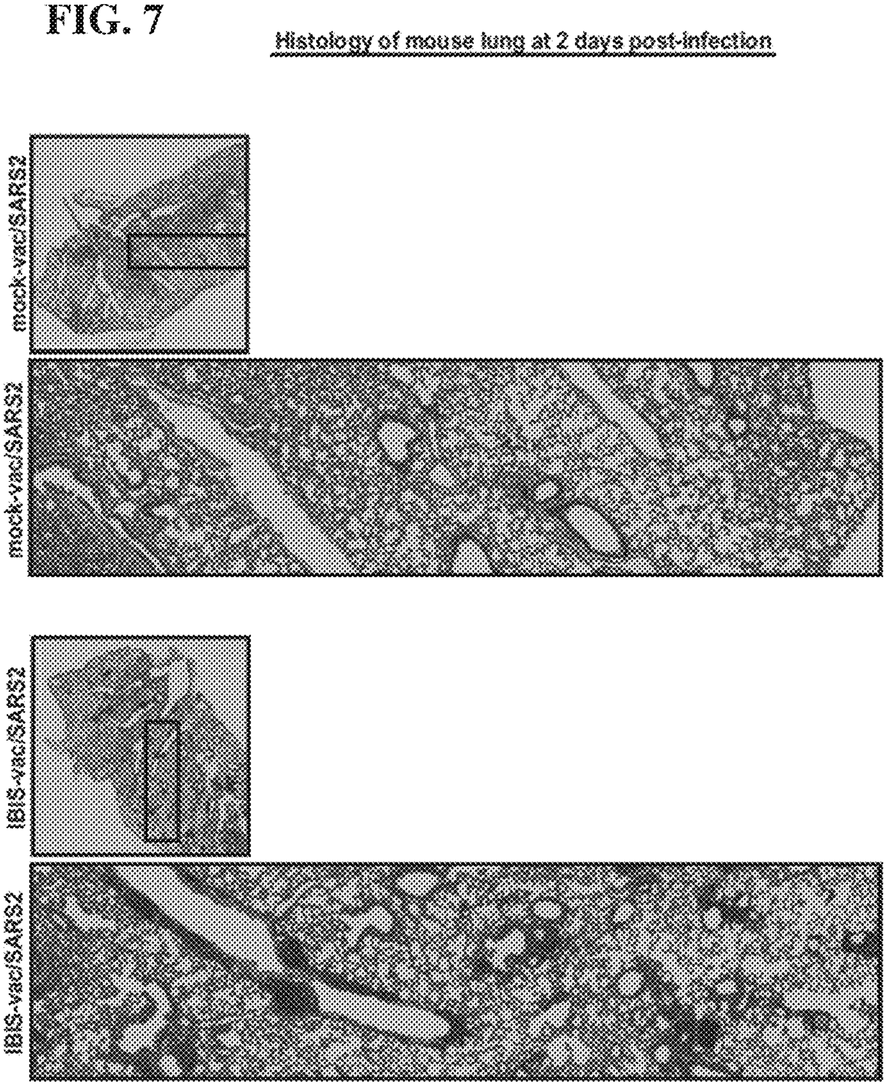
FIG. 7 presents images of H&E-stained mouse lungs that correspond to the data in FIGS. 6J and 6K. PBS- or IBIS-vaccinated K18-hACE2 transgenic mice were infected with SARS-CoV-2 ($1\times10^3$ PFU). Day 2 post-infection, the left lobe of the lungs was harvested and PFA-fixed for H&E staining. Areas in black boxes were enlarged.
Figure 11:
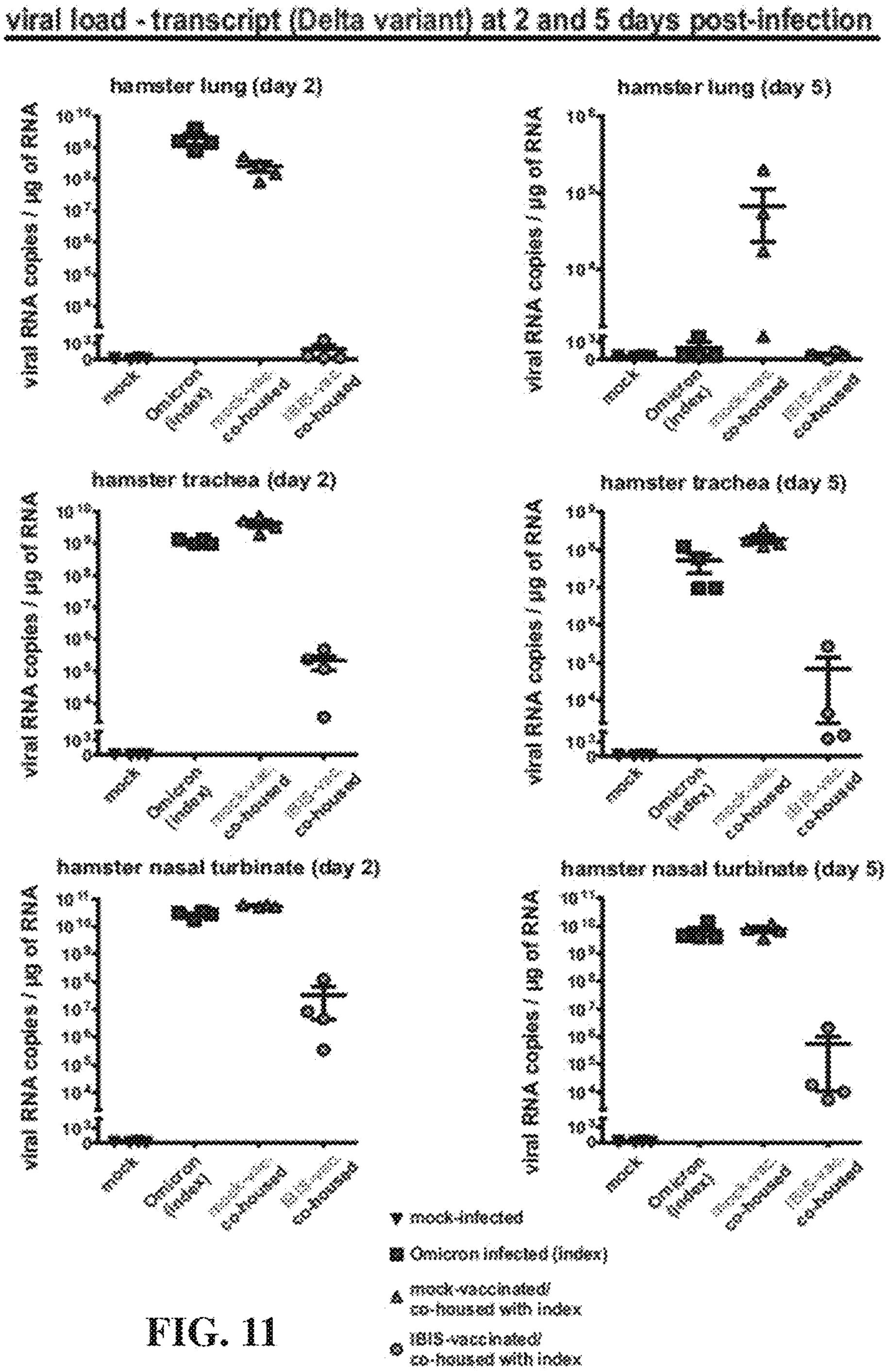
FIG. 11 shows the lungs, trachea, and nasal turbinate of the SARS-CoV-2 (delta variant) infected/co-housed hamsters corresponding to data presented in FIGS. 10D and 10E that were harvested on day2 and day5. Viral transcript level of the tissue homogenate was quantitated by RT-qPCR. The result was summarized in FIG. 10F.
Figure 12:
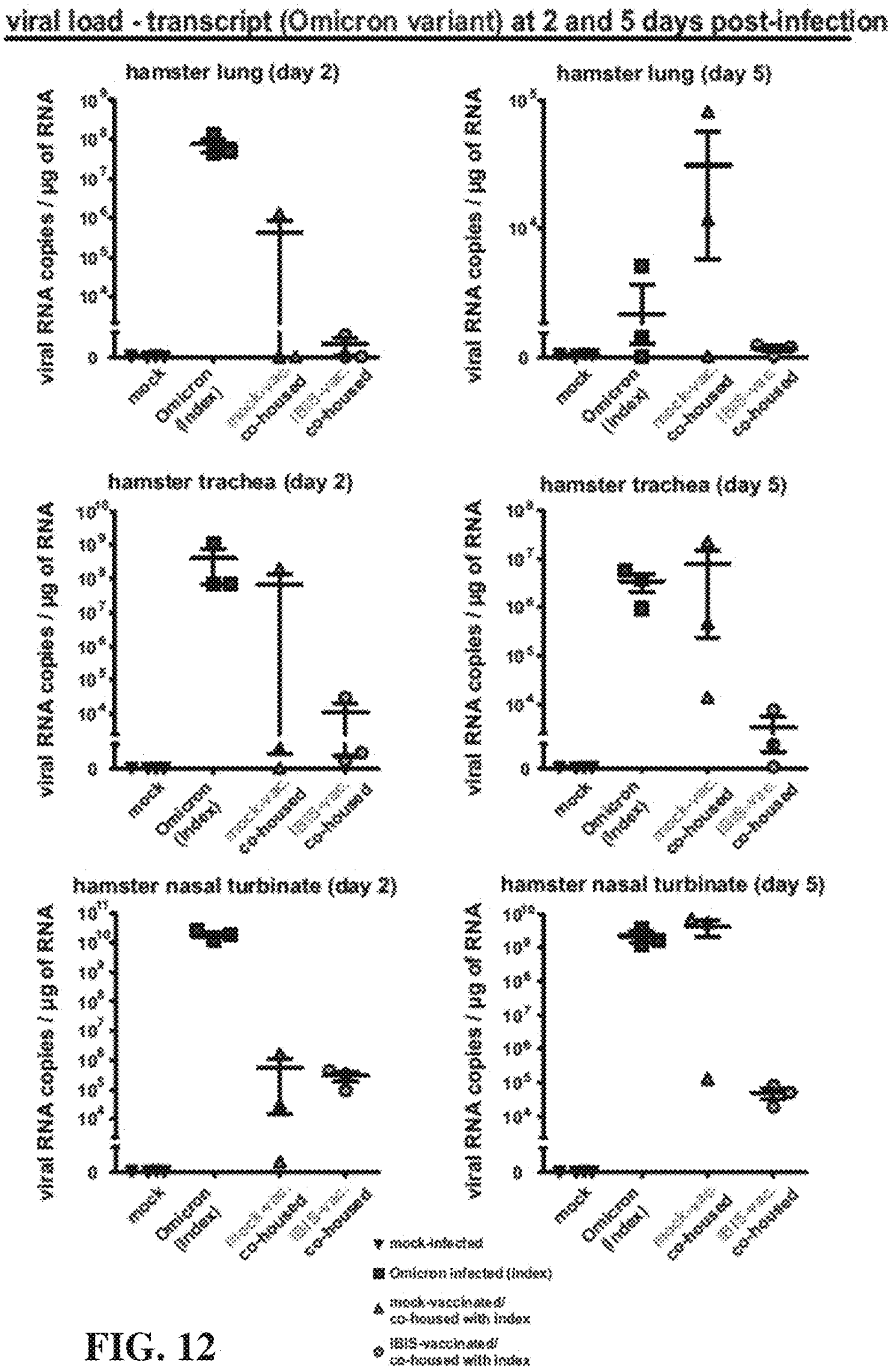
FIG. 12 shows the lungs, trachea, and nasal turbinate of the SARS-CoV-2 (omicron-BA.1 variant) infected/co-housed hamsters corresponding to data presented in FIGS. 10A and 10B were harvested on day2 and day5. Viral transcript level of the tissue homogenate was quantitated by RT-qPCR. The result was summarized in FIG. 10C.

Histological examination also showed the intact structures of bronchi, bronchioles and alveoli, and the absence of hemorrhage in IBIS-vaccinated mice at day-2 post-infection. Whole lung anti-nucleoprotein immunostaining indicated that no viral replication was observed in IBIS-vaccinated mice (FIGS. 6J-6K and FIG. 7). Taken together, the high-titer neutralizing antibody, the high-titer anti-nucleoprotein, and complete protection against lethal infection of homotypic SARS-CoV-2 indicated the successful application of IBIS as a novel live attenuated vaccine strategy.

Example 4: IBIS Vaccination Impedes SARS-CoV-2 Transmission in a Hamster Co-Housing Model Golden Syrian hamsters were used to test the pre-clinical evaluation of the IBIS vaccine for preventing transmission of SARS-CoV-2 (illustrated in FIG. 8A). Two groups of hamsters were either mock vaccinated or vaccinated with two doses of IBIS. Serum samples were harvested for antibody quantitation. Fourteen days after the second dose of the IBIS vaccination, one hamster from each group was co-housed with an index hamster that had also been infected with SARS-CoV-2 one day prior. After 24-hour co-housing, the hamsters were separated for body weight monitoring or time-point tissue harvest (FIG. 8E).

First, anti-spike RBD and anti-nucleoprotein IgG antibodies were induced in serum at 14- and 28-days post IBIS-vaccination (FIGS. 8B-8C). In line with mouse vaccination, serum neutralizing antibody titer in IBIS-vaccinated hamsters was gradually induced to a high-level ranging from $10^3$ to $10^4$ $FRNT_{50}$ (FIG. 8D). At 5 days post-co-housing, mock vaccinated hamsters showed localized alveolar collapse and viral replication across the whole lung (FIG. 8F). In stark contrast, the lungs of IBIS-vaccinated hamsters showed normal alveolar structure without detectable virus replication as indicated by the absence of NP staining (FIG. 8G). In addition, no infectious virus could be recovered from the IBIS-vaccinated hamster lungs, while the mock vaccinated hamsters showed high viral burden at both day 2 and day 5 post-co-housing (FIGS. 8H-8I).

The lowest dose of IBIS vaccine that is sufficient to protect hamsters against homotypic SARS-CoV-2 infection was then tested. Groups of hamsters were vaccinated with a single decreasing dose of IBIS (ranging from $3\times10^6$ to $3\times10^2$ PFU/hamster) for 14 days, followed by SARS-CoV-2 intranasal infection. Surprisingly, $3\times10^2$ PFU of IBIS was already enough to protect vaccinated hamsters from SARS-CoV-2-induced weight loss (FIG. 8J). Hamsters receiving $3\times10^5$ PFU of IBIS vaccination displayed the highest degree of weight gain among all groups tested.

Example 5: IBIS Vaccination Elicits Heterosubtypic Protection Against SARS-CoV-1 Infection IBIS vaccination elicited a potent antibody response and completely protected mice and hamsters from homotypic SARS-CoV-2 infection/transmission. Whether IBIS could also elicit heterosubtypic protection against other sarbecoviruses in both animal models was further examined.

In a SARS-CoV-1 mouse model, IBIS vaccination completely protected K18-hACE2 mice from SARS-CoV-1 lethal infection. No weight-loss was observed in any vaccinated mice (FIG. 9A), and 100% survival of all vaccinated mice was observed (FIG. 9B). Although one out of five vaccinated mice had low but detectable lung viral titer at day 2 post-infection, no virus could be detected in the lungs of any of the five mice at day 5 post-infection (FIG. 9C). Moreover, no infectious virus could be recovered from the nasal turbinate of IBIS-vaccinated mice at either day 2 or day 5 post-infection, suggesting that IBIS was effective in reducing SARS-CoV-1 infection and lethality. This finding was further confirmed using the hamster model.

Hamsters were vaccinated with 2 doses of IBIS, followed by intranasal inoculation of the same titer of SARS-CoV-1 used in mice at 28-days post-vaccination. Lungs, nasal turbinate, and trachea were harvested at day 2 and day 5 post-infection for determination of viral burden. No virus was detected in the lungs of vaccinated hamsters at either day 2 or day 5 (FIG. 9E). Although lower but detectable viral titer was observed in the upper respiratory tract (nasal turbinate and trachea) at day 2, it became marginally detectable (1/3) or undetectable (2/3) on day 5 (FIGS. 9F-9G). Taken together, IBIS vaccination elicited cross-protection against SARS-CoV-1 infection in both mouse and hamster models.

Example 6: IBIS Vaccination Prevents Delta and Omicron Variants Transmission

Since IBIS vaccination protected animals from SARS-CoV-1 infection, IBIS was then tested for its protection against infection of recent emerging SARS-CoV-2 variants such as Delta and Omicron. The hamster transmission model was applied for the study of Delta and Omicron variants because of their enhanced transmissibility and high viral load measured in the upper respiratory tract (see, e.g., Science. 2022 377:428-433, hereby incorporated by reference in entirety). In the same hamster co-housing model as was used for wild-type SARS-CoV-2 transmission, IBIS-vaccinated hamsters did not exhibit weight loss after co-housing with index hamsters pre-infected with either omicron (FIG. 10A) or delta variant (FIG. 10D). Furthermore, no infectious viral particles were detected in respiratory tracts (lung, nasal turbinate and trachea) of all vaccinated hamsters at day 2 and day 5 post-co-housing with omicron- (FIG. 10B) or delta- (FIG. 10E) infected hamsters. Relatively low amount of viral transcript was detected in hamster tissues, indicating that the vaccine-induced immunity restricted the viral replication and spreading, leading to the absence of infectious viral particles (FIG. 10C, FIG. 10F and FIGS. 11-12).

Example 7: IBIS Vaccination Enhances Mucosal Polyfunctional CD4+ T Cell Activation Type-I interferons have been shown to facilitate CD4+ T cell expansion and survival (see, e.g., J Immunol 2006 176:3315-9; Immunity 2014 40:961-73; Immunity 2014 40:949-60), and to inhibit T regulatory cell-mediated suppression of antigen-specific CD4+ T cells (see, e.g., J Exp Med 2014 211:961-74; PLoS Pathog 2018 14:e1006985). Therefore, it was possible that the expression of IFNβ by IBIS could strengthen the vaccine-induced SARS-CoV-2-specific T-cell response.

Figure 13A:
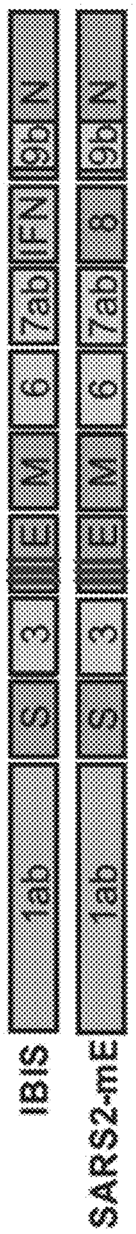
FIG. 13A depicts a schematic overview of the genomic organization of the IBIS and SARS2-mE constructs.

To compare the T-cell response elicited by the vaccine with or without the integrated IFNβ cassette, an identical vaccine was generated (i.e., SARS2-mE) that did not carry the ORF8 replacement by IFNβ (FIG. 13A). K18-hACE2 transgenic mice were either mock-vaccinated or vaccinated with 2 doses of IBIS or SARS2-mE. At 7 days post second-dose vaccination, mice were sacrificed. Dissociated lung cells and bronchoalveolar lavage (BAL)-derived immune cells were harvested for the spike RBD peptide pool stimulation. Cells were then treated with SARS-CoV-2 peptide pool overnight. Activated cells were stained with antibody against CD4, CD8a, IFNγ, TNFα, and IL-2. Flow cytometry data were analyzed by FlowJo v10. Data were statistically analyzed by student's t-test using Prism 8.0 software.

Figure 13B:
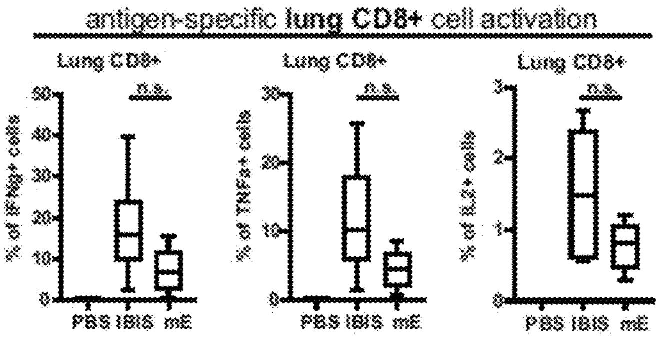
FIGS. 13B and 13C show that IBIS vaccination significantly induced polyfunctional lung CD4+ cells. Mock-vaccinated mice and mice vaccinated with two doses of IBIS or SARS2-mE were sacrificed at 7 days post second-dose of vaccination. Immune cells from dissociated lungs were stimulated by spike peptide pool. Activation of antigen-specific lung CD4+ and CD8+ T cells (IFNγ, TNFα, and IL-2) were quantitated and presented as percentage of the corresponding CD4+ and CD8+ T cells. n.s.: not significant; *: $p<0.05$; mE: SARS2-mE.
Figure 13C:
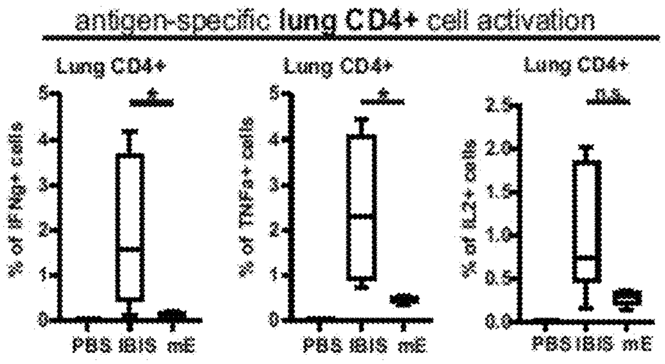
Figure 13D:
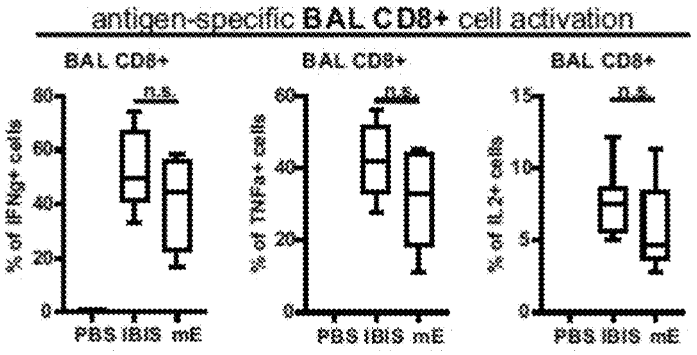
FIGS. 13D and 13E show that IBIS vaccination significantly induced polyfunctional bronchoalveolar lavage (BAL) CD4+ cells. Similar to the analysis of lung cells, immune cells in BAL of vaccinated mice were stimulated with spike peptide pool. Activation of antigen-specific CD4+ and CD8+ T cells (IFNγ, TNFα, and IL-2) were quantitated. n.s.: not significant; *: $p<0.05$; mE: SARS2-mE.
Figure 13E:
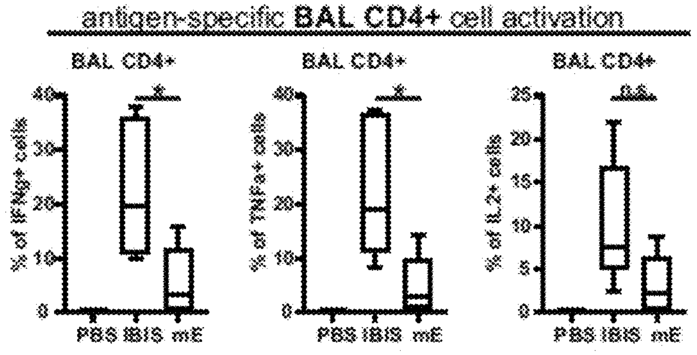

When compared with the SARS2-mE group, no significant enhancement of lung and BAL CD8+ T-cell activation was observed in the IBIS vaccination group (FIG. 13B and FIG. 13D). In contrast, antigen-specific activation of both lung and BAL CD4+ T cells was significantly enhanced (FIG. 13C and FIG. 13E). For the BAL derived cells, the percentage of IFNβ+CD4+ and TNFα+CD4+ T-cell activation (ranging from 11%-37%) in the IBIS vaccination group was much higher than that of the SARS2-mE vaccination group (ranging from 1%-14%) (FIG. 13E). Comparing the vaccination between IBIS and SARS2-mE, it was concluded that integration of IFNβ in IBIS vaccine preferentially enhanced mucosal antigen-specific polyfunctional CD4+ T-cell activation in mouse model.

Figure 14:
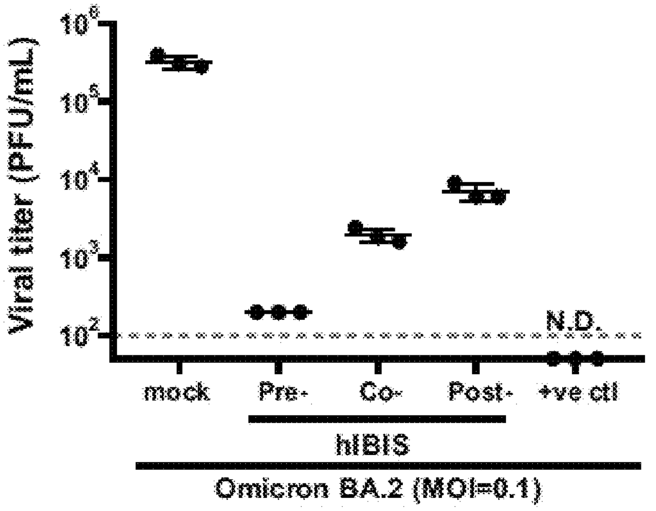
FIG. 14 shows the protective effect of interferon encoded by IBIS against Omicron infection in cells. Human lung fibroblast A549-hACE2-hTMPRSS2 cells were infected with SARS-CoV-2 (Omicron-B A.2) at MOI=0.1, together with pre-, co- or post-treatment of IBIS encoding human IFNβ (hIBIS) at M01=0.2. 48 hr post-infection, and culture supernatant was then collected for viral titer quantitation by plaque assay in VeroE6-hTMPRSS2 cells. Pre-treatment with 1000 IU/mL of recombinant human IFNβ protein served as the positive control (+ve ctl) for the inhibition.

Example 8: Single Round Infection of Human IBIS Suppresses Infection of Omicron BA.2 in Human Cells Mouse IFNβ was able to activate interferon signaling in mouse L929 and monkey Vero cells, but not in human cells. To evaluate the function of IFNβ encoded by IBIS in human cells, a human version of IBIS (hIBIS) that encoded human IFNβ was generated. Activation of interferon signaling was known to promote a host antiviral response. Therefore, expression of IFNβ by IBIS could help to prevent SARS-CoV-2 infection when adaptive immunity had yet to be mounted by the vaccines. Thus, A549-hACE2-hTMPRSS2 cells were infected with SARS-CoV-2 (Omicron BA.2) with or without pre-, co-, or post-treatment of hIBIS (FIG. 14). Pre-treating cells with hIBIS largely suppressed the subsequent infection of omicron (3-log inhibition) from $10^5$ to $10^2$ PFU/mL to a comparable level to recombinant human IFNβ treatment. Co-treatment was also effective in suppressing the infection of omicron (2-log inhibition) from $10^5$ to $10^3$ PFU/mL. Although it was less likely that a COVID-19 patient with a known infection would go for vaccination, treatment of hIBIS post-infection was still able to suppress the omicron replication (1.5-log inhibition). Taken together, IFNβ expressed directly by IBIS could help minimize the risk of co-infection or viral recombination with the circulating virus.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

SEQUENCE LISTING

SEQ ID NO: 1 (SARS-COV-2 DNA sequence)

ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC

-continued

SEQUENCE LISTING

TGACCCTATACATTCTTTAAGAGTTTGTGTAGATACTGTTCGCACAAATGTCTACTTAGCTGTCTTTGATAAAAATC
TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT
GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA
GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT
CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT
TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT

-continued

| SEQUENCE LISTING |
|---|
| GTGATACATTCTGTGCTGGTAGTACATTTATTAGTGATGAAGTTGCGAGAGACTTGTCACTACAGTTTAAAAGACC<br>AATAAATCCTACTGACCAGTCTTCTTACATCGTTGATAGTGTTACAGTGAAGAATGGTTCCATCCATCTTTACTTTG<br>ATAAAGCTGGTCAAAAGACTTATGAAAGACATTCTCTCTCTCATTTTGTTAACTTAGACAACCTGAGAGCTAATAA<br>CACTAAAGGTTCATTGCCTATTAATGTTATAGTTTTTGATGGTAAATCAAAATGTGAAGAATCATCTGCAAAATCA<br>GCGTCTGTTTACTACAGTCAGCTTATGTGTCAACCTATACTGTTACTAGATCAGGCATTAGTGTCTGATGTTGGTGA<br>TAGTGCGGAAGTTGCAGTTAAAATGTTTGATGCTTACGTTAATACGTTTTCATCAACTTTTAACGTACCAATGGAAA<br>AACTCAAAACACTAGTTGCAACTGCAGAAGCTGAACTTGCAAAGAATGTGTCCTTAGACAATGTCTTATCTACTTT<br>TATTTCAGCAGCTCGGCAAGGGTTTGTTGATTCAGATGTAGAAACTAAAGATGTTGTTGAATGTCTTAAATTGTCA<br>CATCAATCTGACATAGAAGTTACTGGCGATAGTTGTAATAACTATATGCTCACCTATAACAAAGTTGAAAACATGA<br>CACCCCGTGACCTTGGTGCTTGTATTGACTGTAGTGCGCGTCATATTAATGCGCAGGTAGCAAAAAGTCACAACAT<br>TGCTTTGATATGGAACGTTAAAGATTTCATGTCATTGTCTGAACAACTACGAAAACAAATACGTAGTGCTGCTAAA<br>AAGAATAACTTACCTTTTAAGTTGACATGTGCAACTACTAGACAAGTTGTTAATGTTGTAACAACAAAGATAGCAC<br>TTAAGGGTGGTAAAATTGTTAATAATTGGTTGAAGCAGTTAATTAAAGTTACACTTGTGTTCCTTTTTGTTGCTGCT<br>ATTTTCTATTTAATAACACCTGTTCATGTCATGTCTAAACATACTGACTTTTCAAGTGAAATCATAGGATACAAGGC<br>TATTGATGGTGGTGTCACTCGTGACATAGCATCTACAGATACTTGTTTTGCTAACAAACATGCTGATTTTGACACAT<br>GGTTTAGCCAGCGTGGTGGTAGTTATACTAATGACAAAGCTTGCCCATTGATTGCTGCAGTCATAACAAGAGAAGT<br>GGGTTTTGTCGTGCCTGGTTTGCCTGGCACGATATTACGCACAACTAATGGTGACTTTTTGCATTTCTTACCTAGAG<br>TTTTTAGTGCAGTTGGTAACATCTGTTACACACCATCAAAACTTATAGAGTACACTGACTTTGCAACATCAGCTTGT<br>GTTTTGGCTGCTGAATGTACAATTTTTAAAGATGCTTCTGGTAAGCCAGTACCATATTGTTATGATACCAATGTACT<br>AGAAGGTTCTGTTGCTTATGAAAGTTTACGCCCTGACACACGTTATGTGCTCATGGATGGCTCTATTATTCAATTTC<br>CTAACACCTACCTTGAAGGTTCTGTTAGAGTGGTAACAACTTTTGATTCTGAGTACTGTAGGCACGGCACTTGTGA<br>AAGATCAGAAGCTGGTGTTTGTGTATCTACTAGTGGTAGATGGGTACTTAACAATGATTATTACAGATCTTTACCA<br>GGAGTTTTCTGTGGTGTAGATGCTGTAAATTTACTTACTAATATGTTTACACCACTAATTCAACCTATTGGTGCTTT<br>GGACATATCAGCATCTATAGTAGCTGGTGGTATTGTAGCTATCGTAGTAACATGCCTTGCCTACTATTTTATGAGGT<br>TTAGAAGAGCTTTTGGTGAATACAGTCATGTAGTTGCCTTTAATACTTTACTATTCCTTATGTCATTCACTGTACTCT<br>GTTTAACACCAGTTTACTCATTCTTACCTGGTGTTTATTCTGTTATTTACTTGTACTTGACATTTTATCTTACTAATG<br>ATGTTTCTTTTTTAGCACATATTCAGTGGATGGTTATGTTCACACCTTTAGTACCTTTCTGGATAACAATTGCTTATA<br>TCATTTGTATTTCCACAAAGCATTTCTATTGGTTCTTTAGTAATTACCTAAAGAGACGTGTAGTCTTTAATGGTGTTT<br>CCTTTAGTACTTTTGAAGAAGCTGCGCTGTGCACCTTTTTGTTAAATAAAGAAATGTATCTAAAGTTGCGTAGTGAT<br>GTGCTATTACCTCTTACGCAATATAATAGATACTTAGCTCTTTATAATAAGTACAAGTATTTTAGTGGAGCAATGGA<br>TACAACTAGCTACAGAGAAGCTGCTTGTTGTCATCTCGCAAAGGCTCTCAATGACTTCAGTAACTCAGGTTCTGAT<br>GTTCTTTACCAACCACCACAAACCTCTATCACCTCAGCTGTTTTGCAGAGTGGTTTTAGAAAAATGGCATTCCCATC<br>TGGTAAAGTTGAGGGTTGTATGGTACAAGTAACTTGTGGTACAACTACACTTAACGGTCTTTGGCTTGATGACGTA<br>GTTTACTGTCCAAGACATGTGATCTGCACCTCTGAAGACATGCTTAACCCTAATTATGAAGATTTACTCATTCGTAA<br>GTCTAATCATAATTTCTTGGTACAGGCTGGTAATGTTCAACTCAGGGTTATTGGACATTCTATGCAAAATTGTGTAC<br>TTAAGCTTAAGGTTGATACAGCCAATCCTAAGACACCTAAGTATAAGTTTGTTCGCATTCAACCAGGACAGACTTT<br>TTCAGTGTTAGCTTGTTACAATGGTTCACCATCTGGTGTTTACCAATGTGCTATGAGGCCCAATTTCACTATTAAGG<br>GTTCATTCCTTAATGGTTCATGTGGTAGTGTTGGTTTTAACATAGATTATGACTGTGTCTCTTTTTGTTACATGCACC<br>ATATGGAATTACCAACTGGAGTTCATGCTGGCACAGACTTAGAAGGTAACTTTTATGGACCTTTTGTTGACAGGCA<br>AACAGCACAAGCAGCTGGTACGGACACAACTATTACAGTTAATGTTTTAGCTTGGTTGTACGCTGCTGTTATAAAT<br>GGAGACAGGTGGTTTCTCAATCGATTTACCACAACTCTTAATGACTTTAACCTTGTGGCTATGAAGTACAATTATG<br>AACCTCTAACACAAGACCATGTTGACATACTAGGACCTCTTTCTGCTCAAACTGGAATTGCCGTTTTAGATATGTGT<br>GCTTCATTAAAAGAATTACTGCAAAATGGTATGAATGGACGTACCATATTGGGTAGTGCTTTATTAGAAGATGAAT<br>TTACACCTTTTGATGTTGTTAGACAATGCTCAGGTGTTACTTTCCAAAGTGCAGTGAAAAGAACAATCAAGGGTAC<br>ACACCACTGGTTGTTACTCACAATTTTGACTTCACTTTTAGTTTTAGTCCAGAGTACTCAATGGTCTTTGTTCTTTTT<br>TTTGTATGAAAATGCCTTTTTACCTTTTGCTATGGGTATTATTGCTATGTCTGCTTTTGCAATGATGTTTGTCAAACA<br>TAAGCATGCATTTCTCTGTTTGTTTTTGTTACCTTCTCTTGCCACTGTAGCTTATTTTAATATGGTCTATATGCCTGCT<br>AGTTGGGTGATGCGTATTATGACATGGTTGGATATGGTTGATACTAGTTTGTCTGGTTTTAAGCTAAAAGACTGTGT<br>TATGTATGCATCAGCTGTAGTGTTACTAATCCTTATGACAGCAAGAACTGTGTATGATGATGGTGCTAGGAGAGTG<br>TGGACACTTATGAATGTCTTGACACTCGTTTATAAAGTTTATTATGGTAATGCTTTAGATCAAGCCATTTCCATGTG<br>GGCTCTTATAATCTCTGTTACTTCTAACTACTCAGGTGTAGTTACAACTGTCATGTTTTTGGCCAGAGGTATTGTTTT |

-continued

| SEQUENCE LISTING |
|---|
| TATGTGTGTTGAGTATTGCCCTATTTTCTTCATAACTGGTAATACACTTCAGTGTATAATGCTAGTTTATTGTTTCTT |
| AGGCTATTTTTGTACTTGTTACTTTGGCCTCTTTTGTTTACTCAACCGCTACTTTAGACTGACTCTTGGTGTTTATGA |
| TTACTTAGTTTCTACACAGGAGTTTAGATATATGAATTCACAGGGACTACTCCCACCCAAGAATAGCATAGATGCC |
| TTCAAACTCAACATTAAATTGTTGGGTGTTGGTGGCAAACCTTGTATCAAAGTAGCCACTGTACAGTCTAAAATGT |
| CAGATGTAAAGTGCACATCAGTAGTCTTACTCTCAGTTTTGCAACAACTCAGAGTAGAATCATCATCTAAATTGTG |
| GGCTCAATGTGTCCAGTTACACAATGACATTCTCTTAGCTAAAGATACTACTGAAGCCTTTGAAAAAATGGTTTCA |
| CTACTTTCTGTTTTGCTTTCCATGCAGGGTGCTGTAGACATAAACAAGCTTTGTGAAGAAATGCTGGACAACAGGG |
| CAACCTTACAAGCTATAGCCTCAGAGTTTAGTTCCCTTCCATCATATGCAGCTTTTGCTACTGCTCAAGAAGCTTAT |
| GAGCAGGCTGTTGCTAATGGTGATTCTGAAGTTGTTCTTAAAAAGTTGAAGAAGTCTTTGAATGTGGCTAAATCTG |
| AATTTGACCGTGATGCAGCCATGCAACGTAAGTTGGAAAAGATGGCTGATCAAGCTATGACCCAAATGTATAAAC |
| AGGCTAGATCTGAGGACAAGAGGGCAAAAGTTACTAGTGCTATGCAGACAATGCTTTTCACTATGCTTAGAAAGTT |
| GGATAATGATGCACTCAACAACATTATCAACAATGCAAGAGATGGTTGTGTTCCCTTGAACATAATACCTCTTACA |
| ACAGCAGCCAAACTAATGGTTGTCATACCAGACTATAACACATATAAAAATACGTGTGATGGTACAACATTTACTT |
| ATGCATCAGCATTGTGGGAAATCCAACAGGTTGTAGATGCAGATAGTAAAATTGTTCAACTTAGTGAAATTAGTAT |
| GGACAATTCACCTAATTTAGCATGGCCTCTTATTGTAACAGCTTTAAGGGCCAATTCTGCTGTCAAATTACAGAAT |
| AATGAGCTTAGTCCTGTTGCACTACGACAGATGTCTTGTGCTGCCGGTACTACACAAACTGCTTGCACTGATGACA |
| ATGCGTTAGCTTACTACAACACAACAAAGGGAGGTAGGTTTGTACTTGCACTGTTATCCGATTTACAGGATTTGAA |
| ATGGGCTAGATTCCCTAAGAGTGATGGAACTGGTACTATCTATACAGAACTGGAACCACCTTGTAGGTTTGTTACA |
| GACACACCTAAAGGTCCTAAAGTGAAGTATTTATACTTTATTAAAGGATTAAACAACCTAAATAGAGGTATGGTAC |
| TTGGTAGTTTAGCTGCCACAGTACGTCTACAAGCTGGTAATGCAACAGAAGTGCCTGCCAATTCAACTGTATTATC |
| TTTCTGTGCTTTTGCTGTAGATGCTGCTAAAGCTTACAAAGATTATCTAGCTAGTGGGGGACAACCAATCACTAATT |
| GTGTTAAGATGTTGTGTACACACACTGGTACTGGTCAGGCAATAACAGTTACACCGGAAGCCAATATGGATCAAG |
| AATCCTTTGGTGGTGCATCGTGTTGTCTGTACTGCCGTTGCCACATAGATCATCCAAATCCTAAAGGATTTTGTGAC |
| TTAAAAGGTAAGTATGTACAAATACCTACAACTTGTGCTAATGACCCTGTGGGTTTTACACTTAAAAACACAGTCT |
| GTACCGTCTGCGGTATGTGGAAAGGTTATGGCTGTAGTTGTGATCAACTCCGCGAACCCATGCTTCAGTCAGCTGA |
| TGCACAATCGTTTTTAAACGGGTTTGCGGTGTAAGTGCAGCCCGTCTTACACCGTGCGGCACAGGCACTAGTACTG |
| ATGTCGTATACAGGGCTTTTGACATCTACAATGATAAAGTAGCTGGTTTTGCTAAATTCCTAAAAACTAATTGTTGT |
| CGCTTCCAAGAAAAGGACGAAGATGACAATTTAATTGATTCTTACTTTGTAGTTAAGAGACACACTTTCTCTAACT |
| ACCAACATGAAGAAACAATTTATAATTTACTTAAGGATTGTCCAGCTGTTGCTAAACATGACTTCTTTAAGTTTAG |
| AATAGACGGTGACATGGTACCACATATATCACGTCAACGTCTTACTAAATACACAATGGCAGACCTCGTCTATGCT |
| TTAAGGCATTTTGATGAAGGTAATTGTGACACATTAAAAGAAATACTTGTCACATACAATTGTTGTGATGATGATT |
| ATTTCAATAAAAAGGACTGGTATGATTTTGTAGAAAACCCAGATATATTACGCGTATACGCCAACTTAGGTGAACG |
| TGTACGCCAAGCTTTGTTAAAAACAGTACAATTCTGTGATGCCATGCGAAATGCTGGTATTGTTGGTGTACTGACA |
| TTAGATAATCAAGATCTCAATGGTAACTGGTATGATTTCGGTGATTTCATACAAACCACGCCAGGTAGTGGAGTTC |
| CTGTTGTAGATTCTTATTATTCATTGTTAATGCCTATATTAACCTTGACCAGGGCTTTAACTGCAGAGTCACATGTT |
| GACACTGACTTAACAAAGCCTTACATTAAGTGGGATTTGTTAAAATATGACTTCACGGAAGAGAGGTTAAAACTCT |
| TTGACCGTTATTTTAAATATTGGGATCAGACATACCACCCAAATTGTGTTAACTGTTTGGATGACAGATGCATTCTG |
| CATTGTGCAAACTTTAATGTTTTATTCTCTACAGTGTTCCCACCTACAAGTTTTGGACCACTAGTGAGAAAAATATT |
| TGTTGATGGTGTTCCATTTGTAGTTTCAACTGGATACCACTTCAGAGAGCTAGGTGTTGTACATAATCAGGATGTAA |
| ACTTACATAGCTCTAGACTTAGTTTTAAGGAATTACTTGTGTATGCTGCTGACCCTGCTATGCACGCTGCTTCTGGT |
| AATCTATTACTAGATAAACGCACTACGTGCTTTTCAGTAGCTGCACTTACTAACAATGTTGCTTTTCAAACTGTCAA |
| ACCCGGTAATTTTAACAAAGACTTCTATGACTTTGCTGTGTCTAAGGGTTTCTTTAAGGAAGGAAGTTCTGTTGAAT |
| TAAAACACTTCTTCTTTGCTCAGGATGGTAATGCTGCTATCAGCGATTATGACTACTATCGTTATAATCTACCAACA |
| ATGTGTGATATCAGACAACTACTATTTGTAGTTGAAGTTGTTGATAAGTACTTTGATTGTTACGATGGTGGCTGTAT |
| TAATGCTAACCAAGTCATCGTCAACAACCTAGACAAATCAGCTGGTTTTCCATTTAATAAATGGGGTAAGGCTAGA |
| CTTTATTATGATTCAATGAGTTATGAGGATCAAGATGCACTTTTCGCATATACAAAACGTAATGTCATCCCTACTAT |
| AACTCAAATGAATCTTAAGTATGCCATTAGTGCAAAGAATAGAGCTCGCACCGTAGCTGGTGTCTCTATCTGTAGT |
| ACTATGACCAATAGACAGTTTCATCAAAAATTATTGAAATCAATAGCCGCCACTAGAGGAGCTACTGTAGTAATTG |
| GAACAAGCAAATTCTATGGTGGTTGGCACAACATGTTAAAAACTGTTTATAGTGATGTAGAAAACCCTCACCTTAT |
| GGGTTGGGATTATCCTAAATGTGATAGAGCCATGCCTAACATGCTTAGAATTATGGCCTCACTTGTTCTTGCTCGCA |
| AACATACAACGTGTTGTAGCTTGTCACACCGTTTCTATAGATTAGCTAATGAGTGTGCTCAAGTATTGAGTGAAAT |

-continued

| SEQUENCE LISTING |
|---|
| GGTCATGTGTGGCGGTTCACTATATGTTAAACCAGGTGGAACCTCATCAGGAGATGCCACAACTGCTTATGCTAAT |
| AGTGTTTTTAACATTTGTCAAGCTGTCACGGCCAATGTTAATGCACTTTTATCTACTGATGGTAACAAAATTGCCGA |
| TAAGTATGTCCGCAATTTACAACACAGACTTTATGAGTGTCTCTATAGAAATAGAGATGTTGACACAGACTTTGTG |
| AATGAGTTTTACGCATATTTGCGTAAACATTTCTCAATGATGATACTCTCTGACGATGCTGTTGTGTGTTTCAATAG |
| CACTTATGCATCTCAAGGTCTAGTGGCTAGCATAAAGAACTTTAAGTCAGTTCTTTATTATCAAAACAATGTTTTTA |
| TGTCTGAAGCAAAATGTTGGACTGAGACTGACCTTACTAAAGGACCTCATGAATTTTGCTCTCAACATACAATGCT |
| AGTTAAACAGGGTGATGATTATGTGTACCTTCCTTACCCAGATCCATCAAGAATCCTAGGGGCCGGCTGTTTTGTA |
| GATGATATCGTAAAAACAGATGGTACACTTATGATTGAACGGTTCGTGTCTTTAGCTATAGATGCTTACCCACTTA |
| CTAAACATCCTAATCAGGAGTATGCTGATGTCTTTCATTTGTACTTACAATACATAAGAAAGCTACATGATGAGTT |
| AACAGGACACATGTTAGACATGTATTCTGTTATGCTTACTAATGATAACACTTCAAGGTATTGGGAACCTGAGTTT |
| TATGAGGCTATGTACACACCGCATACAGTCTTACAGGCTGTTGGGGCTTGTGTTCTTTGCAATTCACAGACTTCATT |
| AAGATGTGGTGCTTGCATACGTAGACCATTCTTATGTTGTAAATGCTGTTACGACCATGTCATATCAACATCACATA |
| AATTAGTCTTGTCTGTTAATCCGTATGTTTGCAATGCTCCAGGTTGTGATGTCACAGATGTGACTCAACTTTACTTA |
| GGAGGTATGAGCTATTATTGTAAATCACATAAACCACCCATTAGTTTTCCATTGTGTGCTAATGGACAAGTTTTTGG |
| TTTATATAAAAATACATGTGTTGGTAGCGATAATGTTACTGACTTTAATGCAATTGCAACATGTGACTGGACAAAT |
| GCTGGTGATTACATTTTAGCTAACACCTGTACTGAAAGACTCAAGCTTTTTGCAGCAGAAACGCTCAAAGCTACTG |
| AGGAGACATTTAAACTGTCTTATGGTATTGCTACTGTACGTGAAGTGCTGTCTGACAGAGAATTACATCTTTCATG |
| GGAAGTTGGTAAACCTAGACCACCACTTAACCGAAATTATGTCTTTACTGGTTATCGTGTAACTAAAAACAGTAAA |
| GTACAAATAGGAGAGTACACCTTTGAAAAAGGTGACTATGGTGATGCTGTTGTTTACCGAGGTACAACAACTTACA |
| AATTAAATGTTGGTGATTATTTTGTGCTGACATCACATACAGTAATGCCATTAAGTGCACCTACACTAGTGCCACA |
| AGAGCACTATGTTAGAATTACTGGCTTATACCCAACACTCAATATCTCAGATGAGTTTTCTAGCAATGTTGCAAATT |
| ATCAAAAGGTTGGTATGCAAAAGTATTCTACACTCCAGGGACCACCTGGTACTGGTAAGAGTCATTTTGCTATTGG |
| CCTAGCTCTCTACTACCCTTCTGCTCGCATAGTGTATACAGCTTGCTCTCATGCCGCTGTTGATGCACTATGTGAGA |
| AGGCATTAAAATATTTGCCTATAGATAAATGTAGTAGAATTATACCTGCACGTGCTCGTGTAGAGTGTTTTGATAA |
| ATTCAAAGTGAATTCAACATTAGAACAGTATGTCTTTTGTACTGTAAATGCATTGCCTGAGACGACAGCAGATATA |
| GTTGTCTTTGATGAAATTTCAATGGCCACAAATTATGATTTGAGTGTTGTCAATGCCAGATTACGTGCTAAGCACTA |
| TGTGTACATTGGCGACCCTGCTCAATTACCTGCACCACGCACATTGCTAACTAAGGGCACACTAGAACCAGAATAT |
| TTCAATTCAGTGTGTAGACTTATGAAAACTATAGGTCCAGACATGTTCCTCGGAACTTGTCGGCGTTGTCCTGCTGA |
| AATTGTTGACACTGTGAGTGCTTTGGTTTATGATAATAAGCTTAAAGCACATAAAGACAAATCAGCTCAATGCTTT |
| AAAATGTTTTATAAGGGTGTTATCACGCATGATGTTTCATCTGCAATTAACAGGCCACAAATAGGCGTGGTAAGAG |
| AATTCCTTACACGTAACCCTGCTTGGAGAAAAGCTGTCTTTATTTCACCTTATAATTCACAGAATGCTGTAGCCTCA |
| AAGATTTTGGGACTACCAACTCAAACTGTTGATTCATCACAGGGCTCAGAATATGACTATGTCATATTCACTCAAA |
| CCACTGAAACAGCTCACTCTTGTAATGTAAACAGATTTAATGTTGCTATTACCAGAGCAAAAGTAGGCATACTTTG |
| CATAATGTCTGATAGAGACCTTTATGACAAGTTGCAATTTACAAGTCTTGAAATTCCACGTAGGAATGTGGCAACT |
| TTACAAGCTGAAAATGTAACAGGACTCTTTAAAGATTGTAGTAAGGTAATCACTGGGTTACATCCTACACAGGCAC |
| CTACACACCTCAGTGTTGACACTAAATTCAAAACTGAAGGTTTATGTGTTGACATACCTGGCATACCTAAGGACAT |
| GACCTATAGAAGACTCATCTCTATGATGGGTTTTAAAATGAATTATCAAGTTAATGGTTACCCTAACATGTTTATCA |
| CCCGCGAAGAAGCTATAAGACATGTACGTGCATGGATTGGCTTCGATGTCGAGGGGTGTCATGCTACTAGAGAAG |
| CTGTTGGTACCAATTTACCTTTACAGCTAGGTTTTTCTACAGGTGTTAACCTAGTTGCTGTACCTACAGGTTATGTT |
| GATACACCTAATAATACAGATTTTTCCAGAGTTAGTGCTAAACCACCGCCTGGAGATCAATTTAAACACCTCATAC |
| CACTTATGTACAAAGGACTTCCTTGGAATGTAGTGCGTATAAAGATTGTACAAATGTTAAGTGACACACTTAAAAA |
| TCTCTCTGACAGAGTCGTATTTGTCTTATGGGCACATGGCTTTGAGTTGACATCTATGAAGTATTTTGTGAAAATAG |
| GACCTGAGCGCACCTGTTGTCTATGTGATAGACGTGCCACATGCTTTTCCACTGCTTCAGACACTTATGCCTGTTGG |
| CATCATTCTATTGGATTTGATTACGTCTATAATCCGTTTATGATTGATGTTCAACAATGGGGTTTTACAGGTAACCT |
| ACAAAGCAACCATGATCTGTATTGTCAAGTCCATGGTAATGCACATGTAGCTAGTTGTGATGCAATCATGACTAGG |
| TGTCTAGCTGTCCACGAGTGCTTTGTTAAGCGTGTTGACTGGACTATTGAATATCCTATAATTGGTGATGAACTGAA |
| GATTAATGCGGCTTGTAGAAAGGTTCAACACATGGTTGTTAAAGCTGCATTATTAGCAGACAAATTCCCAGTTCTT |
| CACGACATTGGTAACCCTAAAGCTATTAAGTGTGTACCTCAAGCTGATGTAGAATGGAAGTTCTATGATGCACAGC |
| CTTGTAGTGACAAAGCTTATAAAATAGAAGAATTATTCTATTCTTATGCCACACATTCTGACAAATTCACAGATGG |
| TGTATGCCTATTTTGGAATTGCAATGTCGATAGATATCCTGCTAATTCCATTGTTTGTAGATTTGACACTAGAGTGC |
| TATCTAACCTTAACTTGCCTGGTTGTGATGGTGGCAGTTTGTATGTAAATAAACATGCATTCCACACACCAGCTTTT |

-continued

| SEQUENCE LISTING |
|---|
| GATAAAAGTGCTTTTGTTAATTTAAAACAATTACCATTTTTCTATTACTCTGACAGTCCATGTGAGTCTCATGGAAA |
| ACAAGTAGTGTCAGATATAGATTATGTACCACTAAAGTCTGCTACGTGTATAACACGTTGCAATTTAGGTGGTGCT |
| GTCTGTAGACATCATGCTAATGAGTACAGATTGTATCTCGATGCTTATAACATGATGATCTCAGCTGGCTTTAGCTT |
| GTGGGTTTACAAACAATTTGATACTTATAACCTCTGGAACACTTTTACAAGACTTCAGAGTTTAGAAAATGTGGCT |
| TTTAATGTTGTAAATAAGGGACACTTTGATGGACAACAGGGTGAAGTACCAGTTTCTATCATTAATAACACTGTTT |
| ACACAAAAGTTGATGGTGTTGATGTAGAATTGTTTGAAAATAAAACAACATTACCTGTTAATGTAGCATTTGAGCT |
| TTGGGCTAAGCGCAACATTAAACCAGTACCAGAGGTGAAAATACTCAATAATTTGGGTGTGGACATTGCTGCTAAT |
| ACTGTGATCTGGGACTACAAAAGAGATGCTCCAGCACATATATCTACTATTGGTGTTTGTTCTATGACTGACATAG |
| CCAAGAAACCAACTGAAACGATTTGTGCACCACTCACTGTCTTTTTTGATGGTAGAGTTGATGGTCAAGTAGACTT |
| ATTTAGAAATGCCCGTAATGGTGTTCTTATTACAGAAGGTAGTGTTAAAGGTTTACAACCATCTGTAGGTCCCAAA |
| CAAGCTAGTCTTAATGGAGTCACATTAATTGGAGAAGCCGTAAAAACACAGTTCAATTATTATAAGAAAGTTGATG |
| GTGTTGTCCAACAATTACCTGAAACTTACTTTACTCAGAGTAGAAATTTACAAGAATTTAAACCCAGGAGTCAAAT |
| GGAAATTGATTTCTTAGAATTAGCTATGGATGAATTCATTGAACGGTATAAATTAGAAGGCTATGCCTTCGAACAT |
| ATCGTTTATGGAGATTTTAGTCATAGTCAGTTAGGTGGTTTACATCTACTGATTGGACTAGCTAAACGTTTTAAGGA |
| ATCACCTTTTGAATTAGAAGATTTTATTCCTATGGACAGTACAGTTAAAAACTATTTCATAACAGATGCGCAAACA |
| GGTTCATCTAAGTGTGTGTGTTCTGTTATTGATTTATTACTTGATGATTTTGTTGAAATAATAAAATCCCAAGATTT |
| ATCTGTAGTTTCTAAGGTTGTCAAAGTGACTATTGACTATACAGAAATTTCATTTATGCTTTGGTGTAAAGATGGCC |
| ATGTAGAAACATTTTACCCAAAATTACAATCTAGTCAAGCGTGGCAACCGGGTGTTGCTATGCCTAATCTTTACAA |
| AATGCAAAGAATGCTATTAGAAAAGTGTGACCTTCAAAATTATGGTGATAGTGCAACATTACCTAAAGGCATAAT |
| GATGAATGTCGCAAAATATACTCAACTGTGTCAATATTTAAACACATTAACATTAGCTGTACCCTATAATATGAGA |
| GTTATACATTTTGGTGCTGGTTCTGATAAAGGAGTTGCACCAGGTACAGCTGTTTTAAGACAGTGGTTGCCTACGG |
| GTACGCTGCTTGTCGATTCAGATCTTAATGACTTTGTCTCTGATGCAGATTCAACTTTGATTGGTGATTGTGCAACT |
| GTACATACAGCTAATAAATGGGATCTCATTATTAGTGATATGTACGACCCTAAGACTAAAAATGTTACAAAAGAA |
| AATGACTCTAAAGAGGGTTTTTTCACTTACATTTGTGGGTTTATACAACAAAAGCTAGCTCTTGGAGGTTCCGTGGC |
| TATAAAGATAACAGAACATTCTTGGAATGCTGATCTTTATAAGCTCATGGGACACTTCGCATGGTGGACAGCCTTT |
| GTTACTAATGTGAATGCGTCATCATCTGAAGCATTTTTAATTGGATGTAATTATCTTGGCAAACCACGCGAACAAA |
| TAGATGGTTATGTCATGCATGCAAATTACATATTTTGGAGGAATACAAATCCAATTCAGTTGTCTTCCTATTCTTTA |
| TTTGACATGAGTAAATTTCCCCTTAAATTAAGGGGTACTGCTGTTATGTCTTTAAAAGAAGGTCAAATCAATGATA |
| TGATTTTATCTCTTCTTAGTAAAGGTAGACTTATAATTAGAGAAAACAACAGAGTTGTTATTTCTAGTGATGTTCTT |
| GTTAACAACTAAACGAACAATGTTTGTTTTTCTTGTTTTATTGCCACTAGTCTCTAGTCAGTGTGTTAATCTTACAAC |
| CAGAACTCAATTACCCCCTGCATACACTAATTCTTTCACACGTGGTGTTTATTACCCTGACAAAGTTTTCAGATCCT |
| CAGTTTTACATTCAACTCAGGACTTGTTCTTACCTTTCTTTTCCAATGTTACTTGGTTCCATGCTATACATGTCTCTG |
| GGACCAATGGTACTAAGAGGTTTGATAACCCTGTCCTACCATTTAATGATGGTGTTTATTTTGCTTCCACTGAGAAG |
| TCTAACATAATAAGAGGCTGGATTTTTGGTACTACTTTAGATTCGAAGACCCAGTCCCTACTTATTGTTAATAACGC |
| TACTAATGTTGTTATTAAAGTCTGTGAATTTCAATTTTGTAATGATCCATTTTTGGGTGTTTATTACCACAAAAACA |
| ACAAAAGTTGGATGGAAAGTGAGTTCAGAGTTTATTCTAGTGCGAATAATTGCACTTTTGAATATGTCTCTCAGCC |
| TTTTCTTATGGACCTTGAAGGAAAACAGGGTAATTTCAAAAATCTTAGGGAATTTGTGTTTAAGAATATTGATGGT |
| TATTTTAAAATATATTCTAAGCACACGCCTATTAATTTAGTGCGTGATCTCCCTCAGGGTTTTTCGGCTTTAGAACC |
| ATTGGTAGATTTGCCAATAGGTATTAACATCACTAGGTTTCAAACTTTACTTGCTTTACATAGAAGTTATTTGACTC |
| CTGGTGATTCTTCTTCAGGTTGGACAGCTGGTGCTGCAGCTTATTATGTGGGTTATCTTCAACCTAGGACTTTTCTA |
| TTAAAATATAATGAAAATGGAACCATTACAGATGCTGTAGACTGTGCACTTGACCCTCTCTCAGAAACAAAGTGTA |
| CGTTGAAATCCTTCACTGTAGAAAAAGGAATCTATCAAACTTCTAACTTTAGAGTCCAACCAACAGAATCTATTGT |
| TAGATTTCCTAATATTACAAACTTGTGCCCTTTTGGTGAAGTTTTTAACGCCACCAGATTTGCATCTGTTTATGCTTG |
| GAACAGGAAGAGAATCAGCAACTGTGTTGCTGATTATTCTGTCCTATATAATTCCGCATCATTTTCCACTTTTAAGT |
| GTTATGGAGTGTCTCCTACTAAATTAAATGATCTCTGCTTTACTAATGTCTATGCAGATTCATTTGTAATTAGAGGT |
| GATGAAGTCAGACAAATCGCTCCAGGGCAAACTGGAAAGATTGCTGATTATAATTATAAATTACCAGATGATTTTA |
| CAGGCTGCGTTATAGCTTGGAATTCTAACAATCTTGATTCTAAGGTTGGTGGTAATTATAATTACCTGTATAGATTG |
| TTTAGGAAGTCTAATCTCAAACCTTTTGAGAGAGATATTTCAACTGAAATCTATCAGGCCGGTAGCACACCTTGTA |
| ATGGTGTTGAAGGTTTTAATTGTTACTTTCCTTTACAATCATATGGTTTCCAACCCACTAATGGTGTTGGTTACCAA |
| CCATACAGAGTAGTAGTACTTTCTTTTGAACTTCTACATGCACCAGCAACTGTTTGTGGACCTAAAAAGTCTACTAA |
| TTTGGTTAAAAACAAATGTGTCAATTTCAACTTCAATGGTTTAACAGGCACAGGTGTTCTTACTGAGTCTAACAAA |

-continued

SEQUENCE LISTING

AAGTTTCTGCCTTTCCAACAATTTGGCAGAGACATTGCTGACACTACTGATGCTGTCCGTGATCCACAGACACTTG
AGATTCTTGACATTACACCATGTTCTTTTGGTGGTGTCAGTGTTATAACACCAGGAACAAATACTTCTAACCAGGTT
GCTGTTCTTTATCAGGATGTTAACTGCACAGAAGTCCCTGTTGCTATTCATGCAGATCAACTTACTCCTACTTGGCG
TGTTTATTCTACAGGTTCTAATGTTTTTCAAACACGTGCAGGCTGTTTAATAGGGGCTGAACATGTCAACAACTCAT
ATGAGTGTGACATACCCATTGGTGCAGGTATATGCGCTAGTTATCAGACTCAGACTAATTCTCCTCGGCGGGCACG
TAGTGTAGCTAGTCAATCCATCATTGCCTACACTATGTCACTTGGTGCAGAAAATTCAGTTGCTTACTCTAATAACT
CTATTGCCATACCCACAAATTTTACTATTAGTGTTACCACAGAAATTCTACCAGTGTCTATGACCAAGACATCAGTA
GATTGTACAATGTACATTTGTGGTGATTCAACTGAATGCAGCAATCTTTTGTTGCAATATGGCAGTTTTTGTACACA
ATTAAACCGTGCTTTAACTGGAATAGCTGTTGAACAAGACAAAAACACCCAAGAAGTTTTTGCACAAGTCAAACA
AATTTACAAAACACCACCAATTAAAGATTTTGGTGGTTTTAATTTTTCACAAATATTACCAGATCCATCAAAACCA
AGCAAGAGGTCATTTATTGAAGATCTACTTTTCAACAAAGTGACACTTGCAGATGCTGGCTTCATCAAACAATATG
GTGATTGCCTTGGTGATATTGCTGCTAGAGACCTCATTTGTGCACAAAAGTTTAACGGCCTTACTGTTTTGCCACCT
TTGCTCACAGATGAAATGATTGCTCAATACACTTCTGCACTGTTAGCGGGTACAATCACTTCTGGTTGGACCTTTGG
TGCAGGTGCTGCATTACAAATACCATTTGCTATGCAAATGGCTTATAGGTTTAATGGTATTGGAGTTACACAGAAT
GTTCTCTATGAGAACCAAAAATTGATTGCCAACCAATTTAATAGTGCTATTGGCAAAATTCAAGACTCACTTTCTTC
CACAGCAAGTGCACTTGGAAAACTTCAAGATGTGGTCAACCAAAATGCACAAGCTTTAAACACGCTTGTTAAACA
ACTTAGCTCCAATTTTGGTGCAATTTCAAGTGTTTTAAATGATATCCTTTCACGTCTTGACAAAGTTGAGGCTGAAG
TGCAAATTGATAGGTTGATCACAGGCAGACTTCAAAGTTTGCAGACATATGTGACTCAACAATTAATTAGAGCTGC
AGAAATCAGAGCTTCTGCTAATCTTGCTGCTACTAAAATGTCAGAGTGTGTACTTGGACAATCAAAAAGAGTTGAT
TTTTGTGGAAAGGGCTATCATCTTATGTCCTTCCCTCAGTCAGCACCTCATGGTGTAGTCTTCTTGCATGTGACTTAT
GTCCCTGCACAAGAAAAGAACTTCACAACTGCTCCTGCCATTTGTCATGATGGAAAAGCACACTTTCCTCGTGAAG
GTGTCTTTGTTTCAAATGGCACACACTGGTTTGTAACACAAAGGAATTTTTATGAACCACAAATCATTACTACAGA
CAACACATTTGTGTCTGGTAACTGTGATGTTGTAATAGGAATTGTCAACAACACAGTTTATGATCCTTTGCAACCTG
AATTAGACTCATTCAAGGAGGAGTTAGATAAATATTTTAAGAATCATACATCACCAGATGTTGATTTAGGTGACAT
CTCTGGCATTAATGCTTCAGTTGTAAACATTCAAAAAGAAATTGACCGCCTCAATGAGGTTGCCAAGAATTTAAAT
GAATCTCTCATCGATCTCCAAGAACTTGGAAAGTATGAGCAGTATATAAAATGGCCATGGTACATTTGGCTAGGTT
TTATAGCTGGCTTGATTGCCATAGTAATGGTGACAATTATGCTTTGCTGTATGACCAGTTGCTGTAGTTGTCTCAAG
GGCTGTTGTTCTTGTGGATCCTGCTGCAAATTTGATGAAGACGACTCTGAGCCAGTGCTCAAAGGAGTCAAATTAC
ATTACACATAAACGAACTTATGGATTTGTTTATGAGAATCTTCACAATTGGAACTGTAACTTTGAAGCAAGGTGAA
ATCAAGGATGCTACTCCTTCAGATTTTGTTCGCGCTACTGCAACGATACCGATACAAGCCTCACTCCCTTTCGGATG
GCTTATTGTTGGCGTTGCACTTCTTGCTGTTTTTCAGAGCGCTTCCAAAATCATAACCCTCAAAAAGAGATGGCAAC
TAGCACTCTCCAAGGGTGTTCACTTTGTTTGCAACTTGCTGTTGTTGTTTGTAACAGTTTACTCACACCTTTTGCTCG
TTGCTGCTGGCCTTGAAGCCCCTTTTCTCTATCTTTATGCTTTAGTCTACTTCTTGCAGAGTATAAACTTTGTAAGAA
TAATAATGAGGCTTTGGCTTTGCTGGAAATGCCGTTCCAAAAACCCATTACTTTATGATGCCAACTATTTTCTTTGC
TGGCATACTAATTGTTACGACTATTGTATACCTTACAATAGTGTAACTTCTTCAATTGTCATTACTTCAGGTGATGG
CACAACAAGTCCTATTTCTGAACATGACTACCAGATTGGTGGTTATACTGAAAAATGGGAATCTGGAGTAAAAGA
CTGTGTTGTATTACACAGTTACTTCACTTCAGACTATTACCAGCTGTACTCAACTCAATTGAGTACAGACACTGGTG
TTGAACATGTTACCTTCTTCATCTACAATAAAATTGTTGATGAGCCTGAAGAACATGTCCAAATTCACACAATCGA
CGGTTCATCCGGAGTTGTTAATCCAGTAATGGAACCAATTTATGATGAACCGACGACGACTACTAGCGTGCCTTTG
TAAGCACAAGCTGATGAGTACGAACTTATGTACTCATTCGTTTCGGAAGAGACAGGTACGTTAATAGTTAATAGCG
TACTTCTTTTTCTTGCTTTCGTGGTATTCTTGCTAGTTACACTAGCCATCCTTACTGCGCTTCGATTGTGTGCGTACT
GCTGCAATATTGTTAACGTGAGTCTTGTAAAACCTTCTTTTTACGTTTACTCTCGTGTTAAAAATCTGAATTCTTCTA
GAGTTCCTGATCTTCTGGTCTAAACGAACTAAATATTATATTAGTTTTTCTGTTTGGAACTTTAATTTTAGCCATGGC
AGATTCCAACGGTACTATTACCGTTGAAGAGCTTAAAAAGCTCCTTGAACAATGGAACCTAGTAATAGGTTTCCTA
TTCCTTACATGGATTTGTCTTCTACAATTTGCCTATGCCAACAGGAATAGGTTTTTGTATATAATTAAGTTAATTTTC
CTCTGGCTGTTATGGCCAGTAACTTTAGCTTGTTTTGTGCTTGCTGCTGTTTACAGAATAAATTGGATCACCGGTGG
AATTGCTATCGCAATGGCTTGTCTTGTAGGCTTGATGTGGCTCAGCTACTTCATTGCTTCTTTCAGACTGTTTGCGC
GTACGCGTTCCATGTGGTCATTCAATCCAGAAACTAACATTCTTCTCAACGTGCCACTCCATGGCACTATTCTGACC
AGACCGCTTCTAGAAAGTGAACTCGTAATCGGAGCTGTGATCCTTCGTGGACATCTTCGTATTGCTGGACACCATC
TAGGACGCTGTGACATCAAGGACCTGCCTAAAGAAATCACTGTTGCTACATCACGAACGCTTTCTTATTACAAATT
GGGAGCTTCGCAGCGTGTAGCAGGTGACTCAGGTTTTGCTGCATACAGTCGCTACAGGATTGGCAACTATAAATTA

-continued

SEQUENCE LISTING

AACACAGACCATTCCAGTAGCAGTGACAATATTGCTTTGCTTGTACAGTAAGTGACAACAGATGTTTCATCTCGTT
GACTTTCAGGTTACTATAGCAGAGATATTACTAATTATTATGAGGACTTTTAAAGTTTCCATTTGGAATCTTGATTA
CATCATAAACCTCATAATTAAAAATTTATCTAAGTCACTAACTGAGAATAAATATTCTCAATTAGATGAAGAGCAA
CCAATGGAGATTGATTAAACGAACATGAAAATTATTCTTTTCTTGGCACTGATAACACTCGCTACTTGTGAGCTTTA
TCACTACCAAGAGTGTGTTAGAGGTACAACAGTACTTTTAAAAGAACCTTGCTCTTCTGGAACATACGAGGGCAAT
TCACCATTTCATCCTCTAGCTGATAACAAATTTGCACTGACTTGCTTTAGCACTCAATTTGCTTTTGCTTGTCCTGAC
GGCGTAAAACACGTCTATCAGTTACGTGCCAGATCAGTTTCACCTAAACTGTTCATCAGACAAGAGGAAGTTCAAG
AACTTTACTCTCCAATTTTTCTTATTGTTGCGGCAATAGTGTTTATAACACTTTGCTTCACACTCAAAAGAAAGACA
GAATGATTGAACTTTCATTAATTGACTTCTATTTGTGCTTTTTAGCCTTTCTGCTATTCCTTGTTTTAATTATGCTTAT
TATCTTTTGGTTCTCACTTGAACTGCAAGATCATAATGAAACTTGTCACGCCTAAACGAACATGAAATTTCTTGTTT
TCTTAGGAATCATCACAACTGTAGCTGCATTTCACCAAGAATGTAGTTTACAGTCATGTACTCAACATCAACCATA
TGTAGTTGATGACCCGTGTCCTATTCACTTCTATTCTAAATGGTATATTAGAGTAGGAGCTAGAAAATCAGCACCTT
TAATTGAATTGTGCGTGGATGAGGCTGGTTCTAAATCACCCATTCAGTACATCGATATCGGTAATTATACAGTTTCC
TGTTTACCTTTTACAATTAATTGCCAGGAACCTAAATTGGGTAGTCTTGTAGTGCGTTGTTCGTTCTATGAAGACTT
TTTAGAGTATCATGACGTTCGTGTTGTTTTAGATTTCATCTAAACGAACAAACTAAAATGTCTGATAATGGACCCCA
AAATCAGCGAAATGCACCCCGCATTACGTTTGGTGGACCCTCAGATTCAACTGGCAGTAACCAGAATGGAGAACG
CAGTGGGGCGCGATCAAAACAACGTCGGCCCCAAGGTTTACCCAATAATACTGCGTCTTGGTTCACCGCTCTCACT
CAACATGGCAAGGAAGACCTTAAATTCCCTCGAGGACAAGGCGTTCCAATTAACACCAATAGCAGTCCAGATGAC
CAAATTGGCTACTACCGAAGAGCTACCAGACGAATTCGTGGTGGTGACGGTAAAATGAAAGATCTCAGTCCAAGA
TGGTATTTCTACTACCTAGGAACTGGGCCAGAAGCTGGACTTCCCTATGGTGCTAACAAAGACGGCATCATATGGG
TTGCAACTGAGGGAGCCTTGAATACACCAAAAGATCACATTGGCACCCGCAATCCTGCTAACAATGCTGCAATCGT
GCTACAACTTCCTCAAGGAACAACATTGCCAAAAGGCTTCTACGCAGAAGGGAGCAGAGGCGGCAGTCAAGCCTC
TTCTCGTTCCTCATCACGTAGTCGCAACAGTTCAAGAAATTCAACTCCAGGCAGCAGTAGGGGAACTTCTCCTGCT
AGAATGGCTGGCAATGGCGGTGATGCTGCTCTTGCTTTGCTGCTGCTTGACAGATTGAACCAGCTTGAGAGCAAAA
TGTCTGGTAAAGGCCAACAACAACAAGGCCAAACTGTCACTAAGAAATCTGCTGCTGAGGCTTCTAAGAAGCCTC
GGCAAAAACGTACTGCCACTAAAGCATACAATGTAACACAAGCTTTCGGCAGACGTGGTCCAGAACAAACCCAAG
GAAATTTTGGGGACCAGGAACTAATCAGACAAGGAACTGATTACAAACATTGGCCGCAAATTGCACAATTTGCCC
CCAGCGCTTCAGCGTTCTTCGGAATGTCGCGCATTGGCATGGAAGTCACACCTTCGGGAACGTGGTTGACCTACAC
AGGTGCCATCAAATTGGATGACAAAGATCCAAATTTCAAAGATCAAGTCATTTTGCTGAATAAGCATATTGACGCA
TACAAAACATTCCCACCAACAGAGCCTAAAAAGGACAAAAAGAAGAAGGCTGATGAAACTCAAGCCTTACCGCA
GAGACAGAAGAAACAGCAAACTGTGACTCTTCTTCCTGCTGCAGATTTGGATGATTTCTCCAAACAATTGCAACAA
TCCATGAGCAGTGCTGACTCAACTCAGGCCTAAACTCATGCAGACCACACAAGGCAGATGGGCTATATAAACGTTT
TCGCTTTTCCGTTTACGATATATAGTCTACTCTTGTGCAGAATGAATTCTCGTAACTACATAGCACAAGTAGATGTA
GTTAACTTTAATCTCACATAGCAATCTTTAATCAGTGTGTAACATTAGGGAGGACTTGAAAGAGCCACCACATTTT
CACCGAGGCCACGCGGAGTACGATCGAGTGTACAGTGAACAATGCTAGGGAGAGCTGCCTATATGGAAGAGCCCT
AATGTGTAAAATTAATTTAGTAGTGCTATCCCCATGTGATTTTAATAGCTTCTTAGGAGAATGACAAAAAAAAAA
AAAAAAAAAAAAAAAAAAAAAAA

SEQ ID NO: 2 (synthetic IBIS DNA construct 1; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA -continued

| SEQUENCE LISTING |
|---|
| CAACTGGACTTTATTGACACTAAGAGGGGTGTATACTGCTGCCGTGAACATGAGCATGAAATTGCTTGGTACACGG<br>AACGTTCTGAAAAGAGCTATGAATTGCAGACACCTTTTGAAATTAAATTGGCAAAGAAATTTGACACCTTCAATGG<br>GGAATGTCCAAATTTTGTATTTCCCTTAAATTCCATAATCAAGACTATTCAACCAAGGGTTGAAAAGAAAAAGCTT<br>GATGGCTTTATGGGTAGAATTCGATCTGTCTATCCAGTTGCGTCACCAAATGAATGCAACCAAATGTGCCTTTCAA<br>CTCTCATGAAGTGTGATCATTGTGGTGAAACTTCATGGCAGACGGGCGATTTTGTTAAAGCCACTTGCGAATTTTGT<br>GGCACTGAGAATTTGACTAAAGAAGGTGCCACTACTTGTGGTTACTTACCCCAAAATGCTGTTGTTAAAATTTATT<br>GTCCAGCATGTCACAATTCAGAAGTAGGACCTGAGCATAGTCTTGCCGAATACCATAATGAATCTGGCTTGAAAAC<br>CATTCTTCGTAAGGGTGGTCGCACTATTGCCTTTGGAGGCTGTGTGTTCTCTTATGTTGGTTGCCATAACAAGTGTG<br>CCTATTGGGTTCCACGTGCTAGCGCTAACATAGGTTGTAACCATACAGGTGTTGTTGGAGAAGGTTCCGAAGGTCT<br>TAATGACAACCTTCTTGAAATACTCCAAAAAGAGAAAGTCAACATCAATATTGTTGGTGACTTTAAACTTAATGAA<br>GAGATCGCCATTATTTTGGCATCTTTTTCTGCTTCCACAAGTGCTTTTGTGGAAACTGTGAAAGGTTTGGATTATAA<br>AGCATTCAAACAAATTGTTGAATCCTGTGGTAATTTTAAAGTTACAAAAGGAAAAGCTAAAAAAGGTGCCTGGAA<br>TATTGGTGAACAGAAATCAATACTGAGTCCTCTTTATGCATTTGCATCAGAGGCTGCTCGTGTTGTACGATCAATTT<br>TCTCCCGCACTCTTGAAACTGCTCAAAATTCTGTGCGTGTTTTACAGAAGGCCGCTATAACAATACTAGATGGAAT<br>TTCACAGTATTCACTGAGACTCATTGATGCTATGATGTTCACATCTGATTTGGCTACTAACAATCTAGTTGTAATGG<br>CCTACATTACAGGTGGTGTTGTTCAGTTGACTTCGCAGTGGCTAACTAACATCTTTGGCACTGTTTATGAAAAACTC<br>AAACCCGTCCTTGATTGGCTTGAAGAGAAGTTTAAGGAAGGTGTAGAGTTTCTTAGAGACGGTTGGGAAATTGTTA<br>AATTTATCTCAACCTGTGCTTGTGAAATTGTCGGTGGACAAATTGTCACCTGTGCAAAGGAAATTAAGGAGAGTGT<br>TCAGACATTCTTTAAGCTTGTAAATAAATTTTTGGCTTTGTGTGCTGACTCTATCATTATTGGTGGAGCTAAACTTA<br>AAGCCTTGAATTTAGGTGAAACATTTGTCACGCACTCAAAGGGATTGTACAGAAAGTGTGTTAAATCCAGAGAAG<br>AAACTGGCCTACTCATGCCTCTAAAAGCCCCAAAAGAAATTATCTTCTTAGAGGGAGAAACACTTCCCACAGAAGT<br>GTTAACAGAGGAAGTTGTCTTGAAAACTGGTGATTTACAACCATTAGAACAACCTACTAGTGAAGCTGTTGAAGCT<br>CCATTGGTTGGTACACCAGTTTGTATTAACGGGCTTATGTTGCTCGAAATCAAAGACACAGAAAAGTACTGTGCCC<br>TTGCACCTAATATGATGGTAACAAACAATACCTTCACACTCAAAGGCGGTGCACCAACAAAGGTTACTTTTGGTGA<br>TGACACTGTGATAGAAGTGCAAGGTTACAAGAGTGTGAATATCACTTTTGAACTTGATGAAAGGATTGATAAAGT<br>ACTTAATGAGAAGTGCTCTGCCTATACAGTTGAACTCGGTACAGAAGTAAATGAGTTCGCCTGTGTTGTGGCAGAT<br>GCTGTCATAAAAACTTTGCAACCAGTATCTGAATTACTTACACCACTGGGCATTGATTTAGATGAGTGGAGTATGG<br>CTACATACTACTTATTTGATGAGTCTGGTGAGTTTAAATTGGCTTCACATATGTATTGTTCTTTCTACCCTCCAGATG<br>AGGATGAAGAAGAAGGTGATTGTGAAGAAGAAGAGTTTGAGCCATCAACTCAATATGAGTATGGTACTGAAGATG<br>ATTACCAAGGTAAACCTTTGGAATTTGGTGCCACTTCTGCTGCTCTTCAACCTGAAGAAGAGCAAGAAGAAGATTG<br>GTTAGATGATGATAGTCAACAAACTGTTGGTCAACAAGACGGCAGTGAGGACAATCAGACAACTACTATTCAAAC<br>AATTGTTGAGGTTCAACCTCAATTAGAGATGGAACTTACACCAGTTGTTCAGACTATTGAAGTGAATAGTTTTAGT<br>GGTTATTTAAAACTTACTGACAATGTATACATTAAAAATGCAGACATTGTGGAAGAAGCTAAAAAGGTAAAACCA<br>ACAGTGGTTGTTAATGCAGCCAATGTTTACCTTAAACATGGAGGAGGTGTTGCAGGAGCCTTAAATAAGGCTACTA<br>ACAATGCCATGCAAGTTGAATCTGATGATTACATAGCTACTAATGGACCACTTAAAGTGGGTGGTAGTTGTGTTTT<br>AAGCGGACACAATCTTGCTAAACACTGTCTTCATGTTGTCGGCCCAAATGTTAACAAAGGTGAAGACATTCAACTT<br>CTTAAGAGTGCTTATGAAAATTTTAATCAGCACGAAGTTCTACTTGCACCATTATTATCAGCTGGTATTTTTGGTGC<br>TGACCCTATACATTCTTTAAGAGTTTGTGTAGATACTGTTCGCACAAATGTCTACTTAGCTGTCTTTGATAAAAATC<br>TCTATGACAAACTTGTTTCAAGCTTTTTGGAAATGAAGAGTGAAAAGCAAGTTGAACAAAAGATCGCTGAGATTCC<br>TAAAGAGGAAGTTAAGCCATTTATAACTGAAAGTAAACCTTCAGTTGAACAGAGAAAACAAGATGATAAGAAAAT<br>CAAAGCTTGTGTTGAAGAAGTTACAACAACTCTGGAAGAAACTAAGTTCCTCACAGAAAACTTGTTACTTTATATT<br>GACATTAATGGCAATCTTCATCCAGATTCTGCCACTCTTGTTAGTGACATTGACATCACTTTCTTAAAGAAAGATGC<br>TCCATATATAGTGGGTGATGTTGTTCAAGAGGGTGTTTTAACTGCTGTGGTTATACCTACTAAAAAGGCTGGTGGC<br>ACTACTGAAATGCTAGCGAAAGCTTTGAGAAAAGTGCCAACAGACAATTATATAACCACTTACCCGGGTCAGGGT<br>TTAAATGGTTACACTGTAGAGGAGGCAAAGACAGTGCTTAAAAAGTGTAAAAGTGCCTTTTACATTCTACCATCTA<br>TTATCTCTAATGAGAAGCAAGAAATTCTTGGAACTGTTTCTTGGAATTTGCGAGAAATGCTTGCACATGCAGAAGA<br>AACACGCAAATTAATGCCTGTCTGTGTGGAAACTAAAGCCATAGTTTCAACTATACAGCGTAAATATAAGGGTATT<br>AAAATACAAGAGGGTGTGGTTGATTATGGTGCTAGATTTTACTTTTACACCAGTAAAACAACTGTAGCGTCACTTA<br>TCAACACACTTAACGATCTAAATGAAACTCTTGTTACAATGCCACTTGGCTATGTAACACATGGCTTAAATTTGGA<br>AGAAGCTGCTCGGTATATGAGATCTCTCAAAGTGCCAGCTACAGTTTCTGTTTCTTCACCTGATGCTGTTACAGCGT<br>ATAATGGTTATCTTACTTCTTCTTCTAAAACACCTGAAGAACATTTTATTGAAACCATCTCACTTGCTGGTTCCTAT |

-continued

| SEQUENCE LISTING |
|---|
| AAAGATTGGTCCTATTCTGGACAATCTACACAACTAGGTATAGAATTTCTTAAGAGAGGTGATAAAAGTGTATATT |
| ACACTAGTAATCCTACCACATTCCACCTAGATGGTGAAGTTATCACCTTTGACAATCTTAAGACACTTCTTTCTTTG |
| AGAGAAGTGAGGACTATTAAGGTGTTTACAACAGTAGACAACATTAACCTCCACACGCAAGTTGTGGACATGTCA |
| ATGACATATGGACAACAGTTTGGTCCAACTTATTTGGATGGAGCTGATGTTACTAAAATAAAACCTCATAATTCAC |
| ATGAAGGTAAAACATTTTATGTTTTACCTAATGATGACACTCTACGTGTTGAGGCTTTTGAGTACTACCACACAACT |
| GATCCTAGTTTTCTGGGTAGGTACATGTCAGCATTAAATCACACTAAAAAGTGGAAATACCCACAAGTTAATGGTT |
| TAACTTCTATTAAATGGGCAGATAACAACTGTTATCTTGCCACTGCATTGTTAACACTCCAACAAATAGAGTTGAA |
| GTTTAATCCACCTGCTCTACAAGATGCTTATTACAGAGCAAGGGCTGGTGAAGCTGCTAACTTTTGTGCACTTATCT |
| TAGCCTACTGTAATAAGACAGTAGGTGAGTTAGGTGATGTTAGAGAAACAATGAGTTACTTGTTTCAACATGCCAA |
| TTTAGATTCTTGCAAAAGAGTCTTGAACGTGGTGTGTAAAACTTGTGGACAACAGCAGACAACCCTTAAGGGTGTA |
| GAAGCTGTTATGTACATGGGCACACTTTCTTATGAACAATTTAAGAAAGGTGTTCAGATACCTTGTACGTGTGGTA |
| AACAAGCTACAAAATATCTAGTACAACAGGAGTCACCTTTTGTTATGATGTCAGCACCACCTGCTCAGTATGAACT |
| TAAGCATGGTACATTTACTTGTGCTAGTGAGTACACTGGTAATTACCAGTGTGGTCACTATAAACATATAACTTCTA |
| AAGAAACTTTGTATTGCATAGACGGTGCTTTACTTACAAAGTCCTCAGAATACAAAGGTCCTATTACGGATGTTTT |
| CTACAAAGAAAACAGTTACACAACAACCATAAAACCAGTTACTTATAAATTGGATGGTGTTGTTTGTACAGAAATT |
| GACCCTAAGTTGGACAATTATTATAAGAAAGACAATTCTTATTTCACAGAGCAACCAATTGATCTTGTACCAAACC |
| AACCATATCCAAACGCAAGCTTCGATAATTTTAAGTTTGTATGTGATAATATCAAATTTGCTGATGATTTAAACCA |
| GTTAACTGGTTATAAGAAACCTGCTTCAAGAGAGCTTAAAGTTACATTTTTCCCTGACTTAAATGGTGATGTGGTG |
| GCTATTGATTATAAACACTACACACCCTCTTTTAAGAAAGGAGCTAAATTGTTACATAAACCTATTGTTTGGCATGT |
| TAACAATGCAACTAATAAAGCCACGTATAAACCAAATACCTGGTGTATACGTTGTCTTTGGAGCACAAAACCAGTT |
| GAAACATCAAATTCGTTTGATGTACTGAAGTCAGAGGACGCGCAGGGAATGGATAATCTTGCCTGCGAAGATCTA |
| AAACCAGTCTCTGAAGAAGTAGTGGAAAATCCTACCATACAGAAAGACGTTCTTGAGTGTAATGTGAAAACTACC |
| GAAGTTGTAGGAGACATTATACTTAAACCAGCAAATAATAGTTTAAAAATTACAGAAGAGGTTGGCCACACAGAT |
| CTAATGGCTGCTTATGTAGACAATTCTAGTCTTACTATTAAGAAACCTAATGAATTATCTAGAGTATTAGGTTTGAA |
| AACCCTTGCTACTCATGGTTTAGCTGCTGTTAATAGTGTCCCTTGGGATACTATAGCTAATTATGCTAAGCCTTTTC |
| TTAACAAAGTTGTTAGTACAACTACTAACATAGTTACACGGTGTTTAAACCGTGTTTGTACTAATTATATGCCTTAT |
| TTCTTTACTTTATTGCTACAATTGTGTACTTTTACTAGAAGTACAAATTCTAGAATTAAAGCATCTATGCCGACTAC |
| TATAGCAAAGAATACTGTTAAGAGTGTCGGTAAATTTTGTCTAGAGGCTTCATTTAATTATTTGAAGTCACCTAATT |
| TTTCTAAACTGATAAATATTATAATTTGGTTTTTACTATTAAGTGTTTGCCTAGGTTCTTTAATCTACTCAACCGCTG |
| CTTTAGGTGTTTTAATGTCTAATTTAGGCATGCCTTCTTACTGTACTGGTTACAGAGAAGGCTATTTGAACTCTACT |
| AATGTCACTATTGCAACCTACTGTACTGGTTCTATACCTTGTAGTGTTTGTCTTAGTGGTTTAGATTCTTTAGACACC |
| TATCCTTCTTTAGAAACTATACAAATTACCATTTCATCTTTTAAATGGGATTTAACTGCTTTTGGCTTAGTTGCAGA |
| GTGGTTTTTGGCATATATTCTTTTCACTAGGTTTTTCTATGTACTTGGATTGGCTGCAATCATGCAATTGTTTTTCAG |
| CTATTTTGCAGTACATTTTATTAGTAATTCTTGGCTTATGTGGTTAATAATTAATCTTGTACAAATGGCCCCGATTTC |
| AGCTATGGTTAGAATGTACATCTTCTTTGCATCATTTTATTATGTATGGAAAAGTTATGTGCATGTTGTAGACGGTT |
| GTAATTCATCAACTTGTATGATGTGTTACAAACGTAATAGAGCAACAAGAGTCGAATGTACAACTATTGTTAATGG |
| TGTTAGAAGGTCCTTTTATGTCTATGCTAATGGAGGTAAAGGCTTTTGCAAACTACACAATTGGAATTGTGTTAATT |
| GTGATACATTCTGTGCTGGTAGTACATTTATTAGTGATGAAGTTGCGAGAGACTTGTCACTACAGTTTAAAAGACC |
| AATAAATCCTACTGACCAGTCTTCTTACATCGTTGATAGTGTTACAGTGAAGAATGGTTCCATCCATCTTTACTTTG |
| ATAAAGCTGGTCAAAAGACTTATGAAAGACATTCTCTCTCTCATTTTGTTAACTTAGACAACCTGAGAGCTAATAA |
| CACTAAAGGTTCATTGCCTATTAATGTTATAGTTTTTGATGGTAAATCAAAATGTGAAGAATCATCTGCAAAATCA |
| GCGTCTGTTTACTACAGTCAGCTTATGTGTCAACCTATACTGTTACTAGATCAGGCATTAGTGTCTGATGTTGGTGA |
| TAGTGCGGAAGTTGCAGTTAAAATGTTTGATGCTTACGTTAATACGTTTTCATCAACTTTTAACGTACCAATGGAAA |
| AACTCAAAACACTAGTTGCAACTGCAGAAGCTGAACTTGCAAAGAATGTGTCCTTAGACAATGTCTTATCTACTTT |
| TATTTCAGCAGCTCGGCAAGGGTTTGTTGATTCAGATGTAGAAACTAAAGATGTTGTTGAATGTCTTAAATTGTCA |
| CATCAATCTGACATAGAAGTTACTGGCGATAGTTGTAATAACTATATGCTCACCTATAACAAAGTTGAAAACATGA |
| CACCCCGTGACCTTGGTGCTTGTATTGACTGTAGTGCGCGTCATATTAATGCGCAGGTAGCAAAAAGTCACAACAT |
| TGCTTTGATATGGAACGTTAAAGATTTCATGTCATTGTCTGAACAACTACGAAAACAAATACGTAGTGCTGCTAAA |
| AAGAATAACTTACCTTTTAAGTTGACATGTGCAACTACTAGACAAGTTGTTAATGTTGTAACAACAAAGATAGCAC |
| TTAAGGGTGGTAAAATTGTTAATAATTGGTTGAAGCAGTTAATTAAAGTTACACTTGTGTTCCTTTTTGTTGCTGCT |
| ATTTTCTATTTAATAACACCTGTTCATGTCATGTCTAAACATACTGACTTTTCAAGTGAAATCATAGGATACAAGGC |

-continued

SEQUENCE LISTING

TATTGATGGTGGTGTCACTCGTGACATAGCATCTACAGATACTTGTTTTGCTAACAAACATGCTGATTTTGACACAT
GGTTTAGCCAGCGTGGTGGTAGTTATACTAATGACAAAGCTTGCCCATTGATTGCTGCAGTCATAACAAGAGAAGT
GGGTTTTGTCGTGCCTGGTTTGCCTGGCACGATATTACGCACAACTAATGGTGACTTTTTGCATTTCTTACCTAGAG
TTTTTAGTGCAGTTGGTAACATCTGTTACACACCATCAAAACTTATAGAGTACACTGACTTTGCAACATCAGCTTGT
GTTTTGGCTGCTGAATGTACAATTTTTAAAGATGCTTCTGGTAAGCCAGTACCATATTGTTATGATACCAATGTACT
AGAAGGTTCTGTTGCTTATGAAAGTTTACGCCCTGACACACGTTATGTGCTCATGGATGGCTCTATTATTCAATTTC
CTAACACCTACCTTGAAGGTTCTGTTAGAGTGGTAACAACTTTTGATTCTGAGTACTGTAGGCACGGCACTTGTGA
AAGATCAGAAGCTGGTGTTTGTGTATCTACTAGTGGTAGATGGGTACTTAACAATGATTATTACAGATCTTTACCA
GGAGTTTTCTGTGGTGTAGATGCTGTAAATTTACTTACTAATATGTTTACACCACTAATTCAACCTATTGGTGCTTT
GGACATATCAGCATCTATAGTAGCTGGTGGTATTGTAGCTATCGTAGTAACATGCCTTGCCTACTATTTTATGAGGT
TTAGAAGAGCTTTTGGTGAATACAGTCATGTAGTTGCCTTTAATACTTTACTATTCCTTATGTCATTCACTGTACTCT
GTTTAACACCAGTTTACTCATTCTTACCTGGTGTTTATTCTGTTATTTACTTGTACTTGACATTTTATCTTACTAATG
ATGTTTCTTTTTTAGCACATATTCAGTGGATGGTTATGTTCACACCTTTAGTACCTTTCTGGATAACAATTGCTTATA
TCATTTGTATTTCCACAAAGCATTTCTATTGGTTCTTTAGTAATTACCTAAAGAGACGTGTAGTCTTTAATGGTGTTT
CCTTTAGTACTTTTGAAGAAGCTGCGCTGTGCACCTTTTTGTTAAATAAAGAAATGTATCTAAAGTTGCGTAGTGAT
GTGCTATTACCTCTTACGCAATATAATAGATACTTAGCTCTTTATAATAAGTACAAGTATTTTAGTGGAGCAATGGA
TACAACTAGCTACAGAGAAGCTGCTTGTTGTCATCTCGCAAAGGCTCTCAATGACTTCAGTAACTCAGGTTCTGAT
GTTCTTTACCAACCACCACAAACCTCTATCACCTCAGCTGTTTTGCAGAGTGGTTTTAGAAAAATGGCATTCCCATC
TGGTAAAGTTGAGGGTTGTATGGTACAAGTAACTTGTGGTACAACTACACTTAACGGTCTTTGGCTTGATGACGTA
GTTTACTGTCCAAGACATGTGATCTGCACCTCTGAAGACATGCTTAACCCTAATTATGAAGATTTACTCATTCGTAA
GTCTAATCATAATTTCTTGGTACAGGCTGGTAATGTTCAACTCAGGGTTATTGGACATTCTATGCAAAATTGTGTAC
TTAAGCTTAAGGTTGATACAGCCAATCCTAAGACACCTAAGTATAAGTTTGTTCGCATTCAACCAGGACAGACTTT
TTCAGTGTTAGCTTGTTACAATGGTTCACCATCTGGTGTTTACCAATGTGCTATGAGGCCCAATTTCACTATTAAGG
GTTCATTCCTTAATGGTTCATGTGGTAGTGTTGGTTTTAACATAGATTATGACTGTGTCTCTTTTTGTTACATGCACC
ATATGGAATTACCAACTGGAGTTCATGCTGGCACAGACTTAGAAGGTAACTTTTATGGACCTTTTGTTGACAGGCA
AACAGCACAAGCAGCTGGTACGGACACAACTATTACAGTTAATGTTTTAGCTTGGTTGTACGCTGCTGTTATAAAT
GGAGACAGGTGGTTTCTCAATCGATTTACCACAACTCTTAATGACTTTAACCTTGTGGCTATGAAGTACAATTATG
AACCTCTAACACAAGACCATGTTGACATACTAGGACCTCTTTCTGCTCAAACTGGAATTGCCGTTTTAGATATGTGT
GCTTCATTAAAAGAATTACTGCAAAATGGTATGAATGGACGTACCATATTGGGTAGTGCTTTATTAGAAGATGAAT
TTACACCTTTTGATGTTGTTAGACAATGCTCAGGTGTTACTTTCCAAAGTGCAGTGAAAAGAACAATCAAGGGTAC
ACACCACTGGTTGTTACTCACAATTTTGACTTCACTTTTAGTTTTAGTCCAGAGTACTCAATGGTCTTTGTTCTTTTT
TTTGTATGAAAATGCCTTTTTACCTTTTGCTATGGGTATTATTGCTATGTCTGCTTTTGCAATGATGTTTGTCAAACA
TAAGCATGCATTTCTCTGTTTGTTTTTGTTACCTTCTCTTGCCACTGTAGCTTATTTTAATATGGTCTATATGCCTGCT
AGTTGGGTGATGCGTATTATGACATGGTTGGATATGGTTGATACTAGTTTGTCTGGTTTTAAGCTAAAAGACTGTGT
TATGTATGCATCAGCTGTAGTGTTACTAATCCTTATGACAGCAAGAACTGTGTATGATGATGGTGCTAGGAGAGTG
TGGACACTTATGAATGTCTTGACACTCGTTTATAAAGTTTATTATGGTAATGCTTTAGATCAAGCCATTTCCATGTG
GGCTCTTATAATCTCTGTTACTTCTAACTACTCAGGTGTAGTTACAACTGTCATGTTTTTGGCCAGAGGTATTGTTTT
TATGTGTGTTGAGTATTGCCCTATTTTCTTCATAACTGGTAATACACTTCAGTGTATAATGCTAGTTTATTGTTTCTT
AGGCTATTTTTGTACTTGTTACTTTGGCCTCTTTTGTTTACTCAACCGCTACTTTAGACTGACTCTTGGTGTTTATGA
TTACTTAGTTTCTACACAGGAGTTTAGATATATGAATTCACAGGGACTACTCCCACCCAAGAATAGCATAGATGCC
TTCAAACTCAACATTAAATTGTTGGGTGTTGGTGGCAAACCTTGTATCAAAGTAGCCACTGTACAGTCTAAAATGT
CAGATGTAAAGTGCACATCAGTAGTCTTACTCTCAGTTTTGCAACAACTCAGAGTAGAATCATCATCTAAATTGTG
GGCTCAATGTGTCCAGTTACACAATGACATTCTCTTAGCTAAAGATACTACTGAAGCCTTTGAAAAAATGGTTTCA
CTACTTTCTGTTTTGCTTTCCATGCAGGGTGCTGTAGACATAAACAAGCTTTGTGAAGAAATGCTGGACAACAGGG
CAACCTTACAAGCTATAGCCTCAGAGTTTAGTTCCCTTCCATCATATGCAGCTTTTGCTACTGCTCAAGAAGCTTAT
GAGCAGGCTGTTGCTAATGGTGATTCTGAAGTTGTTCTTAAAAAGTTGAAGAAGTCTTTGAATGTGGCTAAATCTG
AATTTGACCGTGATGCAGCCATGCAACGTAAGTTGGAAAAGATGGCTGATCAAGCTATGACCCAAATGTATAAAC
AGGCTAGATCTGAGGACAAGAGGGCAAAAGTTACTAGTGCTATGCAGACAATGCTTTTCACTATGCTTAGAAAGTT
GGATAATGATGCACTCAACAACATTATCAACAATGCAAGAGATGGTTGTGTTCCCTTGAACATAATACCTCTTACA
ACAGCAGCCAAACTAATGGTTGTCATACCAGACTATAACACATATAAAAATACGTGTGATGGTACAACATTTACTT
ATGCATCAGCATTGTGGGAAATCCAACAGGTTGTAGATGCAGATAGTAAAATTGTTCAACTTAGTGAAATTAGTAT

-continued

| SEQUENCE LISTING |
|---|
| GGACAATTCACCTAATTTAGCATGGCCTCTTATTGTAACAGCTTTAAGGGCCAATTCTGCTGTCAAATTACAGAAT |
| AATGAGCTTAGTCCTGTTGCACTACGACAGATGTCTTGTGCTGCCGGTACTACACAAACTGCTTGCACTGATGACA |
| ATGCGTTAGCTTACTACAACACAACAAAGGGAGGTAGGTTTGTACTTGCACTGTTATCCGATTTACAGGATTTGAA |
| ATGGGCTAGATTCCCTAAGAGTGATGGAACTGGTACTATCTATACAGAACTGGAACCACCTTGTAGGTTTGTTACA |
| GACACACCTAAAGGTCCTAAAGTGAAGTATTTATACTTTATTAAAGGATTAAACAACCTAAATAGAGGTATGGTAC |
| TTGGTAGTTTAGCTGCCACAGTACGTCTACAAGCTGGTAATGCAACAGAAGTGCCTGCCAATTCAACTGTATTATC |
| TTTCTGTGCTTTTGCTGTAGATGCTGCTAAAGCTTACAAAGATTATCTAGCTAGTGGGGGACAACCAATCACTAATT |
| GTGTTAAGATGTTGTGTACACACACTGGTACTGGTCAGGCAATAACAGTTACACCGGAAGCCAATATGGATCAAG |
| AATCCTTTGGTGGTGCATCGTGTTGTCTGTACTGCCGTTGCCACATAGATCATCCAAATCCTAAAGGATTTTGTGAC |
| TTAAAAGGTAAGTATGTACAAATACCTACAACTTGTGCTAATGACCCTGTGGGTTTTACACTTAAAAACACAGTCT |
| GTACCGTCTGCGGTATGTGGAAAGGTTATGGCTGTAGTTGTGATCAACTCCGCGAACCCATGCTTCAGTCAGCTGA |
| TGCACAATCGTTTTTAAACGGGTTTGCGGTGTAAGTGCAGCCCGTCTTACACCGTGCGGCACAGGCACTAGTACTG |
| ATGTCGTATACAGGGCTTTTGACATCTACAATGATAAAGTAGCTGGTTTTGCTAAATTCCTAAAAACTAATTGTTGT |
| CGCTTCCAAGAAAAGGACGAAGATGACAATTTAATTGATTCTTACTTTGTAGTTAAGAGACACACTTTCTCTAACT |
| ACCAACATGAAGAAACAATTTATAATTTACTTAAGGATTGTCCAGCTGTTGCTAAACATGACTTCTTTAAGTTTAG |
| AATAGACGGTGACATGGTACCACATATATCACGTCAACGTCTTACTAAATACACAATGGCAGACCTCGTCTATGCT |
| TTAAGGCATTTTGATGAAGGTAATTGTGACACATTAAAAGAAATACTTGTCACATACAATTGTTGTGATGATGATT |
| ATTTCAATAAAAAGGACTGGTATGATTTTGTAGAAAACCCAGATATATTACGCGTATACGCCAACTTAGGTGAACG |
| TGTACGCCAAGCTTTGTTAAAAACAGTACAATTCTGTGATGCCATGCGAAATGCTGGTATTGTTGGTGTACTGACA |
| TTAGATAATCAAGATCTCAATGGTAACTGGTATGATTTCGGTGATTTCATACAAACCACGCCAGGTAGTGGAGTTC |
| CTGTTGTAGATTCTTATTATTCATTGTTAATGCCTATATTAACCTTGACCAGGGCTTTAACTGCAGAGTCACATGTT |
| GACACTGACTTAACAAAGCCTTACATTAAGTGGGATTTGTTAAAATATGACTTCACGGAAGAGAGGTTAAAACTCT |
| TTGACCGTTATTTTAAATATTGGGATCAGACATACCACCCAAATTGTGTTAACTGTTTGGATGACAGATGCATTCTG |
| CATTGTGCAAACTTTAATGTTTTATTCTCTACAGTGTTCCCACCTACAAGTTTTGGACCACTAGTGAGAAAAATATT |
| TGTTGATGGTGTTCCATTTGTAGTTTCAACTGGATACCACTTCAGAGAGCTAGGTGTTGTACATAATCAGGATGTAA |
| ACTTACATAGCTCTAGACTTAGTTTTAAGGAATTACTTGTGTATGCTGCTGACCCTGCTATGCACGCTGCTTCTGGT |
| AATCTATTACTAGATAAACGCACTACGTGCTTTTCAGTAGCTGCACTTACTAACAATGTTGCTTTTCAAACTGTCAA |
| ACCCGGTAATTTTAACAAAGACTTCTATGACTTTGCTGTGTCTAAGGGTTTCTTTAAGGAAGGAAGTTCTGTTGAAT |
| TAAAACACTTCTTCTTTGCTCAGGATGGTAATGCTGCTATCAGCGATTATGACTACTATCGTTATAATCTACCAACA |
| ATGTGTGATATCAGACAACTACTATTTGTAGTTGAAGTTGTTGATAAGTACTTTGATTGTTACGATGGTGGCTGTAT |
| TAATGCTAACCAAGTCATCGTCAACAACCTAGACAAATCAGCTGGTTTTCCATTTAATAAATGGGGTAAGGCTAGA |
| CTTTATTATGATTCAATGAGTTATGAGGATCAAGATGCACTTTTCGCATATACAAAACGTAATGTCATCCCTACTAT |
| AACTCAAATGAATCTTAAGTATGCCATTAGTGCAAAGAATAGAGCTCGCACCGTAGCTGGTGTCTCTATCTGTAGT |
| ACTATGACCAATAGACAGTTTCATCAAAAATTATTGAAATCAATAGCCGCCACTAGAGGAGCTACTGTAGTAATTG |
| GAACAAGCAAATTCTATGGTGGTTGGCACAACATGTTAAAAACTGTTTATAGTGATGTAGAAAACCCTCACCTTAT |
| GGGTTGGGATTATCCTAAATGTGATAGAGCCATGCCTAACATGCTTAGAATTATGGCCTCACTTGTTCTTGCTCGCA |
| AACATACAACGTGTTGTAGCTTGTCACACCGTTTCTATAGATTAGCTAATGAGTGTGCTCAAGTATTGAGTGAAAT |
| GGTCATGTGTGGCGGTTCACTATATGTTAAACCAGGTGGAACCTCATCAGGAGATGCCACAACTGCTTATGCTAAT |
| AGTGTTTTTAACATTTGTCAAGCTGTCACGGCCAATGTTAATGCACTTTTATCTACTGATGGTAACAAAATTGCCGA |
| TAAGTATGTCCGCAATTTACAACACAGACTTTATGAGTGTCTCTATAGAAATAGAGATGTTGACACAGACTTTGTG |
| AATGAGTTTTACGCATATTTGCGTAAACATTTCTCAATGATGATACTCTCTGACGATGCTGTTGTGTGTTTCAATAG |
| CACTTATGCATCTCAAGGTCTAGTGGCTAGCATAAAGAACTTTAAGTCAGTTCTTTATTATCAAAACAATGTTTTTA |
| TGTCTGAAGCAAAATGTTGGACTGAGACTGACCTTACTAAAGGACCTCATGAATTTTGCTCTCAACATACAATGCT |
| AGTTAAACAGGGTGATGATTATGTGTACCTTCCTTACCCAGATCCATCAAGAATCCTAGGGGCCGGCTGTTTTGTA |
| GATGATATCGTAAAAACAGATGGTACACTTATGATTGAACGGTTCGTGTCTTTAGCTATAGATGCTTACCCACTTA |
| CTAAACATCCTAATCAGGAGTATGCTGATGTCTTTCATTTGTACTTACAATACATAAGAAAGCTACATGATGAGTT |
| AACAGGACACATGTTAGACATGTATTCTGTTATGCTTACTAATGATAACACTTCAAGGTATTGGGAACCTGAGTTT |
| TATGAGGCTATGTACACACCGCATACAGTCTTACAGGCTGTTGGGGCTTGTGTTCTTTGCAATTCACAGACTTCATT |
| AAGATGTGGTGCTTGCATACGTAGACCATTCTTATGTTGTAAATGCTGTTACGACCATGTCATATCAACATCACATA |
| AATTAGTCTTGTCTGTTAATCCGTATGTTTGCAATGCTCCAGGTTGTGATGTCACAGATGTGACTCAACTTTACTTA |
| GGAGGTATGAGCTATTATTGTAAATCACATAAACCACCCATTAGTTTTCCATTGTGTGCTAATGGACAAGTTTTTGG |

-continued

SEQUENCE LISTING

TTTATATAAAAATACATGTGTTGGTAGCGATAATGTTACTGACTTTAATGCAATTGCAACATGTGACTGGACAAAT
GCTGGTGATTACATTTTAGCTAACACCTGTACTGAAAGACTCAAGCTTTTTGCAGCAGAAACGCTCAAAGCTACTG
AGGAGACATTTAAACTGTCTTATGGTATTGCTACTGTACGTGAAGTGCTGTCTGACAGAGAATTACATCTTTCATG
GGAAGTTGGTAAACCTAGACCACCACTTAACCGAAATTATGTCTTTACTGGTTATCGTGTAACTAAAAACAGTAAA
GTACAAATAGGAGAGTACACCTTTGAAAAAGGTGACTATGGTGATGCTGTTGTTTACCGAGGTACAACAACTTACA
AATTAAATGTTGGTGATTATTTTGTGCTGACATCACATACAGTAATGCCATTAAGTGCACCTACACTAGTGCCACA
AGAGCACTATGTTAGAATTACTGGCTTATACCCAACACTCAATATCTCAGATGAGTTTTCTAGCAATGTTGCAAATT
ATCAAAAGGTTGGTATGCAAAAGTATTCTACACTCCAGGGACCACCTGGTACTGGTAAGAGTCATTTTGCTATTGG
CCTAGCTCTCTACTACCCTTCTGCTCGCATAGTGTATACAGCTTGCTCTCATGCCGCTGTTGATGCACTATGTGAGA
AGGCATTAAAATATTTGCCTATAGATAAATGTAGTAGAATTATACCTGCACGTGCTCGTGTAGAGTGTTTTGATAA
ATTCAAAGTGAATTCAACATTAGAACAGTATGTCTTTTGTACTGTAAATGCATTGCCTGAGACGACAGCAGATATA
GTTGTCTTTGATGAAATTTCAATGGCCACAAATTATGATTTGAGTGTTGTCAATGCCAGATTACGTGCTAAGCACTA
TGTGTACATTGGCGACCCTGCTCAATTACCTGCACCACGCACATTGCTAACTAAGGGCACACTAGAACCAGAATAT
TTCAATTCAGTGTGTAGACTTATGAAAACTATAGGTCCAGACATGTTCCTCGGAACTTGTCGGCGTTGTCCTGCTGA
AATTGTTGACACTGTGAGTGCTTTGGTTTATGATAATAAGCTTAAAGCACATAAAGACAAATCAGCTCAATGCTTT
AAAATGTTTTATAAGGGTGTTATCACGCATGATGTTTCATCTGCAATTAACAGGCCACAAATAGGCGTGGTAAGAG
AATTCCTTACACGTAACCCTGCTTGGAGAAAAGCTGTCTTTATTTCACCTTATAATTCACAGAATGCTGTAGCCTCA
AAGATTTTGGGACTACCAACTCAAACTGTTGATTCATCACAGGGCTCAGAATATGACTATGTCATATTCACTCAAA
CCACTGAAACAGCTCACTCTTGTAATGTAAACAGATTTAATGTTGCTATTACCAGAGCAAAAGTAGGCATACTTTG
CATAATGTCTGATAGAGACCTTTATGACAAGTTGCAATTTACAAGTCTTGAAATTCCACGTAGGAATGTGGCAACT
TTACAAGCTGAAAATGTAACAGGACTCTTTAAAGATTGTAGTAAGGTAATCACTGGGTTACATCCTACACAGGCAC
CTACACACCTCAGTGTTGACACTAAATTCAAAACTGAAGGTTTATGTGTTGACATACCTGGCATACCTAAGGACAT
GACCTATAGAAGACTCATCTCTATGATGGGTTTTAAAATGAATTATCAAGTTAATGGTTACCCTAACATGTTTATCA
CCCGCGAAGAAGCTATAAGACATGTACGTGCATGGATTGGCTTCGATGTCGAGGGGTGTCATGCTACTAGAGAAG
CTGTTGGTACCAATTTACCTTTACAGCTAGGTTTTTCTACAGGTGTTAACCTAGTTGCTGTACCTACAGGTTATGTT
GATACACCTAATAATACAGATTTTTCCAGAGTTAGTGCTAAACCACCGCCTGGAGATCAATTTAAACACCTCATAC
CACTTATGTACAAAGGACTTCCTTGGAATGTAGTGCGTATAAAGATTGTACAAATGTTAAGTGACACACTTAAAAA
TCTCTCTGACAGAGTCGTATTTGTCTTATGGGCACATGGCTTTGAGTTGACATCTATGAAGTATTTTGTGAAAATAG
GACCTGAGCGCACCTGTTGTCTATGTGATAGACGTGCCACATGCTTTTCCACTGCTTCAGACACTTATGCCTGTTGG
CATCATTCTATTGGATTTGATTACGTCTATAATCCGTTTATGATTGATGTTCAACAATGGGGTTTTACAGGTAACCT
ACAAAGCAACCATGATCTGTATTGTCAAGTCCATGGTAATGCACATGTAGCTAGTTGTGATGCAATCATGACTAGG
TGTCTAGCTGTCCACGAGTGCTTTGTTAAGCGTGTTGACTGGACTATTGAATATCCTATAATTGGTGATGAACTGAA
GATTAATGCGGCTTGTAGAAAGGTTCAACACATGGTTGTTAAAGCTGCATTATTAGCAGACAAATTCCCAGTTCTT
CACGACATTGGTAACCCTAAAGCTATTAAGTGTGTACCTCAAGCTGATGTAGAATGGAAGTTCTATGATGCACAGC
CTTGTAGTGACAAAGCTTATAAAATAGAAGAATTATTCTATTCTTATGCCACACATTCTGACAAATTCACAGATGG
TGTATGCCTATTTTGGAATTGCAATGTCGATAGATATCCTGCTAATTCCATTGTTTGTAGATTTGACACTAGAGTGC
TATCTAACCTTAACTTGCCTGGTTGTGATGGTGGCAGTTTGTATGTAAATAAACATGCATTCCACACACCAGCTTTT
GATAAAAGTGCTTTTGTTAATTTAAAACAATTACCATTTTTCTATTACTCTGACAGTCCATGTGAGTCTCATGGAAA
ACAAGTAGTGTCAGATATAGATTATGTACCACTAAAGTCTGCTACGTGTATAACACGTTGCAATTTAGGTGGTGCT
GTCTGTAGACATCATGCTAATGAGTACAGATTGTATCTCGATGCTTATAACATGATGATCTCAGCTGGCTTTAGCTT
GTGGGTTTACAAACAATTTGATACTTATAACCTCTGGAACACTTTTACAAGACTTCAGAGTTTAGAAAATGTGGCT
TTTAATGTTGTAAATAAGGGACACTTTGATGGACAACAGGGTGAAGTACCAGTTTCTATCATTAATAACACTGTTT
ACACAAAAGTTGATGGTGTTGATGTAGAATTGTTTGAAAATAAAACAACATTACCTGTTAATGTAGCATTTGAGCT
TTGGGCTAAGCGCAACATTAAACCAGTACCAGAGGTGAAAATACTCAATAATTTGGGTGTGGACATTGCTGCTAAT
ACTGTGATCTGGGACTACAAAAGAGATGCTCCAGCACATATATCTACTATTGGTGTTTGTTCTATGACTGACATAG
CCAAGAAACCAACTGAAACGATTTGTGCACCACTCACTGTCTTTTTTGATGGTAGAGTTGATGGTCAAGTAGACTT
ATTTAGAAATGCCCGTAATGGTGTTCTTATTACAGAAGGTAGTGTTAAAGGTTTACAACCATCTGTAGGTCCCAAA
CAAGCTAGTCTTAATGGAGTCACATTAATTGGAGAAGCCGTAAAAACACAGTTCAATTATTATAAGAAAGTTGATG
GTGTTGTCCAACAATTACCTGAAACTTACTTTACTCAGAGTAGAAATTTACAAGAATTTAAACCCAGGAGTCAAAT
GGAAATTGATTTCTTAGAATTAGCTATGGATGAATTCATTGAACGGTATAAATTAGAAGGCTATGCCTTCGAACAT
ATCGTTTATGGAGATTTTAGTCATAGTCAGTTAGGTGGTTTACATCTACTGATTGGACTAGCTAAACGTTTTAAGGA

-continued

| SEQUENCE LISTING |
|---|
| ATCACCTTTTGAATTAGAAGATTTTATTCCTATGGACAGTACAGTTAAAAACTATTTCATAACAGATGCGCAAACA<br>GGTTCATCTAAGTGTGTGTGTTCTGTTATTGATTTATTACTTGATGATTTTGTTGAAATAATAAAATCCCAAGATTT<br>ATCTGTAGTTTCTAAGGTTGTCAAAGTGACTATTGACTATACAGAAATTTCATTTATGCTTTGGTGTAAAGATGGCC<br>ATGTAGAAACATTTTACCCAAAATTACAATCTAGTCAAGCGTGGCAACCGGGTGTTGCTATGCCTAATCTTTACAA<br>AATGCAAAGAATGCTATTAGAAAAGTGTGACCTTCAAAATTATGGTGATAGTGCAACATTACCTAAAGGCATAAT<br>GATGAATGTCGCAAAATATACTCAACTGTGTCAATATTTAAACACATTAACATTAGCTGTACCCTATAATATGAGA<br>GTTATACATTTTGGTGCTGGTTCTGATAAAGGAGTTGCACCAGGTACAGCTGTTTTAAGACAGTGGTTGCCTACGG<br>GTACGCTGCTTGTCGATTCAGATCTTAATGACTTTGTCTCTGATGCAGATTCAACTTTGATTGGTGATTGTGCAACT<br>GTACATACAGCTAATAAATGGGATCTCATTATTAGTGATATGTACGACCCTAAGACTAAAAATGTTACAAAAGAA<br>AATGACTCTAAAGAGGGTTTTTTCACTTACATTTGTGGGTTTATACAACAAAAGCTAGCTCTTGGAGGTTCCGTGGC<br>TATAAAGATAACAGAACATTCTTGGAATGCTGATCTTTATAAGCTCATGGGACACTTCGCATGGTGGACAGCCTTT<br>GTTACTAATGTGAATGCGTCATCATCTGAAGCATTTTTAATTGGATGTAATTATCTTGGCAAACCACGCGAACAAA<br>TAGATGGTTATGTCATGCATGCAAATTACATATTTTGGAGGAATACAAATCCAATTCAGTTGTCTTCCTATTCTTTA<br>TTTGACATGAGTAAATTTCCCCTTAAATTAAGGGGTACTGCTGTTATGTCTTTAAAAGAAGGTCAAATCAATGATA<br>TGATTTTATCTCTTCTTAGTAAAGGTAGACTTATAATTAGAGAAAACAACAGAGTTGTTATTTCTAGTGATGTTCTT<br>GTTAACAACTAAACGAACAATGTTTGTTTTTCTTGTTTTATTGCCACTAGTCTCTAGTCAGTGTGTTAATCTTACAAC<br>CAGAACTCAATTACCCCCTGCATACACTAATTCTTTCACACGTGGTGTTTATTACCCTGACAAAGTTTTCAGATCCT<br>CAGTTTTACATTCAACTCAGGACTTGTTCTTACCTTTCTTTTCCAATGTTACTTGGTTCCATGCTATACATGTCTCTG<br>GGACCAATGGTACTAAGAGGTTTGATAACCCTGTCCTACCATTTAATGATGGTGTTTATTTTGCTTCCACTGAGAAG<br>TCTAACATAATAAGAGGCTGGATTTTTGGTACTACTTTAGATTCGAAGACCCAGTCCCTACTTATTGTTAATAACGC<br>TACTAATGTTGTTATTAAAGTCTGTGAATTTCAATTTTGTAATGATCCATTTTTGGGTGTTTATTACCACAAAAACA<br>ACAAAAGTTGGATGGAAAGTGAGTTCAGAGTTTATTCTAGTGCGAATAATTGCACTTTTGAATATGTCTCTCAGCC<br>TTTTCTTATGGACCTTGAAGGAAAACAGGGTAATTTCAAAAATCTTAGGGAATTTGTGTTTAAGAATATTGATGGT<br>TATTTTAAAATATATTCTAAGCACACGCCTATTAATTTAGTGCGTGATCTCCCTCAGGGTTTTTCGGCTTTAGAACC<br>ATTGGTAGATTTGCCAATAGGTATTAACATCACTAGGTTTCAAACTTTACTTGCTTTACATAGAAGTTATTTGACTC<br>CTGGTGATTCTTCTTCAGGTTGGACAGCTGGTGCTGCAGCTTATTATGTGGGTTATCTTCAACCTAGGACTTTTCTA<br>TTAAAATATAATGAAAATGGAACCATTACAGATGCTGTAGACTGTGCACTTGACCCTCTCTCAGAAACAAAGTGTA<br>CGTTGAAATCCTTCACTGTAGAAAAAGGAATCTATCAAACTTCTAACTTTAGAGTCCAACCAACAGAATCTATTGT<br>TAGATTTCCTAATATTACAAACTTGTGCCCTTTTGGTGAAGTTTTTAACGCCACCAGATTTGCATCTGTTTATGCTTG<br>GAACAGGAAGAGAATCAGCAACTGTGTTGCTGATTATTCTGTCCTATATAATTCCGCATCATTTTCCACTTTTAAGT<br>GTTATGGAGTGTCTCCTACTAAATTAAATGATCTCTGCTTTACTAATGTCTATGCAGATTCATTTGTAATTAGAGGT<br>GATGAAGTCAGACAAATCGCTCCAGGGCAAACTGGAAAGATTGCTGATTATAATTATAAATTACCAGATGATTTTA<br>CAGGCTGCGTTATAGCTTGGAATTCTAACAATCTTGATTCTAAGGTTGGTGGTAATTATAATTACCTGTATAGATTG<br>TTTAGGAAGTCTAATCTCAAACCTTTTGAGAGAGATATTTCAACTGAAATCTATCAGGCCGGTAGCACACCTTGTA<br>ATGGTGTTGAAGGTTTTAATTGTTACTTTCCTTTACAATCATATGGTTTCCAACCCACTAATGGTGTTGGTTACCAA<br>CCATACAGAGTAGTAGTACTTTCTTTTGAACTTCTACATGCACCAGCAACTGTTTGTGGACCTAAAAAGTCTACTAA<br>TTTGGTTAAAAACAAATGTGTCAATTTCAACTTCAATGGTTTAACAGGCACAGGTGTTCTTACTGAGTCTAACAAA<br>AAGTTTCTGCCTTTCCAACAATTTGGCAGAGACATTGCTGACACTACTGATGCTGTCCGTGATCCACAGACACTTG<br>AGATTCTTGACATTACACCATGTTCTTTTGGTGGTGTCAGTGTTATAACACCAGGAACAAATACTTCTAACCAGGTT<br>GCTGTTCTTTATCAGGATGTTAACTGCACAGAAGTCCCTGTTGCTATTCATGCAGATCAACTTACTCCTACTTGGCG<br>TGTTTATTCTACAGGTTCTAATGTTTTTCAAACACGTGCAGGCTGTTTAATAGGGGCTGAACATGTCAACAACTCAT<br>ATGAGTGTGACATACCCATTGGTGCAGGTATATGCGCTAGTTATCAGACTCAGACTAATTCTCCTCGGCGGGCACG<br>TAGTGTAGCTAGTCAATCCATCATTGCCTACACTATGTCACTTGGTGCAGAAAATTCAGTTGCTTACTCTAATAACT<br>CTATTGCCATACCCACAAATTTTACTATTAGTGTTACCACAGAAATTCTACCAGTGTCTATGACCAAGACATCAGTA<br>GATTGTACAATGTACATTTGTGGTGATTCAACTGAATGCAGCAATCTTTTGTTGCAATATGGCAGTTTTTGTACACA<br>ATTAAACCGTGCTTTAACTGGAATAGCTGTTGAACAAGACAAAAACACCCAAGAAGTTTTTGCACAAGTCAAACA<br>AATTTACAAAACACCACCAATTAAAGATTTTGGTGGTTTTAATTTTTCACAAATATTACCAGATCCATCAAAACCA<br>AGCAAGAGGTCATTTATTGAAGATCTACTTTTCAACAAAGTGACACTTGCAGATGCTGGCTTCATCAAACAATATG<br>GTGATTGCCTTGGTGATATTGCTGCTAGAGACCTCATTTGTGCACAAAAGTTTAACGGCCTTACTGTTTTGCCACCT<br>TTGCTCACAGATGAAATGATTGCTCAATACACTTCTGCACTGTTAGCGGGTACAATCACTTCTGGTTGGACCTTTGG<br>TGCAGGTGCTGCATTACAAATACCATTTGCTATGCAAATGGCTTATAGGTTTAATGGTATTGGAGTTACACAGAAT |

-continued

SEQUENCE LISTING

GTTCTCTATGAGAACCAAAAATTGATTGCCAACCAATTTAATAGTGCTATTGGCAAAATTCAAGACTCACTTTCTTC
CACAGCAAGTGCACTTGGAAAACTTCAAGATGTGGTCAACCAAAATGCACAAGCTTTAAACACGCTTGTTAAACA
ACTTAGCTCCAATTTTGGTGCAATTTCAAGTGTTTTAAATGATATCCTTTCACGTCTTGACAAAGTTGAGGCTGAAG
TGCAAATTGATAGGTTGATCACAGGCAGACTTCAAAGTTTGCAGACATATGTGACTCAACAATTAATTAGAGCTGC
AGAAATCAGAGCTTCTGCTAATCTTGCTGCTACTAAAATGTCAGAGTGTGTACTTGGACAATCAAAAAGAGTTGAT
TTTTGTGGAAAGGGCTATCATCTTATGTCCTTCCCTCAGTCAGCACCTCATGGTGTAGTCTTCTTGCATGTGACTTAT
GTCCCTGCACAAGAAAAGAACTTCACAACTGCTCCTGCCATTTGTCATGATGGAAAAGCACACTTTCCTCGTGAAG
GTGTCTTTGTTTCAAATGGCACACACTGGTTTGTAACACAAAGGAATTTTTATGAACCACAAATCATTACTACAGA
CAACACATTTGTGTCTGGTAACTGTGATGTTGTAATAGGAATTGTCAACAACACAGTTTATGATCCTTTGCAACCTG
AATTAGACTCATTCAAGGAGGAGTTAGATAAATATTTTAAGAATCATACATCACCAGATGTTGATTTAGGTGACAT
CTCTGGCATTAATGCTTCAGTTGTAAACATTCAAAAAGAAATTGACCGCCTCAATGAGGTTGCCAAGAATTTAAAT
GAATCTCTCATCGATCTCCAAGAACTTGGAAAGTATGAGCAGTATATAAAATGGCCATGGTACATTTGGCTAGGTT
TTATAGCTGGCTTGATTGCCATAGTAATGGTGACAATTATGCTTTGCTGTATGACCAGTTGCTGTAGTTGTCTCAAG
GGCTGTTGTTCTTGTGGATCCTGCTGCAAATTTGATGAAGACGACTCTGAGCCAGTGCTCAAAGGAGTCAAATTAC
ATTACACATAAACGAACTTATGGATTTGTTTATGAGAATCTTCACAATTGGAACTGTAACTTTGAAGCAAGGTGAA
ATCAAGGATGCTACTCCTTCAGATTTTGTTCGCGCTACTGCAACGATACCGATACAAGCCTCACTCCCTTTCGGATG
GCTTATTGTTGGCGTTGCACTTCTTGCTGTTTTTCAGAGCGCTTCCAAAATCATAACCCTCAAAAAGAGATGGCAAC
TAGCACTCTCCAAGGGTGTTCACTTTGTTTGCAACTTGCTGTTGTTGTTTGTAACAGTTTACTCACACCTTTTGCTCG
TTGCTGCTGGCCTTGAAGCCCCTTTTCTCTATCTTTATGCTTTAGTCTACTTCTTGCAGAGTATAAACTTTGTAAGAA
TAATAATGAGGCTTTGGCTTTGCTGGAAATGCCGTTCCAAAAACCCATTACTTTATGATGCCAACTATTTTCTTTGC
TGGCATACTAATTGTTACGACTATTGTATACCTTACAATAGTGTAACTTCTTCAATTGTCATTACTTCAGGTGATGG
CACAACAAGTCCTATTTCTGAACATGACTACCAGATTGGTGGTTATACTGAAAAATGGGAATCTGGAGTAAAAGA
CTGTGTTGTATTACACAGTTACTTCACTTCAGACTATTACCAGCTGTACTCAACTCAATTGAGTACAGACACTGGTG
TTGAACATGTTACCTTCTTCATCTACAATAAAATTGTTGATGAGCCTGAAGAACATGTCCAAATTCACACAATCGA
CGGTTCATCCGGAGTTGTTAATCCAGTAATGGAACCAATTTATGATGAACCGACGACGACTACTAGCGTGCCTTTG
TAAGCACAAGCTGATGAGTACGAACTTATGTACTCATTCGTTTCGGAAGAGACAGGTACGTAAATAGTTAATAGCT
GACTTCTTTTTCTTGCTTTCGTGTGATTCTTGCTAGTTACACTAGCCATCCTTACTGCGCTTCGATTGTGTGCGTACT
GCTGCAATATTGTTAACGTGAGTCTTGTAAAACCTTCTTTTTACGTTTACTCTCGTGTTAAAAATCTGAATTCTTCTA
GAGTTCCTGATCTTCTGGTCTAAACGAACTAAATATTATATTAGTTTTTCTGTTTGGAACTTTAATTTTAGCCATGGC
AGATTCCAACGGTACTATTACCGTTGAAGAGCTTAAAAAGCTCCTTGAACAATGGAACCTAGTAATAGGTTTCCTA
TTCCTTACATGGATTTGTCTTCTACAATTTGCCTATGCCAACAGGAATAGGTTTTTGTATATAATTAAGTTAATTTTC
CTCTGGCTGTTATGGCCAGTAACTTTAGCTTGTTTTGTGCTTGCTGCTGTTTACAGAATAAATTGGATCACCGGTGG
AATTGCTATCGCAATGGCTTGTCTTGTAGGCTTGATGTGGCTCAGCTACTTCATTGCTTCTTTCAGACTGTTTGCGC
GTACGCGTTCCATGTGGTCATTCAATCCAGAAACTAACATTCTTCTCAACGTGCCACTCCATGGCACTATTCTGACC
AGACCGCTTCTAGAAAGTGAACTCGTAATCGGAGCTGTGATCCTTCGTGGACATCTTCGTATTGCTGGACACCATC
TAGGACGCTGTGACATCAAGGACCTGCCTAAAGAAATCACTGTTGCTACATCACGAACGCTTTCTTATTACAAATT
GGGAGCTTCGCAGCGTGTAGCAGGTGACTCAGGTTTTGCTGCATACAGTCGCTACAGGATTGGCAACTATAAATTA
AACACAGACCATTCCAGTAGCAGTGACAATATTGCTTTGCTTGTACAGTAAGTGACAACAGATGTTTCATCTCGTT
GACTTTCAGGTTACTATAGCAGAGATATTACTAATTATTATGAGGACTTTTAAAGTTTCCATTTGGAATCTTGATTA
CATCATAAACCTCATAATTAAAAATTTATCTAAGTCACTAACTGAGAATAAATATTCTCAATTAGATGAAGAGCAA
CCAATGGAGATTGATTAAACGAACATGAAAATTATTCTTTTCTTGGCACTGATAACACTCGCTACTTGTGAGCTTTA
TCACTACCAAGAGTGTGTTAGAGGTACAACAGTACTTTTAAAAGAACCTTGCTCTTCTGGAACATACGAGGGCAAT
TCACCATTTCATCCTCTAGCTGATAACAAATTTGCACTGACTTGCTTTAGCACTCAATTTGCTTTTGCTTGTCCTGAC
GGCGTAAAACACGTCTATCAGTTACGTGCCAGATCAGTTTCACCTAAACTGTTCATCAGACAAGAGGAAGTTCAAG
AACTTTACTCTCCAATTTTTCTTATTGTTGCGGCAATAGTGTTTATAACACTTTGCTTCACACTCAAAAGAAAGACA
GAATGATTGAACTTTCATTAATTGACTTCTATTTGTGCTTTTTAGCCTTTCTGCTATTCCTTGTTTTAATTATGCTTAT
TATCTTTTGGTTCTCACTTGAACTGCAAGATCATAATGAAACTTGTCACGCCTAAACGAACatgaccaacaagtgtctcctccaaat
tgctctcctgttgtgcttctccactacagctctttccatgagctacaacttgcttggattcctacaaagaagcagcaattttcagtgtcagaagctcctgtggcaattgaatgggaggcttgaatact
gcctcaaggacaggatgaactttgacatccctgaggagattaagcagctgcagcagttccagaaggaggacgccgcattaccatctatgagatgctccagaacatctttgctattttcagac
aagattcatctagcactggctggaatgagactattgttgagaacctcctggctaatgtctatcatcagataaaccatctgaagacagtcctggaagaaaaactggagaaagaagatttcaccag
gggaaaactcatgagcagtctgcacctgaaaagatattatgggaggattctgcattacctgaaggccaaggagtacagtcactgtgcctggaccatagtcagagtggaaatcctaaggaactt -continued

SEQUENCE LISTING ttacttcattaacagacttacaggttacctccgaaactgaGACGTTCGTGTTGTTTTAGATTTCATCTAAACGAACAAACTAAAATGTCTGAT
AATGGACCCCAAAATCAGCGAAATGCACCCCGCATTACGTTTGGTGGACCCTCAGATTCAACTGGCAGTAACCAG
AATGGAGAACGCAGTGGGGCGCGATCAAAACAACGTCGGCCCCAAGGTTTACCCAATAATACTGCGTCTTGGTTC
ACCGCTCTCACTCAACATGGCAAGGAAGACCTTAAATTCCCTCGAGGACAAGGCGTTCCAATTAACACCAATAGC
AGTCCAGATGACCAAATTGGCTACTACCGAAGAGCTACCAGACGAATTCGTGGTGGTGACGGTAAAATGAAAGAT
CTCAGTCCAAGATGGTATTTCTACTACCTAGGAACTGGGCCAGAAGCTGGACTTCCCTATGGTGCTAACAAAGACG
GCATCATATGGGTTGCAACTGAGGGAGCCTTGAATACACCAAAAGATCACATTGGCACCCGCAATCCTGCTAACA
ATGCTGCAATCGTGCTACAACTTCCTCAAGGAACAACATTGCCAAAAGGCTTCTACGCAGAAGGGAGCAGAGGCG
GCAGTCAAGCCTCTTCTCGTTCCTCATCACGTAGTCGCAACAGTTCAAGAAATTCAACTCCAGGCAGCAGTAGGGG
AACTTCTCCTGCTAGAATGGCTGGCAATGGCGGTGATGCTGCTCTTGCTTTGCTGCTGCTTGACAGATTGAACCAGC
TTGAGAGCAAAATGTCTGGTAAAGGCCAACAACAACAAGGCCAAACTGTCACTAAGAAATCTGCTGCTGAGGCTT
CTAAGAAGCCTCGGCAAAAACGTACTGCCACTAAAGCATACAATGTAACACAAGCTTTCGGCAGACGTGGTCCAG
AACAAACCCAAGGAAATTTTGGGGACCAGGAACTAATCAGACAAGGAACTGATTACAAACATTGGCCGCAAATTG
CACAATTTGCCCCCAGCGCTTCAGCGTTCTTCGGAATGTCGCGCATTGGCATGGAAGTCACACCTTCGGGAACGTG
GTTGACCTACACAGGTGCCATCAAATTGGATGACAAAGATCCAAATTTCAAAGATCAAGTCATTTTGCTGAATAAG
CATATTGACGCATACAAAACATTCCCACCAACAGAGCCTAAAAAGGACAAAAAGAAGAAGGCTGATGAAACTCA
AGCCTTACCGCAGAGACAGAAGAAACAGCAAACTGTGACTCTTCTTCCTGCTGCAGATTTGGATGATTTCTCCAAA
CAATTGCAACAATCCATGAGCAGTGCTGACTCAACTCAGGCCTAAACTCATGCAGACCACACAAGGCAGATGGGC
TATATAAACGTTTTCGCTTTTCCGTTTACGATATATAGTCTACTCTTGTGCAGAATGAATTCTCGTAACTACATAGC
ACAAGTAGATGTAGTTAACTTTAATCTCACATAGCAATCTTTAATCAGTGTGTAACATTAGGGAGGACTTGAAAGA
GCCACCACATTTTCACCGAGGCCACGCGGAGTACGATCGAGTGTACAGTGAACAATGCTAGGGAGAGCTGCCTAT
ATGGAAGAGCCCTAATGTGTAAAATTAATTTTAGTAGTGCTATCCCCATGTGATTTTAATAGCTTCTTAGGAGAAT
GACAAAAAAAAAAAAAAAAAAAAA SEQ ID NO: 3 (synthetic IBIS DNA construct 1, variant BA.2; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT -continued

SEQUENCE LISTING

TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC
TGACCCTATACATTCTTTAAGAGTTTGTGTAGATACTGTTCGCACAAATGTCTACTTAGCTGTCTTTGATAAAAATC
TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT
GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA
GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT

-continued

SEQUENCE LISTING

CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT
TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT
GTGATACATTCTGTGCTGGTAGTACATTTATTAGTGATGAAGTTGCGAGAGACTTGTCACTACAGTTTAAAAGACC
AATAAATCCTACTGACCAGTCTTCTTACATCGTTGATAGTGTTACAGTGAAGAATGGTTCCATCCATCTTTACTTTG
ATAAAGCTGGTCAAAAGACTTATGAAAGACATTCTCTCTCTCATTTTGTTAACTTAGACAACCTGAGAGCTAATAA
CACTAAAGGTTCATTGCCTATTAATGTTATAGTTTTTGATGGTAAATCAAAATGTGAAGAATCATCTGCAAAATCA
GCGTCTGTTTACTACAGTCAGCTTATGTGTCAACCTATACTGTTACTAGATCAGGCATTAGTGTCTGATGTTGGTGA
TAGTGCGGAAGTTGCAGTTAAAATGTTTGATGCTTACGTTAATACGTTTTCATCAACTTTTAACGTACCAATGGAAA
AACTCAAAACACTAGTTGCAACTGCAGAAGCTGAACTTGCAAAGAATGTGTCCTTAGACAATGTCTTATCTACTTT
TATTTCAGCAGCTCGGCAAGGGTTTGTTGATTCAGATGTAGAAACTAAAGATGTTGTTGAATGTCTTAAATTGTCA
CATCAATCTGACATAGAAGTTACTGGCGATAGTTGTAATAACTATATGCTCACCTATAACAAAGTTGAAAACATGA
CACCCCGTGACCTTGGTGCTTGTATTGACTGTAGTGCGCGTCATATTAATGCGCAGGTAGCAAAAAGTCACAACAT
TGCTTTGATATGGAACGTTAAAGATTTCATGTCATTGTCTGAACAACTACGAAAACAAATACGTAGTGCTGCTAAA
AAGAATAACTTACCTTTTAAGTTGACATGTGCAACTACTAGACAAGTTGTTAATGTTGTAACAACAAAGATAGCAC
TTAAGGGTGGTAAAATTGTTAATAATTGGTTGAAGCAGTTAATTAAAGTTACACTTGTGTTCCTTTTTGTTGCTGCT
ATTTTCTATTTAATAACACCTGTTCATGTCATGTCTAAACATACTGACTTTTCAAGTGAAATCATAGGATACAAGGC
TATTGATGGTGGTGTCACTCGTGACATAGCATCTACAGATACTTGTTTTGCTAACAAACATGCTGATTTTGACACAT
GGTTTAGCCAGCGTGGTGGTAGTTATACTAATGACAAAGCTTGCCCATTGATTGCTGCAGTCATAACAAGAGAAGT
GGGTTTTGTCGTGCCTGGTTTGCCTGGCACGATATTACGCACAACTAATGGTGACTTTTTGCATTTCTTACCTAGAG
TTTTTAGTGCAGTTGGTAACATCTGTTACACACCATCAAAACTTATAGAGTACACTGACTTTGCAACATCAGCTTGT
GTTTTGGCTGCTGAATGTACAATTTTTAAAGATGCTTCTGGTAAGCCAGTACCATATTGTTATGATACCAATGTACT
AGAAGGTTCTGTTGCTTATGAAAGTTTACGCCCTGACACACGTTATGTGCTCATGGATGGCTCTATTATTCAATTTC
CTAACACCTACCTTGAAGGTTCTGTTAGAGTGGTAACAACTTTTGATTCTGAGTACTGTAGGCACGGCACTTGTGA
AAGATCAGAAGCTGGTGTTTGTGTATCTACTAGTGGTAGATGGGTACTTAACAATGATTATTACAGATCTTTACCA
GGAGTTTTCTGTGGTGTAGATGCTGTAAATTTACTTACTAATATGTTTACACCACTAATTCAACCTATTGGTGCTTT
GGACATATCAGCATCTATAGTAGCTGGTGGTATTGTAGCTATCGTAGTAACATGCCTTGCCTACTATTTTATGAGGT
TTAGAAGAGCTTTTGGTGAATACAGTCATGTAGTTGCCTTTAATACTTTACTATTCCTTATGTCATTCACTGTACTCT
GTTTAACACCAGTTTACTCATTCTTACCTGGTGTTTATTCTGTTATTTACTTGTACTTGACATTTTATCTTACTAATG
ATGTTTCTTTTTTAGCACATATTCAGTGGATGGTTATGTTCACACCTTTAGTACCTTTCTGGATAACAATTGCTTATA
TCATTTGTATTTCCACAAAGCATTTCTATTGGTTCTTTAGTAATTACCTAAAGAGACGTGTAGTCTTTAATGGTGTTT

-continued

| SEQUENCE LISTING |
|---|
| CCTTTAGTACTTTTGAAGAAGCTGCGCTGTGCACCTTTTTGTTAAATAAAGAAATGTATCTAAAGTTGCGTAGTGAT |
| GTGCTATTACCTCTTACGCAATATAATAGATACTTAGCTCTTTATAATAAGTACAAGTATTTTAGTGGAGCAATGGA |
| TACAACTAGCTACAGAGAAGCTGCTTGTTGTCATCTCGCAAAGGCTCTCAATGACTTCAGTAACTCAGGTTCTGAT |
| GTTCTTTACCAACCACCACAAACCTCTATCACCTCAGCTGTTTTGCAGAGTGGTTTTAGAAAAATGGCATTCCCATC |
| TGGTAAAGTTGAGGGTTGTATGGTACAAGTAACTTGTGGTACAACTACACTTAACGGTCTTTGGCTTGATGACGTA |
| GTTTACTGTCCAAGACATGTGATCTGCACCTCTGAAGACATGCTTAACCCTAATTATGAAGATTTACTCATTCGTAA |
| GTCTAATCATAATTTCTTGGTACAGGCTGGTAATGTTCAACTCAGGGTTATTGGACATTCTATGCAAAATTGTGTAC |
| TTAAGCTTAAGGTTGATACAGCCAATCCTAAGACACCTAAGTATAAGTTTGTTCGCATTCAACCAGGACAGACTTT |
| TTCAGTGTTAGCTTGTTACAATGGTTCACCATCTGGTGTTTACCAATGTGCTATGAGGCCCAATTTCACTATTAAGG |
| GTTCATTCCTTAATGGTTCATGTGGTAGTGTTGGTTTTAACATAGATTATGACTGTGTCTCTTTTTGTTACATGCACC |
| ATATGGAATTACCAACTGGAGTTCATGCTGGCACAGACTTAGAAGGTAACTTTTATGGACCTTTTGTTGACAGGCA |
| AACAGCACAAGCAGCTGGTACGGACACAACTATTACAGTTAATGTTTTAGCTTGGTTGTACGCTGCTGTTATAAAT |
| GGAGACAGGTGGTTTCTCAATCGATTTACCACAACTCTTAATGACTTTAACCTTGTGGCTATGAAGTACAATTATG |
| AACCTCTAACACAAGACCATGTTGACATACTAGGACCTCTTTCTGCTCAAACTGGAATTGCCGTTTTAGATATGTGT |
| GCTTCATTAAAAGAATTACTGCAAAATGGTATGAATGGACGTACCATATTGGGTAGTGCTTTATTAGAAGATGAAT |
| TTACACCTTTTGATGTTGTTAGACAATGCTCAGGTGTTACTTTCCAAAGTGCAGTGAAAAGAACAATCAAGGGTAC |
| ACACCACTGGTTGTTACTCACAATTTTGACTTCACTTTTAGTTTTAGTCCAGAGTACTCAATGGTCTTTGTTCTTTTT |
| TTTGTATGAAAATGCCTTTTTACCTTTTGCTATGGGTATTATTGCTATGTCTGCTTTTGCAATGATGTTTGTCAAACA |
| TAAGCATGCATTTCTCTGTTTGTTTTTGTTACCTTCTCTTGCCACTGTAGCTTATTTTAATATGGTCTATATGCCTGCT |
| AGTTGGGTGATGCGTATTATGACATGGTTGGATATGGTTGATACTAGTTTGTCTGGTTTTAAGCTAAAAGACTGTGT |
| TATGTATGCATCAGCTGTAGTGTTACTAATCCTTATGACAGCAAGAACTGTGTATGATGATGGTGCTAGGAGAGTG |
| TGGACACTTATGAATGTCTTGACACTCGTTTATAAAGTTTATTATGGTAATGCTTTAGATCAAGCCATTTCCATGTG |
| GGCTCTTATAATCTCTGTTACTTCTAACTACTCAGGTGTAGTTACAACTGTCATGTTTTTGGCCAGAGGTATTGTTTT |
| TATGTGTGTTGAGTATTGCCCTATTTTCTTCATAACTGGTAATACACTTCAGTGTATAATGCTAGTTTATTGTTTCTT |
| AGGCTATTTTTGTACTTGTTACTTTGGCCTCTTTTGTTTACTCAACCGCTACTTTAGACTGACTCTTGGTGTTTATGA |
| TTACTTAGTTTCTACACAGGAGTTTAGATATATGAATTCACAGGGACTACTCCCACCCAAGAATAGCATAGATGCC |
| TTCAAACTCAACATTAAATTGTTGGGTGTTGGTGGCAAACCTTGTATCAAAGTAGCCACTGTACAGTCTAAAATGT |
| CAGATGTAAAGTGCACATCAGTAGTCTTACTCTCAGTTTTGCAACAACTCAGAGTAGAATCATCATCTAAATTGTG |
| GGCTCAATGTGTCCAGTTACACAATGACATTCTCTTAGCTAAAGATACTACTGAAGCCTTTGAAAAAATGGTTTCA |
| CTACTTTCTGTTTTGCTTTCCATGCAGGGTGCTGTAGACATAAACAAGCTTTGTGAAGAAATGCTGGACAACAGGG |
| CAACCTTACAAGCTATAGCCTCAGAGTTTAGTTCCCTTCCATCATATGCAGCTTTTGCTACTGCTCAAGAAGCTTAT |
| GAGCAGGCTGTTGCTAATGGTGATTCTGAAGTTGTTCTTAAAAAGTTGAAGAAGTCTTTGAATGTGGCTAAATCTG |
| AATTTGACCGTGATGCAGCCATGCAACGTAAGTTGGAAAAGATGGCTGATCAAGCTATGACCCAAATGTATAAAC |
| AGGCTAGATCTGAGGACAAGAGGGCAAAAGTTACTAGTGCTATGCAGACAATGCTTTTCACTATGCTTAGAAAGTT |
| GGATAATGATGCACTCAACAACATTATCAACAATGCAAGAGATGGTTGTGTTCCCTTGAACATAATACCTCTTACA |
| ACAGCAGCCAAACTAATGGTTGTCATACCAGACTATAACACATATAAAAATACGTGTGATGGTACAACATTTACTT |
| ATGCATCAGCATTGTGGGAAATCCAACAGGTTGTAGATGCAGATAGTAAAATTGTTCAACTTAGTGAAATTAGTAT |
| GGACAATTCACCTAATTTAGCATGGCCTCTTATTGTAACAGCTTTAAGGGCCAATTCTGCTGTCAAATTACAGAAT |
| AATGAGCTTAGTCCTGTTGCACTACGACAGATGTCTTGTGCTGCCGGTACTACACAAACTGCTTGCACTGATGACA |
| ATGCGTTAGCTTACTACAACACAACAAAGGGAGGTAGGTTTGTACTTGCACTGTTATCCGATTTACAGGATTTGAA |
| ATGGGCTAGATTCCCTAAGAGTGATGGAACTGGTACTATCTATACAGAACTGGAACCACCTTGTAGGTTTGTTACA |
| GACACACCTAAAGGTCCTAAAGTGAAGTATTTATACTTTATTAAAGGATTAAACAACCTAAATAGAGGTATGGTAC |
| TTGGTAGTTTAGCTGCCACAGTACGTCTACAAGCTGGTAATGCAACAGAAGTGCCTGCCAATTCAACTGTATTATC |
| TTTCTGTGCTTTTGCTGTAGATGCTGCTAAAGCTTACAAAGATTATCTAGCTAGTGGGGGACAACCAATCACTAATT |
| GTGTTAAGATGTTGTGTACACACACTGGTACTGGTCAGGCAATAACAGTTACACCGGAAGCCAATATGGATCAAG |
| AATCCTTTGGTGGTGCATCGTGTTGTCTGTACTGCCGTTGCCACATAGATCATCCAAATCCTAAAGGATTTTGTGAC |
| TTAAAAGGTAAGTATGTACAAATACCTACAACTTGTGCTAATGACCCTGTGGGTTTTACACTTAAAAACACAGTCT |
| GTACCGTCTGCGGTATGTGGAAAGGTTATGGCTGTAGTTGTGATCAACTCCGCGAACCCATGCTTCAGTCAGCTGA |
| TGCACAATCGTTTTTAAACGGGTTTGCGGTGTAAGTGCAGCCCGTCTTACACCGTGCGGCACAGGCACTAGTACTG |
| ATGTCGTATACAGGGCTTTTGACATCTACAATGATAAAGTAGCTGGTTTTGCTAAATTCCTAAAAACTAATTGTTGT |
| CGCTTCCAAGAAAAGGACGAAGATGACAATTTAATTGATTCTTACTTTGTAGTTAAGAGACACACTTTCTCTAACT |

-continued

| SEQUENCE LISTING |
|---|
| ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA<br>TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT<br>TAAAACACTTCTTCTTTGCTCAGGATGGTAATGCTGCTATCAGCGATTATGACTACTATCGTTATAATCTACCAACA<br>ATGTGTGATATCAGACAACTACTATTTGTAGTTGAAGTTGTTGATAAGTACTTTGATTGTTACGATGGTGGCTGTAT<br>TAATGCTAACCAAGTCATCGTCAACAACCTAGACAAATCAGCTGGTTTTCCATTTAATAAATGGGGTAAGGCTAGA<br>CTTTATTATGATTCAATGAGTTATGAGGATCAAGATGCACTTTTCGCATATACAAAACGTAATGTCATCCCTACTAT<br>AACTCAAATGAATCTTAAGTATGCCATTAGTGCAAAGAATAGAGCTCGCACCGTAGCTGGTGTCTCTATCTGTAGT<br>ACTATGACCAATAGACAGTTTCATCAAAAATTATTGAAATCAATAGCCGCCACTAGAGGAGCTACTGTAGTAATTG<br>GAACAAGCAAATTCTATGGTGGTTGGCACAACATGTTAAAAACTGTTTATAGTGATGTAGAAAACCCTCACCTTAT<br>GGGTTGGGATTATCCTAAATGTGATAGAGCCATGCCTAACATGCTTAGAATTATGGCCTCACTTGTTCTTGCTCGCA<br>AACATACAACGTGTTGTAGCTTGTCACACCGTTTCTATAGATTAGCTAATGAGTGTGCTCAAGTATTGAGTGAAAT<br>GGTCATGTGTGGCGGTTCACTATATGTTAAACCAGGTGGAACCTCATCAGGAGATGCCACAACTGCTTATGCTAAT<br>AGTGTTTTTAACATTTGTCAAGCTGTCACGGCCAATGTTAATGCACTTTTATCTACTGATGGTAACAAAATTGCCGA<br>TAAGTATGTCCGCAATTTACAACACAGACTTTATGAGTGTCTCTATAGAAATAGAGATGTTGACACAGACTTTGTG<br>AATGAGTTTTACGCATATTTGCGTAAACATTTCTCAATGATGATACTCTCTGACGATGCTGTTGTGTGTTTCAATAG<br>CACTTATGCATCTCAAGGTCTAGTGGCTAGCATAAAGAACTTTAAGTCAGTTCTTTATTATCAAAACAATGTTTTTA<br>TGTCTGAAGCAAAATGTTGGACTGAGACTGACCTTACTAAAGGACCTCATGAATTTTGCTCTCAACATACAATGCT<br>AGTTAAACAGGGTGATGATTATGTGTACCTTCCTTACCCAGATCCATCAAGAATCCTAGGGGCCGGCTGTTTTGTA<br>GATGATATCGTAAAAACAGATGGTACACTTATGATTGAACGGTTCGTGTCTTTAGCTATAGATGCTTACCCACTTA<br>CTAAACATCCTAATCAGGAGTATGCTGATGTCTTTCATTTGTACTTACAATACATAAGAAAGCTACATGATGAGTT<br>AACAGGACACATGTTAGACATGTATTCTGTTATGCTTACTAATGATAACACTTCAAGGTATTGGGAACCTGAGTTT<br>TATGAGGCTATGTACACACCGCATACAGTCTTACAGGCTGTTGGGGCTTGTGTTCTTTGCAATTCACAGACTTCATT<br>AAGATGTGGTGCTTGCATACGTAGACCATTCTTATGTTGTAAATGCTGTTACGACCATGTCATATCAACATCACATA<br>AATTAGTCTTGTCTGTTAATCCGTATGTTTGCAATGCTCCAGGTTGTGATGTCACAGATGTGACTCAACTTTACTTA<br>GGAGGTATGAGCTATTATTGTAAATCACATAAACCACCCATTAGTTTTCCATTGTGTGCTAATGGACAAGTTTTTGG<br>TTTATATAAAAATACATGTGTTGGTAGCGATAATGTTACTGACTTTAATGCAATTGCAACATGTGACTGGACAAAT<br>GCTGGTGATTACATTTTAGCTAACACCTGTACTGAAAGACTCAAGCTTTTTGCAGCAGAAACGCTCAAAGCTACTG<br>AGGAGACATTTAAACTGTCTTATGGTATTGCTACTGTACGTGAAGTGCTGTCTGACAGAGAATTACATCTTTCATG<br>GGAAGTTGGTAAACCTAGACCACCACTTAACCGAAATTATGTCTTTACTGGTTATCGTGTAACTAAAAACAGTAAA<br>GTACAAATAGGAGAGTACACCTTTGAAAAAGGTGACTATGGTGATGCTGTTGTTTACCGAGGTACAACAACTTACA<br>AATTAAATGTTGGTGATTATTTTGTGCTGACATCACATACAGTAATGCCATTAAGTGCACCTACACTAGTGCCACA<br>AGAGCACTATGTTAGAATTACTGGCTTATACCCAACACTCAATATCTCAGATGAGTTTTCTAGCAATGTTGCAAATT<br>ATCAAAAGGTTGGTATGCAAAAGTATTCTACACTCCAGGGACCACCTGGTACTGGTAAGAGTCATTTTGCTATTGG<br>CCTAGCTCTCTACTACCCTTCTGCTCGCATAGTGTATACAGCTTGCTCTCATGCCGCTGTTGATGCACTATGTGAGA<br>AGGCATTAAAATATTTGCCTATAGATAAATGTAGTAGAATTATACCTGCACGTGCTCGTGTAGAGTGTTTTGATAA<br>ATTCAAAGTGAATTCAACATTAGAACAGTATGTCTTTTGTACTGTAAATGCATTGCCTGAGACGACAGCAGATATA<br>GTTGTCTTTGATGAAATTTCAATGGCCACAAATTATGATTTGAGTGTTGTCAATGCCAGATTACGTGCTAAGCACTA<br>TGTGTACATTGGCGACCCTGCTCAATTACCTGCACCACGCACATTGCTAACTAAGGGCACACTAGAACCAGAATAT<br>TTCAATTCAGTGTGTAGACTTATGAAAACTATAGGTCCAGACATGTTCCTCGGAACTTGTCGGCGTTGTCCTGCTGA |

-continued

SEQUENCE LISTING

AATTGTTGACACTGTGAGTGCTTTGGTTTATGATAATAAGCTTAAAGCACATAAAGACAAATCAGCTCAATGCTTT
AAAATGTTTTATAAGGGTGTTATCACGCATGATGTTTCATCTGCAATTAACAGGCCACAAATAGGCGTGGTAAGAG
AATTCCTTACACGTAACCCTGCTTGGAGAAAAGCTGTCTTTATTTCACCTTATAATTCACAGAATGCTGTAGCCTCA
AAGATTTTGGGACTACCAACTCAAACTGTTGATTCATCACAGGGCTCAGAATATGACTATGTCATATTCACTCAAA
CCACTGAAACAGCTCACTCTTGTAATGTAAACAGATTTAATGTTGCTATTACCAGAGCAAAAGTAGGCATACTTTG
CATAATGTCTGATAGAGACCTTTATGACAAGTTGCAATTTACAAGTCTTGAAATTCCACGTAGGAATGTGGCAACT
TTACAAGCTGAAAATGTAACAGGACTCTTTAAAGATTGTAGTAAGGTAATCACTGGGTTACATCCTACACAGGCAC
CTACACACCTCAGTGTTGACACTAAATTCAAAACTGAAGGTTTATGTGTTGACATACCTGGCATACCTAAGGACAT
GACCTATAGAAGACTCATCTCTATGATGGGTTTTAAAATGAATTATCAAGTTAATGGTTACCCTAACATGTTTATCA
CCCGCGAAGAAGCTATAAGACATGTACGTGCATGGATTGGCTTCGATGTCGAGGGGTGTCATGCTACTAGAGAAG
CTGTTGGTACCAATTTACCTTTACAGCTAGGTTTTTCTACAGGTGTTAACCTAGTTGCTGTACCTACAGGTTATGTT
GATACACCTAATAATACAGATTTTTCCAGAGTTAGTGCTAAACCACCGCCTGGAGATCAATTTAAACACCTCATAC
CACTTATGTACAAAGGACTTCCTTGGAATGTAGTGCGTATAAAGATTGTACAAATGTTAAGTGACACACTTAAAAA
TCTCTCTGACAGAGTCGTATTTGTCTTATGGGCACATGGCTTTGAGTTGACATCTATGAAGTATTTTGTGAAAATAG
GACCTGAGCGCACCTGTTGTCTATGTGATAGACGTGCCACATGCTTTTCCACTGCTTCAGACACTTATGCCTGTTGG
CATCATTCTATTGGATTTGATTACGTCTATAATCCGTTTATGATTGATGTTCAACAATGGGGTTTTACAGGTAACCT
ACAAAGCAACCATGATCTGTATTGTCAAGTCCATGGTAATGCACATGTAGCTAGTTGTGATGCAATCATGACTAGG
TGTCTAGCTGTCCACGAGTGCTTTGTTAAGCGTGTTGACTGGACTATTGAATATCCTATAATTGGTGATGAACTGAA
GATTAATGCGGCTTGTAGAAAGGTTCAACACATGGTTGTTAAAGCTGCATTATTAGCAGACAAATTCCCAGTTCTT
CACGACATTGGTAACCCTAAAGCTATTAAGTGTGTACCTCAAGCTGATGTAGAATGGAAGTTCTATGATGCACAGC
CTTGTAGTGACAAAGCTTATAAAATAGAAGAATTATTCTATTCTTATGCCACACATTCTGACAAATTCACAGATGG
TGTATGCCTATTTTGGAATTGCAATGTCGATAGATATCCTGCTAATTCCATTGTTTGTAGATTTGACACTAGAGTGC
TATCTAACCTTAACTTGCCTGGTTGTGATGGTGGCAGTTTGTATGTAAATAAACATGCATTCCACACACCAGCTTTT
GATAAAAGTGCTTTTGTTAATTTAAAACAATTACCATTTTTCTATTACTCTGACAGTCCATGTGAGTCTCATGGAAA
ACAAGTAGTGTCAGATATAGATTATGTACCACTAAAGTCTGCTACGTGTATAACACGTTGCAATTTAGGTGGTGCT
GTCTGTAGACATCATGCTAATGAGTACAGATTGTATCTCGATGCTTATAACATGATGATCTCAGCTGGCTTTAGCTT
GTGGGTTTACAAACAATTTGATACTTATAACCTCTGGAACACTTTTACAAGACTTCAGAGTTTAGAAAATGTGGCT
TTTAATGTTGTAAATAAGGGACACTTTGATGGACAACAGGGTGAAGTACCAGTTTCTATCATTAATAACACTGTTT
ACACAAAAGTTGATGGTGTTGATGTAGAATTGTTTGAAAATAAAACAACATTACCTGTTAATGTAGCATTTGAGCT
TTGGGCTAAGCGCAACATTAAACCAGTACCAGAGGTGAAAATACTCAATAATTTGGGTGTGGACATTGCTGCTAAT
ACTGTGATCTGGGACTACAAAAGAGATGCTCCAGCACATATATCTACTATTGGTGTTTGTTCTATGACTGACATAG
CCAAGAAACCAACTGAAACGATTTGTGCACCACTCACTGTCTTTTTTGATGGTAGAGTTGATGGTCAAGTAGACTT
ATTTAGAAATGCCCGTAATGGTGTTCTTATTACAGAAGGTAGTGTTAAAGGTTTACAACCATCTGTAGGTCCCAAA
CAAGCTAGTCTTAATGGAGTCACATTAATTGGAGAAGCCGTAAAAACACAGTTCAATTATTATAAGAAAGTTGATG
GTGTTGTCCAACAATTACCTGAAACTTACTTTACTCAGAGTAGAAATTTACAAGAATTTAAACCCAGGAGTCAAAT
GGAAATTGATTTCTTAGAATTAGCTATGGATGAATTCATTGAACGGTATAAATTAGAAGGCTATGCCTTCGAACAT
ATCGTTTATGGAGATTTTAGTCATAGTCAGTTAGGTGGTTTACATCTACTGATTGGACTAGCTAAACGTTTTAAGGA
ATCACCTTTTGAATTAGAAGATTTTATTCCTATGGACAGTACAGTTAAAAACTATTTCATAACAGATGCGCAAACA
GGTTCATCTAAGTGTGTGTGTTCTGTTATTGATTTATTACTTGATGATTTTGTTGAAATAATAAAATCCCAAGATTT
ATCTGTAGTTTCTAAGGTTGTCAAAGTGACTATTGACTATACAGAAATTTCATTTATGCTTTGGTGTAAAGATGGCC
ATGTAGAAACATTTTACCCAAAATTACAATCTAGTCAAGCGTGGCAACCGGGTGTTGCTATGCCTAATCTTTACAA
AATGCAAAGAATGCTATTAGAAAAGTGTGACCTTCAAAATTATGGTGATAGTGCAACATTACCTAAAGGCATAAT
GATGAATGTCGCAAAATATACTCAACTGTGTCAATATTTAAACACATTAACATTAGCTGTACCCTATAATATGAGA
GTTATACATTTTGGTGCTGGTTCTGATAAAGGAGTTGCACCAGGTACAGCTGTTTTAAGACAGTGGTTGCCTACGG
GTACGCTGCTTGTCGATTCAGATCTTAATGACTTTGTCTCTGATGCAGATTCAACTTTGATTGGTGATTGTGCAACT
GTACATACAGCTAATAAATGGGATCTCATTATTAGTGATATGTACGACCCTAAGACTAAAAATGTTACAAAAGAA
AATGACTCTAAAGAGGGTTTTTTCACTTACATTTGTGGGTTTATACAACAAAAGCTAGCTCTTGGAGGTTCCGTGGC
TATAAAGATAACAGAACATTCTTGGAATGCTGATCTTTATAAGCTCATGGGACACTTCGCATGGTGGACAGCCTTT
GTTACTAATGTGAATGCGTCATCATCTGAAGCATTTTTAATTGGATGTAATTATCTTGGCAAACCACGCGAACAAA
TAGATGGTTATGTCATGCATGCAAATTACATATTTGGAGGAATACAAATCCAATTCAGTTGTCTTCCTATTCTTTA
TTTGACATGAGTAAATTTCCCCTTAAATTAAGGGGTACTGCTGTTATGTCTTTAAAAGAAGGTCAAATCAATGATA

-continued

| SEQUENCE LISTING |
|---|
| TGATTTTATCTCTTCTTAGTAAAGGTAGACTTATAATTAGAGAAAACAACAGAGTTGTTATTTCTAGTGATGTTCTT |
| GTTAACAACTAAACGAACAATGTTTGTTTTTCTTGTTTTATTGCCACTAGTCTCTAGTCAGTGTGTTAATCTTATAAC |
| CAGAACTCAATCATACACTAATTCTTTCACACGTGGTGTTTATTACCCTGACAAAGTTTTCAGATCCTCAGTTTTAC |
| ATTCAACTCAGGACTTGTTCTTACCTTTCTTTTCCAATGTTACTTGGTTCCATGCTATACATGTCTCTGGGACCAATG |
| GTACTAAGAGGTTTGATAACCCTGTCCTACCATTTAATGATGGTGTTTATTTTGCTTCCACTGAGAAGTCTAACATA |
| ATAAGAGGCTGGATTTTTGGTACTACTTTAGATTCGAAGACCCAGTCCCTACTTATTGTTAATAACGCTACTAATGT |
| TGTTATTAAAGTCTGTGAATTTCAATTTTGTAATGATCCATTTTTGGATGTTTATTACCACAAAAACAACAAAAGTT |
| GGATGGAAAGTGAGTTCAGAGTTTATTCTAGTGCGAATAATTGCACTTTTGAATATGTCTCTCAGCCTTTTCTTATG |
| GACCTTGAAGGAAAACAGGGTAATTTCAAAAATCTTAGGGAATTTGTGTTTAAGAATATTGATGGTTATTTTAAAA |
| TATATTCTAAGCACACGCCTATTAATTTAGGGCGTGATCTCCCTCAGGGTTTTTCGGCTTTAGAACCATTGGTAGAT |
| TTGCCAATAGGTATTAACATCACTAGGTTTCAAACTTTACTTGCTTTACATAGAAGTTATTTGACTCCTGGTGATTC |
| TTCTTCAGGTTGGACAGCTGGTGCTGCAGCTTATTATGTGGGTTATCTTCAACCTAGGACTTTTCTATTAAAATATA |
| ATGAAAATGGAACCATTACAGATGCTGTAGACTGTGCACTTGACCCTCTCTCAGAAACAAAGTGTACGTTGAAATC |
| CTTCACTGTAGAAAAAGGAATCTATCAAACTTCTAACTTTAGAGTCCAACCAACAGAATCTATTGTTAGATTTCCT |
| AATATTACAAACTTGTGCCCTTTTGATGAAGTTTTTAACGCCACCAGATTTGCATCTGTTTATGCTTGGAACAGGAA |
| GAGAATCAGCAACTGTGTTGCTGATTATTCTGTCCTATATAATTTCGCACCATTTTTCGCTTTTAAGTGTTATGGAG |
| TGTCTCCTACTAAATTAAATGATCTCTGCTTTACTAATGTCTATGCAGATTCATTTGTAATTAGAGGTAATGAAGTC |
| AGCCAAATCGCTCCAGGGCAAACTGGAAATATTGCTGATTATAATTATAAATTACCAGATGATTTTACAGGCTGCG |
| TTATAGCTTGGAATTCTAACAAGCTTGATTCTAAGGTTGGTGGTAATTATAATTACCTGTATAGATTGTTTAGGAAG |
| TCTAATCTCAAACCTTTTGAGAGAGATATTTCAACTGAAATCTATCAGGCCGGTAACAAACCTTGTAATGGTGTTG |
| CAGGTTTTAATTGTTACTTTCCTTTACGATCATATGGTTTCCGACCCACTTATGGTGTTGGTCACCAACCATACAGA |
| GTAGTAGTACTTTCTTTTGAACTTCTACATGCACCAGCAACTGTTTGTGGACCTAAAAAGTCTACTAATTTGGTTAA |
| AAACAAATGTGTCAATTTCAACTTCAATGGTTTAACAGGCACAGGTGTTCTTACTGAGTCTAACAAAAAGTTTCTG |
| CCTTTCCAACAATTTGGCAGAGACATTGCTGACACTACTGATGCTGTCCGTGATCCACAGACACTTGAGATTCTTG |
| ACATTACACCATGTTCTTTTGGTGGTGTCAGTGTTATAACACCAGGAACAAATACTTCTAACCAGGTTGCTGTTCTT |
| TATCAGGGTGTTAACTGCACAGAAGTCCCTGTTGCTATTCATGCAGATCAACTTACTCCTACTTGGCGTGTTTATTC |
| TACAGGTTCTAATGTTTTTCAAACACGTGCAGGCTGTTTAATAGGGGCTGAATATGTCAACAACTCATATGAGTGT |
| GACATACCCATTGGTGCAGGTATATGCGCTAGTTATCAGACTCAGACTAAGTCTCATCGGCGGGCACGTAGTGTAG |
| CTAGTCAATCCATCATTGCCTACACTATGTCACTTGGTGCAGAAAATTCAGTTGCTTACTCTAATAACTCTATTGCC |
| ATACCCACAAATTTTACTATTAGTGTTACCACAGAAATTCTACCAGTGTCTATGACCAAGACATCAGTAGATTGTA |
| CAATGTACATTTGTGGTGATTCAACTGAATGCAGCAATCTTTTGTTGCAATATGGCAGTTTTTGTACACAATTAAAA |
| CGTGCTTTAACTGGAATAGCTGTTGAACAAGACAAAAACACCCAAGAAGTTTTTGCACAAGTCAAACAAATTTAC |
| AAAACACCACCAATTAAATATTTTGGTGGTTTTAATTTTTCACAAATATTACCAGATCCATCAAAACCAAGCAAGA |
| GGTCATTTATTGAAGATCTACTTTTCAACAAAGTGACACTTGCAGATGCTGGCTTCATCAAACAATATGGTGATTG |
| CCTTGGTGATATTGCTGCTAGAGACCTCATTTGTGCACAAAAGTTTAACGGCCTTACTGTTTTGCCACCTTTGCTCA |
| CAGATGAAATGATTGCTCAATACACTTCTGCACTGTTAGCGGGTACAATCACTTCTGGTTGGACCTTTGGTGCAGG |
| TGCTGCATTACAAATACCATTTGCTATGCAAATGGCTTATAGGTTTAATGGTATTGGAGTTACACAGAATGTTCTCT |
| ATGAGAACCAAAAATTGATTGCCAACCAATTTAATAGTGCTATTGGCAAAATTCAAGACTCACTTTCTTCCACAGC |
| AAGTGCACTTGGAAAACTTCAAGATGTGGTCAACCATAATGCACAAGCTTTAAACACGCTTGTTAAACAACTTAGC |
| TCCAAATTTGGTGCAATTTCAAGTGTTTTAAATGATATCCTTTCACGTCTTGACAAAGTTGAGGCTGAAGTGCAAAT |
| TGATAGGTTGATCACAGGCAGACTTCAAAGTTTGCAGACATATGTGACTCAACAATTAATTAGAGCTGCAGAAATC |
| AGAGCTTCTGCTAATCTTGCTGCTACTAAAATGTCAGAGTGTGTACTTGGACAATCAAAAAGAGTTGATTTTTGTG |
| GAAAGGGCTATCATCTTATGTCCTTCCCTCAGTCAGCACCTCATGGTGTAGTCTTCTTGCATGTGACTTATGTCCCT |
| GCACAAGAAAAGAACTTCACAACTGCTCCTGCCATTTGTCATGATGGAAAAGCACACTTTCCTCGTGAAGGTGTCT |
| TTGTTTCAAATGGCACACACTGGTTTGTAACACAAAGGAATTTTTATGAACCACAAATCATTACTACAGACAACAC |
| ATTTGTGTCTGGTAACTGTGATGTTGTAATAGGAATTGTCAACAACACAGTTTATGATCCTTTGCAACCTGAATTAG |
| ATTCATTCAAGGAGGAGTTAGATAAATATTTTAAGAATCATACATCACCAGATGTTGATTTAGGTGACATCTCTGG |
| CATTAATGCTTCAGTTGTAAACATTCAAAAAGAAATTGACCGCCTCAATGAGGTTGCCAAGAATTTAAATGAATCT |
| CTCATCGATCTCCAAGAACTTGGAAAGTATGAGCAGTATATAAAATGGCCATGGTACATTTGGCTAGGTTTTATAG |
| CTGGCTTGATTGCCATAGTAATGGTGACAATTATGCTTTGCTGTATGACCAGTTGCTGTAGTTGTCTCAAGGGCTGT |
| TGTTCTTGTGGATCCTGCTGCAAATTTGATGAAGACGACTCTGAGCCAGTGCTCAAAGGAGTCAAATTACATTACA |

-continued

SEQUENCE LISTING

CATAAACGAACTTATGGATTTGTTTATGAGAATCTTCACAATTGGAACTGTAACTTTGAAGCAAGGTGAAATCAAG
GATGCTACTCCTTCAGATTTTGTTCGCGCTACTGCAACGATACCGATACAAGCCTCACTCCCTTTCGGATGGCTTAT
TGTTGGCGTTGCACTTCTTGCTGTTTTTCAGAGCGCTTCCAAAATCATAACCCTCAAAAAGAGATGGCAACTAGCA
CTCTCCAAGGGTGTTCACTTTGTTTGCAACTTGCTGTTGTTGTTTGTAACAGTTTACTCACACCTTTTGCTCGTTGCT
GCTGGCCTTGAAGCCCCTTTTCTCTATCTTTATGCTTTAGTCTACTTCTTGCAGAGTATAAACTTTGTAAGAATAATA
ATGAGGCTTTGGCTTTGCTGGAAATGCCGTTCCAAAAACCCATTACTTTATGATGCCAACTATTTTCTTTGCTGGCA
TACTAATTGTTACGACTATTGTATACCTTACAATAGTGTAACTTCTTCAATTGTCATTACTTCAGGTGATGGCACAA
CAAGTCCTATTTCTGAACATGACTACCAGATTGGTGGTTATACTGAAAAATGGGAATCTGGAGTAAAAGACTGTGT
TGTATTACACAGTTACTTCACTTCAGACTATTACCAGCTGTACTCAACTCAATTGAGTACAGACACTGGTGTTGAAC
ATGTTACCTTCTTCATCTACAATAAAATTGTTGATGAGCCTGAAGAACATGTCCAAATTCACACAATCGACGGTTC
ATCCGGAGTTGTTAATCCAGTAATGGAACCAATTTATGATGAACCGACGACGACTACTAGCGTGCCTTTGTAAGCA
CAAGCTGATGAGTACGAACTTATGTACTCATTCGTTTCGGAAGAGACAGGTACGTAAATAGTTAATAGCTGACTTC
TTTTTCTTGCTTTCGTGTGATTCTTGCTAGTTACACTAGCCATCCTTACTGCGCTTCGATTGTGTGCGTACTGCTGCA
ATATTGTTAACGTGAGTCTTGTAAAACCTTCTTTTTACGTTTACTCTCGTGTTAAAAATCTGAATTCTTCTAGAGTTC
CTGATCTTCTGGTCTAAACGAACTAAATATTATATTAGTTTTTCTGTTTGGAACTTTAATTTTAGCCATGGCAGATTC
CAACGGTACTATTACCGTTGAAGAGCTTAAAAAGCTCCTTGAACAATGGAACCTAGTAATAGGTTTCCTATTCCTT
ACATGGATTTGTCTTCTACAATTTGCCTATGCCAACAGGAATAGGTTTTTGTATATAATTAAGTTAATTTTCCTCTG
GCTGTTATGGCCAGTAACTTTAGCTTGTTTTGTGCTTGCTGCTGTTTACAGAATAAATTGGATCACCGGTGGAATTG
CTATCGCAATGGCTTGTCTTGTAGGCTTGATGTGGCTCAGCTACTTCATTGCTTCTTTCAGACTGTTTGCGCGTACG
CGTTCCATGTGGTCATTCAATCCAGAAACTAACATTCTTCTCAACGTGCCACTCCATGGCACTATTCTGACCAGACC
GCTTCTAGAAAGTGAACTCGTAATCGGAGCTGTGATCCTTCGTGGACATCTTCGTATTGCTGGACACCATCTAGGA
CGCTGTGACATCAAGGACCTGCCTAAAGAAATCACTGTTGCTACATCACGAACGCTTTCTTATTACAAATTGGGAG
CTTCGCAGCGTGTAGCAGGTGACTCAGGTTTTGCTGCATACAGTCGCTACAGGATTGGCAACTATAAATTAAACAC
AGACCATTCCAGTAGCAGTGACAATATTGCTTTGCTTGTACAGTAAGTGACAACAGATGTTTCATCTCGTTGACTTT
CAGGTTACTATAGCAGAGATATTACTAATTATTATGAGGACTTTTAAAGTTTCCATTTGGAATCTTGATTACATCAT
AAACCTCATAATTAAAAATTTATCTAAGTCACTAACTGAGAATAAATATTCTCAATTAGATGAAGAGCAACCAATG
GAGATTGATTAAACGAACATGAAAATTATTCTTTTCTTGGCACTGATAACACTCGCTACTTGTGAGCTTTATCACTA
CCAAGAGTGTGTTAGAGGTACAACAGTACTTTTAAAAGAACCTTGCTCTTCTGGAACATACGAGGGCAATTCACCA
TTTCATCCTCTAGCTGATAACAAATTTGCACTGACTTGCTTTAGCACTCAATTTGCTTTTGCTTGTCCTGACGGCGTA
AAACACGTCTATCAGTTACGTGCCAGATCAGTTTCACCTAAACTGTTCATCAGACAAGAGGAAGTTCAAGAACTTT
ACTCTCCAATTTTTCTTATTGTTGCGGCAATAGTGTTTATAACACTTTGCTTCACACTCAAAAGAAAGACAGAATGA
TTGAACTTTCATTAATTGACTTCTATTTGTGCTTTTTAGCCTTTCTGCTATTCCTTGTTTTAATTATGCTTATTATCTT
TTGGTTCTCACTTGAACTGCAAGATCATAATGAAACTTGTCACGCCTAAACGAACatgaccaacaagtgtctcctccaaattgctctcctg
ttgtgcttctccactacagctctttccatgagctacaacttgcttggattcctacaaagaagcagcaattttcagtgtcagaagctcctgtggcaattgaatgggaggcttgaatactgcctcaagg
acaggatgaactttgacatccctgaggagattaagcagctgcagcagttccagaaggaggacgccgcattgaccatctatgagatgctccagaacatctttgctattttcagacaagattcatct
agcactggctggaatgagactattgttgagaacctcctggctaatgtctatcatcagataaaccatctgaagacagtcctggaagaaaaactggagaaagaagatttcaccaggggaaaactc
atgagcagtctgcacctgaaaagatattatgggaggattctgcattacctgaaggccaaggagtacagtcactgtgcctggaccatagtcagagtggaaatcctaaggaacttttacttcattaa
cagacttacaggttacctccgaaactgaGACGTTCGTGTTGTTTTAGATTTCATCTAAACGAACAAACTAAAATGTCTGATAATGGA
CCCCAAAATCAGCGAAATGCACCCCGCATTACGTTTGGTGGACCCTCAGATTCAACTGGCAGTAACCAGAATGGA
GAACGCAGTGGGGCGCGATCAAAACAACGTCGGCCCCAAGGTTTACCCAATAATACTGCGTCTTGGTTCACCGCTC
TCACTCAACATGGCAAGGAAGACCTTAAATTCCCTCGAGGACAAGGCGTTCCAATTAACACCAATAGCAGTCCAG
ATGACCAAATTGGCTACTACCGAAGAGCTACCAGACGAATTCGTGGTGGTGACGGTAAAATGAAAGATCTCAGTC
CAAGATGGTATTTCTACTACCTAGGAACTGGGCCAGAAGCTGGACTTCCCTATGGTGCTAACAAAGACGGCATCAT
ATGGGTTGCAACTGAGGGAGCCTTGAATACACCAAAAGATCACATTGGCACCCGCAATCCTGCTAACAATGCTGC
AATCGTGCTACAACTTCCTCAAGGAACAACATTGCCAAAAGGCTTCTACGCAGAAGGGAGCAGAGGCGGCAGTCA
AGCCTCTTCTCGTTCCTCATCACGTAGTCGCAACAGTTCAAGAAATTCAACTCCAGGCAGCAGTAGGGGAACTTCT
CCTGCTAGAATGGCTGGCAATGGCGGTGATGCTGCTCTTGCTTTGCTGCTGCTTGACAGATTGAACCAGCTTGAGA
GCAAAATGTCTGGTAAAGGCCAACAACAACAAGGCCAAACTGTCACTAAGAAATCTGCTGCTGAGGCTTCTAAGA
AGCCTCGGCAAAAACGTACTGCCACTAAAGCATACAATGTAACACAAGCTTTCGGCAGACGTGGTCCAGAACAAA
CCCAAGGAAATTTTGGGGACCAGGAACTAATCAGACAAGGAACTGATTACAAACATTGGCCGCAAATTGCACAAT
TTGCCCCCAGCGCTTCAGCGTTCTTCGGAATGTCGCGCATTGGCATGGAAGTCACACCTTCGGGAACGTGGTTGAC -continued

SEQUENCE LISTING

CTACACAGGTGCCATCAAATTGGATGACAAAGATCCAAATTTCAAAGATCAAGTCATTTTGCTGAATAAGCATATT
GACGCATACAAAACATTCCCACCAACAGAGCCTAAAAAGGACAAAAAGAAGAAGGCTGATGAAACTCAAGCCTT
ACCGCAGAGACAGAAGAAACAGCAAACTGTGACTCTTCTTCCTGCTGCAGATTTGGATGATTTCTCCAAACAATTG
CAACAATCCATGAGCAGTGCTGACTCAACTCAGGCCTAAACTCATGCAGACCACACAAGGCAGATGGGCTATATA
AACGTTTTCGCTTTTCCGTTTACGATATATAGTCTACTCTTGTGCAGAATGAATTCTCGTAACTACATAGCACAAGT
AGATGTAGTTAACTTTAATCTCACATAGCAATCTTTAATCAGTGTGTAACATTAGGGAGGACTTGAAAGAGCCACC
ACATTTTCACCGAGGCCACGCGGAGTACGATCGAGTGTACAGTGAACAATGCTAGGGAGAGCTGCCTATATGGAA
GAGCCCTAATGTGTAAAATTAATTTTAGTAGTGCTATCCCCATGTGATTTTAATAGCTTCTTAGGAGAATGACAAA
AAAAAAAAAAAAAAAAAA

SEQ ID NO: 4 (synthetic IBIS DNA construct 1, variant BA.5; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG -continued

SEQUENCE LISTING

AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC
TGACCCTATACATTCTTTAAGAGTTTGTGTAGATACTGTTCGCACAAATGTCTACTTAGCTGTCTTTGATAAAAATC
TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT
GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA
GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT
CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT

-continued

SEQUENCE LISTING

TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT
GTGATACATTCTGTGCTGGTAGTACATTTATTAGTGATGAAGTTGCGAGAGACTTGTCACTACAGTTTAAAAGACC
AATAAATCCTACTGACCAGTCTTCTTACATCGTTGATAGTGTTACAGTGAAGAATGGTTCCATCCATCTTTACTTTG
ATAAAGCTGGTCAAAAGACTTATGAAAGACATTCTCTCTCTCATTTTGTTAACTTAGACAACCTGAGAGCTAATAA
CACTAAAGGTTCATTGCCTATTAATGTTATAGTTTTTGATGGTAAATCAAAATGTGAAGAATCATCTGCAAAATCA
GCGTCTGTTTACTACAGTCAGCTTATGTGTCAACCTATACTGTTACTAGATCAGGCATTAGTGTCTGATGTTGGTGA
TAGTGCGGAAGTTGCAGTTAAAATGTTTGATGCTTACGTTAATACGTTTTCATCAACTTTTAACGTACCAATGGAAA
AACTCAAAACACTAGTTGCAACTGCAGAAGCTGAACTTGCAAAGAATGTGTCCTTAGACAATGTCTTATCTACTTT
TATTTCAGCAGCTCGGCAAGGGTTTGTTGATTCAGATGTAGAAACTAAAGATGTTGTTGAATGTCTTAAATTGTCA
CATCAATCTGACATAGAAGTTACTGGCGATAGTTGTAATAACTATATGCTCACCTATAACAAAGTTGAAAACATGA
CACCCCGTGACCTTGGTGCTTGTATTGACTGTAGTGCGCGTCATATTAATGCGCAGGTAGCAAAAAGTCACAACAT
TGCTTTGATATGGAACGTTAAAGATTTCATGTCATTGTCTGAACAACTACGAAAACAAATACGTAGTGCTGCTAAA
AAGAATAACTTACCTTTTAAGTTGACATGTGCAACTACTAGACAAGTTGTTAATGTTGTAACAACAAAGATAGCAC
TTAAGGGTGGTAAAATTGTTAATAATTGGTTGAAGCAGTTAATTAAAGTTACACTTGTGTTCCTTTTTGTTGCTGCT
ATTTTCTATTTAATAACACCTGTTCATGTCATGTCTAAACATACTGACTTTTCAAGTGAAATCATAGGATACAAGGC
TATTGATGGTGGTGTCACTCGTGACATAGCATCTACAGATACTTGTTTTGCTAACAAACATGCTGATTTTGACACAT
GGTTTAGCCAGCGTGGTGGTAGTTATACTAATGACAAAGCTTGCCCATTGATTGCTGCAGTCATAACAAGAGAAGT
GGGTTTTGTCGTGCCTGGTTTGCCTGGCACGATATTACGCACAACTAATGGTGACTTTTTGCATTTCTTACCTAGAG
TTTTTAGTGCAGTTGGTAACATCTGTTACACACCATCAAAACTTATAGAGTACACTGACTTTGCAACATCAGCTTGT
GTTTTGGCTGCTGAATGTACAATTTTTAAAGATGCTTCTGGTAAGCCAGTACCATATTGTTATGATACCAATGTACT
AGAAGGTTCTGTTGCTTATGAAAGTTTACGCCCTGACACACGTTATGTGCTCATGGATGGCTCTATTATTCAATTTC
CTAACACCTACCTTGAAGGTTCTGTTAGAGTGGTAACAACTTTTGATTCTGAGTACTGTAGGCACGGCACTTGTGA
AAGATCAGAAGCTGGTGTTTGTGTATCTACTAGTGGTAGATGGGTACTTAACAATGATTATTACAGATCTTTACCA
GGAGTTTTCTGTGGTGTAGATGCTGTAAATTTACTTACTAATATGTTTACACCACTAATTCAACCTATTGGTGCTTT
GGACATATCAGCATCTATAGTAGCTGGTGGTATTGTAGCTATCGTAGTAACATGCCTTGCCTACTATTTTATGAGGT
TTAGAAGAGCTTTTGGTGAATACAGTCATGTAGTTGCCTTTAATACTTTACTATTCCTTATGTCATTCACTGTACTCT
GTTTAACACCAGTTTACTCATTCTTACCTGGTGTTTATTCTGTTATTTACTTGTACTTGACATTTTATCTTACTAATG
ATGTTTCTTTTTTAGCACATATTCAGTGGATGGTTATGTTCACACCTTTAGTACCTTTCTGGATAACAATTGCTTATA
TCATTTGTATTTCCACAAAGCATTTCTATTGGTTCTTTAGTAATTACCTAAAGAGACGTGTAGTCTTTAATGGTGTTT
CCTTTAGTACTTTTGAAGAAGCTGCGCTGTGCACCTTTTTGTTAAATAAAGAAATGTATCTAAAGTTGCGTAGTGAT
GTGCTATTACCTCTTACGCAATATAATAGATACTTAGCTCTTTATAATAAGTACAAGTATTTTAGTGGAGCAATGGA
TACAACTAGCTACAGAGAAGCTGCTTGTTGTCATCTCGCAAAGGCTCTCAATGACTTCAGTAACTCAGGTTCTGAT
GTTCTTTACCAACCACCACAAACCTCTATCACCTCAGCTGTTTTGCAGAGTGGTTTTAGAAAAATGGCATTCCCATC
TGGTAAAGTTGAGGGTTGTATGGTACAAGTAACTTGTGGTACAACTACACTTAACGGTCTTTGGCTTGATGACGTA
GTTTACTGTCCAAGACATGTGATCTGCACCTCTGAAGACATGCTTAACCCTAATTATGAAGATTTACTCATTCGTAA
GTCTAATCATAATTTCTTGGTACAGGCTGGTAATGTTCAACTCAGGGTTATTGGACATTCTATGCAAAATTGTGTAC
TTAAGCTTAAGGTTGATACAGCCAATCCTAAGACACCTAAGTATAAGTTTGTTCGCATTCAACCAGGACAGACTTT
TTCAGTGTTAGCTTGTTACAATGGTTCACCATCTGGTGTTTACCAATGTGCTATGAGGCCCAATTTCACTATTAAGG
GTTCATTCCTTAATGGTTCATGTGGTAGTGTTGGTTTTAACATAGATTATGACTGTGTCTCTTTTTGTTACATGCACC
ATATGGAATTACCAACTGGAGTTCATGCTGGCACAGACTTAGAAGGTAACTTTTATGGACCTTTTGTTGACAGGCA
AACAGCACAAGCAGCTGGTACGGACACAACTATTACAGTTAATGTTTTAGCTTGGTTGTACGCTGCTGTTATAAAT
GGAGACAGGTGGTTTCTCAATCGATTTACCACAACTCTTAATGACTTTAACCTTGTGGCTATGAAGTACAATTATG
AACCTCTAACACAAGACCATGTTGACATACTAGGACCTCTTTCTGCTCAAACTGGAATTGCCGTTTTAGATATGTGT

-continued

| SEQUENCE LISTING |
|---|
| GCTTCATTAAAAGAATTACTGCAAAATGGTATGAATGGACGTACCATATTGGGTAGTGCTTTATTAGAAGATGAAT<br>TTACACCTTTTGATGTTGTTAGACAATGCTCAGGTGTTACTTTCCAAAGTGCAGTGAAAAGAACAATCAAGGGTAC<br>ACACCACTGGTTGTTACTCACAATTTTGACTTCACTTTTAGTTTTAGTCCAGAGTACTCAATGGTCTTTGTTCTTTTT<br>TTTGTATGAAAATGCCTTTTTACCTTTTGCTATGGGTATTATTGCTATGTCTGCTTTTGCAATGATGTTTGTCAAACA<br>TAAGCATGCATTTCTCTGTTTGTTTTTGTTACCTTCTCTTGCCACTGTAGCTTATTTTAATATGGTCTATATGCCTGCT<br>AGTTGGGTGATGCGTATTATGACATGGTTGGATATGGTTGATACTAGTTTGTCTGGTTTTAAGCTAAAAGACTGTGT<br>TATGTATGCATCAGCTGTAGTGTTACTAATCCTTATGACAGCAAGAACTGTGTATGATGATGGTGCTAGGAGAGTG<br>TGGACACTTATGAATGTCTTGACACTCGTTTATAAAGTTTATTATGGTAATGCTTTAGATCAAGCCATTTCCATGTG<br>GGCTCTTATAATCTCTGTTACTTCTAACTACTCAGGTGTAGTTACAACTGTCATGTTTTTGGCCAGAGGTATTGTTTT<br>TATGTGTGTTGAGTATTGCCCTATTTTCTTCATAACTGGTAATACACTTCAGTGTATAATGCTAGTTTATTGTTTCTT<br>AGGCTATTTTTGTACTTGTTACTTTGGCCTCTTTTGTTTACTCAACCGCTACTTTAGACTGACTCTTGGTGTTTATGA<br>TTACTTAGTTTCTACACAGGAGTTTAGATATATGAATTCACAGGGACTACTCCCACCCAAGAATAGCATAGATGCC<br>TTCAAACTCAACATTAAATTGTTGGGTGTTGGTGGCAAACCTTGTATCAAAGTAGCCACTGTACAGTCTAAAATGT<br>CAGATGTAAAGTGCACATCAGTAGTCTTACTCTCAGTTTTGCAACAACTCAGAGTAGAATCATCATCTAAATTGTG<br>GGCTCAATGTGTCCAGTTACACAATGACATTCTCTTAGCTAAAGATACTACTGAAGCCTTTGAAAAAATGGTTTCA<br>CTACTTTCTGTTTTGCTTTCCATGCAGGGTGCTGTAGACATAAACAAGCTTTGTGAAGAAATGCTGGACAACAGGG<br>CAACCTTACAAGCTATAGCCTCAGAGTTTAGTTCCCTTCCATCATATGCAGCTTTTGCTACTGCTCAAGAAGCTTAT<br>GAGCAGGCTGTTGCTAATGGTGATTCTGAAGTTGTTCTTAAAAAGTTGAAGAAGTCTTTGAATGTGGCTAAATCTG<br>AATTTGACCGTGATGCAGCCATGCAACGTAAGTTGGAAAAGATGGCTGATCAAGCTATGACCCAAATGTATAAAC<br>AGGCTAGATCTGAGGACAAGAGGGCAAAAGTTACTAGTGCTATGCAGACAATGCTTTTCACTATGCTTAGAAAGTT<br>GGATAATGATGCACTCAACAACATTATCAACAATGCAAGAGATGGTTGTGTTCCCTTGAACATAATACCTCTTACA<br>ACAGCAGCCAAACTAATGGTTGTCATACCAGACTATAACACATATAAAAATACGTGTGATGGTACAACATTTACTT<br>ATGCATCAGCATTGTGGGAAATCCAACAGGTTGTAGATGCAGATAGTAAAATTGTTCAACTTAGTGAAATTAGTAT<br>GGACAATTCACCTAATTTAGCATGGCCTCTTATTGTAACAGCTTTAAGGGCCAATTCTGCTGTCAAATTACAGAAT<br>AATGAGCTTAGTCCTGTTGCACTACGACAGATGTCTTGTGCTGCCGGTACTACACAAACTGCTTGCACTGATGACA<br>ATGCGTTAGCTTACTACAACACAACAAAGGGAGGTAGGTTTGTACTTGCACTGTTATCCGATTTACAGGATTTGAA<br>ATGGGCTAGATTCCCTAAGAGTGATGGAACTGGTACTATCTATACAGAACTGGAACCACCTTGTAGGTTTGTTACA<br>GACACACCTAAAGGTCCTAAAGTGAAGTATTTATACTTTATTAAAGGATTAAACAACCTAAATAGAGGTATGGTAC<br>TTGGTAGTTTAGCTGCCACAGTACGTCTACAAGCTGGTAATGCAACAGAAGTGCCTGCCAATTCAACTGTATTATC<br>TTTCTGTGCTTTTGCTGTAGATGCTGCTAAAGCTTACAAAGATTATCTAGCTAGTGGGGGACAACCAATCACTAATT<br>GTGTTAAGATGTTGTGTACACACACTGGTACTGGTCAGGCAATAACAGTTACACCGGAAGCCAATATGGATCAAG<br>AATCCTTTGGTGGTGCATCGTGTTGTCTGTACTGCCGTTGCCACATAGATCATCCAAATCCTAAAGGATTTTGTGAC<br>TTAAAAGGTAAGTATGTACAAATACCTACAACTTGTGCTAATGACCCTGTGGGTTTTACACTTAAAAACACAGTCT<br>GTACCGTCTGCGGTATGTGGAAAGGTTATGGCTGTAGTTGTGATCAACTCCGCGAACCCATGCTTCAGTCAGCTGA<br>TGCACAATCGTTTTTAAACGGGTTTGCGGTGTAAGTGCAGCCCGTCTTACACCGTGCGGCACAGGCACTAGTACTG<br>ATGTCGTATACAGGGCTTTTGACATCTACAATGATAAAGTAGCTGGTTTTGCTAAATTCCTAAAAACTAATTGTTGT<br>CGCTTCCAAGAAAAGGACGAAGATGACAATTTAATTGATTCTTACTTTGTAGTTAAGAGACACACTTTCTCTAACT<br>ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA<br>TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT |

-continued

SEQUENCE LISTING

TAAAACACTTCTTCTTTGCTCAGGATGGTAATGCTGCTATCAGCGATTATGACTACTATCGTTATAATCTACCAACA
ATGTGTGATATCAGACAACTACTATTTGTAGTTGAAGTTGTTGATAAGTACTTTGATTGTTACGATGGTGGCTGTAT
TAATGCTAACCAAGTCATCGTCAACAACCTAGACAAATCAGCTGGTTTTCCATTTAATAAATGGGGTAAGGCTAGA
CTTTATTATGATTCAATGAGTTATGAGGATCAAGATGCACTTTTCGCATATACAAAACGTAATGTCATCCCTACTAT
AACTCAAATGAATCTTAAGTATGCCATTAGTGCAAAGAATAGAGCTCGCACCGTAGCTGGTGTCTCTATCTGTAGT
ACTATGACCAATAGACAGTTTCATCAAAAATTATTGAAATCAATAGCCGCCACTAGAGGAGCTACTGTAGTAATTG
GAACAAGCAAATTCTATGGTGGTTGGCACAACATGTTAAAAACTGTTTATAGTGATGTAGAAAACCCTCACCTTAT
GGGTTGGGATTATCCTAAATGTGATAGAGCCATGCCTAACATGCTTAGAATTATGGCCTCACTTGTTCTTGCTCGCA
AACATACAACGTGTTGTAGCTTGTCACACCGTTTCTATAGATTAGCTAATGAGTGTGCTCAAGTATTGAGTGAAAT
GGTCATGTGTGGCGGTTCACTATATGTTAAACCAGGTGGAACCTCATCAGGAGATGCCACAACTGCTTATGCTAAT
AGTGTTTTTAACATTTGTCAAGCTGTCACGGCCAATGTTAATGCACTTTTATCTACTGATGGTAACAAAATTGCCGA
TAAGTATGTCCGCAATTTACAACACAGACTTTATGAGTGTCTCTATAGAAATAGAGATGTTGACACAGACTTTGTG
AATGAGTTTTACGCATATTTGCGTAAACATTTCTCAATGATGATACTCTCTGACGATGCTGTTGTGTGTTTCAATAG
CACTTATGCATCTCAAGGTCTAGTGGCTAGCATAAAGAACTTTAAGTCAGTTCTTTATTATCAAAACAATGTTTTTA
TGTCTGAAGCAAAATGTTGGACTGAGACTGACCTTACTAAAGGACCTCATGAATTTTGCTCTCAACATACAATGCT
AGTTAAACAGGGTGATGATTATGTGTACCTTCCTTACCCAGATCCATCAAGAATCCTAGGGGCCGGCTGTTTTGTA
GATGATATCGTAAAAACAGATGGTACACTTATGATTGAACGGTTCGTGTCTTTAGCTATAGATGCTTACCCACTTA
CTAAACATCCTAATCAGGAGTATGCTGATGTCTTTCATTTGTACTTACAATACATAAGAAAGCTACATGATGAGTT
AACAGGACACATGTTAGACATGTATTCTGTTATGCTTACTAATGATAACACTTCAAGGTATTGGGAACCTGAGTTT
TATGAGGCTATGTACACACCGCATACAGTCTTACAGGCTGTTGGGGCTTGTGTTCTTTGCAATTCACAGACTTCATT
AAGATGTGGTGCTTGCATACGTAGACCATTCTTATGTTGTAAATGCTGTTACGACCATGTCATATCAACATCACATA
AATTAGTCTTGTCTGTTAATCCGTATGTTTGCAATGCTCCAGGTTGTGATGTCACAGATGTGACTCAACTTTACTTA
GGAGGTATGAGCTATTATTGTAAATCACATAAACCACCCATTAGTTTTCCATTGTGTGCTAATGGACAAGTTTTTGG
TTTATATAAAAATACATGTGTTGGTAGCGATAATGTTACTGACTTTAATGCAATTGCAACATGTGACTGGACAAAT
GCTGGTGATTACATTTTAGCTAACACCTGTACTGAAAGACTCAAGCTTTTTGCAGCAGAAACGCTCAAAGCTACTG
AGGAGACATTTAAACTGTCTTATGGTATTGCTACTGTACGTGAAGTGCTGTCTGACAGAGAATTACATCTTTCATG
GGAAGTTGGTAAACCTAGACCACCACTTAACCGAAATTATGTCTTTACTGGTTATCGTGTAACTAAAAACAGTAAA
GTACAAATAGGAGAGTACACCTTTGAAAAAGGTGACTATGGTGATGCTGTTGTTTACCGAGGTACAACAACTTACA
AATTAAATGTTGGTGATTATTTTGTGCTGACATCACATACAGTAATGCCATTAAGTGCACCTACACTAGTGCCACA
AGAGCACTATGTTAGAATTACTGGCTTATACCCAACACTCAATATCTCAGATGAGTTTTCTAGCAATGTTGCAAATT
ATCAAAAGGTTGGTATGCAAAAGTATTCTACACTCCAGGGACCACCTGGTACTGGTAAGAGTCATTTTGCTATTGG
CCTAGCTCTCTACTACCCTTCTGCTCGCATAGTGTATACAGCTTGCTCTCATGCCGCTGTTGATGCACTATGTGAGA
AGGCATTAAAATATTTGCCTATAGATAAATGTAGTAGAATTATACCTGCACGTGCTCGTGTAGAGTGTTTTGATAA
ATTCAAAGTGAATTCAACATTAGAACAGTATGTCTTTTGTACTGTAAATGCATTGCCTGAGACGACAGCAGATATA
GTTGTCTTTGATGAAATTTCAATGGCCACAAATTATGATTTGAGTGTTGTCAATGCCAGATTACGTGCTAAGCACTA
TGTGTACATTGGCGACCCTGCTCAATTACCTGCACCACGCACATTGCTAACTAAGGGCACACTAGAACCAGAATAT
TTCAATTCAGTGTGTAGACTTATGAAAACTATAGGTCCAGACATGTTCCTCGGAACTTGTCGGCGTTGTCCTGCTGA
AATTGTTGACACTGTGAGTGCTTTGGTTTATGATAATAAGCTTAAAGCACATAAAGACAAATCAGCTCAATGCTTT
AAAATGTTTTATAAGGGTGTTATCACGCATGATGTTTCATCTGCAATTAACAGGCCACAAATAGGCGTGGTAAGAG
AATTCCTTACACGTAACCCTGCTTGGAGAAAAGCTGTCTTTATTTCACCTTATAATTCACAGAATGCTGTAGCCTCA
AAGATTTTGGGACTACCAACTCAAACTGTTGATTCATCACAGGGCTCAGAATATGACTATGTCATATTCACTCAAA
CCACTGAAACAGCTCACTCTTGTAATGTAAACAGATTTAATGTTGCTATTACCAGAGCAAAAGTAGGCATACTTTG
CATAATGTCTGATAGAGACCTTTATGACAAGTTGCAATTTACAAGTCTTGAAATTCCACGTAGGAATGTGGCAACT
TTACAAGCTGAAAATGTAACAGGACTCTTTAAAGATTGTAGTAAGGTAATCACTGGGTTACATCCTACACAGGCAC
CTACACACCTCAGTGTTGACACTAAATTCAAAACTGAAGGTTTATGTGTTGACATACCTGGCATACCTAAGGACAT
GACCTATAGAAGACTCATCTCTATGATGGGTTTTAAAATGAATTATCAAGTTAATGGTTACCCTAACATGTTTATCA
CCCGCGAAGAAGCTATAAGACATGTACGTGCATGGATTGGCTTCGATGTCGAGGGGTGTCATGCTACTAGAGAAG
CTGTTGGTACCAATTTACCTTTACAGCTAGGTTTTTCTACAGGTGTTAACCTAGTTGCTGTACCTACAGGTTATGTT
GATACACCTAATAATACAGATTTTTCCAGAGTTAGTGCTAAACCACCGCCTGGAGATCAATTTAAACACCTCATAC
CACTTATGTACAAAGGACTTCCTTGGAATGTAGTGCGTATAAAGATTGTACAAATGTTAAGTGACACACTTAAAAA
TCTCTCTGACAGAGTCGTATTTGTCTTATGGGCACATGGCTTTGAGTTGACATCTATGAAGTATTTTGTGAAAATAG

-continued

SEQUENCE LISTING

GACCTGAGCGCACCTGTTGTCTATGTGATAGACGTGCCACATGCTTTTCCACTGCTTCAGACACTTATGCCTGTTGG
CATCATTCTATTGGATTTGATTACGTCTATAATCCGTTTATGATTGATGTTCAACAATGGGGTTTTACAGGTAACCT
ACAAAGCAACCATGATCTGTATTGTCAAGTCCATGGTAATGCACATGTAGCTAGTTGTGATGCAATCATGACTAGG
TGTCTAGCTGTCCACGAGTGCTTTGTTAAGCGTGTTGACTGGACTATTGAATATCCTATAATTGGTGATGAACTGAA
GATTAATGCGGCTTGTAGAAAGGTTCAACACATGGTTGTTAAAGCTGCATTATTAGCAGACAAATTCCCAGTTCTT
CACGACATTGGTAACCCTAAAGCTATTAAGTGTGTACCTCAAGCTGATGTAGAATGGAAGTTCTATGATGCACAGC
CTTGTAGTGACAAAGCTTATAAAATAGAAGAATTATTCTATTCTTATGCCACACATTCTGACAAATTCACAGATGG
TGTATGCCTATTTTGGAATTGCAATGTCGATAGATATCCTGCTAATTCCATTGTTTGTAGATTTGACACTAGAGTGC
TATCTAACCTTAACTTGCCTGGTTGTGATGGTGGCAGTTTGTATGTAAATAAACATGCATTCCACACACCAGCTTTT
GATAAAAGTGCTTTTGTTAATTTAAAACAATTACCATTTTTCTATTACTCTGACAGTCCATGTGAGTCTCATGGAAA
ACAAGTAGTGTCAGATATAGATTATGTACCACTAAAGTCTGCTACGTGTATAACACGTTGCAATTTAGGTGGTGCT
GTCTGTAGACATCATGCTAATGAGTACAGATTGTATCTCGATGCTTATAACATGATGATCTCAGCTGGCTTTAGCTT
GTGGGTTTACAAACAATTTGATACTTATAACCTCTGGAACACTTTTACAAGACTTCAGAGTTTAGAAAATGTGGCT
TTTAATGTTGTAAATAAGGGACACTTTGATGGACAACAGGGTGAAGTACCAGTTTCTATCATTAATAACACTGTTT
ACACAAAAGTTGATGGTGTTGATGTAGAATTGTTTGAAAATAAAACAACATTACCTGTTAATGTAGCATTTGAGCT
TTGGGCTAAGCGCAACATTAAACCAGTACCAGAGGTGAAAATACTCAATAATTTGGGTGTGGACATTGCTGCTAAT
ACTGTGATCTGGGACTACAAAAGAGATGCTCCAGCACATATATCTACTATTGGTGTTTGTTCTATGACTGACATAG
CCAAGAAACCAACTGAAACGATTTGTGCACCACTCACTGTCTTTTTTGATGGTAGAGTTGATGGTCAAGTAGACTT
ATTTAGAAATGCCCGTAATGGTGTTCTTATTACAGAAGGTAGTGTTAAAGGTTTACAACCATCTGTAGGTCCCAAA
CAAGCTAGTCTTAATGGAGTCACATTAATTGGAGAAGCCGTAAAAACACAGTTCAATTATTATAAGAAAGTTGATG
GTGTTGTCCAACAATTACCTGAAACTTACTTTACTCAGAGTAGAAATTTACAAGAATTTAAACCCAGGAGTCAAAT
GGAAATTGATTTCTTAGAATTAGCTATGGATGAATTCATTGAACGGTATAAATTAGAAGGCTATGCCTTCGAACAT
ATCGTTTATGGAGATTTTAGTCATAGTCAGTTAGGTGGTTTACATCTACTGATTGGACTAGCTAAACGTTTTAAGGA
ATCACCTTTTGAATTAGAAGATTTTATTCCTATGGACAGTACAGTTAAAAACTATTTCATAACAGATGCGCAAACA
GGTTCATCTAAGTGTGTGTGTTCTGTTATTGATTTATTACTTGATGATTTTGTTGAAATAATAAAATCCCAAGATTT
ATCTGTAGTTTCTAAGGTTGTCAAAGTGACTATTGACTATACAGAAATTTCATTTATGCTTTGGTGTAAAGATGGCC
ATGTAGAAACATTTTACCCAAAATTACAATCTAGTCAAGCGTGGCAACCGGGTGTTGCTATGCCTAATCTTTACAA
AATGCAAAGAATGCTATTAGAAAAGTGTGACCTTCAAAATTATGGTGATAGTGCAACATTACCTAAAGGCATAAT
GATGAATGTCGCAAAATATACTCAACTGTGTCAATATTTAAACACATTAACATTAGCTGTACCCTATAATATGAGA
GTTATACATTTTGGTGCTGGTTCTGATAAAGGAGTTGCACCAGGTACAGCTGTTTTAAGACAGTGGTTGCCTACGG
GTACGCTGCTTGTCGATTCAGATCTTAATGACTTTGTCTCTGATGCAGATTCAACTTTGATTGGTGATTGTGCAACT
GTACATACAGCTAATAAATGGGATCTCATTATTAGTGATATGTACGACCCTAAGACTAAAAATGTTACAAAAGAA
AATGACTCTAAAGAGGGTTTTTTCACTTACATTTGTGGGTTTATACAACAAAAGCTAGCTCTTGGAGGTTCCGTGGC
TATAAAGATAACAGAACATTCTTGGAATGCTGATCTTTATAAGCTCATGGGACACTTCGCATGGTGGACAGCCTTT
GTTACTAATGTGAATGCGTCATCATCTGAAGCATTTTTAATTGGATGTAATTATCTTGGCAAACCACGCGAACAAA
TAGATGGTTATGTCATGCATGCAAATTACATATTTTGGAGGAATACAAATCCAATTCAGTTGTCTTCCTATTCTTTA
TTTGACATGAGTAAATTTCCCCTTAAATTAAGGGGTACTGCTGTTATGTCTTTAAAAGAAGGTCAAATCAATGATA
TGATTTTATCTCTTCTTAGTAAAGGTAGACTTATAATTAGAGAAAACAACAGAGTTGTTATTTCTAGTGATGTTCTT
GTTAACAACTAAACGAACAATGTTTGTTTTTCTTGTTTTATTGCCACTAGTCTCTAGTCAGTGTGTTAATCTTATAAC
CAGAACTCAATCATACACTAATTCTTTCACACGTGGTGTTTATTACCCTGACAAAGTTTTCAGATCCTCAGTTTTAC
ATTCAACTCAGGACTTGTTCTTACCTTTCTTTTCCAATGTTACTTGGTTCCATGCTATCTCTGGGACCAATGGTACTA
AGAGGTTTGATAACCCTGTCCTACCATTTAATGATGGTGTTTATTTTGCTTCCACTGAGAAGTCTAACATAATAAGA
GGCTGGATTTTTGGTACTACTTTAGATTCGAAGACCCAGTCCCTACTTATTGTTAATAACGCTACTAATGTTGTTAT
TAAAGTCTGTGAATTTCAATTTTGTAATGATCCATTTTTGGATGTTTATTACCACAAAAACAACAAAAGTTGGATGG
AAAGTGAGTTCAGAGTTTATTCTAGTGCGAATAATTGCACTTTTGAATATGTCTCTCAGCCTTTTCTTATGGACCTT
GAAGGAAAACAGGGTAATTTCAAAAATCTTAGGGAATTTGTGTTTAAGAATATTGATGGTTATTTTAAAATATATT
CTAAGCACACGCCTATTAATTTAGGGCGTGATCTCCCTCAGGGTTTTTCGGCTTTAGAACCATTGGTAGATTTGCCA
ATAGGTATTAACATCACTAGGTTTCAAACTTTACTTGCTTTACATAGAAGTTATTTGACTCCTGGTGATTCTTCTTCA
GGTTGGACAGCTGGTGCTGCAGCTTATTATGTGGGTTATCTTCAACCTAGGACTTTTCTATTAAAATATAATGAAAA
TGGAACCATTACAGATGCTGTAGACTGTGCACTTGACCCTCTCTCAGAAACAAAGTGTACGTTGAAATCCTTCACT
GTAGAAAAAGGAATCTATCAAACTTCTAACTTTAGAGTCCAACCAACAGAATCTATTGTTAGATTTCCTAATATTA

-continued

| SEQUENCE LISTING |
|---|

CAAACTTGTGCCCTTTTGATGAAGTTTTTAACGCCACCAGATTTGCATCTGTTTATGCTTGGAACAGGAAGAGAATC
AGCAACTGTGTTGCTGATTATTCTGTCCTATATAATTTCGCACCATTTTTCGCTTTTAAGTGTTATGGAGTGTCTCCT
ACTAAATTAAATGATCTCTGCTTTACTAATGTCTATGCAGATTCATTTGTAATTAGAGGTAATGAAGTCAGCCAAAT
CGCTCCAGGGCAAACTGGAAATATTGCTGATTATAATTATAAATTACCAGATGATTTTACAGGCTGCGTTATAGCT
TGGAATTCTAACAAGCTTGATTCTAAGGTTGGTGGTAATTATAATTACCGGTATAGATTGTTTAGGAAGTCTAATCT
CAAACCTTTTGAGAGAGATATTTCAACTGAAATCTATCAGGCCGGTAACAAACCTTGTAATGGTGTTGCAGGTGTT
AATTGTTACTTTCCTTTACAATCATATGGTTTCCGACCCACTTATGGTGTTGGTCACCAACCATACAGAGTAGTAGT
ACTTTCTTTTGAACTTCTACATGCACCAGCAACTGTTTGTGGACCTAAAAAGTCTACTAATTTGGTTAAAAACAAAT
GTGTCAATTTCAACTTCAATGGTTTAACAGGCACAGGTGTTCTTACTGAGTCTAACAAAAAGTTTCTGCCTTTCCAA
CAATTTGGCAGAGACATTGCTGACACTACTGATGCTGTCCGTGATCCACAGACACTTGAGATTCTTGACATTACAC
CATGTTCTTTTGGTGGTGTCAGTGTTATAACACCAGGAACAAATACTTCTAACCAGGTTGCTGTTCTTTATCAGGGT
GTTAACTGCACAGAAGTCCCTGTTGCTATTCATGCAGATCAACTTACTCCTACTTGGCGTGTTTATTCTACAGGTTC
TAATGTTTTTCAAACACGTGCAGGCTGTTTAATAGGGGCTGAATATGTCAACAACTCATATGAGTGTGACATACCC
ATTGGTGCAGGTATATGCGCTAGTTATCAGACTCAGACTAAGTCTCATCGGCGGGCACGTAGTGTAGCTAGTCAAT
CCATCATTGCCTACACTATGTCACTTGGTGCAGAAAATTCAGTTGCTTACTCTAATAACTCTATTGCCATACCCACA
AATTTTACTATTAGTGTTACCACAGAAATTCTACCAGTGTCTATGACCAAGACATCAGTAGATTGTACAATGTACA
TTTGTGGTGATTCAACTGAATGCAGCAATCTTTTGTTGCAATATGGCAGTTTTTGTACACAATTAAAACGTGCTTTA
ACTGGAATAGCTGTTGAACAAGACAAAAACACCCAAGAAGTTTTTGCACAAGTCAAACAAATTTACAAAACACCA
CCAATTAAATATTTTGGTGGTTTTAATTTTTCACAAATATTACCAGATCCATCAAAACCAAGCAAGAGGTCATTTAT
TGAAGATCTACTTTTCAACAAAGTGACACTTGCAGATGCTGGCTTCATCAAACAATATGGTGATTGCCTTGGTGAT
ATTGCTGCTAGAGACCTCATTTGTGCACAAAAGTTTAACGGCCTTACTGTTTTGCCACCTTTGCTCACAGATGAAAT
GATTGCTCAATACACTTCTGCACTGTTAGCGGGTACAATCACTTCTGGTTGGACCTTTGGTGCAGGTGCTGCATTAC
AAATACCATTTGCTATGCAAATGGCTTATAGGTTTAATGGTATTGGAGTTACACAGAATGTTCTCTATGAGAACCA
AAAATTGATTGCCAACCAATTTAATAGTGCTATTGGCAAAATTCAAGACTCACTTTCTTCCACAGCAAGTGCACTT
GGAAAACTTCAAGATGTGGTCAACCATAATGCACAAGCTTTAAACACGCTTGTTAAACAACTTAGCTCCAAATTTG
GTGCAATTTCAAGTGTTTTAAATGATATCCTTTCACGTCTTGACAAAGTTGAGGCTGAAGTGCAAATTGATAGGTT
GATCACAGGCAGACTTCAAAGTTTGCAGACATATGTGACTCAACAATTAATTAGAGCTGCAGAAATCAGAGCTTCT
GCTAATCTTGCTGCTACTAAAATGTCAGAGTGTGTACTTGGACAATCAAAAAGAGTTGATTTTTGTGGAAAGGGCT
ATCATCTTATGTCCTTCCCTCAGTCAGCACCTCATGGTGTAGTCTTCTTGCATGTGACTTATGTCCCTGCACAAGAA
AAGAACTTCACAACTGCTCCTGCCATTTGTCATGATGGAAAAGCACACTTTCCTCGTGAAGGTGTCTTTGTTTCAAA
TGGCACACACTGGTTTGTAACACAAAGGAATTTTTATGAACCACAAATCATTACTACAGACAACACATTTGTGTCT
GGTAACTGTGATGTTGTAATAGGAATTGTCAACAACACAGTTTATGATCCTTTGCAACCTGAATTAGATTCATTCA
AGGAGGAGTTAGATAAATATTTTAAGAATCATACATCACCAGATGTTGATTTAGGTGACATCTCTGGCATTAATGC
TTCAGTTGTAAACATTCAAAAAGAAATTGACCGCCTCAATGAGGTTGCCAAGAATTTAAATGAATCTCTCATCGAT
CTCCAAGAACTTGGAAAGTATGAGCAGTATATAAAATGGCCATGGTACATTTGGCTAGGTTTTATAGCTGGCTTGA
TTGCCATAGTAATGGTGACAATTATGCTTTGCTGTATGACCAGTTGCTGTAGTTGTCTCAAGGGCTGTTGTTCTTGT
GGATCCTGCTGCAAATTTGATGAAGACGACTCTGAGCCAGTGCTCAAAGGAGTCAAATTACATTACACATAAACG
AACTTATGGATTTGTTTATGAGAATCTTCACAATTGGAACTGTAACTTTGAAGCAAGGTGAAATCAAGGATGCTAC
TCCTTCAGATTTTGTTCGCGCTACTGCAACGATACCGATACAAGCCTCACTCCCTTTCGGATGGCTTATTGTTGGCG
TTGCACTTCTTGCTGTTTTTCAGAGCGCTTCCAAAATCATAACCCTCAAAAAGAGATGGCAACTAGCACTCTCCAA
GGGTGTTCACTTTGTTTGCAACTTGCTGTTGTTGTTTGTAACAGTTTACTCACACCTTTTGCTCGTTGCTGCTGGCCT
TGAAGCCCCTTTTCTCTATCTTTATGCTTTAGTCTACTTCTTGCAGAGTATAAACTTTGTAAGAATAATAATGAGGC
TTTGGCTTTGCTGGAAATGCCGTTCCAAAAACCCATTACTTTATGATGCCAACTATTTTCTTTGCTGGCATACTAAT
TGTTACGACTATTGTATACCTTACAATAGTGTAACTTCTTCAATTGTCATTACTTCAGGTGATGGCACAACAAGTCC
TATTTCTGAACATGACTACCAGATTGGTGGTTATACTGAAAAATGGGAATCTGGAGTAAAAGACTGTGTTGTATTA
CACAGTTACTTCACTTCAGACTATTACCAGCTGTACTCAACTCAATTGAGTACAGACACTGGTGTTGAACATGTTAC
CTTCTTCATCTACAATAAAATTGTTGATGAGCCTGAAGAACATGTCCAAATTCACACAATCGACGGTTCATCCGGA
GTTGTTAATCCAGTAATGGAACCAATTTATGATGAACCGACGACGACTACTAGCGTGCCTTTGTAAGCACAAGCTG
ATGAGTACGAACTTATGTACTCATTCGTTTCGGAAGAGACAGGTACGTAAATAGTTAATAGCTGACTTCTTTTTCTT
GCTTTCGTGTGATTCTTGCTAGTTACACTAGCCATCCTTACTGCGCTTCGATTGTGTGCGTACTGCTGCAATATTGTT
AACGTGAGTCTTGTAAAACCTTCTTTTTACGTTTACTCTCGTGTTAAAAATCTGAATTCTTCTAGAGTTCCTGATCTT

-continued

SEQUENCE LISTING

CTGGTCTAAACGAACTAAATATTATATTAGTTTTTCTGTTTGGAACTTTAATTTTAGCCATGGCAGATTCCAACGGT
ACTATTACCGTTGAAGAGCTTAAAAAGCTCCTTGAACAATGGAACCTAGTAATAGGTTTCCTATTCCTTACATGGA
TTTGTCTTCTACAATTTGCCTATGCCAACAGGAATAGGTTTTTGTATATAATTAAGTTAATTTTCCTCTGGCTGTTAT
GGCCAGTAACTTTAGCTTGTTTTGTGCTTGCTGCTGTTTACAGAATAAATTGGATCACCGGTGGAATTGCTATCGCA
ATGGCTTGTCTTGTAGGCTTGATGTGGCTCAGCTACTTCATTGCTTCTTTCAGACTGTTTGCGCGTACGCGTTCCATG
TGGTCATTCAATCCAGAAACTAACATTCTTCTCAACGTGCCACTCCATGGCACTATTCTGACCAGACCGCTTCTAGA
AAGTGAACTCGTAATCGGAGCTGTGATCCTTCGTGGACATCTTCGTATTGCTGGACACCATCTAGGACGCTGTGAC
ATCAAGGACCTGCCTAAAGAAATCACTGTTGCTACATCACGAACGCTTTCTTATTACAAATTGGGAGCTTCGCAGC
GTGTAGCAGGTGACTCAGGTTTTGCTGCATACAGTCGCTACAGGATTGGCAACTATAAATTAAACACAGACCATTC
CAGTAGCAGTGACAATATTGCTTTGCTTGTACAGTAAGTGACAACAGATGTTTCATCTCGTTGACTTTCAGGTTACT
ATAGCAGAGATATTACTAATTATTATGAGGACTTTTAAAGTTTCCATTTGGAATCTTGATTACATCATAAACCTCAT
AATTAAAAATTTATCTAAGTCACTAACTGAGAATAAATATTCTCAATTAGATGAAGAGCAACCAATGGAGATTGAT
TAAACGAACATGAAAATTATTCTTTTCTTGGCACTGATAACACTCGCTACTTGTGAGCTTTATCACTACCAAGAGTG
TGTTAGAGGTACAACAGTACTTTTAAAAGAACCTTGCTCTTCTGGAACATACGAGGGCAATTCACCATTTCATCCT
CTAGCTGATAACAAATTTGCACTGACTTGCTTTAGCACTCAATTTGCTTTTGCTTGTCCTGACGGCGTAAAACACGT
CTATCAGTTACGTGCCAGATCAGTTTCACCTAAACTGTTCATCAGACAAGAGGAAGTTCAAGAACTTTACTCTCCA
ATTTTTCTTATTGTTGCGGCAATAGTGTTTATAACACTTTGCTTCACACTCAAAAGAAAGACAGAATGATTGAACTT
TCATTAATTGACTTCTATTTGTGCTTTTTAGCCTTTCTGCTATTCCTTGTTTTAATTATGCTTATTATCTTTTGGTTCTC
ACTTGAACTGCAAGATCATAATGAAACTTGTCACGCCTAAACGAACatgaccaacaagtgtctcctccaaattgctctcctgttgtgcttctccact
acagctctttccatgagctacaacttgcttggattcctacaaagaagcagcaattttcagtgtcagaagctcctgtggcaattgaatgggaggcttgaatactgcctcaaggacaggatgaacttt
gacatccctgaggagattaagcagctgcagcagttccagaaggaggacgccgcattgaccatctatgagatgctccagaacatctttgctattttcagacaagattcatctagcactggctgga
atgagactattgttgagaacctcctggctaatgtctatcatcagataaaccatctgaagacagtcctggaagaaaaactggagaaagaagatttcaccaggggaaaactcatgagcagtctgc
acctgaaaagatattatgggaggattctgcattacctgaaggccaaggagtacagtcactgtgcctggaccatagtcagagtggaaatcctaaggaacttttacttcattaacagacttacaggt
tacctccgaaactgaGACGTTCGTGTTGTTTTAGATTTCATCTAAACGAACAAACTAAAATGTCTGATAATGGACCCCAAAA
TCAGCGAAATGCACCCCGCATTACGTTTGGTGGACCCTCAGATTCAACTGGCAGTAACCAGAATGGAGAACGCAG
TGGGGCGCGATCAAAACAACGTCGGCCCCAAGGTTTACCCAATAATACTGCGTCTTGGTTCACCGCTCTCACTCAA
CATGGCAAGGAAGACCTTAAATTCCCTCGAGGACAAGGCGTTCCAATTAACACCAATAGCAGTCCAGATGACCAA
ATTGGCTACTACCGAAGAGCTACCAGACGAATTCGTGGTGGTGACGGTAAAATGAAAGATCTCAGTCCAAGATGG
TATTTCTACTACCTAGGAACTGGGCCAGAAGCTGGACTTCCCTATGGTGCTAACAAAGACGGCATCATATGGGTTG
CAACTGAGGGAGCCTTGAATACACCAAAAGATCACATTGGCACCCGCAATCCTGCTAACAATGCTGCAATCGTGC
TACAACTTCCTCAAGGAACAACATTGCCAAAAGGCTTCTACGCAGAAGGGAGCAGAGGCGGCAGTCAAGCCTCTT
CTCGTTCCTCATCACGTAGTCGCAACAGTTCAAGAAATTCAACTCCAGGCAGCAGTAGGGGAACTTCTCCTGCTAG
AATGGCTGGCAATGGCGGTGATGCTGCTCTTGCTTTGCTGCTGCTTGACAGATTGAACCAGCTTGAGAGCAAAATG
TCTGGTAAAGGCCAACAACAACAAGGCCAAACTGTCACTAAGAAATCTGCTGCTGAGGCTTCTAAGAAGCCTCGG
CAAAAACGTACTGCCACTAAAGCATACAATGTAACACAAGCTTTCGGCAGACGTGGTCCAGAACAAACCCAAGGA
AATTTTGGGGACCAGGAACTAATCAGACAAGGAACTGATTACAAACATTGGCCGCAAATTGCACAATTTGCCCCC
AGCGCTTCAGCGTTCTTCGGAATGTCGCGCATTGGCATGGAAGTCACACCTTCGGGAACGTGGTTGACCTACACAG
GTGCCATCAAATTGGATGACAAAGATCCAAATTTCAAAGATCAAGTCATTTTGCTGAATAAGCATATTGACGCATA
CAAAACATTCCCACCAACAGAGCCTAAAAAGGACAAAAAGAAGAAGGCTGATGAAACTCAAGCCTTACCGCAGA
GACAGAAGAAACAGCAAACTGTGACTCTTCTTCCTGCTGCAGATTTGGATGATTTCTCCAAACAATTGCAACAATC
CATGAGCAGTGCTGACTCAACTCAGGCCTAAACTCATGCAGACCACACAAGGCAGATGGGCTATATAAACGTTTTC
GCTTTTCCGTTTACGATATATAGTCTACTCTTGTGCAGAATGAATTCTCGTAACTACATAGCACAAGTAGATGTAGT
TAACTTTAATCTCACATAGCAATCTTTAATCAGTGTGTAACATTAGGGAGGACTTGAAAGAGCCACCACATTTTCA
CCGAGGCCACGCGGAGTACGATCGAGTGTACAGTGAACAATGCTAGGGAGAGCTGCCTATATGGAAGAGCCCTAA
TGTGTAAAATTAATTTTAGTAGTGCTATCCCCATGTGATTTTAATAGCTTCTTAGGAGAATGACAAAAAAAAAAAA
AAAAAAAAA -continued

SEQUENCE LISTING

SEQ ID NO: 5 (synthetic IBIS DNA construct 2; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC
TGACCCTATACATTCTTTAAGAGTTTGTGTAGATACTGTTCGCACAAATGTCTACTTAGCTGTCTTTGATAAAAATC -continued

SEQUENCE LISTING

TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT
GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA
GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT
CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT
TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT
GTGATACATTCTGTGCTGGTAGTACATTTATTAGTGATGAAGTTGCGAGAGACTTGTCACTACAGTTTAAAAGACC

-continued

| SEQUENCE LISTING |
| --- |
| AATAAATCCTACTGACCAGTCTTCTTACATCGTTGATAGTGTTACAGTGAAGAATGGTTCCATCCATCTTTACTTTG<br>ATAAAGCTGGTCAAAAGACTTATGAAAGACATTCTCTCTCTCATTTTGTTAACTTAGACAACCTGAGAGCTAATAA<br>CACTAAAGGTTCATTGCCTATTAATGTTATAGTTTTGATGGTAAATCAAAATGTGAAGAATCATCTGCAAAATCA<br>GCGTCTGTTTACTACAGTCAGCTTATGTGTCAACCTATACTGTTACTAGATCAGGCATTAGTGTCTGATGTTGGTGA<br>TAGTGCGGAAGTTGCAGTTAAAATGTTTGATGCTTACGTTAATACGTTTTCATCAACTTTTAACGTACCAATGGAAA<br>AACTCAAAACACTAGTTGCAACTGCAGAAGCTGAACTTGCAAAGAATGTGTCCTTAGACAATGTCTTATCTACTTT<br>TATTTCAGCAGCTCGGCAAGGGTTTGTTGATTCAGATGTAGAAACTAAAGATGTTGTTGAATGTCTTAAATTGTCA<br>CATCAATCTGACATAGAAGTTACTGGCGATAGTTGTAATAACTATATGCTCACCTATAACAAAGTTGAAAACATGA<br>CACCCCGTGACCTTGGTGCTTGTATTGACTGTAGTGCGCGTCATATTAATGCGCAGGTAGCAAAAAGTCACAACAT<br>TGCTTTGATATGGAACGTTAAAGATTTCATGTCATTGTCTGAACAACTACGAAAACAAATACGTAGTGCTGCTAAA<br>AAGAATAACTTACCTTTTAAGTTGACATGTGCAACTACTAGACAAGTTGTTAATGTTGTAACAACAAAGATAGCAC<br>TTAAGGGTGGTAAAATTGTTAATAATTGGTTGAAGCAGTTAATTAAAGTTACACTTGTGTTCCTTTTTGTTGCTGCT<br>ATTTTCTATTTAATAACACCTGTTCATGTCATGTCTAAACATACTGACTTTTCAAGTGAAATCATAGGATACAAGGC<br>TATTGATGGTGGTGTCACTCGTGACATAGCATCTACAGATACTTGTTTTGCTAACAAACATGCTGATTTTGACACAT<br>GGTTTAGCCAGCGTGGTGGTAGTTATACTAATGACAAAGCTTGCCCATTGATTGCTGCAGTCATAACAAGAGAAGT<br>GGGTTTTGTCGTGCCTGGTTTGCCTGGCACGATATTACGCACAACTAATGGTGACTTTTTGCATTTCTTACCTAGAG<br>TTTTTAGTGCAGTTGGTAACATCTGTTACACACCATCAAAACTTATAGAGTACACTGACTTTGCAACATCAGCTTGT<br>GTTTTGGCTGCTGAATGTACAATTTTTAAAGATGCTTCTGGTAAGCCAGTACCATATTGTTATGATACCAATGTACT<br>AGAAGGTTCTGTTGCTTATGAAAGTTTACGCCCTGACACACGTTATGTGCTCATGGATGGCTCTATTATTCAATTTC<br>CTAACACCTACCTTGAAGGTTCTGTTAGAGTGGTAACAACTTTTGATTCTGAGTACTGTAGGCACGGCACTTGTGA<br>AAGATCAGAAGCTGGTGTTTGTGTATCTACTAGTGGTAGATGGGTACTTAACAATGATTATTACAGATCTTTACCA<br>GGAGTTTTCTGTGGTGTAGATGCTGTAAATTTACTTACTAATATGTTTACACCACTAATTCAACCTATTGGTGCTTT<br>GGACATATCAGCATCTATAGTAGCTGGTGGTATTGTAGCTATCGTAGTAACATGCCTTGCCTACTATTTTATGAGGT<br>TTAGAAGAGCTTTTGGTGAATACAGTCATGTAGTTGCCTTTAATACTTTACTATTCCTTATGTCATTCACTGTACTCT<br>GTTTAACACCAGTTTACTCATTCTTACCTGGTGTTTATTCTGTTATTTACTTGTACTTGACATTTTATCTTACTAATG<br>ATGTTTCTTTTTTAGCACATATTCAGTGGATGGTTATGTTCACACCTTTAGTACCTTTCTGGATAACAATTGCTTATA<br>TCATTTGTATTTCCACAAAGCATTTCTATTGGTTCTTTAGTAATTACCTAAAGAGACGTGTAGTCTTTAATGGTGTTT<br>CCTTTAGTACTTTTGAAGAAGCTGCGCTGTGCACCTTTTTGTTAAATAAAGAAATGTATCTAAAGTTGCGTAGTGAT<br>GTGCTATTACCTCTTACGCAATATAATAGATACTTAGCTCTTTATAATAAGTACAAGTATTTTAGTGGAGCAATGGA<br>TACAACTAGCTACAGAGAAGCTGCTTGTTGTCATCTCGCAAAGGCTCTCAATGACTTCAGTAACTCAGGTTCTGAT<br>GTTCTTTACCAACCACCACAAACCTCTATCACCTCAGCTGTTTTGCAGAGTGGTTTTAGAAAAATGGCATTCCCATC<br>TGGTAAAGTTGAGGGTTGTATGGTACAAGTAACTTGTGGTACAACTACACTTAACGGTCTTTGGCTTGATGACGTA<br>GTTTACTGTCCAAGACATGTGATCTGCACCTCTGAAGACATGCTTAACCCTAATTATGAAGATTTACTCATTCGTAA<br>GTCTAATCATAATTTCTTGGTACAGGCTGGTAATGTTCAACTCAGGGTTATTGGACATTCTATGCAAAATTGTGTAC<br>TTAAGCTTAAGGTTGATACAGCCAATCCTAAGACACCTAAGTATAAGTTTGTTCGCATTCAACCAGGACAGACTTT<br>TTCAGTGTTAGCTTGTTACAATGGTTCACCATCTGGTGTTTACCAATGTGCTATGAGGCCCAATTTCACTATTAAGG<br>GTTCATTCCTTAATGGTTCATGTGGTAGTGTTGGTTTTAACATAGATTATGACTGTGTCTCTTTTTGTTACATGCACC<br>ATATGGAATTACCAACTGGAGTTCATGCTGGCACAGACTTAGAAGGTAACTTTTATGGACCTTTTGTTGACAGGCA<br>AACAGCACAAGCAGCTGGTACGGACACAACTATTACAGTTAATGTTTTAGCTTGGTTGTACGCTGCTGTTATAAAT<br>GGAGACAGGTGGTTTCTCAATCGATTTACCACAACTCTTAATGACTTTAACCTTGTGGCTATGAAGTACAATTATG<br>AACCTCTAACACAAGACCATGTTGACATACTAGGACCTCTTTCTGCTCAAACTGGAATTGCCGTTTTAGATATGTGT<br>GCTTCATTAAAAGAATTACTGCAAAATGGTATGAATGGACGTACCATATTGGGTAGTGCTTTATTAGAAGATGAAT<br>TTACACCTTTTGATGTTGTTAGACAATGCTCAGGTGTTACTTTCCAAAGTGCAGTGAAAAGAACAATCAAGGGTAC<br>ACACCACTGGTTGTTACTCACAATTTTGACTTCACTTTTAGTTTTAGTCCAGAGTACTCAATGGTCTTTGTTCTTTTT<br>TTTGTATGAAAATGCCTTTTTACCTTTTGCTATGGGTATTATTGCTATGTCTGCTTTTGCAATGATGTTTGTCAAACA<br>TAAGCATGCATTTCTCTGTTTGTTTTTGTTACCTTCTCTTGCCACTGTAGCTTATTTTAATATGGTCTATATGCCTGCT<br>AGTTGGGTGATGCGTATTATGACATGGTTGGATATGGTTGATACTAGTTTGTCTGGTTTTAAGCTAAAAGACTGTGT<br>TATGTATGCATCAGCTGTAGTGTTACTAATCCTTATGACAGCAAGAACTGTGTATGATGATGGTGCTAGGAGAGTG<br>TGGACACTTATGAATGTCTTGACACTCGTTTATAAAGTTTATTATGGTAATGCTTTAGATCAAGCCATTTCCATGTG<br>GGCTCTTATAATCTCTGTTACTTCTAACTACTCAGGTGTAGTTACAACTGTCATGTTTTTGGCCAGAGGTATTGTTTT<br>TATGTGTGTTGAGTATTGCCCTATTTTCTTCATAACTGGTAATACACTTCAGTGTATAATGCTAGTTTATTGTTTCTT |

-continued

| SEQUENCE LISTING |
|---|
| AGGCTATTTTTGTACTTGTTACTTTGGCCTCTTTTGTTTACTCAACCGCTACTTTAGACTGACTCTTGGTGTTTATGA<br>TTACTTAGTTTCTACACAGGAGTTTAGATATATGAATTCACAGGGACTACTCCCACCCAAGAATAGCATAGATGCC<br>TTCAAACTCAACATTAAATTGTTGGGTGTTGGTGGCAAACCTTGTATCAAAGTAGCCACTGTACAGTCTAAAATGT<br>CAGATGTAAAGTGCACATCAGTAGTCTTACTCTCAGTTTTGCAACAACTCAGAGTAGAATCATCATCTAAATTGTG<br>GGCTCAATGTGTCCAGTTACACAATGACATTCTCTTAGCTAAAGATACTACTGAAGCCTTTGAAAAAATGGTTTCA<br>CTACTTTCTGTTTTGCTTTCCATGCAGGGTGCTGTAGACATAAACAAGCTTTGTGAAGAAATGCTGGACAACAGGG<br>CAACCTTACAAGCTATAGCCTCAGAGTTTAGTTCCCTTCCATCATATGCAGCTTTTGCTACTGCTCAAGAAGCTTAT<br>GAGCAGGCTGTTGCTAATGGTGATTCTGAAGTTGTTCTTAAAAAGTTGAAGAAGTCTTTGAATGTGGCTAAATCTG<br>AATTTGACCGTGATGCAGCCATGCAACGTAAGTTGGAAAAGATGGCTGATCAAGCTATGACCCAAATGTATAAAC<br>AGGCTAGATCTGAGGACAAGAGGGCAAAAGTTACTAGTGCTATGCAGACAATGCTTTTCACTATGCTTAGAAAGTT<br>GGATAATGATGCACTCAACAACATTATCAACAATGCAAGAGATGGTTGTGTTCCCTTGAACATAATACCTCTTACA<br>ACAGCAGCCAAACTAATGGTTGTCATACCAGACTATAACACATATAAAAATACGTGTGATGGTACAACATTTACTT<br>ATGCATCAGCATTGTGGGAAATCCAACAGGTTGTAGATGCAGATAGTAAAATTGTTCAACTTAGTGAAATTAGTAT<br>GGACAATTCACCTAATTTAGCATGGCCTCTTATTGTAACAGCTTTAAGGGCCAATTCTGCTGTCAAATTACAGAAT<br>AATGAGCTTAGTCCTGTTGCACTACGACAGATGTCTTGTGCTGCCGGTACTACACAAACTGCTTGCACTGATGACA<br>ATGCGTTAGCTTACTACAACACAACAAAGGGAGGTAGGTTTGTACTTGCACTGTTATCCGATTTACAGGATTTGAA<br>ATGGGCTAGATTCCCTAAGAGTGATGGAACTGGTACTATCTATACAGAACTGGAACCACCTTGTAGGTTTGTTACA<br>GACACACCTAAAGGTCCTAAAGTGAAGTATTTATACTTTATTAAAGGATTAAACAACCTAAATAGAGGTATGGTAC<br>TTGGTAGTTTAGCTGCCACAGTACGTCTACAAGCTGGTAATGCAACAGAAGTGCCTGCCAATTCAACTGTATTATC<br>TTTCTGTGCTTTTGCTGTAGATGCTGCTAAAGCTTACAAAGATTATCTAGCTAGTGGGGGACAACCAATCACTAATT<br>GTGTTAAGATGTTGTGTACACACACTGGTACTGGTCAGGCAATAACAGTTACACCGGAAGCCAATATGGATCAAG<br>AATCCTTTGGTGGTGCATCGTGTTGTCTGTACTGCCGTTGCCACATAGATCATCCAAATCCTAAAGGATTTTGTGAC<br>TTAAAAGGTAAGTATGTACAAATACCTACAACTTGTGCTAATGACCCTGTGGGTTTTACACTTAAAAACACAGTCT<br>GTACCGTCTGCGGTATGTGGAAAGGTTATGGCTGTAGTTGTGATCAACTCCGCGAACCCATGCTTCAGTCAGCTGA<br>TGCACAATCGTTTTTAAACGGGTTTGCGGTGTAAGTGCAGCCCGTCTTACACCGTGCGGCACAGGCACTAGTACTG<br>ATGTCGTATACAGGGCTTTTGACATCTACAATGATAAAGTAGCTGGTTTTGCTAAATTCCTAAAAACTAATTGTTGT<br>CGCTTCCAAGAAAAGGACGAAGATGACAATTTAATTGATTCTTACTTTGTAGTTAAGAGACACACTTTCTCTAACT<br>ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA<br>TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT<br>TAAAACACTTCTTCTTTGCTCAGGATGGTAATGCTGCTATCAGCGATTATGACTACTATCGTTATAATCTACCAACA<br>ATGTGTGATATCAGACAACTACTATTTGTAGTTGAAGTTGTTGATAAGTACTTTGATTGTTACGATGGTGGCTGTAT<br>TAATGCTAACCAAGTCATCGTCAACAACCTAGACAAATCAGCTGGTTTTCCATTTAATAAATGGGGTAAGGCTAGA<br>CTTTATTATGATTCAATGAGTTATGAGGATCAAGATGCACTTTTCGCATATACAAAACGTAATGTCATCCCTACTAT<br>AACTCAAATGAATCTTAAGTATGCCATTAGTGCAAAGAATAGAGCTCGCACCGTAGCTGGTGTCTCTATCTGTAGT<br>ACTATGACCAATAGACAGTTTCATCAAAAATTATTGAAATCAATAGCCGCCACTAGAGGAGCTACTGTAGTAATTG<br>GAACAAGCAAATTCTATGGTGGTTGGCACAACATGTTAAAAACTGTTTATAGTGATGTAGAAAACCCTCACCTTAT<br>GGGTTGGGATTATCCTAAATGTGATAGAGCCATGCCTAACATGCTTAGAATTATGGCCTCACTTGTTCTTGCTCGCA<br>AACATACAACGTGTTGTAGCTTGTCACACCGTTTCTATAGATTAGCTAATGAGTGTGCTCAAGTATTGAGTGAAAT<br>GGTCATGTGTGGCGGTTCACTATATGTTAAACCAGGTGGAACCTCATCAGGAGATGCCACAACTGCTTATGCTAAT |

-continued

SEQUENCE LISTING

AGTGTTTTTAACATTTGTCAAGCTGTCACGGCCAATGTTAATGCACTTTTATCTACTGATGGTAACAAAATTGCCGA
TAAGTATGTCCGCAATTTACAACACAGACTTTATGAGTGTCTCTATAGAAATAGAGATGTTGACACAGACTTTGTG
AATGAGTTTTACGCATATTTGCGTAAACATTTCTCAATGATGATACTCTCTGACGATGCTGTTGTGTGTTTCAATAG
CACTTATGCATCTCAAGGTCTAGTGGCTAGCATAAAGAACTTTAAGTCAGTTCTTTATTATCAAAACAATGTTTTTA
TGTCTGAAGCAAAATGTTGGACTGAGACTGACCTTACTAAAGGACCTCATGAATTTTGCTCTCAACATACAATGCT
AGTTAAACAGGGTGATGATTATGTGTACCTTCCTTACCCAGATCCATCAAGAATCCTAGGGGCCGGCTGTTTTGTA
GATGATATCGTAAAAACAGATGGTACACTTATGATTGAACGGTTCGTGTCTTTAGCTATAGATGCTTACCCACTTA
CTAAACATCCTAATCAGGAGTATGCTGATGTCTTTCATTTGTACTTACAATACATAAGAAAGCTACATGATGAGTT
AACAGGACACATGTTAGACATGTATTCTGTTATGCTTACTAATGATAACACTTCAAGGTATTGGGAACCTGAGTTT
TATGAGGCTATGTACACACCGCATACAGTCTTACAGGCTGTTGGGGCTTGTGTTCTTTGCAATTCACAGACTTCATT
AAGATGTGGTGCTTGCATACGTAGACCATTCTTATGTTGTAAATGCTGTTACGACCATGTCATATCAACATCACATA
AATTAGTCTTGTCTGTTAATCCGTATGTTTGCAATGCTCCAGGTTGTGATGTCACAGATGTGACTCAACTTTACTTA
GGAGGTATGAGCTATTATTGTAAATCACATAAACCACCCATTAGTTTTCCATTGTGTGCTAATGGACAAGTTTTTGG
TTTATATAAAAATACATGTGTTGGTAGCGATAATGTTACTGACTTTAATGCAATTGCAACATGTGACTGGACAAAT
GCTGGTGATTACATTTTAGCTAACACCTGTACTGAAAGACTCAAGCTTTTTGCAGCAGAAACGCTCAAAGCTACTG
AGGAGACATTTAAACTGTCTTATGGTATTGCTACTGTACGTGAAGTGCTGTCTGACAGAGAATTACATCTTTCATG
GGAAGTTGGTAAACCTAGACCACCACTTAACCGAAATTATGTCTTTACTGGTTATCGTGTAACTAAAAACAGTAAA
GTACAAATAGGAGAGTACACCTTTGAAAAAGGTGACTATGGTGATGCTGTTGTTTACCGAGGTACAACAACTTACA
AATTAAATGTTGGTGATTATTTTGTGCTGACATCACATACAGTAATGCCATTAAGTGCACCTACACTAGTGCCACA
AGAGCACTATGTTAGAATTACTGGCTTATACCCAACACTCAATATCTCAGATGAGTTTTCTAGCAATGTTGCAAATT
ATCAAAAGGTTGGTATGCAAAAGTATTCTACACTCCAGGGACCACCTGGTACTGGTAAGAGTCATTTTGCTATTGG
CCTAGCTCTCTACTACCCTTCTGCTCGCATAGTGTATACAGCTTGCTCTCATGCCGCTGTTGATGCACTATGTGAGA
AGGCATTAAAATATTTGCCTATAGATAAATGTAGTAGAATTATACCTGCACGTGCTCGTGTAGAGTGTTTTGATAA
ATTCAAAGTGAATTCAACATTAGAACAGTATGTCTTTTGTACTGTAAATGCATTGCCTGAGACGACAGCAGATATA
GTTGTCTTTGATGAAATTTCAATGGCCACAAATTATGATTTGAGTGTTGTCAATGCCAGATTACGTGCTAAGCACTA
TGTGTACATTGGCGACCCTGCTCAATTACCTGCACCACGCACATTGCTAACTAAGGGCACACTAGAACCAGAATAT
TTCAATTCAGTGTGTAGACTTATGAAAACTATAGGTCCAGACATGTTCCTCGGAACTTGTCGGCGTTGTCCTGCTGA
AATTGTTGACACTGTGAGTGCTTTGGTTTATGATAATAAGCTTAAAGCACATAAAGACAAATCAGCTCAATGCTTT
AAAATGTTTTATAAGGGTGTTATCACGCATGATGTTTCATCTGCAATTAACAGGCCACAAATAGGCGTGGTAAGAG
AATTCCTTACACGTAACCCTGCTTGGAGAAAAGCTGTCTTTATTTCACCTTATAATTCACAGAATGCTGTAGCCTCA
AAGATTTTGGGACTACCAACTCAAACTGTTGATTCATCACAGGGCTCAGAATATGACTATGTCATATTCACTCAAA
CCACTGAAACAGCTCACTCTTGTAATGTAAACAGATTTAATGTTGCTATTACCAGAGCAAAAGTAGGCATACTTTG
CATAATGTCTGATAGAGACCTTTATGACAAGTTGCAATTTACAAGTCTTGAAATTCCACGTAGGAATGTGGCAACT
TTACAAGCTGAAAATGTAACAGGACTCTTTAAAGATTGTAGTAAGGTAATCACTGGGTTACATCCTACACAGGCAC
CTACACACCTCAGTGTTGACACTAAATTCAAAACTGAAGGTTTATGTGTTGACATACCTGGCATACCTAAGGACAT
GACCTATAGAAGACTCATCTCTATGATGGGTTTTAAAATGAATTATCAAGTTAATGGTTACCCTAACATGTTTATCA
CCCGCGAAGAAGCTATAAGACATGTACGTGCATGGATTGGCTTCGATGTCGAGGGGTGTCATGCTACTAGAGAAG
CTGTTGGTACCAATTTACCTTTACAGCTAGGTTTTTCTACAGGTGTTAACCTAGTTGCTGTACCTACAGGTTATGTT
GATACACCTAATAATACAGATTTTTCCAGAGTTAGTGCTAAACCACCGCCTGGAGATCAATTTAAACACCTCATAC
CACTTATGTACAAAGGACTTCCTTGGAATGTAGTGCGTATAAAGATTGTACAAATGTTAAGTGACACACTTAAAAA
TCTCTCTGACAGAGTCGTATTTGTCTTATGGGCACATGGCTTTGAGTTGACATCTATGAAGTATTTTGTGAAAATAG
GACCTGAGCGCACCTGTTGTCTATGTGATAGACGTGCCACATGCTTTTCCACTGCTTCAGACACTTATGCCTGTTGG
CATCATTCTATTGGATTTGATTACGTCTATAATCCGTTTATGATTGATGTTCAACAATGGGGTTTTACAGGTAACCT
ACAAAGCAACCATGATCTGTATTGTCAAGTCCATGGTAATGCACATGTAGCTAGTTGTGATGCAATCATGACTAGG
TGTCTAGCTGTCCACGAGTGCTTTGTTAAGCGTGTTGACTGGACTATTGAATATCCTATAATTGGTGATGAACTGAA
GATTAATGCGGCTTGTAGAAAGGTTCAACACATGGTTGTTAAAGCTGCATTATTAGCAGACAAATTCCCAGTTCTT
CACGACATTGGTAACCCTAAAGCTATTAAGTGTGTACCTCAAGCTGATGTAGAATGGAAGTTCTATGATGCACAGC
CTTGTAGTGACAAAGCTTATAAAATAGAAGAATTATTCTATTCTTATGCCACACATTCTGACAAATTCACAGATGG
TGTATGCCTATTTTGGAATTGCAATGTCGATAGATATCCTGCTAATTCCATTGTTTGTAGATTTGACACTAGAGTGC
TATCTAACCTTAACTTGCCTGGTTGTGATGGTGGCAGTTTGTATGTAAATAAACATGCATTCCACACACCAGCTTTT
GATAAAAGTGCTTTTGTTAATTTAAAACAATTACCATTTTTCTATTACTCTGACAGTCCATGTGAGTCTCATGGAAA

-continued

| SEQUENCE LISTING |
| --- |
| ACAAGTAGTGTCAGATATAGATTATGTACCACTAAAGTCTGCTACGTGTATAACACGTTGCAATTTAGGTGGTGCT |
| GTCTGTAGACATCATGCTAATGAGTACAGATTGTATCTCGATGCTTATAACATGATGATCTCAGCTGGCTTTAGCTT |
| GTGGGTTTACAAACAATTTGATACTTATAACCTCTGGAACACTTTTACAAGACTTCAGAGTTTAGAAAATGTGGCT |
| TTTAATGTTGTAAATAAGGGACACTTTGATGGACAACAGGGTGAAGTACCAGTTTCTATCATTAATAACACTGTTT |
| ACACAAAAGTTGATGGTGTTGATGTAGAATTGTTTGAAAATAAAACAACATTACCTGTTAATGTAGCATTTGAGCT |
| TTGGGCTAAGCGCAACATTAAACCAGTACCAGAGGTGAAAATACTCAATAATTTGGGTGTGGACATTGCTGCTAAT |
| ACTGTGATCTGGGACTACAAAAGAGATGCTCCAGCACATATATCTACTATTGGTGTTTGTTCTATGACTGACATAG |
| CCAAGAAACCAACTGAAACGATTTGTGCACCACTCACTGTCTTTTTTGATGGTAGAGTTGATGGTCAAGTAGACTT |
| ATTTAGAAATGCCCGTAATGGTGTTCTTATTACAGAAGGTAGTGTTAAAGGTTTACAACCATCTGTAGGTCCCAAA |
| CAAGCTAGTCTTAATGGAGTCACATTAATTGGAGAAGCCGTAAAAACACAGTTCAATTATTATAAGAAAGTTGATG |
| GTGTTGTCCAACAATTACCTGAAACTTACTTTACTCAGAGTAGAAATTTACAAGAATTTAAACCCAGGAGTCAAAT |
| GGAAATTGATTTCTTAGAATTAGCTATGGATGAATTCATTGAACGGTATAAATTAGAAGGCTATGCCTTCGAACAT |
| ATCGTTTATGGAGATTTTAGTCATAGTCAGTTAGGTGGTTTACATCTACTGATTGGACTAGCTAAACGTTTTAAGGA |
| ATCACCTTTTGAATTAGAAGATTTTATTCCTATGGACAGTACAGTTAAAAACTATTTCATAACAGATGCGCAAACA |
| GGTTCATCTAAGTGTGTGTGTTCTGTTATTGATTTATTACTTGATGATTTTGTTGAAATAATAAAATCCCAAGATTT |
| ATCTGTAGTTTCTAAGGTTGTCAAAGTGACTATTGACTATACAGAAATTTCATTTATGCTTTGGTGTAAAGATGGCC |
| ATGTAGAAACATTTTACCCAAAATTACAATCTAGTCAAGCGTGGCAACCGGGTGTTGCTATGCCTAATCTTTACAA |
| AATGCAAAGAATGCTATTAGAAAAGTGTGACCTTCAAAATTATGGTGATAGTGCAACATTACCTAAAGGCATAAT |
| GATGAATGTCGCAAAATATACTCAACTGTGTCAATATTTAAACACATTAACATTAGCTGTACCCTATAATATGAGA |
| GTTATACATTTTGGTGCTGGTTCTGATAAAGGAGTTGCACCAGGTACAGCTGTTTTAAGACAGTGGTTGCCTACGG |
| GTACGCTGCTTGTCGATTCAGATCTTAATGACTTTGTCTCTGATGCAGATTCAACTTTGATTGGTGATTGTGCAACT |
| GTACATACAGCTAATAAATGGGATCTCATTATTAGTGATATGTACGACCCTAAGACTAAAAATGTTACAAAAGAA |
| AATGACTCTAAAGAGGGTTTTTTCACTTACATTTGTGGGTTTATACAACAAAAGCTAGCTCTTGGAGGTTCCGTGGC |
| TATAAAGATAACAGAACATTCTTGGAATGCTGATCTTTATAAGCTCATGGGACACTTCGCATGGTGGACAGCCTTT |
| GTTACTAATGTGAATGCGTCATCATCTGAAGCATTTTTAATTGGATGTAATTATCTTGGCAAACCACGCGAACAAA |
| TAGATGGTTATGTCATGCATGCAAATTACATATTTTGGAGGAATACAAATCCAATTCAGTTGTCTTCCTATTCTTTA |
| TTTGACATGAGTAAATTTCCCCTTAAATTAAGGGGTACTGCTGTTATGTCTTTAAAAGAAGGTCAAATCAATGATA |
| TGATTTTATCTCTTCTTAGTAAAGGTAGACTTATAATTAGAGAAAACAACAGAGTTGTTATTTCTAGTGATGTTCTT |
| GTTAACAACTAAACGAACAATGTTTGTTTTTCTTGTTTTATTGCCACTAGTCTCTAGTCAGTGTGTTAATCTTACAAC |
| CAGAACTCAATTACCCCCTGCATACACTAATTCTTTCACACGTGGTGTTTATTACCCTGACAAAGTTTTCAGATCCT |
| CAGTTTTACATTCAACTCAGGACTTGTTCTTACCTTTCTTTTCCAATGTTACTTGGTTCCATGCTATACATGTCTCTG |
| GGACCAATGGTACTAAGAGGTTTGATAACCCTGTCCTACCATTTAATGATGGTGTTTATTTTGCTTCCACTGAGAAG |
| TCTAACATAATAAGAGGCTGGATTTTTGGTACTACTTTAGATTCGAAGACCCAGTCCCTACTTATTGTTAATAACGC |
| TACTAATGTTGTTATTAAAGTCTGTGAATTTCAATTTTGTAATGATCCATTTTTGGGTGTTTATTACCACAAAAACA |
| ACAAAAGTTGGATGGAAAGTGAGTTCAGAGTTTATTCTAGTGCGAATAATTGCACTTTTGAATATGTCTCTCAGCC |
| TTTTCTTATGGACCTTGAAGGAAAACAGGGTAATTTCAAAAATCTTAGGGAATTTGTGTTTAAGAATATTGATGGT |
| TATTTTAAAATATATTCTAAGCACACGCCTATTAATTTAGTGCGTGATCTCCCTCAGGGTTTTTCGGCTTTAGAACC |
| ATTGGTAGATTTGCCAATAGGTATTAACATCACTAGGTTTCAAACTTTACTTGCTTTACATAGAAGTTATTTGACTC |
| CTGGTGATTCTTCTTCAGGTTGGACAGCTGGTGCTGCAGCTTATTATGTGGGTTATCTTCAACCTAGGACTTTTCTA |
| TTAAAATATAATGAAAATGGAACCATTACAGATGCTGTAGACTGTGCACTTGACCCTCTCTCAGAAACAAAGTGTA |
| CGTTGAAATCCTTCACTGTAGAAAAAGGAATCTATCAAACTTCTAACTTTAGAGTCCAACCAACAGAATCTATTGT |
| TAGATTTCCTAATATTACAAACTTGTGCCCTTTTGGTGAAGTTTTTAACGCCACCAGATTTGCATCTGTTTATGCTTG |
| GAACAGGAAGAGAATCAGCAACTGTGTTGCTGATTATTCTGTCCTATATAATTCCGCATCATTTTCCACTTTTAAGT |
| GTTATGGAGTGTCTCCTACTAAATTAAATGATCTCTGCTTTACTAATGTCTATGCAGATTCATTTGTAATTAGAGGT |
| GATGAAGTCAGACAAATCGCTCCAGGGCAAACTGGAAAGATTGCTGATTATAATTATAAATTACCAGATGATTTTA |
| CAGGCTGCGTTATAGCTTGGAATTCTAACAATCTTGATTCTAAGGTTGGTGGTAATTATAATTACCTGTATAGATTG |
| TTTAGGAAGTCTAATCTCAAACCTTTTGAGAGAGATATTTCAACTGAAATCTATCAGGCCGGTAGCACACCTTGTA |
| ATGGTGTTGAAGGTTTTAATTGTTACTTTCCTTTACAATCATATGGTTTCCAACCCACTAATGGTGTTGGTTACCAA |
| CCATACAGAGTAGTAGTACTTTCTTTTGAACTTCTACATGCACCAGCAACTGTTTGTGGACCTAAAAAGTCTACTAA |
| TTTGGTTAAAAACAAATGTGTCAATTTCAACTTCAATGGTTTAACAGGCACAGGTGTTCTTACTGAGTCTAACAAA |
| AAGTTTCTGCCTTTCCAACAATTTGGCAGAGACATTGCTGACACTACTGATGCTGTCCGTGATCCACAGACACTTG |

-continued

SEQUENCE LISTING

AGATTCTTGACATTACACCATGTTCTTTTGGTGGTGTCAGTGTTATAACACCAGGAACAAATACTTCTAACCAGGTT
GCTGTTCTTTATCAGGATGTTAACTGCACAGAAGTCCCTGTTGCTATTCATGCAGATCAACTTACTCCTACTTGGCG
TGTTTATTCTACAGGTTCTAATGTTTTTCAAACACGTGCAGGCTGTTTAATAGGGGCTGAACATGTCAACAACTCAT
ATGAGTGTGACATACCCATTGGTGCAGGTATATGCGCTAGTTATCAGACTCAGACTAATTCTCCTCGGCGGGCACG
TAGTGTAGCTAGTCAATCCATCATTGCCTACACTATGTCACTTGGTGCAGAAAATTCAGTTGCTTACTCTAATAACT
CTATTGCCATACCCACAAATTTTACTATTAGTGTTACCACAGAAATTCTACCAGTGTCTATGACCAAGACATCAGTA
GATTGTACAATGTACATTTGTGGTGATTCAACTGAATGCAGCAATCTTTTGTTGCAATATGGCAGTTTTTGTACACA
ATTAAACCGTGCTTTAACTGGAATAGCTGTTGAACAAGACAAAAACACCCAAGAAGTTTTTGCACAAGTCAAACA
AATTTACAAAACACCACCAATTAAAGATTTTGGTGGTTTTAATTTTTCACAAATATTACCAGATCCATCAAAACCA
AGCAAGAGGTCATTTATTGAAGATCTACTTTTCAACAAAGTGACACTTGCAGATGCTGGCTTCATCAAACAATATG
GTGATTGCCTTGGTGATATTGCTGCTAGAGACCTCATTTGTGCACAAAAGTTTAACGGCCTTACTGTTTTGCCACCT
TTGCTCACAGATGAAATGATTGCTCAATACACTTCTGCACTGTTAGCGGGTACAATCACTTCTGGTTGGACCTTTGG
TGCAGGTGCTGCATTACAAATACCATTTGCTATGCAAATGGCTTATAGGTTTAATGGTATTGGAGTTACACAGAAT
GTTCTCTATGAGAACCAAAAATTGATTGCCAACCAATTTAATAGTGCTATTGGCAAAATTCAAGACTCACTTTCTTC
CACAGCAAGTGCACTTGGAAAACTTCAAGATGTGGTCAACCAAAATGCACAAGCTTTAAACACGCTTGTTAAACA
ACTTAGCTCCAATTTTGGTGCAATTTCAAGTGTTTTAAATGATATCCTTTCACGTCTTGACAAAGTTGAGGCTGAAG
TGCAAATTGATAGGTTGATCACAGGCAGACTTCAAAGTTTGCAGACATATGTGACTCAACAATTAATTAGAGCTGC
AGAAATCAGAGCTTCTGCTAATCTTGCTGCTACTAAAATGTCAGAGTGTGTACTTGGACAATCAAAAAGAGTTGAT
TTTTGTGGAAAGGGCTATCATCTTATGTCCTTCCCTCAGTCAGCACCTCATGGTGTAGTCTTCTTGCATGTGACTTAT
GTCCCTGCACAAGAAAAGAACTTCACAACTGCTCCTGCCATTTGTCATGATGGAAAAGCACACTTTCCTCGTGAAG
GTGTCTTTGTTTCAAATGGCACACACTGGTTTGTAACACAAAGGAATTTTTATGAACCACAAATCATTACTACAGA
CAACACATTTGTGTCTGGTAACTGTGATGTTGTAATAGGAATTGTCAACAACACAGTTTATGATCCTTTGCAACCTG
AATTAGACTCATTCAAGGAGGAGTTAGATAAATATTTTAAGAATCATACATCACCAGATGTTGATTTAGGTGACAT
CTCTGGCATTAATGCTTCAGTTGTAAACATTCAAAAAGAAATTGACCGCCTCAATGAGGTTGCCAAGAATTTAAAT
GAATCTCTCATCGATCTCCAAGAACTTGGAAAGTATGAGCAGTATATAAAATGGCCATGGTACATTTGGCTAGGTT
TTATAGCTGGCTTGATTGCCATAGTAATGGTGACAATTATGCTTTGCTGTATGACCAGTTGCTGTAGTTGTCTCAAG
GGCTGTTGTTCTTGTGGATCCTGCTGCAAATTTGATGAAGACGACTCTGAGCCAGTGCTCAAAGGAGTCAAATTAC
ATTACACATAAACGAACTTATGGATTTGTTTATGAGAATCTTCACAATTGGAACTGTAACTTTGAAGCAAGGTGAA
ATCAAGGATGCTACTCCTTCAGATTTTGTTCGCGCTACTGCAACGATACCGATACAAGCCTCACTCCCTTTCGGATG
GCTTATTGTTGGCGTTGCACTTCTTGCTGTTTTTCAGAGCGCTTCCAAAATCATAACCCTCAAAAAGAGATGGCAAC
TAGCACTCTCCAAGGGTGTTCACTTTGTTTGCAACTTGCTGTTGTTGTTTGTAACAGTTTACTCACACCTTTTGCTCG
TTGCTGCTGGCCTTGAAGCCCCTTTTCTCTATCTTTATGCTTTAGTCTACTTCTTGCAGAGTATAAACTTTGTAAGAA
TAATAATGAGGCTTTGGCTTTGCTGGAAATGCCGTTCCAAAAACCCATTACTTTATGATGCCAACTATTTTCTTTGC
TGGCATACTAATTGTTACGACTATTGTATACCTTACAATAGTGTAACTTCTTCAATTGTCATTACTTCAGGTGATGG
CACAACAAGTCCTATTTCTGAACATGACTACCAGATTGGTGGTTATACTGAAAAATGGGAATCTGGAGTAAAAGA
CTGTGTTGTATTACACAGTTACTTCACTTCAGACTATTACCAGCTGTACTCAACTCAATTGAGTACAGACACTGGTG
TTGAACATGTTACCTTCTTCATCTACAATAAAATTGTTGATGAGCCTGAAGAACATGTCCAAATTCACACAATCGA
CGGTTCATCCGGAGTTGTTAATCCAGTAATGGAACCAATTTATGATGAACCGACGACGACTACTAGCGTGCCTTTG
TAAGCACAAGCTGATGAGTACGAACTTATGTACTCATTCGTTTCGGAAGAGACAGGTACGTAAATAGTTAATAGCT
GACTTCTTTTTCTTGCTTTCGTGTGATTCTTGCTAGTTACACTAGCCATCCTTACTGCGCTTCGATTGTGTGCGTACT
GCTGCAATATTGTTAACGTGAGTCTTGTAAAACCTTCTTTTTACGTTTACTCTCGTGTTAAAAATCTGAATTCTTCTA
GAGTTCCTGATCTTCTGGTCTAAACGAACTAAATATTATATTAGTTTTTCTGTTTGGAACTTTAATTTTAGCCATGGC
AGATTCCAACGGTACTATTACCGTTGAAGAGCTTAAAAAGCTCCTTGAACAATGGAACCTAGTAATAGGTTTCCTA
TTCCTTACATGGATTTGTCTTCTACAATTTGCCTATGCCAACAGGAATAGGTTTTTGTATATAATTAAGTTAATTTTC
CTCTGGCTGTTATGGCCAGTAACTTTAGCTTGTTTTGTGCTTGCTGCTGTTTACAGAATAAATTGGATCACCGGTGG
AATTGCTATCGCAATGGCTTGTCTTGTAGGCTTGATGTGGCTCAGCTACTTCATTGCTTCTTTCAGACTGTTTGCGC
GTACGCGTTCCATGTGGTCATTCAATCCAGAAACTAACATTCTTCTCAACGTGCCACTCCATGGCACTATTCTGACC
AGACCGCTTCTAGAAAGTGAACTCGTAATCGGAGCTGTGATCCTTCGTGGACATCTTCGTATTGCTGGACACCATC
TAGGACGCTGTGACATCAAGGACCTGCCTAAAGAAATCACTGTTGCTACATCACGAACGCTTTCTTATTACAAATT
GGGAGCTTCGCAGCGTGTAGCAGGTGACTCAGGTTTTGCTGCATACAGTCGCTACAGGATTGGCAACTATAAATTA
AACACAGACCATTCCAGTAGCAGTGACAATATTGCTTTGCTTGTACAATGATAATGAAACTTGTCACGCCTAAACG

-continued

SEQUENCE LISTING

AACatgaccaacaagtgtctcctccaaattgctctcctgttgtgcttctccactacagctctttccatgagctacaacttgcttggattcctacaaagaagcagcaattttcagtgtcagaagctc
ctgtggcaattgaatgggaggcttgaatactgcctcaaggacaggatgaactttgacatccctgaggagattaagcagctgcagcagttccagaaggaggacgccgcattgaccatctatga
gatgctccagaacatctttgctattttcagacaagattcatctagcactggctggaatgagactattgttgagaacctcctggctaatgtctatcatcagataaaccatctgaagacagtcctggaa
gaaaaactggagaaagaagatttcaccaggggaaaactcatgagcagtctgcacctgaaaagatattatgggaggattctgcattacctgaaggccaaggagtacagtcactgtgcctgga
ccatagtcagagtggaaatcctaaggaacttttacttcattaacagacttacaggttacctccgaaactgaGACGTTCGTGTTGTTTTAGATTTCATCTAAACGA
ACAAACTAAAATGTCTGATAATGGACCCCAAAATCAGCGAAATGCACCCCGCATTACGTTTGGTGGACCCTCAGAT
TCAACTGGCAGTAACCAGAATGGAGAACGCAGTGGGGCGCGATCAAAACAACGTCGGCCCCAAGGTTTACCCAAT
AATACTGCGTCTTGGTTCACCGCTCTCACTCAACATGGCAAGGAAGACCTTAAATTCCCTCGAGGACAAGGCGTTC
CAATTAACACCAATAGCAGTCCAGATGACCAAATTGGCTACTACCGAAGAGCTACCAGACGAATTCGTGGTGGTG
ACGGTAAAATGAAAGATCTCAGTCCAAGATGGTATTTCTACTACCTAGGAACTGGGCCAGAAGCTGGACTTCCCTA
TGGTGCTAACAAAGACGGCATCATATGGGTTGCAACTGAGGGAGCCTTGAATACACCAAAAGATCACATTGGCAC
CCGCAATCCTGCTAACAATGCTGCAATCGTGCTACAACTTCCTCAAGGAACAACATTGCCAAAAGGCTTCTACGCA
GAAGGGAGCAGAGGCGGCAGTCAAGCCTCTTCTCGTTCCTCATCACGTAGTCGCAACAGTTCAAGAAATTCAACTC
CAGGCAGCAGTAGGGGAACTTCTCCTGCTAGAATGGCTGGCAATGGCGGTGATGCTGCTCTTGCTTTGCTGCTGCT
TGACAGATTGAACCAGCTTGAGAGCAAAATGTCTGGTAAAGGCCAACAACAACAAGGCCAAACTGTCACTAAGAA
ATCTGCTGCTGAGGCTTCTAAGAAGCCTCGGCAAAAACGTACTGCCACTAAAGCATACAATGTAACACAAGCTTTC
GGCAGACGTGGTCCAGAACAAACCCAAGGAAATTTTGGGGACCAGGAACTAATCAGACAAGGAACTGATTACAA
ACATTGGCCGCAAATTGCACAATTTGCCCCCAGCGCTTCAGCGTTCTTCGGAATGTCGCGCATTGGCATGGAAGTC
ACACCTTCGGGAACGTGGTTGACCTACACAGGTGCCATCAAATTGGATGACAAAGATCCAAATTTCAAAGATCAA
GTCATTTTGCTGAATAAGCATATTGACGCATACAAAACATTCCCACCAACAGAGCCTAAAAAGGACAAAAAGAAG
AAGGCTGATGAAACTCAAGCCTTACCGCAGAGACAGAAGAAACAGCAAACTGTGACTCTTCTTCCTGCTGCAGAT
TTGGATGATTTCTCCAAACAATTGCAACAATCCATGAGCAGTGCTGACTCAACTCAGGCCTAAACTCATGCAGACC
ACACAAGGCAGATGGGCTATATAAACGTTTTCGCTTTTCCGTTTACGATATATAGTCTACTCTTGTGCAGAATGAAT
TCTCGTAACTACATAGCACAAGTAGATGTAGTTAACTTTAATCTCACATAGCAATCTTTAATCAGTGTGTAACATTA
GGGAGGACTTGAAAGAGCCACCACATTTTCACCGAGGCCACGCGGAGTACGATCGAGTGTACAGTGAACAATGCT
AGGGAGAGCTGCCTATATGGAAGAGCCCTAATGTGTAAAATTAATTTTAGTAGTGCTATCCCCATGTGATTTTAAT
AGCTTCTTAGGAGAATGACAAAAAAAAAAAAAAAAAAAAA SEQ ID NO: 6 (synthetic IBIS DNA construct 2, variant BA.2; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA -continued

SEQUENCE LISTING

GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC
TGACCCTATACATTCTTTAAGAGTTTGTGTAGATACTGTTCGCACAAATGTCTACTTAGCTGTCTTTGATAAAAATC
TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT
GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA

-continued

SEQUENCE LISTING

GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT
CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT
TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT
GTGATACATTCTGTGCTGGTAGTACATTTATTAGTGATGAAGTTGCGAGAGACTTGTCACTACAGTTTAAAAGACC
AATAAATCCTACTGACCAGTCTTCTTACATCGTTGATAGTGTTACAGTGAAGAATGGTTCCATCCATCTTTACTTTG
ATAAAGCTGGTCAAAAGACTTATGAAAGACATTCTCTCTCTCATTTTGTTAACTTAGACAACCTGAGAGCTAATAA
CACTAAAGGTTCATTGCCTATTAATGTTATAGTTTTTGATGGTAAATCAAAATGTGAAGAATCATCTGCAAAATCA
GCGTCTGTTTACTACAGTCAGCTTATGTGTCAACCTATACTGTTACTAGATCAGGCATTAGTGTCTGATGTTGGTGA
TAGTGCGGAAGTTGCAGTTAAAATGTTTGATGCTTACGTTAATACGTTTTCATCAACTTTTAACGTACCAATGGAAA
AACTCAAAACACTAGTTGCAACTGCAGAAGCTGAACTTGCAAAGAATGTGTCCTTAGACAATGTCTTATCTACTTT
TATTTCAGCAGCTCGGCAAGGGTTTGTTGATTCAGATGTAGAAACTAAAGATGTTGTTGAATGTCTTAAATTGTCA
CATCAATCTGACATAGAAGTTACTGGCGATAGTTGTAATAACTATATGCTCACCTATAACAAAGTTGAAAACATGA
CACCCCGTGACCTTGGTGCTTGTATTGACTGTAGTGCGCGTCATATTAATGCGCAGGTAGCAAAAAGTCACAACAT
TGCTTTGATATGGAACGTTAAAGATTTCATGTCATTGTCTGAACAACTACGAAAACAAATACGTAGTGCTGCTAAA
AAGAATAACTTACCTTTTAAGTTGACATGTGCAACTACTAGACAAGTTGTTAATGTTGTAACAACAAAGATAGCAC
TTAAGGGTGGTAAAATTGTTAATAATTGGTTGAAGCAGTTAATTAAAGTTACACTTGTGTTCCTTTTTGTTGCTGCT
ATTTTCTATTTAATAACACCTGTTCATGTCATGTCTAAACATACTGACTTTTCAAGTGAAATCATAGGATACAAGGC
TATTGATGGTGGTGTCACTCGTGACATAGCATCTACAGATACTTGTTTTGCTAACAAACATGCTGATTTTGACACAT
GGTTTAGCCAGCGTGGTGGTAGTTATACTAATGACAAAGCTTGCCCATTGATTGCTGCAGTCATAACAAGAGAAGT
GGGTTTTGTCGTGCCTGGTTTGCCTGGCACGATATTACGCACAACTAATGGTGACTTTTTGCATTTCTTACCTAGAG
TTTTTAGTGCAGTTGGTAACATCTGTTACACACCATCAAAACTTATAGAGTACACTGACTTTGCAACATCAGCTTGT
GTTTTGGCTGCTGAATGTACAATTTTTAAAGATGCTTCTGGTAAGCCAGTACCATATTGTTATGATACCAATGTACT
AGAAGGTTCTGTTGCTTATGAAAGTTTACGCCCTGACACACGTTATGTGCTCATGGATGGCTCTATTATTCAATTTC
CTAACACCTACCTTGAAGGTTCTGTTAGAGTGGTAACAACTTTTGATTCTGAGTACTGTAGGCACGGCACTTGTGA
AAGATCAGAAGCTGGTGTTTGTGTATCTACTAGTGGTAGATGGGTACTTAACAATGATTATTACAGATCTTTACCA
GGAGTTTTCTGTGGTGTAGATGCTGTAAATTTACTTACTAATATGTTTACACCACTAATTCAACCTATTGGTGCTTT
GGACATATCAGCATCTATAGTAGCTGGTGGTATTGTAGCTATCGTAGTAACATGCCTTGCCTACTATTTTATGAGGT

-continued

SEQUENCE LISTING

```
TTAGAAGAGCTTTTGGTGAATACAGTCATGTAGTTGCCTTTAATACTTTACTATTCCTTATGTCATTCACTGTACTCT
GTTTAACACCAGTTTACTCATTCTTACCTGGTGTTTATTCTGTTATTTACTTGTACTTGACATTTTATCTTACTAATG
ATGTTTCTTTTTTAGCACATATTCAGTGGATGGTTATGTTCACACCTTTAGTACCTTTCTGGATAACAATTGCTTATA
TCATTTGTATTTCCACAAAGCATTTCTATTGGTTCTTTAGTAATTACCTAAAGAGACGTGTAGTCTTTAATGGTGTTT
CCTTTAGTACTTTTGAAGAAGCTGCGCTGTGCACCTTTTTGTTAAATAAAGAAATGTATCTAAAGTTGCGTAGTGAT
GTGCTATTACCTCTTACGCAATATAATAGATACTTAGCTCTTTATAATAAGTACAAGTATTTTAGTGGAGCAATGGA
TACAACTAGCTACAGAGAAGCTGCTTGTTGTCATCTCGCAAAGGCTCTCAATGACTTCAGTAACTCAGGTTCTGAT
GTTCTTTACCAACCACCACAAACCTCTATCACCTCAGCTGTTTTGCAGAGTGGTTTTAGAAAAATGGCATTCCCATC
TGGTAAAGTTGAGGGTTGTATGGTACAAGTAACTTGTGGTACAACTACACTTAACGGTCTTTGGCTTGATGACGTA
GTTTACTGTCCAAGACATGTGATCTGCACCTCTGAAGACATGCTTAACCCTAATTATGAAGATTTACTCATTCGTAA
GTCTAATCATAATTTCTTGGTACAGGCTGGTAATGTTCAACTCAGGGTTATTGGACATTCTATGCAAAATTGTGTAC
TTAAGCTTAAGGTTGATACAGCCAATCCTAAGACACCTAAGTATAAGTTTGTTCGCATTCAACCAGGACAGACTTT
TTCAGTGTTAGCTTGTTACAATGGTTCACCATCTGGTGTTTACCAATGTGCTATGAGGCCCAATTTCACTATTAAGG
GTTCATTCCTTAATGGTTCATGTGGTAGTGTTGGTTTTAACATAGATTATGACTGTGTCTCTTTTTGTTACATGCACC
ATATGGAATTACCAACTGGAGTTCATGCTGGCACAGACTTAGAAGGTAACTTTTATGGACCTTTTGTTGACAGGCA
AACAGCACAAGCAGCTGGTACGGACACAACTATTACAGTTAATGTTTTAGCTTGGTTGTACGCTGCTGTTATAAAT
GGAGACAGGTGGTTTCTCAATCGATTTACCACAACTCTTAATGACTTTAACCTTGTGGCTATGAAGTACAATTATG
AACCTCTAACACAAGACCATGTTGACATACTAGGACCTCTTTCTGCTCAAACTGGAATTGCCGTTTTAGATATGTGT
GCTTCATTAAAAGAATTACTGCAAAATGGTATGAATGGACGTACCATATTGGGTAGTGCTTTATTAGAAGATGAAT
TTACACCTTTTGATGTTGTTAGACAATGCTCAGGTGTTACTTTCCAAAGTGCAGTGAAAAGAACAATCAAGGGTAC
ACACCACTGGTTGTTACTCACAATTTTGACTTCACTTTTAGTTTTAGTCCAGAGTACTCAATGGTCTTTGTTCTTTTT
TTTGTATGAAAATGCCTTTTTACCTTTTGCTATGGGTATTATTGCTATGTCTGCTTTTGCAATGATGTTTGTCAAACA
TAAGCATGCATTTCTCTGTTTGTTTTTGTTACCTTCTCTTGCCACTGTAGCTTATTTTAATATGGTCTATATGCCTGCT
AGTTGGGTGATGCGTATTATGACATGGTTGGATATGGTTGATACTAGTTTGTCTGGTTTTAAGCTAAAAGACTGTGT
TATGTATGCATCAGCTGTAGTGTTACTAATCCTTATGACAGCAAGAACTGTGTATGATGATGGTGCTAGGAGAGTG
TGGACACTTATGAATGTCTTGACACTCGTTTATAAAGTTTATTATGGTAATGCTTTAGATCAAGCCATTTCCATGTG
GGCTCTTATAATCTCTGTTACTTCTAACTACTCAGGTGTAGTTACAACTGTCATGTTTTTGGCCAGAGGTATTGTTTT
TATGTGTGTTGAGTATTGCCCTATTTTCTTCATAACTGGTAATACACTTCAGTGTATAATGCTAGTTTATTGTTTCTT
AGGCTATTTTTGTACTTGTTACTTTGGCCTCTTTTGTTTACTCAACCGCTACTTTAGACTGACTCTTGGTGTTTATGA
TTACTTAGTTTCTACACAGGAGTTTAGATATATGAATTCACAGGGACTACTCCCACCCAAGAATAGCATAGATGCC
TTCAAACTCAACATTAAATTGTTGGGTGTTGGTGGCAAACCTTGTATCAAAGTAGCCACTGTACAGTCTAAAATGT
CAGATGTAAAGTGCACATCAGTAGTCTTACTCTCAGTTTTGCAACAACTCAGAGTAGAATCATCATCTAAATTGTG
GGCTCAATGTGTCCAGTTACACAATGACATTCTCTTAGCTAAAGATACTACTGAAGCCTTTGAAAAAATGGTTTCA
CTACTTTCTGTTTTGCTTTCCATGCAGGGTGCTGTAGACATAAACAAGCTTTGTGAAGAAATGCTGGACAACAGGG
CAACCTTACAAGCTATAGCCTCAGAGTTTAGTTCCCTTCCATCATATGCAGCTTTTGCTACTGCTCAAGAAGCTTAT
GAGCAGGCTGTTGCTAATGGTGATTCTGAAGTTGTTCTTAAAAAGTTGAAGAAGTCTTTGAATGTGGCTAAATCTG
AATTTGACCGTGATGCAGCCATGCAACGTAAGTTGGAAAAGATGGCTGATCAAGCTATGACCCAAATGTATAAAC
AGGCTAGATCTGAGGACAAGAGGGCAAAAGTTACTAGTGCTATGCAGACAATGCTTTTCACTATGCTTAGAAAGTT
GGATAATGATGCACTCAACAACATTATCAACAATGCAAGAGATGGTTGTGTTCCCTTGAACATAATACCTCTTACA
ACAGCAGCCAAACTAATGGTTGTCATACCAGACTATAACACATATAAAAATACGTGTGATGGTACAACATTTACTT
ATGCATCAGCATTGTGGGAAATCCAACAGGTTGTAGATGCAGATAGTAAAATTGTTCAACTTAGTGAAATTAGTAT
GGACAATTCACCTAATTTAGCATGGCCTCTTATTGTAACAGCTTTAAGGGCCAATTCTGCTGTCAAATTACAGAAT
AATGAGCTTAGTCCTGTTGCACTACGACAGATGTCTTGTGCTGCCGGTACTACACAAACTGCTTGCACTGATGACA
ATGCGTTAGCTTACTACAACACAACAAAGGGAGGTAGGTTTGTACTTGCACTGTTATCCGATTTACAGGATTTGAA
ATGGGCTAGATTCCCTAAGAGTGATGGAACTGGTACTATCTATACAGAACTGGAACCACCTTGTAGGTTTGTTACA
GACACACCTAAAGGTCCTAAAGTGAAGTATTTATACTTTATTAAAGGATTAAACAACCTAAATAGAGGTATGGTAC
TTGGTAGTTTAGCTGCCACAGTACGTCTACAAGCTGGTAATGCAACAGAAGTGCCTGCCAATTCAACTGTATTATC
TTTCTGTGCTTTTGCTGTAGATGCTGCTAAAGCTTACAAAGATTATCTAGCTAGTGGGGGACAACCAATCACTAATT
GTGTTAAGATGTTGTGTACACACACTGGTACTGGTCAGGCAATAACAGTTACACCGGAAGCCAATATGGATCAAG
AATCCTTTGGTGGTGCATCGTGTTGTCTGTACTGCCGTTGCCACATAGATCATCCAAATCCTAAAGGATTTTGTGAC
TTAAAAGGTAAGTATGTACAAATACCTACAACTTGTGCTAATGACCCTGTGGGTTTTACACTTAAAAACACAGTCT
```

-continued

| SEQUENCE LISTING |
| --- |
| GTACCGTCTGCGGTATGTGGAAAGGTTATGGCTGTAGTTGTGATCAACTCCGCGAACCCATGCTTCAGTCAGCTGA<br>TGCACAATCGTTTTTAAACGGGTTTGCGGTGTAAGTGCAGCCCGTCTTACACCGTGCGGCACAGGCACTAGTACTG<br>ATGTCGTATACAGGGCTTTTGACATCTACAATGATAAAGTAGCTGGTTTTGCTAAATTCCTAAAAACTAATTGTTGT<br>CGCTTCCAAGAAAAGGACGAAGATGACAATTTAATTGATTCTTACTTTGTAGTTAAGAGACACACTTTCTCTAACT<br>ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA<br>TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT<br>TAAAACACTTCTTCTTTGCTCAGGATGGTAATGCTGCTATCAGCGATTATGACTACTATCGTTATAATCTACCAACA<br>ATGTGTGATATCAGACAACTACTATTTGTAGTTGAAGTTGTTGATAAGTACTTTGATTGTTACGATGGTGGCTGTAT<br>TAATGCTAACCAAGTCATCGTCAACAACCTAGACAAATCAGCTGGTTTTCCATTTAATAAATGGGGTAAGGCTAGA<br>CTTTATTATGATTCAATGAGTTATGAGGATCAAGATGCACTTTTCGCATATACAAAACGTAATGTCATCCCTACTAT<br>AACTCAAATGAATCTTAAGTATGCCATTAGTGCAAAGAATAGAGCTCGCACCGTAGCTGGTGTCTCTATCTGTAGT<br>ACTATGACCAATAGACAGTTTCATCAAAAATTATTGAAATCAATAGCCGCCACTAGAGGAGCTACTGTAGTAATTG<br>GAACAAGCAAATTCTATGGTGGTTGGCACAACATGTTAAAAACTGTTTATAGTGATGTAGAAAACCCTCACCTTAT<br>GGGTTGGGATTATCCTAAATGTGATAGAGCCATGCCTAACATGCTTAGAATTATGGCCTCACTTGTTCTTGCTCGCA<br>AACATACAACGTGTTGTAGCTTGTCACACCGTTTCTATAGATTAGCTAATGAGTGTGCTCAAGTATTGAGTGAAAT<br>GGTCATGTGTGGCGGTTCACTATATGTTAAACCAGGTGGAACCTCATCAGGAGATGCCACAACTGCTTATGCTAAT<br>AGTGTTTTTAACATTTGTCAAGCTGTCACGGCCAATGTTAATGCACTTTTATCTACTGATGGTAACAAAATTGCCGA<br>TAAGTATGTCCGCAATTTACAACACAGACTTTATGAGTGTCTCTATAGAAATAGAGATGTTGACACAGACTTTGTG<br>AATGAGTTTTACGCATATTTGCGTAAACATTTCTCAATGATGATACTCTCTGACGATGCTGTTGTGTGTTTCAATAG<br>CACTTATGCATCTCAAGGTCTAGTGGCTAGCATAAAGAACTTTAAGTCAGTTCTTTATTATCAAAACAATGTTTTTA<br>TGTCTGAAGCAAAATGTTGGACTGAGACTGACCTTACTAAAGGACCTCATGAATTTTGCTCTCAACATACAATGCT<br>AGTTAAACAGGGTGATGATTATGTGTACCTTCCTTACCCAGATCCATCAAGAATCCTAGGGGCCGGCTGTTTTGTA<br>GATGATATCGTAAAAACAGATGGTACACTTATGATTGAACGGTTCGTGTCTTTAGCTATAGATGCTTACCCACTTA<br>CTAAACATCCTAATCAGGAGTATGCTGATGTCTTTCATTTGTACTTACAATACATAAGAAAGCTACATGATGAGTT<br>AACAGGACACATGTTAGACATGTATTCTGTTATGCTTACTAATGATAACACTTCAAGGTATTGGGAACCTGAGTTT<br>TATGAGGCTATGTACACACCGCATACAGTCTTACAGGCTGTTGGGGCTTGTGTTCTTTGCAATTCACAGACTTCATT<br>AAGATGTGGTGCTTGCATACGTAGACCATTCTTATGTTGTAAATGCTGTTACGACCATGTCATATCAACATCACATA<br>AATTAGTCTTGTCTGTTAATCCGTATGTTTGCAATGCTCCAGGTTGTGATGTCACAGATGTGACTCAACTTTACTTA<br>GGAGGTATGAGCTATTATTGTAAATCACATAAACCACCCATTAGTTTTCCATTGTGTGCTAATGGACAAGTTTTTGG<br>TTTATATAAAAATACATGTGTTGGTAGCGATAATGTTACTGACTTTAATGCAATTGCAACATGTGACTGGACAAAT<br>GCTGGTGATTACATTTTAGCTAACACCTGTACTGAAAGACTCAAGCTTTTTGCAGCAGAAACGCTCAAAGCTACTG<br>AGGAGACATTTAAACTGTCTTATGGTATTGCTACTGTACGTGAAGTGCTGTCTGACAGAGAATTACATCTTTCATG<br>GGAAGTTGGTAAACCTAGACCACCACTTAACCGAAATTATGTCTTTACTGGTTATCGTGTAACTAAAAACAGTAAA<br>GTACAAATAGGAGAGTACACCTTTGAAAAAGGTGACTATGGTGATGCTGTTGTTTACCGAGGTACAACAACTTACA<br>AATTAAATGTTGGTGATTATTTTGTGCTGACATCACATACAGTAATGCCATTAAGTGCACCTACACTAGTGCCACA<br>AGAGCACTATGTTAGAATTACTGGCTTATACCCAACACTCAATATCTCAGATGAGTTTTCTAGCAATGTTGCAAATT<br>ATCAAAAGGTTGGTATGCAAAAGTATTCTACACTCCAGGGACCACCTGGTACTGGTAAGAGTCATTTTGCTATTGG<br>CCTAGCTCTCTACTACCCTTCTGCTCGCATAGTGTATACAGCTTGCTCTCATGCCGCTGTTGATGCACTATGTGAGA<br>AGGCATTAAAATATTTGCCTATAGATAAATGTAGTAGAATTATACCTGCACGTGCTCGTGTAGAGTGTTTTGATAA |

-continued

| SEQUENCE LISTING |
|---|
| ATTCAAAGTGAATTCAACATTAGAACAGTATGTCTTTTGTACTGTAAATGCATTGCCTGAGACGACAGCAGATATA<br>GTTGTCTTTGATGAAATTTCAATGGCCACAAATTATGATTTGAGTGTTGTCAATGCCAGATTACGTGCTAAGCACTA<br>TGTGTACATTGGCGACCCTGCTCAATTACCTGCACCACGCACATTGCTAACTAAGGGCACACTAGAACCAGAATAT<br>TTCAATTCAGTGTGTAGACTTATGAAAACTATAGGTCCAGACATGTTCCTCGGAACTTGTCGGCGTTGTCCTGCTGA<br>AATTGTTGACACTGTGAGTGCTTTGGTTTATGATAATAAGCTTAAAGCACATAAAGACAAATCAGCTCAATGCTTT<br>AAAATGTTTTATAAGGGTGTTATCACGCATGATGTTTCATCTGCAATTAACAGGCCACAAATAGGCGTGGTAAGAG<br>AATTCCTTACACGTAACCCTGCTTGGAGAAAAGCTGTCTTTATTTCACCTTATAATTCACAGAATGCTGTAGCCTCA<br>AAGATTTTGGGACTACCAACTCAAACTGTTGATTCATCACAGGGCTCAGAATATGACTATGTCATATTCACTCAAA<br>CCACTGAAACAGCTCACTCTTGTAATGTAAACAGATTTAATGTTGCTATTACCAGAGCAAAAGTAGGCATACTTTG<br>CATAATGTCTGATAGAGACCTTTATGACAAGTTGCAATTTACAAGTCTTGAAATTCCACGTAGGAATGTGGCAACT<br>TTACAAGCTGAAAATGTAACAGGACTCTTTAAAGATTGTAGTAAGGTAATCACTGGGTTACATCCTACACAGGCAC<br>CTACACACCTCAGTGTTGACACTAAATTCAAAACTGAAGGTTTATGTGTTGACATACCTGGCATACCTAAGGACAT<br>GACCTATAGAAGACTCATCTCTATGATGGGTTTTAAAATGAATTATCAAGTTAATGGTTACCCTAACATGTTTATCA<br>CCCGCGAAGAAGCTATAAGACATGTACGTGCATGGATTGGCTTCGATGTCGAGGGGTGTCATGCTACTAGAGAAG<br>CTGTTGGTACCAATTTACCTTTACAGCTAGGTTTTTCTACAGGTGTTAACCTAGTTGCTGTACCTACAGGTTATGTT<br>GATACACCTAATAATACAGATTTTTCCAGAGTTAGTGCTAAACCACCGCCTGGAGATCAATTTAAACACCTCATAC<br>CACTTATGTACAAAGGACTTCCTTGGAATGTAGTGCGTATAAAGATTGTACAAATGTTAAGTGACACACTTAAAAA<br>TCTCTCTGACAGAGTCGTATTTGTCTTATGGGCACATGGCTTTGAGTTGACATCTATGAAGTATTTTGTGAAAATAG<br>GACCTGAGCGCACCTGTTGTCTATGTGATAGACGTGCCACATGCTTTTCCACTGCTTCAGACACTTATGCCTGTTGG<br>CATCATTCTATTGGATTTGATTACGTCTATAATCCGTTTATGATTGATGTTCAACAATGGGGTTTTACAGGTAACCT<br>ACAAAGCAACCATGATCTGTATTGTCAAGTCCATGGTAATGCACATGTAGCTAGTTGTGATGCAATCATGACTAGG<br>TGTCTAGCTGTCCACGAGTGCTTTGTTAAGCGTGTTGACTGGACTATTGAATATCCTATAATTGGTGATGAACTGAA<br>GATTAATGCGGCTTGTAGAAAGGTTCAACACATGGTTGTTAAAGCTGCATTATTAGCAGACAAATTCCCAGTTCTT<br>CACGACATTGGTAACCCTAAAGCTATTAAGTGTGTACCTCAAGCTGATGTAGAATGGAAGTTCTATGATGCACAGC<br>CTTGTAGTGACAAAGCTTATAAAATAGAAGAATTATTCTATTCTTATGCCACACATTCTGACAAATTCACAGATGG<br>TGTATGCCTATTTTGGAATTGCAATGTCGATAGATATCCTGCTAATTCCATTGTTTGTAGATTTGACACTAGAGTGC<br>TATCTAACCTTAACTTGCCTGGTTGTGATGGTGGCAGTTTGTATGTAAATAAACATGCATTCCACACACCAGCTTTT<br>GATAAAAGTGCTTTTGTTAATTTAAAACAATTACCATTTTTCTATTACTCTGACAGTCCATGTGAGTCTCATGGAAA<br>ACAAGTAGTGTCAGATATAGATTATGTACCACTAAAGTCTGCTACGTGTATAACACGTTGCAATTTAGGTGGTGCT<br>GTCTGTAGACATCATGCTAATGAGTACAGATTGTATCTCGATGCTTATAACATGATGATCTCAGCTGGCTTTAGCTT<br>GTGGGTTTACAAACAATTTGATACTTATAACCTCTGGAACACTTTTACAAGACTTCAGAGTTTAGAAAATGTGGCT<br>TTTAATGTTGTAAATAAGGGACACTTTGATGGACAACAGGGTGAAGTACCAGTTTCTATCATTAATAACACTGTTT<br>ACACAAAAGTTGATGGTGTTGATGTAGAATTGTTTGAAAATAAAACAACATTACCTGTTAATGTAGCATTTGAGCT<br>TTGGGCTAAGCGCAACATTAAACCAGTACCAGAGGTGAAAATACTCAATAATTTGGGTGTGGACATTGCTGCTAAT<br>ACTGTGATCTGGGACTACAAAAGAGATGCTCCAGCACATATATCTACTATTGGTGTTTGTTCTATGACTGACATAG<br>CCAAGAAACCAACTGAAACGATTTGTGCACCACTCACTGTCTTTTTTGATGGTAGAGTTGATGGTCAAGTAGACTT<br>ATTTAGAAATGCCCGTAATGGTGTTCTTATTACAGAAGGTAGTGTTAAAGGTTTACAACCATCTGTAGGTCCCAAA<br>CAAGCTAGTCTTAATGGAGTCACATTAATTGGAGAAGCCGTAAAAACACAGTTCAATTATTATAAGAAAGTTGATG<br>GTGTTGTCCAACAATTACCTGAAACTTACTTTACTCAGAGTAGAAATTTACAAGAATTTAAACCCAGGAGTCAAAT<br>GGAAATTGATTTCTTAGAATTAGCTATGGATGAATTCATTGAACGGTATAAATTAGAAGGCTATGCCTTCGAACAT<br>ATCGTTTATGGAGATTTTAGTCATAGTCAGTTAGGTGGTTTACATCTACTGATTGGACTAGCTAAACGTTTTAAGGA<br>ATCACCTTTTGAATTAGAAGATTTTATTCCTATGGACAGTACAGTTAAAAACTATTTCATAACAGATGCGCAAACA<br>GGTTCATCTAAGTGTGTGTGTTCTGTTATTGATTTATTACTTGATGATTTTGTTGAAATAATAAAATCCCAAGATTT<br>ATCTGTAGTTTCTAAGGTTGTCAAAGTGACTATTGACTATACAGAAATTTCATTTATGCTTTGGTGTAAAGATGGCC<br>ATGTAGAAACATTTTACCCAAAATTACAATCTAGTCAAGCGTGGCAACCGGGTGTTGCTATGCCTAATCTTTACAA<br>AATGCAAAGAATGCTATTAGAAAAGTGTGACCTTCAAAATTATGGTGATAGTGCAACATTACCTAAAGGCATAAT<br>GATGAATGTCGCAAAATATACTCAACTGTGTCAATATTTAAACACATTAACATTAGCTGTACCCTATAATATGAGA<br>GTTATACATTTTGGTGCTGGTTCTGATAAAGGAGTTGCACCAGGTACAGCTGTTTTAAGACAGTGGTTGCCTACGG<br>GTACGCTGCTTGTCGATTCAGATCTTAATGACTTTGTCTCTGATGCAGATTCAACTTTGATTGGTGATTGTGCAACT<br>GTACATACAGCTAATAAATGGGATCTCATTATTAGTGATATGTACGACCCTAAGACTAAAAATGTTACAAAAGAA<br>AATGACTCTAAAGAGGGTTTTTTCACTTACATTTGTGGGTTTATACAACAAAAGCTAGCTCTTGGAGGTTCCGTGGC |

-continued

SEQUENCE LISTING

TATAAAGATAACAGAACATTCTTGGAATGCTGATCTTTATAAGCTCATGGGACACTTCGCATGGTGGACAGCCTTT
GTTACTAATGTGAATGCGTCATCATCTGAAGCATTTTTAATTGGATGTAATTATCTTGGCAAACCACGCGAACAAA
TAGATGGTTATGTCATGCATGCAAATTACATATTTGGAGGAATACAAATCCAATTCAGTTGTCTTCCTATTCTTTA
TTTGACATGAGTAAATTTCCCCTTAAATTAAGGGGTACTGCTGTTATGTCTTTAAAAGAAGGTCAAATCAATGATA
TGATTTTATCTCTTCTTAGTAAAGGTAGACTTATAATTAGAGAAAACAACAGAGTTGTTATTTCTAGTGATGTTCTT
GTTAACAACTAAACGAACAATGTTTGTTTTTCTTGTTTTATTGCCACTAGTCTCTAGTCAGTGTGTTAATCTTATAAC
CAGAACTCAATCATACACTAATTCTTTCACACGTGGTGTTTATTACCCTGACAAAGTTTTCAGATCCTCAGTTTTAC
ATTCAACTCAGGACTTGTTCTTACCTTTCTTTTCCAATGTTACTTGGTTCCATGCTATACATGTCTCTGGGACCAATG
GTACTAAGAGGTTTGATAACCCTGTCCTACCATTTAATGATGGTGTTTATTTTGCTTCCACTGAGAAGTCTAACATA
ATAAGAGGCTGGATTTTTGGTACTACTTTAGATTCGAAGACCCAGTCCCTACTTATTGTTAATAACGCTACTAATGT
TGTTATTAAAGTCTGTGAATTTCAATTTTGTAATGATCCATTTTTGGATGTTTATTACCACAAAAACAACAAAAGTT
GGATGGAAAGTGAGTTCAGAGTTTATTCTAGTGCGAATAATTGCACTTTTGAATATGTCTCTCAGCCTTTTCTTATG
GACCTTGAAGGAAAACAGGGTAATTTCAAAAATCTTAGGGAATTTGTGTTTAAGAATATTGATGGTTATTTTAAAA
TATATTCTAAGCACACGCCTATTAATTTAGGGCGTGATCTCCCTCAGGGTTTTTCGGCTTTAGAACCATTGGTAGAT
TTGCCAATAGGTATTAACATCACTAGGTTTCAAACTTTACTTGCTTTACATAGAAGTTATTTGACTCCTGGTGATTC
TTCTTCAGGTTGGACAGCTGGTGCTGCAGCTTATTATGTGGGTTATCTTCAACCTAGGACTTTTCTATTAAAATATA
ATGAAAATGGAACCATTACAGATGCTGTAGACTGTGCACTTGACCCTCTCTCAGAAACAAAGTGTACGTTGAAATC
CTTCACTGTAGAAAAAGGAATCTATCAAACTTCTAACTTTAGAGTCCAACCAACAGAATCTATTGTTAGATTTCCT
AATATTACAAACTTGTGCCCTTTTGATGAAGTTTTTAACGCCACCAGATTTGCATCTGTTTATGCTTGGAACAGGAA
GAGAATCAGCAACTGTGTTGCTGATTATTCTGTCCTATATAATTTCGCACCATTTTTCGCTTTTAAGTGTTATGGAG
TGTCTCCTACTAAATTAAATGATCTCTGCTTTACTAATGTCTATGCAGATTCATTTGTAATTAGAGGTAATGAAGTC
AGCCAAATCGCTCCAGGGCAAACTGGAAATATTGCTGATTATAATTATAAATTACCAGATGATTTTACAGGCTGCG
TTATAGCTTGGAATTCTAACAAGCTTGATTCTAAGGTTGGTGGTAATTATAATTACCTGTATAGATTGTTTAGGAAG
TCTAATCTCAAACCTTTTGAGAGAGATATTTCAACTGAAATCTATCAGGCCGGTAACAAACCTTGTAATGGTGTTG
CAGGTTTTAATTGTTACTTTCCTTTACGATCATATGGTTTCCGACCCACTTATGGTGTTGGTCACCAACCATACAGA
GTAGTAGTACTTTCTTTTGAACTTCTACATGCACCAGCAACTGTTTGTGGACCTAAAAAGTCTACTAATTTGGTTAA
AAACAAATGTGTCAATTTCAACTTCAATGGTTTAACAGGCACAGGTGTTCTTACTGAGTCTAACAAAAAGTTTCTG
CCTTTCCAACAATTTGGCAGAGACATTGCTGACACTACTGATGCTGTCCGTGATCCACAGACACTTGAGATTCTTG
ACATTACACCATGTTCTTTTGGTGGTGTCAGTGTTATAACACCAGGAACAAATACTTCTAACCAGGTTGCTGTTCTT
TATCAGGGTGTTAACTGCACAGAAGTCCCTGTTGCTATTCATGCAGATCAACTTACTCCTACTTGGCGTGTTTATTC
TACAGGTTCTAATGTTTTTCAAACACGTGCAGGCTGTTTAATAGGGGCTGAATATGTCAACAACTCATATGAGTGT
GACATACCCATTGGTGCAGGTATATGCGCTAGTTATCAGACTCAGACTAAGTCTCATCGGCGGGCACGTAGTGTAG
CTAGTCAATCCATCATTGCCTACACTATGTCACTTGGTGCAGAAAATTCAGTTGCTTACTCTAATAACTCTATTGCC
ATACCCACAAATTTTACTATTAGTGTTACCACAGAAATTCTACCAGTGTCTATGACCAAGACATCAGTAGATTGTA
CAATGTACATTTGTGGTGATTCAACTGAATGCAGCAATCTTTTGTTGCAATATGGCAGTTTTTGTACACAATTAAAA
CGTGCTTTAACTGGAATAGCTGTTGAACAAGACAAAAACACCCAAGAAGTTTTTGCACAAGTCAAACAAATTTAC
AAAACACCACCAATTAAATATTTTGGTGGTTTTAATTTTTCACAAATATTACCAGATCCATCAAAACCAAGCAAGA
GGTCATTTATTGAAGATCTACTTTTCAACAAAGTGACACTTGCAGATGCTGGCTTCATCAAACAATATGGTGATTG
CCTTGGTGATATTGCTGCTAGAGACCTCATTTGTGCACAAAAGTTTAACGGCCTTACTGTTTTGCCACCTTTGCTCA
CAGATGAAATGATTGCTCAATACACTTCTGCACTGTTAGCGGGTACAATCACTTCTGGTTGGACCTTTGGTGCAGG
TGCTGCATTACAAATACCATTTGCTATGCAAATGGCTTATAGGTTTAATGGTATTGGAGTTACACAGAATGTTCTCT
ATGAGAACCAAAAATTGATTGCCAACCAATTTAATAGTGCTATTGGCAAAATTCAAGACTCACTTTCTTCCACAGC
AAGTGCACTTGGAAAACTTCAAGATGTGGTCAACCATAATGCACAAGCTTTAAACACGCTTGTTAAACAACTTAGC
TCCAAATTTGGTGCAATTTCAAGTGTTTTAAATGATATCCTTTCACGTCTTGACAAAGTTGAGGCTGAAGTGCAAAT
TGATAGGTTGATCACAGGCAGACTTCAAAGTTTGCAGACATATGTGACTCAACAATTAATTAGAGCTGCAGAAATC
AGAGCTTCTGCTAATCTTGCTGCTACTAAAATGTCAGAGTGTGTACTTGGACAATCAAAAAGAGTTGATTTTTGTG
GAAAGGGCTATCATCTTATGTCCTTCCCTCAGTCAGCACCTCATGGTGTAGTCTTCTTGCATGTGACTTATGTCCCT
GCACAAGAAAAGAACTTCACAACTGCTCCTGCCATTTGTCATGATGGAAAAGCACACTTTCCTCGTGAAGGTGTCT
TTGTTTCAAATGGCACACACTGGTTTGTAACACAAAGGAATTTTTATGAACCACAAATCATTACTACAGACAACAC
ATTTGTGTCTGGTAACTGTGATGTTGTAATAGGAATTGTCAACAACACAGTTTATGATCCTTTGCAACCTGAATTAG
ATTCATTCAAGGAGGAGTTAGATAAATATTTTAAGAATCATACATCACCAGATGTTGATTTAGGTGACATCTCTGG

-continued

SEQUENCE LISTING

CATTAATGCTTCAGTTGTAAACATTCAAAAAGAAATTGACCGCCTCAATGAGGTTGCCAAGAATTTAAATGAATCT
CTCATCGATCTCCAAGAACTTGGAAAGTATGAGCAGTATATAAAATGGCCATGGTACATTTGGCTAGGTTTTATAG
CTGGCTTGATTGCCATAGTAATGGTGACAATTATGCTTTGCTGTATGACCAGTTGCTGTAGTTGTCTCAAGGGCTGT
TGTTCTTGTGGATCCTGCTGCAAATTTGATGAAGACGACTCTGAGCCAGTGCTCAAAGGAGTCAAATTACATTACA
CATAAACGAACTTATGGATTTGTTTATGAGAATCTTCACAATTGGAACTGTAACTTTGAAGCAAGGTGAAATCAAG
GATGCTACTCCTTCAGATTTTGTTCGCGCTACTGCAACGATACCGATACAAGCCTCACTCCCTTTCGGATGGCTTAT
TGTTGGCGTTGCACTTCTTGCTGTTTTTCAGAGCGCTTCCAAAATCATAACCCTCAAAAAGAGATGGCAACTAGCA
CTCTCCAAGGGTGTTCACTTTGTTTGCAACTTGCTGTTGTTGTTTGTAACAGTTTACTCACACCTTTTGCTCGTTGCT
GCTGGCCTTGAAGCCCCTTTTCTCTATCTTTATGCTTTAGTCTACTTCTTGCAGAGTATAAACTTTGTAAGAATAATA
ATGAGGCTTTGGCTTTGCTGGAAATGCCGTTCCAAAAACCCATTACTTTATGATGCCAACTATTTTCTTTGCTGGCA
TACTAATTGTTACGACTATTGTATACCTTACAATAGTGTAACTTCTTCAATTGTCATTACTTCAGGTGATGGCACAA
CAAGTCCTATTTCTGAACATGACTACCAGATTGGTGGTTATACTGAAAAATGGGAATCTGGAGTAAAAGACTGTGT
TGTATTACACAGTTACTTCACTTCAGACTATTACCAGCTGTACTCAACTCAATTGAGTACAGACACTGGTGTTGAAC
ATGTTACCTTCTTCATCTACAATAAAATTGTTGATGAGCCTGAAGAACATGTCCAAATTCACACAATCGACGGTTC
ATCCGGAGTTGTTAATCCAGTAATGGAACCAATTTATGATGAACCGACGACGACTACTAGCGTGCCTTTGTAAGCA
CAAGCTGATGAGTACGAACTTATGTACTCATTCGTTTCGGAAGAGACAGGTACGTAAATAGTTAATAGCTGACTTC
TTTTTCTTGCTTTCGTGTGATTCTTGCTAGTTACACTAGCCATCCTTACTGCGCTTCGATTGTGTGCGTACTGCTGCA
ATATTGTTAACGTGAGTCTTGTAAAACCTTCTTTTTACGTTTACTCTCGTGTTAAAAATCTGAATTCTTCTAGAGTTC
CTGATCTTCTGGTCTAAACGAACTAAATATTATATTAGTTTTTCTGTTTGGAACTTTAATTTTAGCCATGGCAGATTC
CAACGGTACTATTACCGTTGAAGAGCTTAAAAAGCTCCTTGAACAATGGAACCTAGTAATAGGTTTCCTATTCCTT
ACATGGATTTGTCTTCTACAATTTGCCTATGCCAACAGGAATAGGTTTTTGTATATAATTAAGTTAATTTTCCTCTG
GCTGTTATGGCCAGTAACTTTAGCTTGTTTTGTGCTTGCTGCTGTTTACAGAATAAATTGGATCACCGGTGGAATTG
CTATCGCAATGGCTTGTCTTGTAGGCTTGATGTGGCTCAGCTACTTCATTGCTTCTTTCAGACTGTTTGCGCGTACG
CGTTCCATGTGGTCATTCAATCCAGAAACTAACATTCTTCTCAACGTGCCACTCCATGGCACTATTCTGACCAGACC
GCTTCTAGAAAGTGAACTCGTAATCGGAGCTGTGATCCTTCGTGGACATCTTCGTATTGCTGGACACCATCTAGGA
CGCTGTGACATCAAGGACCTGCCTAAAGAAATCACTGTTGCTACATCACGAACGCTTTCTTATTACAAATTGGGAG
CTTCGCAGCGTGTAGCAGGTGACTCAGGTTTTGCTGCATACAGTCGCTACAGGATTGGCAACTATAAATTAAACAC
AGACCATTCCAGTAGCAGTGACAATATTGCTTTGCTTGTACAATGATAATGAAACTTGTCACGCCTAAACGAACatga
ccaacaagtgtctcctccaaattgctctcctgttgtgcttctccactacagctctttccatgagctacaacttgcttggattcctacaaagaagcagcaattttcagtgtcagaagctcctgtggcaa
ttgaatgggaggcttgaatactgcctcaaggacaggatgaactttgacatccctgaggagattaagcagctgcagcagttccagaaggaggacgccgcattgaccatctatgagatgctcca
gaacatctttgctattttcagacaagattcatctagcactggctggaatgagactattgttgagaacctcctggctaatgtctatcatcagataaaccatctgaagacagtcctggaagaaaaactg
gagaaagaagatttcaccaggggaaaactcatgagcagtctgcacctgaaaagatattatgggaggattctgcattacctgaaggccaaggagtacagtcactgtgcctggaccatagtcag
agtggaaatcctaaggaacttttacttcattaacagacttacaggttacctccgaaactgaGACGTTCGTGTTGTTTTAGATTTCATCTAAACGAACAAAC
TAAAATGTCTGATAATGGACCCCAAAATCAGCGAAATGCACCCCGCATTACGTTTGGTGGACCCTCAGATTCAACT
GGCAGTAACCAGAATGGAGAACGCAGTGGGGCGCGATCAAAACAACGTCGGCCCCAAGGTTTACCCAATAATACT
GCGTCTTGGTTCACCGCTCTCACTCAACATGGCAAGGAAGACCTTAAATTCCCTCGAGGACAAGGCGTTCCAATTA
ACACCAATAGCAGTCCAGATGACCAAATTGGCTACTACCGAAGAGCTACCAGACGAATTCGTGGTGGTGACGGTA
AAATGAAAGATCTCAGTCCAAGATGGTATTTCTACTACCTAGGAACTGGGCCAGAAGCTGGACTTCCCTATGGTGC
TAACAAAGACGGCATCATATGGGTTGCAACTGAGGGAGCCTTGAATACACCAAAAGATCACATTGGCACCCGCAA
TCCTGCTAACAATGCTGCAATCGTGCTACAACTTCCTCAAGGAACAACATTGCCAAAAGGCTTCTACGCAGAAGGG
AGCAGAGGCGGCAGTCAAGCCTCTTCTCGTTCCTCATCACGTAGTCGCAACAGTTCAAGAAATTCAACTCCAGGCA
GCAGTAGGGGAACTTCTCCTGCTAGAATGGCTGGCAATGGCGGTGATGCTGCTCTTGCTTTGCTGCTGCTTGACAG
ATTGAACCAGCTTGAGAGCAAAATGTCTGGTAAAGGCCAACAACAACAAGGCCAAACTGTCACTAAGAAATCTGC
TGCTGAGGCTTCTAAGAAGCCTCGGCAAAAACGTACTGCCACTAAAGCATACAATGTAACACAAGCTTTCGGCAG
ACGTGGTCCAGAACAAACCCAAGGAAATTTTGGGGACCAGGAACTAATCAGACAAGGAACTGATTACAAACATTG
GCCGCAAATTGCACAATTTGCCCCCAGCGCTTCAGCGTTCTTCGGAATGTCGCGCATTGGCATGGAAGTCACACCT
TCGGGAACGTGGTTGACCTACACAGGTGCCATCAAATTGGATGACAAAGATCCAAATTTCAAAGATCAAGTCATTT
TGCTGAATAAGCATATTGACGCATACAAAACATTCCCACCAACAGAGCCTAAAAAGGACAAAAAGAAGAAGGCT
GATGAAACTCAAGCCTTACCGCAGAGACAGAAGAAACAGCAAACTGTGACTCTTCTTCCTGCTGCAGATTTGGATG
ATTTCTCCAAACAATTGCAACAATCCATGAGCAGTGCTGACTCAACTCAGGCCTAAACTCATGCAGACCACACAAG
GCAGATGGGCTATATAAACGTTTTCGCTTTTCCGTTTACGATATATAGTCTACTCTTGTGCAGAATGAATTCTCGTA -continued

SEQUENCE LISTING

ACTACATAGCACAAGTAGATGTAGTTAACTTTAATCTCACATAGCAATCTTTAATCAGTGTGTAACATTAGGGAGG
ACTTGAAAGAGCCACCACATTTTCACCGAGGCCACGCGGAGTACGATCGAGTGTACAGTGAACAATGCTAGGGAG
AGCTGCCTATATGGAAGAGCCCTAATGTGTAAAATTAATTTTAGTAGTGCTATCCCCATGTGATTTTAATAGCTTCT
TAGGAGAATGACAAAAAAAAAAAAAAAAAAAAA

SEQ ID NO: 7 (synthetic IBIS DNA construct 2, variant BA.5; human IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA -continued

| SEQUENCE LISTING |
|---|
| ACAGTGGTTGTTAATGCAGCCAATGTTTACCTTAAACATGGAGGAGGTGTTGCAGGAGCCTTAAATAAGGCTACTA |
| ACAATGCCATGCAAGTTGAATCTGATGATTACATAGCTACTAATGGACCACTTAAAGTGGGTGGTAGTTGTGTTTT |
| AAGCGGACACAATCTTGCTAAACACTGTCTTCATGTTGTCGGCCCAAATGTTAACAAAGGTGAAGACATTCAACTT |
| CTTAAGAGTGCTTATGAAAATTTTAATCAGCACGAAGTTCTACTTGCACCATTATTATCAGCTGGTATTTTTGGTGC |
| TGACCCTATACATTCTTTAAGAGTTTGTGTAGATACTGTTCGCACAAATGTCTACTTAGCTGTCTTTGATAAAAATC |
| TCTATGACAAACTTGTTTCAAGCTTTTTGGAAATGAAGAGTGAAAAGCAAGTTGAACAAAAGATCGCTGAGATTCC |
| TAAAGAGGAAGTTAAGCCATTTATAACTGAAAGTAAACCTTCAGTTGAACAGAGAAAACAAGATGATAAGAAAAT |
| CAAAGCTTGTGTTGAAGAAGTTACAACAACTCTGGAAGAAACTAAGTTCCTCACAGAAAACTTGTTACTTTATATT |
| GACATTAATGGCAATCTTCATCCAGATTCTGCCACTCTTGTTAGTGACATTGACATCACTTTCTTAAAGAAAGATGC |
| TCCATATATAGTGGGTGATGTTGTTCAAGAGGGTGTTTTAACTGCTGTGGTTATACCTACTAAAAAGGCTGGTGGC |
| ACTACTGAAATGCTAGCGAAAGCTTTGAGAAAAGTGCCAACAGACAATTATATAACCACTTACCCGGGTCAGGGT |
| TTAAATGGTTACACTGTAGAGGAGGCAAAGACAGTGCTTAAAAAGTGTAAAAGTGCCTTTTACATTCTACCATCTA |
| TTATCTCTAATGAGAAGCAAGAAATTCTTGGAACTGTTTCTTGGAATTTGCGAGAAATGCTTGCACATGCAGAAGA |
| AACACGCAAATTAATGCCTGTCTGTGTGGAAACTAAAGCCATAGTTTCAACTATACAGCGTAAATATAAGGGTATT |
| AAAATACAAGAGGGTGTGGTTGATTATGGTGCTAGATTTTACTTTTACACCAGTAAAACAACTGTAGCGTCACTTA |
| TCAACACACTTAACGATCTAAATGAAACTCTTGTTACAATGCCACTTGGCTATGTAACACATGGCTTAAATTTGGA |
| AGAAGCTGCTCGGTATATGAGATCTCTCAAAGTGCCAGCTACAGTTTCTGTTTCTTCACCTGATGCTGTTACAGCGT |
| ATAATGGTTATCTTACTTCTTCTTCTAAAACACCTGAAGAACATTTTATTGAAACCATCTCACTTGCTGGTTCCTAT |
| AAAGATTGGTCCTATTCTGGACAATCTACACAACTAGGTATAGAATTTCTTAAGAGAGGTGATAAAAGTGTATATT |
| ACACTAGTAATCCTACCACATTCCACCTAGATGGTGAAGTTATCACCTTTGACAATCTTAAGACACTTCTTTCTTTG |
| AGAGAAGTGAGGACTATTAAGGTGTTTACAACAGTAGACAACATTAACCTCCACACGCAAGTTGTGGACATGTCA |
| ATGACATATGGACAACAGTTTGGTCCAACTTATTTGGATGGAGCTGATGTTACTAAAATAAAACCTCATAATTCAC |
| ATGAAGGTAAAACATTTTATGTTTTACCTAATGATGACACTCTACGTGTTGAGGCTTTTGAGTACTACCACACAACT |
| GATCCTAGTTTTCTGGGTAGGTACATGTCAGCATTAAATCACACTAAAAAGTGGAAATACCCACAAGTTAATGGTT |
| TAACTTCTATTAAATGGGCAGATAACAACTGTTATCTTGCCACTGCATTGTTAACACTCCAACAAATAGAGTTGAA |
| GTTTAATCCACCTGCTCTACAAGATGCTTATTACAGAGCAAGGGCTGGTGAAGCTGCTAACTTTTGTGCACTTATCT |
| TAGCCTACTGTAATAAGACAGTAGGTGAGTTAGGTGATGTTAGAGAAACAATGAGTTACTTGTTTCAACATGCCAA |
| TTTAGATTCTTGCAAAAGAGTCTTGAACGTGGTGTGTAAAACTTGTGGACAACAGCAGACAACCCTTAAGGGTGTA |
| GAAGCTGTTATGTACATGGGCACACTTTCTTATGAACAATTTAAGAAAGGTGTTCAGATACCTTGTACGTGTGGTA |
| AACAAGCTACAAAATATCTAGTACAACAGGAGTCACCTTTTGTTATGATGTCAGCACCACCTGCTCAGTATGAACT |
| TAAGCATGGTACATTTACTTGTGCTAGTGAGTACACTGGTAATTACCAGTGTGGTCACTATAAACATATAACTTCTA |
| AAGAAACTTTGTATTGCATAGACGGTGCTTTACTTACAAAGTCCTCAGAATACAAAGGTCCTATTACGGATGTTTT |
| CTACAAAGAAAACAGTTACACAACAACCATAAAACCAGTTACTTATAAATTGGATGGTGTTGTTTGTACAGAAATT |
| GACCCTAAGTTGGACAATTATTATAAGAAAGACAATTCTTATTTCACAGAGCAACCAATTGATCTTGTACCAAACC |
| AACCATATCCAAACGCAAGCTTCGATAATTTTAAGTTTGTATGTGATAATATCAAATTTGCTGATGATTTAAACCA |
| GTTAACTGGTTATAAGAAACCTGCTTCAAGAGAGCTTAAAGTTACATTTTTCCCTGACTTAAATGGTGATGTGGTG |
| GCTATTGATTATAAACACTACACACCCTCTTTTAAGAAAGGAGCTAAATTGTTACATAAACCTATTGTTTGGCATGT |
| TAACAATGCAACTAATAAAGCCACGTATAAACCAAATACCTGGTGTATACGTTGTCTTTGGAGCACAAAACCAGTT |
| GAAACATCAAATTCGTTTGATGTACTGAAGTCAGAGGACGCGCAGGGAATGGATAATCTTGCCTGCGAAGATCTA |
| AAACCAGTCTCTGAAGAAGTAGTGGAAAATCCTACCATACAGAAAGACGTTCTTGAGTGTAATGTGAAAACTACC |
| GAAGTTGTAGGAGACATTATACTTAAACCAGCAAATAATAGTTTAAAAATTACAGAAGAGGTTGGCCACACAGAT |
| CTAATGGCTGCTTATGTAGACAATTCTAGTCTTACTATTAAGAAACCTAATGAATTATCTAGAGTATTAGGTTTGAA |
| AACCCTTGCTACTCATGGTTTAGCTGCTGTTAATAGTGTCCCTTGGGATACTATAGCTAATTATGCTAAGCCTTTTC |
| TTAACAAAGTTGTTAGTACAACTACTAACATAGTTACACGGTGTTTAAACCGTGTTTGTACTAATTATATGCCTTAT |
| TTCTTTACTTTATTGCTACAATTGTGTACTTTTACTAGAAGTACAAATTCTAGAATTAAAGCATCTATGCCGACTAC |
| TATAGCAAAGAATACTGTTAAGAGTGTCGGTAAATTTTGTCTAGAGGCTTCATTTAATTATTTGAAGTCACCTAATT |
| TTTCTAAACTGATAAATATTATAATTTGGTTTTTACTATTAAGTGTTTGCCTAGGTTCTTTAATCTACTCAACCGCTG |
| CTTTAGGTGTTTTAATGTCTAATTTAGGCATGCCTTCTTACTGTACTGGTTACAGAGAAGGCTATTTGAACTCTACT |
| AATGTCACTATTGCAACCTACTGTACTGGTTCTATACCTTGTAGTGTTTGTCTTAGTGGTTTAGATTCTTTAGACACC |
| TATCCTTCTTTAGAAACTATACAAATTACCATTTCATCTTTTAAATGGGATTTAACTGCTTTTGGCTTAGTTGCAGA |
| GTGGTTTTTGGCATATATTCTTTTCACTAGGTTTTTCTATGTACTTGGATTGGCTGCAATCATGCAATTGTTTTTCAG |

-continued

| SEQUENCE LISTING |
| --- |
| CTATTTTGCAGTACATTTTATTAGTAATTCTTGGCTTATGTGGTTAATAATTAATCTTGTACAAATGGCCCCGATTTC |
| AGCTATGGTTAGAATGTACATCTTCTTTGCATCATTTTATTATGTATGGAAAAGTTATGTGCATGTTGTAGACGGTT |
| GTAATTCATCAACTTGTATGATGTGTTACAAACGTAATAGAGCAACAAGAGTCGAATGTACAACTATTGTTAATGG |
| TGTTAGAAGGTCCTTTTATGTCTATGCTAATGGAGGTAAAGGCTTTTGCAAACTACACAATTGGAATTGTGTTAATT |
| GTGATACATTCTGTGCTGGTAGTACATTTATTAGTGATGAAGTTGCGAGAGACTTGTCACTACAGTTTAAAAGACC |
| AATAAATCCTACTGACCAGTCTTCTTACATCGTTGATAGTGTTACAGTGAAGAATGGTTCCATCCATCTTTACTTTG |
| ATAAAGCTGGTCAAAAGACTTATGAAAGACATTCTCTCTCTCATTTTGTTAACTTAGACAACCTGAGAGCTAATAA |
| CACTAAAGGTTCATTGCCTATTAATGTTATAGTTTTGATGGTAAATCAAAATGTGAAGAATCATCTGCAAAATCA |
| GCGTCTGTTTACTACAGTCAGCTTATGTGTCAACCTATACTGTTACTAGATCAGGCATTAGTGTCTGATGTTGGTGA |
| TAGTGCGGAAGTTGCAGTTAAAATGTTTGATGCTTACGTTAATACGTTTTCATCAACTTTTAACGTACCAATGGAAA |
| AACTCAAAACACTAGTTGCAACTGCAGAAGCTGAACTTGCAAAGAATGTGTCCTTAGACAATGTCTTATCTACTTT |
| TATTTCAGCAGCTCGGCAAGGGTTTGTTGATTCAGATGTAGAAACTAAAGATGTTGTTGAATGTCTTAAATTGTCA |
| CATCAATCTGACATAGAAGTTACTGGCGATAGTTGTAATAACTATATGCTCACCTATAACAAAGTTGAAAACATGA |
| CACCCCGTGACCTTGGTGCTTGTATTGACTGTAGTGCGCGTCATATTAATGCGCAGGTAGCAAAAAGTCACAACAT |
| TGCTTTGATATGGAACGTTAAAGATTTCATGTCATTGTCTGAACAACTACGAAAACAAATACGTAGTGCTGCTAAA |
| AAGAATAACTTACCTTTTAAGTTGACATGTGCAACTACTAGACAAGTTGTTAATGTTGTAACAACAAAGATAGCAC |
| TTAAGGGTGGTAAAATTGTTAATAATTGGTTGAAGCAGTTAATTAAAGTTACACTTGTGTTCCTTTTTGTTGCTGCT |
| ATTTTCTATTTAATAACACCTGTTCATGTCATGTCTAAACATACTGACTTTTCAAGTGAAATCATAGGATACAAGGC |
| TATTGATGGTGGTGTCACTCGTGACATAGCATCTACAGATACTTGTTTTGCTAACAAACATGCTGATTTTGACACAT |
| GGTTTAGCCAGCGTGGTGGTAGTTATACTAATGACAAAGCTTGCCCATTGATTGCTGCAGTCATAACAAGAGAAGT |
| GGGTTTTGTCGTGCCTGGTTTGCCTGGCACGATATTACGCACAACTAATGGTGACTTTTTGCATTTCTTACCTAGAG |
| TTTTTAGTGCAGTTGGTAACATCTGTTACACACCATCAAAACTTATAGAGTACACTGACTTTGCAACATCAGCTTGT |
| GTTTTGGCTGCTGAATGTACAATTTTTAAAGATGCTTCTGGTAAGCCAGTACCATATTGTTATGATACCAATGTACT |
| AGAAGGTTCTGTTGCTTATGAAAGTTTACGCCCTGACACACGTTATGTGCTCATGGATGGCTCTATTATTCAATTTC |
| CTAACACCTACCTTGAAGGTTCTGTTAGAGTGGTAACAACTTTTGATTCTGAGTACTGTAGGCACGGCACTTGTGA |
| AAGATCAGAAGCTGGTGTTTGTGTATCTACTAGTGGTAGATGGGTACTTAACAATGATTATTACAGATCTTTACCA |
| GGAGTTTTCTGTGGTGTAGATGCTGTAAATTTACTTACTAATATGTTTACACCACTAATTCAACCTATTGGTGCTTT |
| GGACATATCAGCATCTATAGTAGCTGGTGGTATTGTAGCTATCGTAGTAACATGCCTTGCCTACTATTTTATGAGGT |
| TTAGAAGAGCTTTTGGTGAATACAGTCATGTAGTTGCCTTTAATACTTTACTATTCCTTATGTCATTCACTGTACTCT |
| GTTTAACACCAGTTTACTCATTCTTACCTGGTGTTTATTCTGTTATTTACTTGTACTTGACATTTTATCTTACTAATG |
| ATGTTTCTTTTTTAGCACATATTCAGTGGATGGTTATGTTCACACCTTTAGTACCTTTCTGGATAACAATTGCTTATA |
| TCATTTGTATTTCCACAAAGCATTTCTATTGGTTCTTTAGTAATTACCTAAAGAGACGTGTAGTCTTTAATGGTGTTT |
| CCTTTAGTACTTTTGAAGAAGCTGCGCTGTGCACCTTTTTGTTAAATAAAGAAATGTATCTAAAGTTGCGTAGTGAT |
| GTGCTATTACCTCTTACGCAATATAATAGATACTTAGCTCTTTATAATAAGTACAAGTATTTTAGTGGAGCAATGGA |
| TACAACTAGCTACAGAGAAGCTGCTTGTTGTCATCTCGCAAAGGCTCTCAATGACTTCAGTAACTCAGGTTCTGAT |
| GTTCTTTACCAACCACCACAAACCTCTATCACCTCAGCTGTTTTGCAGAGTGGTTTTAGAAAAATGGCATTCCCATC |
| TGGTAAAGTTGAGGGTTGTATGGTACAAGTAACTTGTGGTACAACTACACTTAACGGTCTTTGGCTTGATGACGTA |
| GTTTACTGTCCAAGACATGTGATCTGCACCTCTGAAGACATGCTTAACCCTAATTATGAAGATTTACTCATTCGTAA |
| GTCTAATCATAATTTCTTGGTACAGGCTGGTAATGTTCAACTCAGGGTTATTGGACATTCTATGCAAAATTGTGTAC |
| TTAAGCTTAAGGTTGATACAGCCAATCCTAAGACACCTAAGTATAAGTTTGTTCGCATTCAACCAGGACAGACTTT |
| TTCAGTGTTAGCTTGTTACAATGGTTCACCATCTGGTGTTTACCAATGTGCTATGAGGCCCAATTTCACTATTAAGG |
| GTTCATTCCTTAATGGTTCATGTGGTAGTGTTGGTTTTAACATAGATTATGACTGTGTCTCTTTTTGTTACATGCACC |
| ATATGGAATTACCAACTGGAGTTCATGCTGGCACAGACTTAGAAGGTAACTTTTATGGACCTTTTGTTGACAGGCA |
| AACAGCACAAGCAGCTGGTACGGACACAACTATTACAGTTAATGTTTTAGCTTGGTTGTACGCTGCTGTTATAAAT |
| GGAGACAGGTGGTTTCTCAATCGATTTACCACAACTCTTAATGACTTTAACCTTGTGGCTATGAAGTACAATTATG |
| AACCTCTAACACAAGACCATGTTGACATACTAGGACCTCTTTCTGCTCAAACTGGAATTGCCGTTTTAGATATGTGT |
| GCTTCATTAAAAGAATTACTGCAAAATGGTATGAATGGACGTACCATATTGGGTAGTGCTTTATTAGAAGATGAAT |
| TTACACCTTTTGATGTTGTTAGACAATGCTCAGGTGTTACTTTCCAAAGTGCAGTGAAAAGAACAATCAAGGGTAC |
| ACACCACTGGTTGTTACTCACAATTTTGACTTCACTTTTAGTTTTAGTCCAGAGTACTCAATGGTCTTTGTTCTTTTT |
| TTTGTATGAAAATGCCTTTTTACCTTTTGCTATGGGTATTATTGCTATGTCTGCTTTTGCAATGATGTTTGTCAAACA |
| TAAGCATGCATTTCTCTGTTTGTTTTTGTTACCTTCTCTTGCCACTGTAGCTTATTTTAATATGGTCTATATGCCTGCT |

-continued

| SEQUENCE LISTING |
|---|
| AGTTGGGTGATGCGTATTATGACATGGTTGGATATGGTTGATACTAGTTTGTCTGGTTTTAAGCTAAAAGACTGTGT<br>TATGTATGCATCAGCTGTAGTGTTACTAATCCTTATGACAGCAAGAACTGTGTATGATGATGGTGCTAGGAGAGTG<br>TGGACACTTATGAATGTCTTGACACTCGTTTATAAAGTTTATTATGGTAATGCTTTAGATCAAGCCATTTCCATGTG<br>GGCTCTTATAATCTCTGTTACTTCTAACTACTCAGGTGTAGTTACAACTGTCATGTTTTTGGCCAGAGGTATTGTTTT<br>TATGTGTGTTGAGTATTGCCCTATTTTCTTCATAACTGGTAATACACTTCAGTGTATAATGCTAGTTTATTGTTTCTT<br>AGGCTATTTTTGTACTTGTTACTTTGGCCTCTTTTGTTTACTCAACCGCTACTTTAGACTGACTCTTGGTGTTTATGA<br>TTACTTAGTTTCTACACAGGAGTTTAGATATATGAATTCACAGGGACTACTCCCACCCAAGAATAGCATAGATGCC<br>TTCAAACTCAACATTAAATTGTTGGGTGTTGGTGGCAAACCTTGTATCAAAGTAGCCACTGTACAGTCTAAAATGT<br>CAGATGTAAAGTGCACATCAGTAGTCTTACTCTCAGTTTTGCAACAACTCAGAGTAGAATCATCATCTAAATTGTG<br>GGCTCAATGTGTCCAGTTACACAATGACATTCTCTTAGCTAAAGATACTACTGAAGCCTTTGAAAAAATGGTTTCA<br>CTACTTTCTGTTTTGCTTTCCATGCAGGGTGCTGTAGACATAAACAAGCTTTGTGAAGAAATGCTGGACAACAGGG<br>CAACCTTACAAGCTATAGCCTCAGAGTTTAGTTCCCTTCCATCATATGCAGCTTTTGCTACTGCTCAAGAAGCTTAT<br>GAGCAGGCTGTTGCTAATGGTGATTCTGAAGTTGTTCTTAAAAAGTTGAAGAAGTCTTTGAATGTGGCTAAATCTG<br>AATTTGACCGTGATGCAGCCATGCAACGTAAGTTGGAAAAGATGGCTGATCAAGCTATGACCCAAATGTATAAAC<br>AGGCTAGATCTGAGGACAAGAGGGCAAAAGTTACTAGTGCTATGCAGACAATGCTTTTCACTATGCTTAGAAAGTT<br>GGATAATGATGCACTCAACAACATTATCAACAATGCAAGAGATGGTTGTGTTCCCTTGAACATAATACCTCTTACA<br>ACAGCAGCCAAACTAATGGTTGTCATACCAGACTATAACACATATAAAAATACGTGTGATGGTACAACATTTACTT<br>ATGCATCAGCATTGTGGGAAATCCAACAGGTTGTAGATGCAGATAGTAAAATTGTTCAACTTAGTGAAATTAGTAT<br>GGACAATTCACCTAATTTAGCATGGCCTCTTATTGTAACAGCTTTAAGGGCCAATTCTGCTGTCAAATTACAGAAT<br>AATGAGCTTAGTCCTGTTGCACTACGACAGATGTCTTGTGCTGCCGGTACTACACAAACTGCTTGCACTGATGACA<br>ATGCGTTAGCTTACTACAACACAACAAAGGGAGGTAGGTTTGTACTTGCACTGTTATCCGATTTACAGGATTTGAA<br>ATGGGCTAGATTCCCTAAGAGTGATGGAACTGGTACTATCTATACAGAACTGGAACCACCTTGTAGGTTTGTTACA<br>GACACACCTAAAGGTCCTAAAGTGAAGTATTTATACTTTATTAAAGGATTAAACAACCTAAATAGAGGTATGGTAC<br>TTGGTAGTTTAGCTGCCACAGTACGTCTACAAGCTGGTAATGCAACAGAAGTGCCTGCCAATTCAACTGTATTATC<br>TTTCTGTGCTTTTGCTGTAGATGCTGCTAAAGCTTACAAAGATTATCTAGCTAGTGGGGGACAACCAATCACTAATT<br>GTGTTAAGATGTTGTGTACACACACTGGTACTGGTCAGGCAATAACAGTTACACCGGAAGCCAATATGGATCAAG<br>AATCCTTTGGTGGTGCATCGTGTTGTCTGTACTGCCGTTGCCACATAGATCATCCAAATCCTAAAGGATTTTGTGAC<br>TTAAAAGGTAAGTATGTACAAATACCTACAACTTGTGCTAATGACCCTGTGGGTTTTACACTTAAAAACACAGTCT<br>GTACCGTCTGCGGTATGTGGAAAGGTTATGGCTGTAGTTGTGATCAACTCCGCGAACCCATGCTTCAGTCAGCTGA<br>TGCACAATCGTTTTTAAACGGGTTTGCGGTGTAAGTGCAGCCCGTCTTACACCGTGCGGCACAGGCACTAGTACTG<br>ATGTCGTATACAGGGCTTTTGACATCTACAATGATAAAGTAGCTGGTTTTGCTAAATTCCTAAAAACTAATTGTTGT<br>CGCTTCCAAGAAAAGGACGAAGATGACAATTTAATTGATTCTTACTTTGTAGTTAAGAGACACACTTTCTCTAACT<br>ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA<br>TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT<br>TAAAACACTTCTTCTTTGCTCAGGATGGTAATGCTGCTATCAGCGATTATGACTACTATCGTTATAATCTACCAACA<br>ATGTGTGATATCAGACAACTACTATTTGTAGTTGAAGTTGTTGATAAGTACTTTGATTGTTACGATGGTGGCTGTAT<br>TAATGCTAACCAAGTCATCGTCAACAACCTAGACAAATCAGCTGGTTTTCCATTTAATAAATGGGGTAAGGCTAGA<br>CTTTATTATGATTCAATGAGTTATGAGGATCAAGATGCACTTTTCGCATATACAAAACGTAATGTCATCCCTACTAT<br>AACTCAAATGAATCTTAAGTATGCCATTAGTGCAAAGAATAGAGCTCGCACCGTAGCTGGTGTCTCTATCTGTAGT |

-continued

| SEQUENCE LISTING |
|---|
| ACTATGACCAATAGACAGTTTCATCAAAAATTATTGAAATCAATAGCCGCCACTAGAGGAGCTACTGTAGTAATTG |
| GAACAAGCAAATTCTATGGTGGTTGGCACAACATGTTAAAAACTGTTTATAGTGATGTAGAAAACCCTCACCTTAT |
| GGGTTGGGATTATCCTAAATGTGATAGAGCCATGCCTAACATGCTTAGAATTATGGCCTCACTTGTTCTTGCTCGCA |
| AACATACAACGTGTTGTAGCTTGTCACACCGTTTCTATAGATTAGCTAATGAGTGTGCTCAAGTATTGAGTGAAAT |
| GGTCATGTGTGGCGGTTCACTATATGTTAAACCAGGTGGAACCTCATCAGGAGATGCCACAACTGCTTATGCTAAT |
| AGTGTTTTTAACATTTGTCAAGCTGTCACGGCCAATGTTAATGCACTTTTATCTACTGATGGTAACAAAATTGCCGA |
| TAAGTATGTCCGCAATTTACAACACAGACTTTATGAGTGTCTCTATAGAAATAGAGATGTTGACACAGACTTTGTG |
| AATGAGTTTTACGCATATTTGCGTAAACATTTCTCAATGATGATACTCTCTGACGATGCTGTTGTGTGTTTCAATAG |
| CACTTATGCATCTCAAGGTCTAGTGGCTAGCATAAAGAACTTTAAGTCAGTTCTTTATTATCAAAACAATGTTTTTA |
| TGTCTGAAGCAAAATGTTGGACTGAGACTGACCTTACTAAAGGACCTCATGAATTTTGCTCTCAACATACAATGCT |
| AGTTAAACAGGGTGATGATTATGTGTACCTTCCTTACCCAGATCCATCAAGAATCCTAGGGGCCGGCTGTTTTGTA |
| GATGATATCGTAAAAACAGATGGTACACTTATGATTGAACGGTTCGTGTCTTTAGCTATAGATGCTTACCCACTTA |
| CTAAACATCCTAATCAGGAGTATGCTGATGTCTTTCATTTGTACTTACAATACATAAGAAAGCTACATGATGAGTT |
| AACAGGACACATGTTAGACATGTATTCTGTTATGCTTACTAATGATAACACTTCAAGGTATTGGGAACCTGAGTTT |
| TATGAGGCTATGTACACACCGCATACAGTCTTACAGGCTGTTGGGGCTTGTGTTCTTTGCAATTCACAGACTTCATT |
| AAGATGTGGTGCTTGCATACGTAGACCATTCTTATGTTGTAAATGCTGTTACGACCATGTCATATCAACATCACATA |
| AATTAGTCTTGTCTGTTAATCCGTATGTTTGCAATGCTCCAGGTTGTGATGTCACAGATGTGACTCAACTTTACTTA |
| GGAGGTATGAGCTATTATTGTAAATCACATAAACCACCCATTAGTTTTCCATTGTGTGCTAATGGACAAGTTTTTGG |
| TTTATATAAAAATACATGTGTTGGTAGCGATAATGTTACTGACTTTAATGCAATTGCAACATGTGACTGGACAAAT |
| GCTGGTGATTACATTTTAGCTAACACCTGTACTGAAAGACTCAAGCTTTTTGCAGCAGAAACGCTCAAAGCTACTG |
| AGGAGACATTTAAACTGTCTTATGGTATTGCTACTGTACGTGAAGTGCTGTCTGACAGAGAATTACATCTTTCATG |
| GGAAGTTGGTAAACCTAGACCACCACTTAACCGAAATTATGTCTTTACTGGTTATCGTGTAACTAAAAACAGTAAA |
| GTACAAATAGGAGAGTACACCTTTGAAAAAGGTGACTATGGTGATGCTGTTGTTTACCGAGGTACAACAACTTACA |
| AATTAAATGTTGGTGATTATTTTGTGCTGACATCACATACAGTAATGCCATTAAGTGCACCTACACTAGTGCCACA |
| AGAGCACTATGTTAGAATTACTGGCTTATACCCAACACTCAATATCTCAGATGAGTTTTCTAGCAATGTTGCAAATT |
| ATCAAAAGGTTGGTATGCAAAAGTATTCTACACTCCAGGGACCACCTGGTACTGGTAAGAGTCATTTTGCTATTGG |
| CCTAGCTCTCTACTACCCTTCTGCTCGCATAGTGTATACAGCTTGCTCTCATGCCGCTGTTGATGCACTATGTGAGA |
| AGGCATTAAAATATTTGCCTATAGATAAATGTAGTAGAATTATACCTGCACGTGCTCGTGTAGAGTGTTTTGATAA |
| ATTCAAAGTGAATTCAACATTAGAACAGTATGTCTTTTGTACTGTAAATGCATTGCCTGAGACGACAGCAGATATA |
| GTTGTCTTTGATGAAATTTCAATGGCCACAAATTATGATTTGAGTGTTGTCAATGCCAGATTACGTGCTAAGCACTA |
| TGTGTACATTGGCGACCCTGCTCAATTACCTGCACCACGCACATTGCTAACTAAGGGCACACTAGAACCAGAATAT |
| TTCAATTCAGTGTGTAGACTTATGAAAACTATAGGTCCAGACATGTTCCTCGGAACTTGTCGGCGTTGTCCTGCTGA |
| AATTGTTGACACTGTGAGTGCTTTGGTTTATGATAATAAGCTTAAAGCACATAAAGACAAATCAGCTCAATGCTTT |
| AAAATGTTTTATAAGGGTGTTATCACGCATGATGTTTCATCTGCAATTAACAGGCCACAAATAGGCGTGGTAAGAG |
| AATTCCTTACACGTAACCCTGCTTGGAGAAAAGCTGTCTTTATTTCACCTTATAATTCACAGAATGCTGTAGCCTCA |
| AAGATTTTGGGACTACCAACTCAAACTGTTGATTCATCACAGGGCTCAGAATATGACTATGTCATATTCACTCAAA |
| CCACTGAAACAGCTCACTCTTGTAATGTAAACAGATTTAATGTTGCTATTACCAGAGCAAAAGTAGGCATACTTTG |
| CATAATGTCTGATAGAGACCTTTATGACAAGTTGCAATTTACAAGTCTTGAAATTCCACGTAGGAATGTGGCAACT |
| TTACAAGCTGAAAATGTAACAGGACTCTTTAAAGATTGTAGTAAGGTAATCACTGGGTTACATCCTACACAGGCAC |
| CTACACACCTCAGTGTTGACACTAAATTCAAAACTGAAGGTTTATGTGTTGACATACCTGGCATACCTAAGGACAT |
| GACCTATAGAAGACTCATCTCTATGATGGGTTTTAAAATGAATTATCAAGTTAATGGTTACCCTAACATGTTTATCA |
| CCCGCGAAGAAGCTATAAGACATGTACGTGCATGGATTGGCTTCGATGTCGAGGGGTGTCATGCTACTAGAGAAG |
| CTGTTGGTACCAATTTACCTTTACAGCTAGGTTTTTCTACAGGTGTTAACCTAGTTGCTGTACCTACAGGTTATGTT |
| GATACACCTAATAATACAGATTTTTCCAGAGTTAGTGCTAAACCACCGCCTGGAGATCAATTTAAACACCTCATAC |
| CACTTATGTACAAAGGACTTCCTTGGAATGTAGTGCGTATAAAGATTGTACAAATGTTAAGTGACACACTTAAAAA |
| TCTCTCTGACAGAGTCGTATTTGTCTTATGGGCACATGGCTTTGAGTTGACATCTATGAAGTATTTTGTGAAAATAG |
| GACCTGAGCGCACCTGTTGTCTATGTGATAGACGTGCCACATGCTTTTCCACTGCTTCAGACACTTATGCCTGTTGG |
| CATCATTCTATTGGATTTGATTACGTCTATAATCCGTTTATGATTGATGTTCAACAATGGGGTTTTACAGGTAACCT |
| ACAAAGCAACCATGATCTGTATTGTCAAGTCCATGGTAATGCACATGTAGCTAGTTGTGATGCAATCATGACTAGG |
| TGTCTAGCTGTCCACGAGTGCTTTGTTAAGCGTGTTGACTGGACTATTGAATATCCTATAATTGGTGATGAACTGAA |
| GATTAATGCGGCTTGTAGAAAGGTTCAACACATGGTTGTTAAAGCTGCATTATTAGCAGACAAATTCCCAGTTCTT |

-continued

| SEQUENCE LISTING |
|---|
| CACGACATTGGTAACCCTAAAGCTATTAAGTGTGTACCTCAAGCTGATGTAGAATGGAAGTTCTATGATGCACAGC<br>CTTGTAGTGACAAAGCTTATAAAATAGAAGAATTATTCTATTCTTATGCCACACATTCTGACAAATTCACAGATGG<br>TGTATGCCTATTTTGGAATTGCAATGTCGATAGATATCCTGCTAATTCCATTGTTTGTAGATTTGACACTAGAGTGC<br>TATCTAACCTTAACTTGCCTGGTTGTGATGGTGGCAGTTTGTATGTAAATAAACATGCATTCCACACACCAGCTTTT<br>GATAAAAGTGCTTTTGTTAATTTAAAACAATTACCATTTTTCTATTACTCTGACAGTCCATGTGAGTCTCATGGAAA<br>ACAAGTAGTGTCAGATATAGATTATGTACCACTAAAGTCTGCTACGTGTATAACACGTTGCAATTTAGGTGGTGCT<br>GTCTGTAGACATCATGCTAATGAGTACAGATTGTATCTCGATGCTTATAACATGATGATCTCAGCTGGCTTTAGCTT<br>GTGGGTTTACAAACAATTTGATACTTATAACCTCTGGAACACTTTTACAAGACTTCAGAGTTTAGAAAATGTGGCT<br>TTTAATGTTGTAAATAAGGGACACTTTGATGGACAACAGGGTGAAGTACCAGTTTCTATCATTAATAACACTGTTT<br>ACACAAAAGTTGATGGTGTTGATGTAGAATTGTTTGAAAATAAAACAACATTACCTGTTAATGTAGCATTTGAGCT<br>TTGGGCTAAGCGCAACATTAAACCAGTACCAGAGGTGAAAATACTCAATAATTTGGGTGTGGACATTGCTGCTAAT<br>ACTGTGATCTGGGACTACAAAAGAGATGCTCCAGCACATATATCTACTATTGGTGTTTGTTCTATGACTGACATAG<br>CCAAGAAACCAACTGAAACGATTTGTGCACCACTCACTGTCTTTTTGATGGTAGAGTTGATGGTCAAGTAGACTT<br>ATTTAGAAATGCCCGTAATGGTGTTCTTATTACAGAAGGTAGTGTTAAAGGTTTACAACCATCTGTAGGTCCCAAA<br>CAAGCTAGTCTTAATGGAGTCACATTAATTGGAGAAGCCGTAAAAACACAGTTCAATTATTATAAGAAAGTTGATG<br>GTGTTGTCCAACAATTACCTGAAACTTACTTTACTCAGAGTAGAAATTTACAAGAATTTAAACCCAGGAGTCAAAT<br>GGAAATTGATTTCTTAGAATTAGCTATGGATGAATTCATTGAACGGTATAAATTAGAAGGCTATGCCTTCGAACAT<br>ATCGTTTATGGAGATTTTAGTCATAGTCAGTTAGGTGGTTTACATCTACTGATTGGACTAGCTAAACGTTTTAAGGA<br>ATCACCTTTTGAATTAGAAGATTTTATTCCTATGGACAGTACAGTTAAAAACTATTTCATAACAGATGCGCAAACA<br>GGTTCATCTAAGTGTGTGTGTTCTGTTATTGATTTATTACTTGATGATTTTGTTGAAATAATAAAATCCCAAGATTT<br>ATCTGTAGTTTCTAAGGTTGTCAAAGTGACTATTGACTATACAGAAATTTCATTTATGCTTTGGTGTAAAGATGGCC<br>ATGTAGAAACATTTTACCCAAAATTACAATCTAGTCAAGCGTGGCAACCGGGTGTTGCTATGCCTAATCTTTACAA<br>AATGCAAAGAATGCTATTAGAAAAGTGTGACCTTCAAAATTATGGTGATAGTGCAACATTACCTAAAGGCATAAT<br>GATGAATGTCGCAAAATATACTCAACTGTGTCAATATTTAAACACATTAACATTAGCTGTACCCTATAATATGAGA<br>GTTATACATTTTGGTGCTGGTTCTGATAAAGGAGTTGCACCAGGTACAGCTGTTTTAAGACAGTGGTTGCCTACGG<br>GTACGCTGCTTGTCGATTCAGATCTTAATGACTTTGTCTCTGATGCAGATTCAACTTTGATTGGTGATTGTGCAACT<br>GTACATACAGCTAATAAATGGGATCTCATTATTAGTGATATGTACGACCCTAAGACTAAAAATGTTACAAAAGAA<br>AATGACTCTAAAGAGGGTTTTTCACTTACATTTGTGGGTTTATACAACAAAAGCTAGCTCTTGGAGGTTCCGTGGC<br>TATAAAGATAACAGAACATTCTTGGAATGCTGATCTTTATAAGCTCATGGGACACTTCGCATGGTGGACAGCCTTT<br>GTTACTAATGTGAATGCGTCATCATCTGAAGCATTTTTAATTGGATGTAATTATCTTGGCAAACCACGCGAACAAA<br>TAGATGGTTATGTCATGCATGCAAATTACATATTTTGGAGGAATACAAATCCAATTCAGTTGTCTTCCTATTCTTTA<br>TTTGACATGAGTAAATTTCCCCTTAAATTAAGGGGTACTGCTGTTATGTCTTTAAAAGAAGGTCAAATCAATGATA<br>TGATTTTATCTCTTCTTAGTAAAGGTAGACTTATAATTAGAGAAAACAACAGAGTTGTTATTTCTAGTGATGTTCTT<br>GTTAACAACTAAACGAACAATGTTTGTTTTTCTTGTTTTATTGCCACTAGTCTCTAGTCAGTGTGTTAATCTTATAAC<br>CAGAACTCAATCATACACTAATTCTTTCACACGTGGTGTTTATTACCCTGACAAAGTTTTCAGATCCTCAGTTTTAC<br>ATTCAACTCAGGACTTGTTCTTACCTTTCTTTTCCAATGTTACTTGGTTCCATGCTATCTCTGGGACCAATGGTACTA<br>AGAGGTTTGATAACCCTGTCCTACCATTTAATGATGGTGTTTATTTTGCTTCCACTGAGAAGTCTAACATAATAAGA<br>GGCTGGATTTTTGGTACTACTTTAGATTCGAAGACCCAGTCCCTACTTATTGTTAATAACGCTACTAATGTTGTTAT<br>TAAAGTCTGTGAATTTCAATTTTGTAATGATCCATTTTTGGATGTTTATTACCACAAAAACAACAAAAGTTGGATGG<br>AAAGTGAGTTCAGAGTTTATTCTAGTGCGAATAATTGCACTTTTGAATATGTCTCTCAGCCTTTTCTTATGGACCTT<br>GAAGGAAAACAGGGTAATTTCAAAAATCTTAGGGAATTTGTGTTTAAGAATATTGATGGTTATTTTAAAATATATT<br>CTAAGCACACGCCTATTAATTTAGGGCGTGATCTCCCTCAGGGTTTTTCGGCTTTAGAACCATTGGTAGATTTGCCA<br>ATAGGTATTAACATCACTAGGTTTCAAACTTTACTTGCTTTACATAGAAGTTATTTGACTCCTGGTGATTCTTCTTCA<br>GGTTGGACAGCTGGTGCTGCAGCTTATTATGTGGGTTATCTTCAACCTAGGACTTTTCTATTAAAATATAATGAAAA<br>TGGAACCATTACAGATGCTGTAGACTGTGCACTTGACCCTCTCTCAGAAACAAAGTGTACGTTGAAATCCTTCACT<br>GTAGAAAAAGGAATCTATCAAACTTCTAACTTTAGAGTCCAACCAACAGAATCTATTGTTAGATTTCCTAATATTA<br>CAAACTTGTGCCCTTTTGATGAAGTTTTTAACGCCACCAGATTTGCATCTGTTTATGCTTGGAACAGGAAGAGAATC<br>AGCAACTGTGTTGCTGATTATTCTGTCCTATATAATTTCGCACCATTTTTCGCTTTTAAGTGTTATGGAGTGTCTCCT<br>ACTAAATTAAATGATCTCTGCTTTACTAATGTCTATGCAGATTCATTTGTAATTAGAGGTAATGAAGTCAGCCAAAT<br>CGCTCCAGGGCAAACTGGAAATATTGCTGATTATAATTATAAATTACCAGATGATTTTACAGGCTGCGTTATAGCT<br>TGGAATTCTAACAAGCTTGATTCTAAGGTTGGTGGTAATTATAATTACCGGTATAGATTGTTTAGGAAGTCTAATCT |

-continued

SEQUENCE LISTING

CAAACCTTTTGAGAGAGATATTTCAACTGAAATCTATCAGGCCGGTAACAAACCTTGTAATGGTGTTGCAGGTGTT
AATTGTTACTTTCCTTTACAATCATATGGTTTCCGACCCACTTATGGTGTTGGTCACCAACCATACAGAGTAGTAGT
ACTTTCTTTTGAACTTCTACATGCACCAGCAACTGTTTGTGGACCTAAAAAGTCTACTAATTTGGTTAAAAACAAAT
GTGTCAATTTCAACTTCAATGGTTTAACAGGCACAGGTGTTCTTACTGAGTCTAACAAAAAGTTTCTGCCTTTCCAA
CAATTTGGCAGAGACATTGCTGACACTACTGATGCTGTCCGTGATCCACAGACACTTGAGATTCTTGACATTACAC
CATGTTCTTTTGGTGGTGTCAGTGTTATAACACCAGGAACAAATACTTCTAACCAGGTTGCTGTTCTTTATCAGGGT
GTTAACTGCACAGAAGTCCCTGTTGCTATTCATGCAGATCAACTTACTCCTACTTGGCGTGTTTATTCTACAGGTTC
TAATGTTTTTCAAACACGTGCAGGCTGTTTAATAGGGGCTGAATATGTCAACAACTCATATGAGTGTGACATACCC
ATTGGTGCAGGTATATGCGCTAGTTATCAGACTCAGACTAAGTCTCATCGGCGGGCACGTAGTGTAGCTAGTCAAT
CCATCATTGCCTACACTATGTCACTTGGTGCAGAAAATTCAGTTGCTTACTCTAATAACTCTATTGCCATACCCACA
AATTTTACTATTAGTGTTACCACAGAAATTCTACCAGTGTCTATGACCAAGACATCAGTAGATTGTACAATGTACA
TTTGTGGTGATTCAACTGAATGCAGCAATCTTTTGTTGCAATATGGCAGTTTTTGTACACAATTAAAACGTGCTTTA
ACTGGAATAGCTGTTGAACAAGACAAAAACACCCAAGAAGTTTTTGCACAAGTCAAACAAATTTACAAAACACCA
CCAATTAAATATTTTGGTGGTTTTAATTTTTCACAAATATTACCAGATCCATCAAAACCAAGCAAGAGGTCATTTAT
TGAAGATCTACTTTTCAACAAAGTGACACTTGCAGATGCTGGCTTCATCAAACAATATGGTGATTGCCTTGGTGAT
ATTGCTGCTAGAGACCTCATTTGTGCACAAAAGTTTAACGGCCTTACTGTTTTGCCACCTTTGCTCACAGATGAAAT
GATTGCTCAATACACTTCTGCACTGTTAGCGGGTACAATCACTTCTGGTTGGACCTTTGGTGCAGGTGCTGCATTAC
AAATACCATTTGCTATGCAAATGGCTTATAGGTTTAATGGTATTGGAGTTACACAGAATGTTCTCTATGAGAACCA
AAAATTGATTGCCAACCAATTTAATAGTGCTATTGGCAAAATTCAAGACTCACTTTCTTCCACAGCAAGTGCACTT
GGAAAACTTCAAGATGTGGTCAACCATAATGCACAAGCTTTAAACACGCTTGTTAAACAACTTAGCTCCAAATTTG
GTGCAATTTCAAGTGTTTTAAATGATATCCTTTCACGTCTTGACAAAGTTGAGGCTGAAGTGCAAATTGATAGGTT
GATCACAGGCAGACTTCAAAGTTTGCAGACATATGTGACTCAACAATTAATTAGAGCTGCAGAAATCAGAGCTTCT
GCTAATCTTGCTGCTACTAAAATGTCAGAGTGTGTACTTGGACAATCAAAAAGAGTTGATTTTTGTGGAAAGGGCT
ATCATCTTATGTCCTTCCCTCAGTCAGCACCTCATGGTGTAGTCTTCTTGCATGTGACTTATGTCCCTGCACAAGAA
AAGAACTTCACAACTGCTCCTGCCATTTGTCATGATGGAAAAGCACACTTTCCTCGTGAAGGTGTCTTTGTTTCAAA
TGGCACACACTGGTTTGTAACACAAAGGAATTTTTATGAACCACAAATCATTACTACAGACAACACATTTGTGTCT
GGTAACTGTGATGTTGTAATAGGAATTGTCAACAACACAGTTTATGATCCTTTGCAACCTGAATTAGATTCATTCA
AGGAGGAGTTAGATAAATATTTTAAGAATCATACATCACCAGATGTTGATTTAGGTGACATCTCTGGCATTAATGC
TTCAGTTGTAAACATTCAAAAAGAAATTGACCGCCTCAATGAGGTTGCCAAGAATTTAAATGAATCTCTCATCGAT
CTCCAAGAACTTGGAAAGTATGAGCAGTATATAAAATGGCCATGGTACATTTGGCTAGGTTTTATAGCTGGCTTGA
TTGCCATAGTAATGGTGACAATTATGCTTTGCTGTATGACCAGTTGCTGTAGTTGTCTCAAGGGCTGTTGTTCTTGT
GGATCCTGCTGCAAATTTGATGAAGACGACTCTGAGCCAGTGCTCAAAGGAGTCAAATTACATTACACATAAACG
AACTTATGGATTTGTTTATGAGAATCTTCACAATTGGAACTGTAACTTTGAAGCAAGGTGAAATCAAGGATGCTAC
TCCTTCAGATTTTGTTCGCGCTACTGCAACGATACCGATACAAGCCTCACTCCCTTTCGGATGGCTTATTGTTGGCG
TTGCACTTCTTGCTGTTTTTCAGAGCGCTTCCAAAATCATAACCCTCAAAAAGAGATGGCAACTAGCACTCTCCAA
GGGTGTTCACTTTGTTTGCAACTTGCTGTTGTTGTTTGTAACAGTTTACTCACACCTTTTGCTCGTTGCTGCTGGCCT
TGAAGCCCCTTTTCTCTATCTTTATGCTTTAGTCTACTTCTTGCAGAGTATAAACTTTGTAAGAATAATAATGAGGC
TTTGGCTTTGCTGGAAATGCCGTTCCAAAAACCCATTACTTTATGATGCCAACTATTTTCTTTGCTGGCATACTAAT
TGTTACGACTATTGTATACCTTACAATAGTGTAACTTCTTCAATTGTCATTACTTCAGGTGATGGCACAACAAGTCC
TATTTCTGAACATGACTACCAGATTGGTGGTTATACTGAAAAATGGGAATCTGGAGTAAAAGACTGTGTTGTATTA
CACAGTTACTTCACTTCAGACTATTACCAGCTGTACTCAACTCAATTGAGTACAGACACTGGTGTTGAACATGTTAC
CTTCTTCATCTACAATAAAATTGTTGATGAGCCTGAAGAACATGTCCAAATTCACACAATCGACGGTTCATCCGGA
GTTGTTAATCCAGTAATGGAACCAATTTATGATGAACCGACGACGACTACTAGCGTGCCTTTGTAAGCACAAGCTG
ATGAGTACGAACTTATGTACTCATTCGTTTCGGAAGAGACAGGTACGTAAATAGTTAATAGCTGACTTCTTTTTCTT
GCTTTCGTGTGATTCTTGCTAGTTACACTAGCCATCCTTACTGCGCTTCGATTGTGTGCGTACTGCTGCAATATTGTT
AACGTGAGTCTTGTAAAACCTTCTTTTTACGTTTACTCTCGTGTTAAAAATCTGAATTCTTCTAGAGTTCCTGATCTT
CTGGTCTAAACGAACTAAATATTATATTAGTTTTTCTGTTTGGAACTTTAATTTTAGCCATGGCAGATTCCAACGGT
ACTATTACCGTTGAAGAGCTTAAAAAGCTCCTTGAACAATGGAACCTAGTAATAGGTTTCCTATTCCTTACATGGA
TTTGTCTTCTACAATTTGCCTATGCCAACAGGAATAGGTTTTTGTATATAATTAAGTTAATTTTCCTCTGGCTGTTAT
GGCCAGTAACTTTAGCTTGTTTTGTGCTTGCTGCTGTTTACAGAATAAATTGGATCACCGGTGGAATTGCTATCGCA
ATGGCTTGTCTTGTAGGCTTGATGTGGCTCAGCTACTTCATTGCTTCTTTCAGACTGTTTGCGCGTACGCGTTCCATG

-continued

SEQUENCE LISTING

TGGTCATTCAATCCAGAAACTAACATTCTTCTCAACGTGCCACTCCATGGCACTATTCTGACCAGACCGCTTCTAGA
AAGTGAACTCGTAATCGGAGCTGTGATCCTTCGTGGACATCTTCGTATTGCTGGACACCATCTAGGACGCTGTGAC
ATCAAGGACCTGCCTAAAGAAATCACTGTTGCTACATCACGAACGCTTTCTTATTACAAATTGGGAGCTTCGCAGC
GTGTAGCAGGTGACTCAGGTTTTGCTGCATACAGTCGCTACAGGATTGGCAACTATAAATTAAACACAGACCATTC
CAGTAGCAGTGACAATATTGCTTTGCTTGTACAATGATAATGAAACTTGTCACGCCTAAACGAACatgaccaacaagtgtctc
ctccaaattgctctcctgttgtgcttctccactacagctctttccatgagctacaacttgcttggattcctacaaagaagcagcaattttcagtgtcagaagctcctgtggcaattgaatgggaggct
tgaatactgcctcaaggacaggatgaactttgacatccctgaggagattaagcagctgcagcagttccagaaggaggacgccgcattgaccatctatgagatgctccagaacatctttgctatt
ttcagacaagattcatctagcactggctggaatgagactattgttgagaacctcctggctaatgtctatcatcagataaaccatctgaagacagtcctggaagaaaaactggagaaagaagattt
caccaggggaaaactcatgagcagtctgcacctgaaaagatattatgggaggattctgcattacctgaaggccaaggagtacagtcactgtgcctggaccatagtcagagtggaaatcctaa
ggaactttttacttcattaacagacttacaggttacctccgaaactgaGACGTTCGTGTTGTTTTAGATTTCATCTAAACGAACAAACTAAAATGTC
TGATAATGGACCCCAAAATCAGCGAAATGCACCCCGCATTACGTTTGGTGGACCCTCAGATTCAACTGGCAGTAAC
CAGAATGGAGAACGCAGTGGGGCGCGATCAAAACAACGTCGGCCCCAAGGTTTACCCAATAATACTGCGTCTTGG
TTCACCGCTCTCACTCAACATGGCAAGGAAGACCTTAAATTCCCTCGAGGACAAGGCGTTCCAATTAACACCAATA
GCAGTCCAGATGACCAAATTGGCTACTACCGAAGAGCTACCAGACGAATTCGTGGTGGTGACGGTAAAATGAAAG
ATCTCAGTCCAAGATGGTATTTCTACTACCTAGGAACTGGGCCAGAAGCTGGACTTCCCTATGGTGCTAACAAAGA
CGGCATCATATGGGTTGCAACTGAGGGAGCCTTGAATACACCAAAAGATCACATTGGCACCCGCAATCCTGCTAA
CAATGCTGCAATCGTGCTACAACTTCCTCAAGGAACAACATTGCCAAAAGGCTTCTACGCAGAAGGGAGCAGAGG
CGGCAGTCAAGCCTCTTCTCGTTCCTCATCACGTAGTCGCAACAGTTCAAGAAATTCAACTCCAGGCAGCAGTAGG
GGAACTTCTCCTGCTAGAATGGCTGGCAATGGCGGTGATGCTGCTCTTGCTTTGCTGCTGCTTGACAGATTGAACC
AGCTTGAGAGCAAAATGTCTGGTAAAGGCCAACAACAACAAGGCCAAACTGTCACTAAGAAATCTGCTGCTGAGG
CTTCTAAGAAGCCTCGGCAAAAACGTACTGCCACTAAAGCATACAATGTAACACAAGCTTTCGGCAGACGTGGTC
CAGAACAAACCCAAGGAAATTTTGGGGACCAGGAACTAATCAGACAAGGAACTGATTACAAACATTGGCCGCAA
ATTGCACAATTTGCCCCCAGCGCTTCAGCGTTCTTCGGAATGTCGCGCATTGGCATGGAAGTCACACCTTCGGGAA
CGTGGTTGACCTACACAGGTGCCATCAAATTGGATGACAAAGATCCAAATTTCAAAGATCAAGTCATTTTGCTGAA
TAAGCATATTGACGCATACAAAACATTCCCACCAACAGAGCCTAAAAAGGACAAAAAGAAGAAGGCTGATGAAA
CTCAAGCCTTACCGCAGAGACAGAAGAAACAGCAAACTGTGACTCTTCTTCCTGCTGCAGATTTGGATGATTTCTC
CAAACAATTGCAACAATCCATGAGCAGTGCTGACTCAACTCAGGCCTAAACTCATGCAGACCACACAAGGCAGAT
GGGCTATATAAACGTTTTCGCTTTTCCGTTTACGATATATAGTCTACTCTTGTGCAGAATGAATTCTCGTAACTACA
TAGCACAAGTAGATGTAGTTAACTTTAATCTCACATAGCAATCTTTAATCAGTGTGTAACATTAGGGAGGACTTGA
AAGAGCCACCACATTTTCACCGAGGCCACGCGGAGTACGATCGAGTGTACAGTGAACAATGCTAGGGAGAGCTGC
CTATATGGAAGAGCCCTAATGTGTAAAATTAATTTTAGTAGTGCTATCCCCATGTGATTTTAATAGCTTCTTAGGAG
AATGACAAAAAAAAAAAAAAAAAAAAA SEQ ID NO: 8 (synthetic IBIS DNA construct 1; mouse IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT -continued

SEQUENCE LISTING

GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA
AAGCCTTGAATTTAGGTGAAACATTTGTCACGCACTCAAAGGGATTGTACAGAAAGTGTGTTAAATCCAGAGAAG
AAACTGGCCTACTCATGCCTCTAAAAGCCCCAAAAGAAATTATCTTCTTAGAGGGAGAAACACTTCCCACAGAAGT
GTTAACAGAGGAAGTTGTCTTGAAAACTGGTGATTTACAACCATTAGAACAACCTACTAGTGAAGCTGTTGAAGCT
CCATTGGTTGGTACACCAGTTTGTATTAACGGGCTTATGTTGCTCGAAATCAAAGACACAGAAAAGTACTGTGCCC
TTGCACCTAATATGATGGTAACAAACAATACCTTCACACTCAAAGGCGGTGCACCAACAAAGGTTACTTTTGGTGA
TGACACTGTGATAGAAGTGCAAGGTTACAAGAGTGTGAATATCACTTTTGAACTTGATGAAAGGATTGATAAAGT
ACTTAATGAGAAGTGCTCTGCCTATACAGTTGAACTCGGTACAGAAGTAAATGAGTTCGCCTGTGTTGTGGCAGAT
GCTGTCATAAAAACTTTGCAACCAGTATCTGAATTACTTACACCACTGGGCATTGATTTAGATGAGTGGAGTATGG
CTACATACTACTTATTTGATGAGTCTGGTGAGTTTAAATTGGCTTCACATATGTATTGTTCTTTCTACCCTCCAGATG
AGGATGAAGAAGAAGGTGATTGTGAAGAAGAAGAGTTTGAGCCATCAACTCAATATGAGTATGGTACTGAAGATG
ATTACCAAGGTAAACCTTTGGAATTTGGTGCCACTTCTGCTGCTCTTCAACCTGAAGAAGAGCAAGAAGAAGATTG
GTTAGATGATGATAGTCAACAAACTGTTGGTCAACAAGACGGCAGTGAGGACAATCAGACAACTACTATTCAAAC
AATTGTTGAGGTTCAACCTCAATTAGAGATGGAACTTACACCAGTTGTTCAGACTATTGAAGTGAATAGTTTTAGT
GGTTATTTAAAACTTACTGACAATGTATACATTAAAAATGCAGACATTGTGGAAGAAGCTAAAAAGGTAAAACCA
ACAGTGGTTGTTAATGCAGCCAATGTTTACCTTAAACATGGAGGAGGTGTTGCAGGAGCCTTAAATAAGGCTACTA
ACAATGCCATGCAAGTTGAATCTGATGATTACATAGCTACTAATGGACCACTTAAAGTGGGTGGTAGTTGTGTTTT
AAGCGGACACAATCTTGCTAAACACTGTCTTCATGTTGTCGGCCCAAATGTTAACAAAGGTGAAGACATTCAACTT
CTTAAGAGTGCTTATGAAAATTTTAATCAGCACGAAGTTCTACTTGCACCATTATTATCAGCTGGTATTTTTGGTGC
TGACCCTATACATTCTTTAAGAGTTTGTGTAGATACTGTTCGCACAAATGTCTACTTAGCTGTCTTTGATAAAAATC
TCTATGACAAACTTGTTTCAAGCTTTTTGGAAATGAAGAGTGAAAAGCAAGTTGAACAAAAGATCGCTGAGATTCC
TAAAGAGGAAGTTAAGCCATTTATAACTGAAAGTAAACCTTCAGTTGAACAGAGAAAACAAGATGATAAGAAAAT
CAAAGCTTGTGTTGAAGAAGTTACAACAACTCTGGAAGAAACTAAGTTCCTCACAGAAAACTTGTTACTTTATATT
GACATTAATGGCAATCTTCATCCAGATTCTGCCACTCTTGTTAGTGACATTGACATCACTTTCTTAAAGAAAGATGC
TCCATATATAGTGGGTGATGTTGTTCAAGAGGGTGTTTTAACTGCTGTGGTTATACCTACTAAAAAGGCTGGTGGC
ACTACTGAAATGCTAGCGAAAGCTTTGAGAAAAGTGCCAACAGACAATTATATAACCACTTACCCGGGTCAGGGT
TTAAATGGTTACACTGTAGAGGAGGCAAAGACAGTGCTTAAAAAGTGTAAAAGTGCCTTTTACATTCTACCATCTA
TTATCTCTAATGAGAAGCAAGAAATTCTTGGAACTGTTTCTTGGAATTTGCGAGAAATGCTTGCACATGCAGAAGA
AACACGCAAATTAATGCCTGTCTGTGTGGAAACTAAAGCCATAGTTTCAACTATACAGCGTAAATATAAGGGTATT
AAAATACAAGAGGGTGTGGTTGATTATGGTGCTAGATTTTACTTTTACACCAGTAAAACAACTGTAGCGTCACTTA
TCAACACACTTAACGATCTAAATGAAACTCTTGTTACAATGCCACTTGGCTATGTAACACATGGCTTAAATTTGGA
AGAAGCTGCTCGGTATATGAGATCTCTCAAAGTGCCAGCTACAGTTTCTGTTTCTTCACCTGATGCTGTTACAGCGT
ATAATGGTTATCTTACTTCTTCTTCTAAAACACCTGAAGAACATTTTATTGAAACCATCTCACTTGCTGGTTCCTAT
AAAGATTGGTCCTATTCTGGACAATCTACACAACTAGGTATAGAATTTCTTAAGAGAGGTGATAAAAGTGTATATT
ACACTAGTAATCCTACCACATTCCACCTAGATGGTGAAGTTATCACCTTTGACAATCTTAAGACACTTCTTTCTTTG
AGAGAAGTGAGGACTATTAAGGTGTTTACAACAGTAGACAACATTAACCTCCACACGCAAGTTGTGGACATGTCA
ATGACATATGGACAACAGTTTGGTCCAACTTATTTGGATGGAGCTGATGTTACTAAAATAAAACCTCATAATTCAC
ATGAAGGTAAAACATTTTATGTTTTACCTAATGATGACACTCTACGTGTTGAGGCTTTTGAGTACTACCACACAACT

-continued

SEQUENCE LISTING

GATCCTAGTTTTCTGGGTAGGTACATGTCAGCATTAAATCACACTAAAAAGTGGAAATACCCACAAGTTAATGGTT
TAACTTCTATTAAATGGGCAGATAACAACTGTTATCTTGCCACTGCATTGTTAACACTCCAACAAATAGAGTTGAA
GTTTAATCCACCTGCTCTACAAGATGCTTATTACAGAGCAAGGGCTGGTGAAGCTGCTAACTTTTGTGCACTTATCT
TAGCCTACTGTAATAAGACAGTAGGTGAGTTAGGTGATGTTAGAGAAACAATGAGTTACTTGTTTCAACATGCCAA
TTTAGATTCTTGCAAAAGAGTCTTGAACGTGGTGTGTAAAACTTGTGGACAACAGCAGACAACCCTTAAGGGTGTA
GAAGCTGTTATGTACATGGGCACACTTTCTTATGAACAATTTAAGAAAGGTGTTCAGATACCTTGTACGTGTGGTA
AACAAGCTACAAAATATCTAGTACAACAGGAGTCACCTTTTGTTATGATGTCAGCACCACCTGCTCAGTATGAACT
TAAGCATGGTACATTTACTTGTGCTAGTGAGTACACTGGTAATTACCAGTGTGGTCACTATAAACATATAACTTCTA
AAGAAACTTTGTATTGCATAGACGGTGCTTTACTTACAAAGTCCTCAGAATACAAAGGTCCTATTACGGATGTTTT
CTACAAAGAAAACAGTTACACAACAACCATAAAACCAGTTACTTATAAATTGGATGGTGTTGTTTGTACAGAAATT
GACCCTAAGTTGGACAATTATTATAAGAAAGACAATTCTTATTTCACAGAGCAACCAATTGATCTTGTACCAAACC
AACCATATCCAAACGCAAGCTTCGATAATTTTAAGTTTGTATGTGATAATATCAAATTTGCTGATGATTTAAACCA
GTTAACTGGTTATAAGAAACCTGCTTCAAGAGAGCTTAAAGTTACATTTTTCCCTGACTTAAATGGTGATGTGGTG
GCTATTGATTATAAACACTACACACCCTCTTTTAAGAAAGGAGCTAAATTGTTACATAAACCTATTGTTTGGCATGT
TAACAATGCAACTAATAAAGCCACGTATAAACCAAATACCTGGTGTATACGTTGTCTTTGGAGCACAAAACCAGTT
GAAACATCAAATTCGTTTGATGTACTGAAGTCAGAGGACGCGCAGGGAATGGATAATCTTGCCTGCGAAGATCTA
AAACCAGTCTCTGAAGAAGTAGTGGAAAATCCTACCATACAGAAAGACGTTCTTGAGTGTAATGTGAAAACTACC
GAAGTTGTAGGAGACATTATACTTAAACCAGCAAATAATAGTTTAAAAATTACAGAAGAGGTTGGCCACACAGAT
CTAATGGCTGCTTATGTAGACAATTCTAGTCTTACTATTAAGAAACCTAATGAATTATCTAGAGTATTAGGTTTGAA
AACCCTTGCTACTCATGGTTTAGCTGCTGTTAATAGTGTCCCTTGGGATACTATAGCTAATTATGCTAAGCCTTTTC
TTAACAAAGTTGTTAGTACAACTACTAACATAGTTACACGGTGTTTAAACCGTGTTTGTACTAATTATATGCCTTAT
TTCTTTACTTTATTGCTACAATTGTGTACTTTTACTAGAAGTACAAATTCTAGAATTAAAGCATCTATGCCGACTAC
TATAGCAAAGAATACTGTTAAGAGTGTCGGTAAATTTTGTCTAGAGGCTTCATTTAATTATTTGAAGTCACCTAATT
TTTCTAAACTGATAAATATTATAATTTGGTTTTTACTATTAAGTGTTTGCCTAGGTTCTTTAATCTACTCAACCGCTG
CTTTAGGTGTTTTAATGTCTAATTTAGGCATGCCTTCTTACTGTACTGGTTACAGAGAAGGCTATTTGAACTCTACT
AATGTCACTATTGCAACCTACTGTACTGGTTCTATACCTTGTAGTGTTTGTCTTAGTGGTTTAGATTCTTTAGACACC
TATCCTTCTTTAGAAACTATACAAATTACCATTTCATCTTTTAAATGGGATTTAACTGCTTTTGGCTTAGTTGCAGA
GTGGTTTTTGGCATATATTCTTTTCACTAGGTTTTTCTATGTACTTGGATTGGCTGCAATCATGCAATTGTTTTTCAG
CTATTTTGCAGTACATTTTATTAGTAATTCTTGGCTTATGTGGTTAATAATTAATCTTGTACAAATGGCCCCGATTTC
AGCTATGGTTAGAATGTACATCTTCTTTGCATCATTTTATTATGTATGGAAAAGTTATGTGCATGTTGTAGACGGTT
GTAATTCATCAACTTGTATGATGTGTTACAAACGTAATAGAGCAACAAGAGTCGAATGTACAACTATTGTTAATGG
TGTTAGAAGGTCCTTTTATGTCTATGCTAATGGAGGTAAAGGCTTTTGCAAACTACACAATTGGAATTGTGTTAATT
GTGATACATTCTGTGCTGGTAGTACATTTATTAGTGATGAAGTTGCGAGAGACTTGTCACTACAGTTTAAAAGACC
AATAAATCCTACTGACCAGTCTTCTTACATCGTTGATAGTGTTACAGTGAAGAATGGTTCCATCCATCTTTACTTTG
ATAAAGCTGGTCAAAAGACTTATGAAAGACATTCTCTCTCTCATTTTGTTAACTTAGACAACCTGAGAGCTAATAA
CACTAAAGGTTCATTGCCTATTAATGTTATAGTTTTTGATGGTAAATCAAAATGTGAAGAATCATCTGCAAAATCA
GCGTCTGTTTACTACAGTCAGCTTATGTGTCAACCTATACTGTTACTAGATCAGGCATTAGTGTCTGATGTTGGTGA
TAGTGCGGAAGTTGCAGTTAAAATGTTTGATGCTTACGTTAATACGTTTTCATCAACTTTTAACGTACCAATGGAAA
AACTCAAAACACTAGTTGCAACTGCAGAAGCTGAACTTGCAAAGAATGTGTCCTTAGACAATGTCTTATCTACTTT
TATTTCAGCAGCTCGGCAAGGGTTTGTTGATTCAGATGTAGAAACTAAAGATGTTGTTGAATGTCTTAAATTGTCA
CATCAATCTGACATAGAAGTTACTGGCGATAGTTGTAATAACTATATGCTCACCTATAACAAAGTTGAAAACATGA
CACCCCGTGACCTTGGTGCTTGTATTGACTGTAGTGCGCGTCATATTAATGCGCAGGTAGCAAAAAGTCACAACAT
TGCTTTGATATGGAACGTTAAAGATTTCATGTCATTGTCTGAACAACTACGAAAACAAATACGTAGTGCTGCTAAA
AAGAATAACTTACCTTTTAAGTTGACATGTGCAACTACTAGACAAGTTGTTAATGTTGTAACAACAAAGATAGCAC
TTAAGGGTGGTAAAATTGTTAATAATTGGTTGAAGCAGTTAATTAAAGTTACACTTGTGTTCCTTTTTGTTGCTGCT
ATTTTCTATTTAATAACACCTGTTCATGTCATGTCTAAACATACTGACTTTTCAAGTGAAATCATAGGATACAAGGC
TATTGATGGTGGTGTCACTCGTGACATAGCATCTACAGATACTTGTTTTGCTAACAAACATGCTGATTTTGACACAT
GGTTTAGCCAGCGTGGTGGTAGTTATACTAATGACAAAGCTTGCCCATTGATTGCTGCAGTCATAACAAGAGAAGT
GGGTTTTGTCGTGCCTGGTTTGCCTGGCACGATATTACGCACAACTAATGGTGACTTTTTGCATTTCTTACCTAGAG
TTTTTAGTGCAGTTGGTAACATCTGTTACACACCATCAAAACTTATAGAGTACACTGACTTTGCAACATCAGCTTGT
GTTTTGGCTGCTGAATGTACAATTTTTAAAGATGCTTCTGGTAAGCCAGTACCATATTGTTATGATACCAATGTACT

-continued

| SEQUENCE LISTING |
|---|
| AGAAGGTTCTGTTGCTTATGAAAGTTTACGCCCTGACACACGTTATGTGCTCATGGATGGCTCTATTATTCAATTTC |
| CTAACACCTACCTTGAAGGTTCTGTTAGAGTGGTAACAACTTTTGATTCTGAGTACTGTAGGCACGGCACTTGTGA |
| AAGATCAGAAGCTGGTGTTTGTGTATCTACTAGTGGTAGATGGGTACTTAACAATGATTATTACAGATCTTTACCA |
| GGAGTTTTCTGTGGTGTAGATGCTGTAAATTTACTTACTAATATGTTTACACCACTAATTCAACCTATTGGTGCTTT |
| GGACATATCAGCATCTATAGTAGCTGGTGGTATTGTAGCTATCGTAGTAACATGCCTTGCCTACTATTTTATGAGGT |
| TTAGAAGAGCTTTTGGTGAATACAGTCATGTAGTTGCCTTTAATACTTTACTATTCCTTATGTCATTCACTGTACTCT |
| GTTTAACACCAGTTTACTCATTCTTACCTGGTGTTTATTCTGTTATTTACTTGTACTTGACATTTTATCTTACTAATG |
| ATGTTTCTTTTTTAGCACATATTCAGTGGATGGTTATGTTCACACCTTTAGTACCTTTCTGGATAACAATTGCTTATA |
| TCATTTGTATTTCCACAAAGCATTTCTATTGGTTCTTTAGTAATTACCTAAAGAGACGTGTAGTCTTTAATGGTGTTT |
| CCTTTAGTACTTTTGAAGAAGCTGCGCTGTGCACCTTTTTGTTAAATAAAGAAATGTATCTAAAGTTGCGTAGTGAT |
| GTGCTATTACCTCTTACGCAATATAATAGATACTTAGCTCTTTATAATAAGTACAAGTATTTTAGTGGAGCAATGGA |
| TACAACTAGCTACAGAGAAGCTGCTTGTTGTCATCTCGCAAAGGCTCTCAATGACTTCAGTAACTCAGGTTCTGAT |
| GTTCTTTACCAACCACCACAAACCTCTATCACCTCAGCTGTTTTGCAGAGTGGTTTTAGAAAAATGGCATTCCCATC |
| TGGTAAAGTTGAGGGTTGTATGGTACAAGTAACTTGTGGTACAACTACACTTAACGGTCTTTGGCTTGATGACGTA |
| GTTTACTGTCCAAGACATGTGATCTGCACCTCTGAAGACATGCTTAACCCTAATTATGAAGATTTACTCATTCGTAA |
| GTCTAATCATAATTTCTTGGTACAGGCTGGTAATGTTCAACTCAGGGTTATTGGACATTCTATGCAAAATTGTGTAC |
| TTAAGCTTAAGGTTGATACAGCCAATCCTAAGACACCTAAGTATAAGTTTGTTCGCATTCAACCAGGACAGACTTT |
| TTCAGTGTTAGCTTGTTACAATGGTTCACCATCTGGTGTTTACCAATGTGCTATGAGGCCCAATTTCACTATTAAGG |
| GTTCATTCCTTAATGGTTCATGTGGTAGTGTTGGTTTTAACATAGATTATGACTGTGTCTCTTTTTGTTACATGCACC |
| ATATGGAATTACCAACTGGAGTTCATGCTGGCACAGACTTAGAAGGTAACTTTTATGGACCTTTTGTTGACAGGCA |
| AACAGCACAAGCAGCTGGTACGGACACAACTATTACAGTTAATGTTTTAGCTTGGTTGTACGCTGCTGTTATAAAT |
| GGAGACAGGTGGTTTCTCAATCGATTTACCACAACTCTTAATGACTTTAACCTTGTGGCTATGAAGTACAATTATG |
| AACCTCTAACACAAGACCATGTTGACATACTAGGACCTCTTTCTGCTCAAACTGGAATTGCCGTTTTAGATATGTGT |
| GCTTCATTAAAAGAATTACTGCAAAATGGTATGAATGGACGTACCATATTGGGTAGTGCTTTATTAGAAGATGAAT |
| TTACACCTTTTGATGTTGTTAGACAATGCTCAGGTGTTACTTTCCAAAGTGCAGTGAAAAGAACAATCAAGGGTAC |
| ACACCACTGGTTGTTACTCACAATTTTGACTTCACTTTTAGTTTTAGTCCAGAGTACTCAATGGTCTTTGTTCTTTTT |
| TTTGTATGAAAATGCCTTTTTACCTTTTGCTATGGGTATTATTGCTATGTCTGCTTTTGCAATGATGTTTGTCAAACA |
| TAAGCATGCATTTCTCTGTTTGTTTTTGTTACCTTCTCTTGCCACTGTAGCTTATTTTAATATGGTCTATATGCCTGCT |
| AGTTGGGTGATGCGTATTATGACATGGTTGGATATGGTTGATACTAGTTTGTCTGGTTTTAAGCTAAAAGACTGTGT |
| TATGTATGCATCAGCTGTAGTGTTACTAATCCTTATGACAGCAAGAACTGTGTATGATGATGGTGCTAGGAGAGTG |
| TGGACACTTATGAATGTCTTGACACTCGTTTATAAAGTTTATTATGGTAATGCTTTAGATCAAGCCATTTCCATGTG |
| GGCTCTTATAATCTCTGTTACTTCTAACTACTCAGGTGTAGTTACAACTGTCATGTTTTTGGCCAGAGGTATTGTTTT |
| TATGTGTGTTGAGTATTGCCCTATTTTCTTCATAACTGGTAATACACTTCAGTGTATAATGCTAGTTTATTGTTTCTT |
| AGGCTATTTTTGTACTTGTTACTTTGGCCTCTTTTGTTTACTCAACCGCTACTTTAGACTGACTCTTGGTGTTTATGA |
| TTACTTAGTTTCTACACAGGAGTTTAGATATATGAATTCACAGGGACTACTCCCACCCAAGAATAGCATAGATGCC |
| TTCAAACTCAACATTAAATTGTTGGGTGTTGGTGGCAAACCTTGTATCAAAGTAGCCACTGTACAGTCTAAAATGT |
| CAGATGTAAAGTGCACATCAGTAGTCTTACTCTCAGTTTTGCAACAACTCAGAGTAGAATCATCATCTAAATTGTG |
| GGCTCAATGTGTCCAGTTACACAATGACATTCTCTTAGCTAAAGATACTACTGAAGCCTTTGAAAAAATGGTTTCA |
| CTACTTTCTGTTTTGCTTTCCATGCAGGGTGCTGTAGACATAAACAAGCTTTGTGAAGAAATGCTGGACAACAGGG |
| CAACCTTACAAGCTATAGCCTCAGAGTTTAGTTCCCTTCCATCATATGCAGCTTTTGCTACTGCTCAAGAAGCTTAT |
| GAGCAGGCTGTTGCTAATGGTGATTCTGAAGTTGTTCTTAAAAAGTTGAAGAAGTCTTTGAATGTGGCTAAATCTG |
| AATTTGACCGTGATGCAGCCATGCAACGTAAGTTGGAAAAGATGGCTGATCAAGCTATGACCCAAATGTATAAAC |
| AGGCTAGATCTGAGGACAAGAGGGCAAAAGTTACTAGTGCTATGCAGACAATGCTTTTCACTATGCTTAGAAAGTT |
| GGATAATGATGCACTCAACAACATTATCAACAATGCAAGAGATGGTTGTGTTCCCTTGAACATAATACCTCTTACA |
| ACAGCAGCCAAACTAATGGTTGTCATACCAGACTATAACACATATAAAAATACGTGTGATGGTACAACATTTACTT |
| ATGCATCAGCATTGTGGGAAATCCAACAGGTTGTAGATGCAGATAGTAAAATTGTTCAACTTAGTGAAATTAGTAT |
| GGACAATTCACCTAATTTAGCATGGCCTCTTATTGTAACAGCTTTAAGGGCCAATTCTGCTGTCAAATTACAGAAT |
| AATGAGCTTAGTCCTGTTGCACTACGACAGATGTCTTGTGCTGCCGGTACTACACAAACTGCTTGCACTGATGACA |
| ATGCGTTAGCTTACTACAACACAACAAAGGGAGGTAGGTTTGTACTTGCACTGTTATCCGATTTACAGGATTTGAA |
| ATGGGCTAGATTCCCTAAGAGTGATGGAACTGGTACTATCTATACAGAACTGGAACCACCTTGTAGGTTTGTTACA |
| GACACACCTAAAGGTCCTAAAGTGAAGTATTTATACTTTATTAAAGGATTAAACAACCTAAATAGAGGTATGGTAC |

-continued

| SEQUENCE LISTING |
|---|
| TTGGTAGTTTAGCTGCCACAGTACGTCTACAAGCTGGTAATGCAACAGAAGTGCCTGCCAATTCAACTGTATTATC |
| TTTCTGTGCTTTTGCTGTAGATGCTGCTAAAGCTTACAAAGATTATCTAGCTAGTGGGGACAACCAATCACTAATT |
| GTGTTAAGATGTTGTGTACACACACTGGTACTGGTCAGGCAATAACAGTTACACCGGAAGCCAATATGGATCAAG |
| AATCCTTTGGTGGTGCATCGTGTTGTCTGTACTGCCGTTGCCACATAGATCATCCAAATCCTAAAGGATTTTGTGAC |
| TTAAAAGGTAAGTATGTACAAATACCTACAACTTGTGCTAATGACCCTGTGGGTTTTACACTTAAAAACACAGTCT |
| GTACCGTCTGCGGTATGTGGAAAGGTTATGGCTGTAGTTGTGATCAACTCCGCGAACCCATGCTTCAGTCAGCTGA |
| TGCACAATCGTTTTTAAACGGGTTTGCGGTGTAAGTGCAGCCCGTCTTACACCGTGCGGCACAGGCACTAGTACTG |
| ATGTCGTATACAGGGCTTTTGACATCTACAATGATAAAGTAGCTGGTTTTGCTAAATTCCTAAAAACTAATTGTTGT |
| CGCTTCCAAGAAAAGGACGAAGATGACAATTTAATTGATTCTTACTTTGTAGTTAAGAGACACACTTTCTCTAACT |
| ACCAACATGAAGAAACAATTTATAATTTACTTAAGGATTGTCCAGCTGTTGCTAAACATGACTTCTTTAAGTTTAG |
| AATAGACGGTGACATGGTACCACATATATCACGTCAACGTCTTACTAAATACACAATGGCAGACCTCGTCTATGCT |
| TTAAGGCATTTTGATGAAGGTAATTGTGACACATTAAAAGAAATACTTGTCACATACAATTGTTGTGATGATGATT |
| ATTTCAATAAAAAGGACTGGTATGATTTTGTAGAAAACCCAGATATATTACGCGTATACGCCAACTTAGGTGAACG |
| TGTACGCCAAGCTTTGTTAAAAACAGTACAATTCTGTGATGCCATGCGAAATGCTGGTATTGTTGGTGTACTGACA |
| TTAGATAATCAAGATCTCAATGGTAACTGGTATGATTTCGGTGATTTCATACAAACCACGCCAGGTAGTGGAGTTC |
| CTGTTGTAGATTCTTATTATTCATTGTTAATGCCTATATTAACCTTGACCAGGGCTTTAACTGCAGAGTCACATGTT |
| GACACTGACTTAACAAAGCCTTACATTAAGTGGGATTTGTTAAAATATGACTTCACGGAAGAGAGGTTAAAACTCT |
| TTGACCGTTATTTTAAATATTGGGATCAGACATACCACCCAAATTGTGTTAACTGTTTGGATGACAGATGCATTCTG |
| CATTGTGCAAACTTTAATGTTTTATTCTCTACAGTGTTCCCACCTACAAGTTTTGGACCACTAGTGAGAAAAATATT |
| TGTTGATGGTGTTCCATTTGTAGTTTCAACTGGATACCACTTCAGAGAGCTAGGTGTTGTACATAATCAGGATGTAA |
| ACTTACATAGCTCTAGACTTAGTTTTAAGGAATTACTTGTGTATGCTGCTGACCCTGCTATGCACGCTGCTTCTGGT |
| AATCTATTACTAGATAAACGCACTACGTGCTTTTCAGTAGCTGCACTTACTAACAATGTTGCTTTTCAAACTGTCAA |
| ACCCGGTAATTTTAACAAAGACTTCTATGACTTTGCTGTGTCTAAGGGTTTCTTTAAGGAAGGAAGTTCTGTTGAAT |
| TAAAACACTTCTTCTTTGCTCAGGATGGTAATGCTGCTATCAGCGATTATGACTACTATCGTTATAATCTACCAACA |
| ATGTGTGATATCAGACAACTACTATTTGTAGTTGAAGTTGTTGATAAGTACTTTGATTGTTACGATGGTGGCTGTAT |
| TAATGCTAACCAAGTCATCGTCAACAACCTAGACAAATCAGCTGGTTTTCCATTTAATAAATGGGGTAAGGCTAGA |
| CTTTATTATGATTCAATGAGTTATGAGGATCAAGATGCACTTTTCGCATATACAAAACGTAATGTCATCCCTACTAT |
| AACTCAAATGAATCTTAAGTATGCCATTAGTGCAAAGAATAGAGCTCGCACCGTAGCTGGTGTCTCTATCTGTAGT |
| ACTATGACCAATAGACAGTTTCATCAAAAATTATTGAAATCAATAGCCGCCACTAGAGGAGCTACTGTAGTAATTG |
| GAACAAGCAAATTCTATGGTGGTTGGCACAACATGTTAAAAACTGTTTATAGTGATGTAGAAAACCCTCACCTTAT |
| GGGTTGGGATTATCCTAAATGTGATAGAGCCATGCCTAACATGCTTAGAATTATGGCCTCACTTGTTCTTGCTCGCA |
| AACATACAACGTGTTGTAGCTTGTCACACCGTTTCTATAGATTAGCTAATGAGTGTGCTCAAGTATTGAGTGAAAT |
| GGTCATGTGTGGCGGTTCACTATATGTTAAACCAGGTGGAACCTCATCAGGAGATGCCACAACTGCTTATGCTAAT |
| AGTGTTTTTAACATTTGTCAAGCTGTCACGGCCAATGTTAATGCACTTTTATCTACTGATGGTAACAAAATTGCCGA |
| TAAGTATGTCCGCAATTTACAACACAGACTTTATGAGTGTCTCTATAGAAATAGAGATGTTGACACAGACTTTGTG |
| AATGAGTTTTACGCATATTTGCGTAAACATTTCTCAATGATGATACTCTCTGACGATGCTGTTGTGTGTTTCAATAG |
| CACTTATGCATCTCAAGGTCTAGTGGCTAGCATAAAGAACTTTAAGTCAGTTCTTTATTATCAAAACAATGTTTTTA |
| TGTCTGAAGCAAAATGTTGGACTGAGACTGACCTTACTAAAGGACCTCATGAATTTTGCTCTCAACATACAATGCT |
| AGTTAAACAGGGTGATGATTATGTGTACCTTCCTTACCCAGATCCATCAAGAATCCTAGGGGCCGGCTGTTTTGTA |
| GATGATATCGTAAAAACAGATGGTACACTTATGATTGAACGGTTCGTGTCTTTAGCTATAGATGCTTACCCACTTA |
| CTAAACATCCTAATCAGGAGTATGCTGATGTCTTTCATTTGTACTTACAATACATAAGAAAGCTACATGATGAGTT |
| AACAGGACACATGTTAGACATGTATTCTGTTATGCTTACTAATGATAACACTTCAAGGTATTGGGAACCTGAGTTT |
| TATGAGGCTATGTACACACCGCATACAGTCTTACAGGCTGTTGGGGCTTGTGTTCTTTGCAATTCACAGACTTCATT |
| AAGATGTGGTGCTTGCATACGTAGACCATTCTTATGTTGTAAATGCTGTTACGACCATGTCATATCAACATCACATA |
| AATTAGTCTTGTCTGTTAATCCGTATGTTTGCAATGCTCCAGGTTGTGATGTCACAGATGTGACTCAACTTTACTTA |
| GGAGGTATGAGCTATTATTGTAAATCACATAAACCACCCATTAGTTTTCCATTGTGTGCTAATGGACAAGTTTTTGG |
| TTTATATAAAAATACATGTGTTGGTAGCGATAATGTTACTGACTTTAATGCAATTGCAACATGTGACTGGACAAAT |
| GCTGGTGATTACATTTTAGCTAACACCTGTACTGAAAGACTCAAGCTTTTTGCAGCAGAAACGCTCAAAGCTACTG |
| AGGAGACATTTAAACTGTCTTATGGTATTGCTACTGTACGTGAAGTGCTGTCTGACAGAGAATTACATCTTTCATG |
| GGAAGTTGGTAAACCTAGACCACCACTTAACCGAAATTATGTCTTTACTGGTTATCGTGTAACTAAAAACAGTAAA |
| GTACAAATAGGAGAGTACACCTTTGAAAAAGGTGACTATGGTGATGCTGTTGTTTACCGAGGTACAACAACTTACA |

-continued

SEQUENCE LISTING

AATTAAATGTTGGTGATTATTTTGTGCTGACATCACATACAGTAATGCCATTAAGTGCACCTACACTAGTGCCACA
AGAGCACTATGTTAGAATTACTGGCTTATACCCAACACTCAATATCTCAGATGAGTTTTCTAGCAATGTTGCAAATT
ATCAAAAGGTTGGTATGCAAAAGTATTCTACACTCCAGGGACCACCTGGTACTGGTAAGAGTCATTTTGCTATTGG
CCTAGCTCTCTACTACCCTTCTGCTCGCATAGTGTATACAGCTTGCTCTCATGCCGCTGTTGATGCACTATGTGAGA
AGGCATTAAAATATTTGCCTATAGATAAATGTAGTAGAATTATACCTGCACGTGCTCGTGTAGAGTGTTTTGATAA
ATTCAAAGTGAATTCAACATTAGAACAGTATGTCTTTTGTACTGTAAATGCATTGCCTGAGACGACAGCAGATATA
GTTGTCTTTGATGAAATTTCAATGGCCACAAATTATGATTTGAGTGTTGTCAATGCCAGATTACGTGCTAAGCACTA
TGTGTACATTGGCGACCCTGCTCAATTACCTGCACCACGCACATTGCTAACTAAGGGCACACTAGAACCAGAATAT
TTCAATTCAGTGTGTAGACTTATGAAAACTATAGGTCCAGACATGTTCCTCGGAACTTGTCGGCGTTGTCCTGCTGA
AATTGTTGACACTGTGAGTGCTTTGGTTTATGATAATAAGCTTAAAGCACATAAAGACAAATCAGCTCAATGCTTT
AAAATGTTTTATAAGGGTGTTATCACGCATGATGTTTCATCTGCAATTAACAGGCCACAAATAGGCGTGGTAAGAG
AATTCCTTACACGTAACCCTGCTTGGAGAAAAGCTGTCTTTATTTCACCTTATAATTCACAGAATGCTGTAGCCTCA
AAGATTTTGGGACTACCAACTCAAACTGTTGATTCATCACAGGGCTCAGAATATGACTATGTCATATTCACTCAAA
CCACTGAAACAGCTCACTCTTGTAATGTAAACAGATTTAATGTTGCTATTACCAGAGCAAAAGTAGGCATACTTTG
CATAATGTCTGATAGAGACCTTTATGACAAGTTGCAATTTACAAGTCTTGAAATTCCACGTAGGAATGTGGCAACT
TTACAAGCTGAAAATGTAACAGGACTCTTTAAAGATTGTAGTAAGGTAATCACTGGGTTACATCCTACACAGGCAC
CTACACACCTCAGTGTTGACACTAAATTCAAAACTGAAGGTTTATGTGTTGACATACCTGGCATACCTAAGGACAT
GACCTATAGAAGACTCATCTCTATGATGGGTTTTAAAATGAATTATCAAGTTAATGGTTACCCTAACATGTTTATCA
CCCGCGAAGAAGCTATAAGACATGTACGTGCATGGATTGGCTTCGATGTCGAGGGGTGTCATGCTACTAGAGAAG
CTGTTGGTACCAATTTACCTTTACAGCTAGGTTTTTCTACAGGTGTTAACCTAGTTGCTGTACCTACAGGTTATGTT
GATACACCTAATAATACAGATTTTTCCAGAGTTAGTGCTAAACCACCGCCTGGAGATCAATTTAAACACCTCATAC
CACTTATGTACAAAGGACTTCCTTGGAATGTAGTGCGTATAAAGATTGTACAAATGTTAAGTGACACACTTAAAAA
TCTCTCTGACAGAGTCGTATTTGTCTTATGGGCACATGGCTTTGAGTTGACATCTATGAAGTATTTTGTGAAAATAG
GACCTGAGCGCACCTGTTGTCTATGTGATAGACGTGCCACATGCTTTTCCACTGCTTCAGACACTTATGCCTGTTGG
CATCATTCTATTGGATTTGATTACGTCTATAATCCGTTTATGATTGATGTTCAACAATGGGGTTTTACAGGTAACCT
ACAAAGCAACCATGATCTGTATTGTCAAGTCCATGGTAATGCACATGTAGCTAGTTGTGATGCAATCATGACTAGG
TGTCTAGCTGTCCACGAGTGCTTTGTTAAGCGTGTTGACTGGACTATTGAATATCCTATAATTGGTGATGAACTGAA
GATTAATGCGGCTTGTAGAAAGGTTCAACACATGGTTGTTAAAGCTGCATTATTAGCAGACAAATTCCCAGTTCTT
CACGACATTGGTAACCCTAAAGCTATTAAGTGTGTACCTCAAGCTGATGTAGAATGGAAGTTCTATGATGCACAGC
CTTGTAGTGACAAAGCTTATAAAATAGAAGAATTATTCTATTCTTATGCCACACATTCTGACAAATTCACAGATGG
TGTATGCCTATTTTGGAATTGCAATGTCGATAGATATCCTGCTAATTCCATTGTTTGTAGATTTGACACTAGAGTGC
TATCTAACCTTAACTTGCCTGGTTGTGATGGTGGCAGTTTGTATGTAAATAAACATGCATTCCACACACCAGCTTTT
GATAAAAGTGCTTTTGTTAATTTAAAACAATTACCATTTTTCTATTACTCTGACAGTCCATGTGAGTCTCATGGAAA
ACAAGTAGTGTCAGATATAGATTATGTACCACTAAAGTCTGCTACGTGTATAACACGTTGCAATTTAGGTGGTGCT
GTCTGTAGACATCATGCTAATGAGTACAGATTGTATCTCGATGCTTATAACATGATGATCTCAGCTGGCTTTAGCTT
GTGGGTTTACAAACAATTTGATACTTATAACCTCTGGAACACTTTTACAAGACTTCAGAGTTTAGAAAATGTGGCT
TTTAATGTTGTAAATAAGGGACACTTTGATGGACAACAGGGTGAAGTACCAGTTTCTATCATTAATAACACTGTTT
ACACAAAAGTTGATGGTGTTGATGTAGAATTGTTTGAAAATAAAACAACATTACCTGTTAATGTAGCATTTGAGCT
TTGGGCTAAGCGCAACATTAAACCAGTACCAGAGGTGAAAATACTCAATAATTTGGGTGTGGACATTGCTGCTAAT
ACTGTGATCTGGGACTACAAAAGAGATGCTCCAGCACATATATCTACTATTGGTGTTTGTTCTATGACTGACATAG
CCAAGAAACCAACTGAAACGATTTGTGCACCACTCACTGTCTTTTTTGATGGTAGAGTTGATGGTCAAGTAGACTT
ATTTAGAAATGCCCGTAATGGTGTTCTTATTACAGAAGGTAGTGTTAAAGGTTTACAACCATCTGTAGGTCCCAAA
CAAGCTAGTCTTAATGGAGTCACATTAATTGGAGAAGCCGTAAAAACACAGTTCAATTATTATAAGAAAGTTGATG
GTGTTGTCCAACAATTACCTGAAACTTACTTTACTCAGAGTAGAAATTTACAAGAATTTAAACCCAGGAGTCAAAT
GGAAATTGATTTCTTAGAATTAGCTATGGATGAATTCATTGAACGGTATAAATTAGAAGGCTATGCCTTCGAACAT
ATCGTTTATGGAGATTTTAGTCATAGTCAGTTAGGTGGTTTACATCTACTGATTGGACTAGCTAAACGTTTTAAGGA
ATCACCTTTTGAATTAGAAGATTTTATTCCTATGGACAGTACAGTTAAAAACTATTTCATAACAGATGCGCAAACA
GGTTCATCTAAGTGTGTGTGTTCTGTTATTGATTTATTACTTGATGATTTTGTTGAAATAATAAAATCCCAAGATTT
ATCTGTAGTTTCTAAGGTTGTCAAAGTGACTATTGACTATACAGAAATTTCATTTATGCTTTGGTGTAAAGATGGCC
ATGTAGAAACATTTTACCCAAAATTACAATCTAGTCAAGCGTGGCAACCGGGTGTTGCTATGCCTAATCTTTACAA
AATGCAAAGAATGCTATTAGAAAAGTGTGACCTTCAAAATTATGGTGATAGTGCAACATTACCTAAAGGCATAAT

-continued

SEQUENCE LISTING

GATGAATGTCGCAAAATATACTCAACTGTGTCAATATTTAAACACATTAACATTAGCTGTACCCTATAATATGAGA
GTTATACATTTTGGTGCTGGTTCTGATAAAGGAGTTGCACCAGGTACAGCTGTTTTAAGACAGTGGTTGCCTACGG
GTACGCTGCTTGTCGATTCAGATCTTAATGACTTTGTCTCTGATGCAGATTCAACTTTGATTGGTGATTGTGCAACT
GTACATACAGCTAATAAATGGGATCTCATTATTAGTGATATGTACGACCCTAAGACTAAAAATGTTACAAAAGAA
AATGACTCTAAAGAGGGTTTTTTCACTTACATTTGTGGGTTTATACAACAAAAGCTAGCTCTTGGAGGTTCCGTGGC
TATAAAGATAACAGAACATTCTTGGAATGCTGATCTTTATAAGCTCATGGGACACTTCGCATGGTGGACAGCCTTT
GTTACTAATGTGAATGCGTCATCATCTGAAGCATTTTTAATTGGATGTAATTATCTTGGCAAACCACGCGAACAAA
TAGATGGTTATGTCATGCATGCAAATTACATATTTGGAGGAATACAAATCCAATTCAGTTGTCTTCCTATTCTTTA
TTTGACATGAGTAAATTTCCCCTTAAATTAAGGGGTACTGCTGTTATGTCTTTAAAAGAAGGTCAAATCAATGATA
TGATTTTATCTCTTCTTAGTAAAGGTAGACTTATAATTAGAGAAAACAACAGAGTTGTTATTTCTAGTGATGTTCTT
GTTAACAACTAAACGAACAATGTTTGTTTTTCTTGTTTTATTGCCACTAGTCTCTAGTCAGTGTGTTAATCTTACAAC
CAGAACTCAATTACCCCCTGCATACACTAATTCTTTCACACGTGGTGTTTATTACCCTGACAAAGTTTTCAGATCCT
CAGTTTTACATTCAACTCAGGACTTGTTCTTACCTTTCTTTTCCAATGTTACTTGGTTCCATGCTATACATGTCTCTG
GGACCAATGGTACTAAGAGGTTTGATAACCCTGTCCTACCATTTAATGATGGTGTTTATTTTGCTTCCACTGAGAAG
TCTAACATAATAAGAGGCTGGATTTTTGGTACTACTTTAGATTCGAAGACCCAGTCCCTACTTATTGTTAATAACGC
TACTAATGTTGTTATTAAAGTCTGTGAATTTCAATTTTGTAATGATCCATTTTTGGGTGTTTATTACCACAAAAACA
ACAAAAGTTGGATGGAAAGTGAGTTCAGAGTTTATTCTAGTGCGAATAATTGCACTTTTGAATATGTCTCTCAGCC
TTTTCTTATGGACCTTGAAGGAAAACAGGGTAATTTCAAAAATCTTAGGGAATTTGTGTTTAAGAATATTGATGGT
TATTTTAAAATATATTCTAAGCACACGCCTATTAATTTAGTGCGTGATCTCCCTCAGGGTTTTTCGGCTTTAGAACC
ATTGGTAGATTTGCCAATAGGTATTAACATCACTAGGTTTCAAACTTTACTTGCTTTACATAGAAGTTATTTGACTC
CTGGTGATTCTTCTTCAGGTTGGACAGCTGGTGCTGCAGCTTATTATGTGGGTTATCTTCAACCTAGGACTTTTCTA
TTAAAATATAATGAAAATGGAACCATTACAGATGCTGTAGACTGTGCACTTGACCCTCTCTCAGAAACAAAGTGTA
CGTTGAAATCCTTCACTGTAGAAAAAGGAATCTATCAAACTTCTAACTTTAGAGTCCAACCAACAGAATCTATTGT
TAGATTTCCTAATATTACAAACTTGTGCCCTTTTGGTGAAGTTTTTAACGCCACCAGATTTGCATCTGTTTATGCTTG
GAACAGGAAGAGAATCAGCAACTGTGTTGCTGATTATTCTGTCCTATATAATTCCGCATCATTTTCCACTTTTAAGT
GTTATGGAGTGTCTCCTACTAAATTAAATGATCTCTGCTTTACTAATGTCTATGCAGATTCATTTGTAATTAGAGGT
GATGAAGTCAGACAAATCGCTCCAGGGCAAACTGGAAAGATTGCTGATTATAATTATAAATTACCAGATGATTTTA
CAGGCTGCGTTATAGCTTGGAATTCTAACAATCTTGATTCTAAGGTTGGTGGTAATTATAATTACCTGTATAGATTG
TTTAGGAAGTCTAATCTCAAACCTTTTGAGAGAGATATTTCAACTGAAATCTATCAGGCCGGTAGCACACCTTGTA
ATGGTGTTGAAGGTTTTAATTGTTACTTTCCTTTACAATCATATGGTTTCCAACCCACTAATGGTGTTGGTTACCAA
CCATACAGAGTAGTAGTACTTTCTTTTGAACTTCTACATGCACCAGCAACTGTTTGTGGACCTAAAAAGTCTACTAA
TTTGGTTAAAAACAAATGTGTCAATTTCAACTTCAATGGTTTAACAGGCACAGGTGTTCTTACTGAGTCTAACAAA
AAGTTTCTGCCTTTCCAACAATTTGGCAGAGACATTGCTGACACTACTGATGCTGTCCGTGATCCACAGACACTTG
AGATTCTTGACATTACACCATGTTCTTTTGGTGGTGTCAGTGTTATAACACCAGGAACAAATACTTCTAACCAGGTT
GCTGTTCTTTATCAGGATGTTAACTGCACAGAAGTCCCTGTTGCTATTCATGCAGATCAACTTACTCCTACTTGGCG
TGTTTATTCTACAGGTTCTAATGTTTTTCAAACACGTGCAGGCTGTTTAATAGGGGCTGAACATGTCAACAACTCAT
ATGAGTGTGACATACCCATTGGTGCAGGTATATGCGCTAGTTATCAGACTCAGACTAATTCTCCTCGGGGGCACG
TAGTGTAGCTAGTCAATCCATCATTGCCTACACTATGTCACTTGGTGCAGAAAATTCAGTTGCTTACTCTAATAACT
CTATTGCCATACCCACAAATTTTACTATTAGTGTTACCACAGAAATTCTACCAGTGTCTATGACCAAGACATCAGTA
GATTGTACAATGTACATTTGTGGTGATTCAACTGAATGCAGCAATCTTTTGTTGCAATATGGCAGTTTTTGTACACA
ATTAAACCGTGCTTTAACTGGAATAGCTGTTGAACAAGACAAAAACACCCAAGAAGTTTTTGCACAAGTCAAACA
AATTTACAAAACACCACCAATTAAAGATTTTGGTGGTTTTAATTTTTCACAAATATTACCAGATCCATCAAAACCA
AGCAAGAGGTCATTTATTGAAGATCTACTTTTCAACAAAGTGACACTTGCAGATGCTGGCTTCATCAAACAATATG
GTGATTGCCTTGGTGATATTGCTGCTAGAGACCTCATTTGTGCACAAAAGTTTAACGGCCTTACTGTTTTGCCACCT
TTGCTCACAGATGAAATGATTGCTCAATACACTTCTGCACTGTTAGCGGGTACAATCACTTCTGGTTGGACCTTTGG
TGCAGGTGCTGCATTACAAATACCATTTGCTATGCAAATGGCTTATAGGTTTAATGGTATTGGAGTTACACAGAAT
GTTCTCTATGAGAACCAAAAATTGATTGCCAACCAATTTAATAGTGCTATTGGCAAAATTCAAGACTCACTTTCTTC
CACAGCAAGTGCACTTGGAAAACTTCAAGATGTGGTCAACCAAAATGCACAAGCTTTAAACACGCTTGTTAAACA
ACTTAGCTCCAATTTTGGTGCAATTTCAAGTGTTTTAAATGATATCCTTTCACGTCTTGACAAAGTTGAGGCTGAAG
TGCAAATTGATAGGTTGATCACAGGCAGACTTCAAAGTTTGCAGACATATGTGACTCAACAATTAATTAGAGCTGC
AGAAATCAGAGCTTCTGCTAATCTTGCTGCTACTAAAATGTCAGAGTGTGTACTTGGACAATCAAAAAGAGTTGAT

-continued

SEQUENCE LISTING

TTTTGTGGAAAGGGCTATCATCTTATGTCCTTCCCTCAGTCAGCACCTCATGGTGTAGTCTTCTTGCATGTGACTTAT
GTCCCTGCACAAGAAAAGAACTTCACAACTGCTCCTGCCATTTGTCATGATGGAAAAGCACACTTTCCTCGTGAAG
GTGTCTTTGTTTCAAATGGCACACACTGGTTTGTAACACAAAGGAATTTTTATGAACCACAAATCATTACTACAGA
CAACACATTTGTGTCTGGTAACTGTGATGTTGTAATAGGAATTGTCAACAACACAGTTTATGATCCTTTGCAACCTG
AATTAGACTCATTCAAGGAGGAGTTAGATAAATATTTTAAGAATCATACATCACCAGATGTTGATTTAGGTGACAT
CTCTGGCATTAATGCTTCAGTTGTAAACATTCAAAAAGAAATTGACCGCCTCAATGAGGTTGCCAAGAATTTAAAT
GAATCTCTCATCGATCTCCAAGAACTTGGAAAGTATGAGCAGTATATAAAATGGCCATGGTACATTTGGCTAGGTT
TTATAGCTGGCTTGATTGCCATAGTAATGGTGACAATTATGCTTTGCTGTATGACCAGTTGCTGTAGTTGTCTCAAG
GGCTGTTGTTCTTGTGGATCCTGCTGCAAATTTGATGAAGACGACTCTGAGCCAGTGCTCAAAGGAGTCAAATTAC
ATTACACATAAACGAACTTATGGATTTGTTTATGAGAATCTTCACAATTGGAACTGTAACTTTGAAGCAAGGTGAA
ATCAAGGATGCTACTCCTTCAGATTTTGTTCGCGCTACTGCAACGATACCGATACAAGCCTCACTCCCTTTCGGATG
GCTTATTGTTGGCGTTGCACTTCTTGCTGTTTTTCAGAGCGCTTCCAAAATCATAACCCTCAAAAAGAGATGGCAAC
TAGCACTCTCCAAGGGTGTTCACTTTGTTTGCAACTTGCTGTTGTTGTTTGTAACAGTTTACTCACACCTTTTGCTCG
TTGCTGCTGGCCTTGAAGCCCCTTTTCTCTATCTTTATGCTTTAGTCTACTTCTTGCAGAGTATAAACTTTGTAAGAA
TAATAATGAGGCTTTGGCTTTGCTGGAAATGCCGTTCCAAAAACCCATTACTTTATGATGCCAACTATTTTCTTTGC
TGGCATACTAATTGTTACGACTATTGTATACCTTACAATAGTGTAACTTCTTCAATTGTCATTACTTCAGGTGATGG
CACAACAAGTCCTATTTCTGAACATGACTACCAGATTGGTGGTTATACTGAAAAATGGGAATCTGGAGTAAAAGA
CTGTGTTGTATTACACAGTTACTTCACTTCAGACTATTACCAGCTGTACTCAACTCAATTGAGTACAGACACTGGTG
TTGAACATGTTACCTTCTTCATCTACAATAAAATTGTTGATGAGCCTGAAGAACATGTCCAAATTCACACAATCGA
CGGTTCATCCGGAGTTGTTAATCCAGTAATGGAACCAATTTATGATGAACCGACGACGACTACTAGCGTGCCTTTG
TAAGCACAAGCTGATGAGTACGAACTTATGTACTCATTCGTTTCGGAAGAGACAGGTACGTAAATAGTTAATAGCT
GACTTCTTTTTCTTGCTTTCGTGTGATTCTTGCTAGTTACACTAGCCATCCTTACTGCGCTTCGATTGTGTGCGTACT
GCTGCAATATTGTTAACGTGAGTCTTGTAAAACCTTCTTTTTACGTTTACTCTCGTGTTAAAAATCTGAATTCTTCTA
GAGTTCCTGATCTTCTGGTCTAAACGAACTAAATATTATATTAGTTTTTCTGTTTGGAACTTTAATTTTAGCCATGGC
AGATTCCAACGGTACTATTACCGTTGAAGAGCTTAAAAAGCTCCTTGAACAATGGAACCTAGTAATAGGTTTCCTA
TTCCTTACATGGATTTGTCTTCTACAATTTGCCTATGCCAACAGGAATAGGTTTTTGTATATAATTAAGTTAATTTTC
CTCTGGCTGTTATGGCCAGTAACTTTAGCTTGTTTTGTGCTTGCTGCTGTTTACAGAATAAATTGGATCACCGGTGG
AATTGCTATCGCAATGGCTTGTCTTGTAGGCTTGATGTGGCTCAGCTACTTCATTGCTTCTTTCAGACTGTTTGCGC
GTACGCGTTCCATGTGGTCATTCAATCCAGAAACTAACATTCTTCTCAACGTGCCACTCCATGGCACTATTCTGACC
AGACCGCTTCTAGAAAGTGAACTCGTAATCGGAGCTGTGATCCTTCGTGGACATCTTCGTATTGCTGGACACCATC
TAGGACGCTGTGACATCAAGGACCTGCCTAAAGAAATCACTGTTGCTACATCACGAACGCTTTCTTATTACAAATT
GGGAGCTTCGCAGCGTGTAGCAGGTGACTCAGGTTTTGCTGCATACAGTCGCTACAGGATTGGCAACTATAAATTA
AACACAGACCATTCCAGTAGCAGTGACAATATTGCTTTGCTTGTACAGTAAGTGACAACAGATGTTTCATCTCGTT
GACTTTCAGGTTACTATAGCAGAGATATTACTAATTATTATGAGGACTTTTAAAGTTTCCATTTGGAATCTTGATTA
CATCATAAACCTCATAATTAAAAATTTATCTAAGTCACTAACTGAGAATAAATATTCTCAATTAGATGAAGAGCAA
CCAATGGAGATTGATTAAACGAACATGAAAATTATTCTTTTCTTGGCACTGATAACACTCGCTACTTGTGAGCTTTA
TCACTACCAAGAGTGTGTTAGAGGTACAACAGTACTTTTAAAAGAACCTTGCTCTTCTGGAACATACGAGGGCAAT
TCACCATTTCATCCTCTAGCTGATAACAAATTTGCACTGACTTGCTTTAGCACTCAATTTGCTTTTGCTTGTCCTGAC
GGCGTAAAACACGTCTATCAGTTACGTGCCAGATCAGTTTCACCTAAACTGTTCATCAGACAAGAGGAAGTTCAAG
AACTTTACTCTCCAATTTTTCTTATTGTTGCGGCAATAGTGTTTATAACACTTTGCTTCACACTCAAAAGAAAGACA
GAATGATTGAACTTTCATTAATTGACTTCTATTTGTGCTTTTTAGCCTTTCTGCTATTCCTTGTTTTAATTATGCTTAT
TATCTTTTGGTTCTCACTTGAACTGCAAGATCATAATGAAACTTGTCACGCCTAAACGAACatgaacaacaggtggatcctccacg
ctgcgttcctgctgtgcttctccaccacagccctctccatcaactataagcagctccagctccaagaaaggacgaacattcggaaatgtcaggagctcctggagcagctgaatggaaagatca
acctcacctacagggcggacttcaagatccctatggagatgacggagaagatgcagaagagttacactgcctttgccatccaagagatgctccagaatgtctttettgtcttcagaaacaatttc
tccagcactgggtggaatgagactattgttgtacgtctcctggatgaactccaccagcagacagtgtttctgaagacagtactagaggaaaagcaagaggaaagattgacgtgggagatgtc
ctcaactgctctccacttgaagagctattactggagggtocaaaggtaccttaaactcatgaagtacaacagctacgcctggatggtggtccgagcagagatcttcaggaactttctcatcattc
gaagacttaccagaaacttccaaaactgaGACGTTCGTGTTGTTTTAGATTTCATCTAAACGAACAAACTAAAATGTCTGATAATGG
ACCCCAAAATCAGCGAAATGCACCCCGCATTACGTTTGGTGGACCCTCAGATTCAACTGGCAGTAACCAGAATGG
AGAACGCAGTGGGGCGCGATCAAAACAACGTCGGCCCCAAGGTTTACCCAATAATACTGCGTCTTGGTTCACCGC
TCTCACTCAACATGGCAAGGAAGACCTTAAATTCCCTCGAGGACAAGGCGTTCCAATTAACACCAATAGCAGTCC
AGATGACCAAATTGGCTACTACCGAAGAGCTACCAGACGAATTCGTGGTGGTGACGGTAAAATGAAAGATCTCAG -continued

SEQUENCE LISTING

TCCAAGATGGTATTTCTACTACCTAGGAACTGGGCCAGAAGCTGGACTTCCCTATGGTGCTAACAAAGACGGCATC
ATATGGGTTGCAACTGAGGGAGCCTTGAATACACCAAAAGATCACATTGGCACCCGCAATCCTGCTAACAATGCT
GCAATCGTGCTACAACTTCCTCAAGGAACAACATTGCCAAAAGGCTTCTACGCAGAAGGGAGCAGAGGCGGCAGT
CAAGCCTCTTCTCGTTCCTCATCACGTAGTCGCAACAGTTCAAGAAATTCAACTCCAGGCAGCAGTAGGGGAACTT
CTCCTGCTAGAATGGCTGGCAATGGCGGTGATGCTGCTCTTGCTTTGCTGCTGCTTGACAGATTGAACCAGCTTGA
GAGCAAAATGTCTGGTAAAGGCCAACAACAACAAGGCCAAACTGTCACTAAGAAATCTGCTGCTGAGGCTTCTAA
GAAGCCTCGGCAAAAACGTACTGCCACTAAAGCATACAATGTAACACAAGCTTTCGGCAGACGTGGTCCAGAACA
AACCCAAGGAAATTTTGGGGACCAGGAACTAATCAGACAAGGAACTGATTACAAACATTGGCCGCAAATTGCACA
ATTTGCCCCCAGCGCTTCAGCGTTCTTCGGAATGTCGCGCATTGGCATGGAAGTCACACCTTCGGGAACGTGGTTG
ACCTACACAGGTGCCATCAAATTGGATGACAAAGATCCAAATTTCAAAGATCAAGTCATTTTGCTGAATAAGCATA
TTGACGCATACAAAACATTCCCACCAACAGAGCCTAAAAAGGACAAAAAGAAGAAGGCTGATGAAACTCAAGCC
TTACCGCAGAGACAGAAGAAACAGCAAACTGTGACTCTTCTTCCTGCTGCAGATTTGGATGATTTCTCCAAACAAT
TGCAACAATCCATGAGCAGTGCTGACTCAACTCAGGCCTAAACTCATGCAGACCACACAAGGCAGATGGGCTATA
TAAACGTTTTCGCTTTTCCGTTTACGATATATAGTCTACTCTTGTGCAGAATGAATTCTCGTAACTACATAGCACAA
GTAGATGTAGTTAACTTTAATCTCACATAGCAATCTTTAATCAGTGTGTAACATTAGGGAGGACTTGAAAGAGCCA
CCACATTTTCACCGAGGCCACGCGGAGTACGATCGAGTGTACAGTGAACAATGCTAGGGAGAGCTGCCTATATGG
AAGAGCCCTAATGTGTAAAATTAATTTTAGTAGTGCTATCCCCATGTGATTTTAATAGCTTCTTAGGAGAATGACA
AAAAAAAAAAAAAAAAAAAA

SEQ ID NO: 9 (synthetic IBIS DNA construct 2; mouse IFN-beta transgene underlined)
ATTAAAGGTTTATACCTTCCCAGGTAACAAACCAACCAACTTTCGATCTCTTGTAGATCTGTTCTCTAAACGAACTT
TAAAATCTGTGTGGCTGTCACTCGGCTGCATGCTTAGTGCACTCACGCAGTATAATTAATAACTAATTACTGTCGTT
GACAGGACACGAGTAACTCGTCTATCTTCTGCAGGCTGCTTACGGTTTCGTCCGTGTTGCAGCCGATCATCAGCAC
ATCTAGGTTTCGTCCGGGTGTGACCGAAAGGTAAGATGGAGAGCCTTGTCCCTGGTTTCAACGAGAAAACACACGT
CCAACTCAGTTTGCCTGTTTTACAGGTTCGCGACGTGCTCGTACGTGGCTTTGGAGACTCCGTGGAGGAGGTCTTAT
CAGAGGCACGTCAACATCTTAAAGATGGCACTTGTGGCTTAGTAGAAGTTGAAAAAGGCGTTTTGCCTCAACTTGA
ACAGCCCTATGTGTTCATCAAACGTTCGGATGCTCGAACTGCACCTCATGGTCATGTTATGGTTGAGCTGGTAGCA
GAACTCGAAGGCATTCAGTACGGTCGTAGTGGTGAGACACTTGGTGTCCTTGTCCCTCATGTGGGCGAAATACCAG
TGGCTTACCGCAAGGTTCTTCTTCGTAAGAACGGTAATAAAGGAGCTGGTGGCCATAGTTACGGCGCCGATCTAAA
GTCATTTGACTTAGGCGACGAGCTTGGCACTGATCCTTATGAAGATTTTCAAGAAAACTGGAACACTAAACATAGC
AGTGGTGTTACCCGTGAACTCATGCGTGAGCTTAACGGAGGGGCATACACTCGCTATGTCGATAACAACTTCTGTG
GCCCTGATGGCTACCCTCTTGAGTGCATTAAAGACCTTCTAGCACGTGCTGGTAAAGCTTCATGCACTTTGTCCGAA
CAACTGGACTTTATTGACACTAAGAGGGGTGTATACTGCTGCCGTGAACATGAGCATGAAATTGCTTGGTACACGG
AACGTTCTGAAAAGAGCTATGAATTGCAGACACCTTTTGAAATTAAATTGGCAAAGAAATTTGACACCTTCAATGG
GGAATGTCCAAATTTTGTATTTCCCTTAAATTCCATAATCAAGACTATTCAACCAAGGGTTGAAAAGAAAAAGCTT
GATGGCTTTATGGGTAGAATTCGATCTGTCTATCCAGTTGCGTCACCAAATGAATGCAACCAAATGTGCCTTTCAA
CTCTCATGAAGTGTGATCATTGTGGTGAAACTTCATGGCAGACGGGCGATTTTGTTAAAGCCACTTGCGAATTTTGT
GGCACTGAGAATTTGACTAAAGAAGGTGCCACTACTTGTGGTTACTTACCCCAAAATGCTGTTGTTAAAATTTATT
GTCCAGCATGTCACAATTCAGAAGTAGGACCTGAGCATAGTCTTGCCGAATACCATAATGAATCTGGCTTGAAAAC
CATTCTTCGTAAGGGTGGTCGCACTATTGCCTTTGGAGGCTGTGTGTTCTCTTATGTTGGTTGCCATAACAAGTGTG
CCTATTGGGTTCCACGTGCTAGCGCTAACATAGGTTGTAACCATACAGGTGTTGTTGGAGAAGGTTCCGAAGGTCT
TAATGACAACCTTCTTGAAATACTCCAAAAAGAGAAAGTCAACATCAATATTGTTGGTGACTTTAAACTTAATGAA
GAGATCGCCATTATTTTGGCATCTTTTTCTGCTTCCACAAGTGCTTTTGTGGAAACTGTGAAAGGTTTGGATTATAA
AGCATTCAAACAAATTGTTGAATCCTGTGGTAATTTTAAAGTTACAAAAGGAAAAGCTAAAAAAGGTGCCTGGAA
TATTGGTGAACAGAAATCAATACTGAGTCCTCTTTATGCATTTGCATCAGAGGCTGCTCGTGTTGTACGATCAATTT
TCTCCCGCACTCTTGAAACTGCTCAAAATTCTGTGCGTGTTTTACAGAAGGCCGCTATAACAATACTAGATGGAAT
TTCACAGTATTCACTGAGACTCATTGATGCTATGATGTTCACATCTGATTTGGCTACTAACAATCTAGTTGTAATGG
CCTACATTACAGGTGGTGTTGTTCAGTTGACTTCGCAGTGGCTAACTAACATCTTTGGCACTGTTTATGAAAAACTC
AAACCCGTCCTTGATTGGCTTGAAGAGAAGTTTAAGGAAGGTGTAGAGTTTCTTAGAGACGGTTGGGAAATTGTTA
AATTTATCTCAACCTGTGCTTGTGAAATTGTCGGTGGACAAATTGTCACCTGTGCAAAGGAAATTAAGGAGAGTGT
TCAGACATTCTTTAAGCTTGTAAATAAATTTTTGGCTTTGTGTGCTGACTCTATCATTATTGGTGGAGCTAAACTTA -continued

| SEQUENCE LISTING |
|---|
| AAGCCTTGAATTTAGGTGAAACATTTGTCACGCACTCAAAGGGATTGTACAGAAAGTGTGTTAAATCCAGAGAAG<br>AAACTGGCCTACTCATGCCTCTAAAAGCCCCAAAAGAAATTATCTTCTTAGAGGGAGAAACACTTCCCACAGAAGT<br>GTTAACAGAGGAAGTTGTCTTGAAAACTGGTGATTTACAACCATTAGAACAACCTACTAGTGAAGCTGTTGAAGCT<br>CCATTGGTTGGTACACCAGTTTGTATTAACGGGCTTATGTTGCTCGAAATCAAAGACACAGAAAAGTACTGTGCCC<br>TTGCACCTAATATGATGGTAACAAACAATACCTTCACACTCAAAGGCGGTGCACCAACAAAGGTTACTTTTGGTGA<br>TGACACTGTGATAGAAGTGCAAGGTTACAAGAGTGTGAATATCACTTTTGAACTTGATGAAAGGATTGATAAAGT<br>ACTTAATGAGAAGTGCTCTGCCTATACAGTTGAACTCGGTACAGAAGTAAATGAGTTCGCCTGTGTTGTGGCAGAT<br>GCTGTCATAAAAACTTTGCAACCAGTATCTGAATTACTTACACCACTGGGCATTGATTTAGATGAGTGGAGTATGG<br>CTACATACTACTTATTTGATGAGTCTGGTGAGTTTAAATTGGCTTCACATATGTATTGTTCTTTCTACCCTCCAGATG<br>AGGATGAAGAAGAAGGTGATTGTGAAGAAGAAGAGTTTGAGCCATCAACTCAATATGAGTATGGTACTGAAGATG<br>ATTACCAAGGTAAACCTTTGGAATTTGGTGCCACTTCTGCTGCTCTTCAACCTGAAGAAGAGCAAGAAGAAGATTG<br>GTTAGATGATGATAGTCAACAAACTGTTGGTCAACAAGACGGCAGTGAGGACAATCAGACAACTACTATTCAAAC<br>AATTGTTGAGGTTCAACCTCAATTAGAGATGGAACTTACACCAGTTGTTCAGACTATTGAAGTGAATAGTTTTAGT<br>GGTTATTTAAAACTTACTGACAATGTATACATTAAAAATGCAGACATTGTGGAAGAAGCTAAAAAGGTAAAACCA<br>ACAGTGGTTGTTAATGCAGCCAATGTTTACCTTAAACATGGAGGAGGTGTTGCAGGAGCCTTAAATAAGGCTACTA<br>ACAATGCCATGCAAGTTGAATCTGATGATTACATAGCTACTAATGGACCACTTAAAGTGGGTGGTAGTTGTGTTTT<br>AAGCGGACACAATCTTGCTAAACACTGTCTTCATGTTGTCGGCCCAAATGTTAACAAAGGTGAAGACATTCAACTT<br>CTTAAGAGTGCTTATGAAAATTTTAATCAGCACGAAGTTCTACTTGCACCATTATTATCAGCTGGTATTTTTGGTGC<br>TGACCCTATACATTCTTTAAGAGTTTGTGTAGATACTGTTCGCACAAATGTCTACTTAGCTGTCTTTGATAAAAATC<br>TCTATGACAAACTTGTTTCAAGCTTTTTGGAAATGAAGAGTGAAAAGCAAGTTGAACAAAAGATCGCTGAGATTCC<br>TAAAGAGGAAGTTAAGCCATTTATAACTGAAAGTAAACCTTCAGTTGAACAGAGAAAACAAGATGATAAGAAAAT<br>CAAAGCTTGTGTTGAAGAAGTTACAACAACTCTGGAAGAAACTAAGTTCCTCACAGAAAACTTGTTACTTTATATT<br>GACATTAATGGCAATCTTCATCCAGATTCTGCCACTCTTGTTAGTGACATTGACATCACTTTCTTAAAGAAAGATGC<br>TCCATATATAGTGGGTGATGTTGTTCAAGAGGGTGTTTTAACTGCTGTGGTTATACCTACTAAAAAGGCTGGTGGC<br>ACTACTGAAATGCTAGCGAAAGCTTTGAGAAAAGTGCCAACAGACAATTATATAACCACTTACCCGGGTCAGGGT<br>TTAAATGGTTACACTGTAGAGGAGGCAAAGACAGTGCTTAAAAAGTGTAAAAGTGCCTTTTACATTCTACCATCTA<br>TTATCTCTAATGAGAAGCAAGAAATTCTTGGAACTGTTTCTTGGAATTTGCGAGAAATGCTTGCACATGCAGAAGA<br>AACACGCAAATTAATGCCTGTCTGTGTGGAAACTAAAGCCATAGTTTCAACTATACAGCGTAAATATAAGGGTATT<br>AAAATACAAGAGGGTGTGGTTGATTATGGTGCTAGATTTTACTTTTACACCAGTAAAACAACTGTAGCGTCACTTA<br>TCAACACACTTAACGATCTAAATGAAACTCTTGTTACAATGCCACTTGGCTATGTAACACATGGCTTAAATTTGGA<br>AGAAGCTGCTCGGTATATGAGATCTCTCAAAGTGCCAGCTACAGTTTCTGTTTCTTCACCTGATGCTGTTACAGCGT<br>ATAATGGTTATCTTACTTCTTCTTCTAAAACACCTGAAGAACATTTTATTGAAACCATCTCACTTGCTGGTTCCTAT<br>AAAGATTGGTCCTATTCTGGACAATCTACACAACTAGGTATAGAATTTCTTAAGAGAGGTGATAAAAGTGTATATT<br>ACACTAGTAATCCTACCACATTCCACCTAGATGGTGAAGTTATCACCTTTGACAATCTTAAGACACTTCTTTCTTTG<br>AGAGAAGTGAGGACTATTAAGGTGTTTACAACAGTAGACAACATTAACCTCCACACGCAAGTTGTGGACATGTCA<br>ATGACATATGGACAACAGTTTGGTCCAACTTATTTGGATGGAGCTGATGTTACTAAAATAAAACCTCATAATTCAC<br>ATGAAGGTAAAACATTTTATGTTTTACCTAATGATGACACTCTACGTGTTGAGGCTTTTGAGTACTACCACACAACT<br>GATCCTAGTTTTCTGGGTAGGTACATGTCAGCATTAAATCACACTAAAAAGTGGAAATACCCACAAGTTAATGGTT<br>TAACTTCTATTAAATGGGCAGATAACAACTGTTATCTTGCCACTGCATTGTTAACACTCCAACAAATAGAGTTGAA<br>GTTTAATCCACCTGCTCTACAAGATGCTTATTACAGAGCAAGGGCTGGTGAAGCTGCTAACTTTTGTGCACTTATCT<br>TAGCCTACTGTAATAAGACAGTAGGTGAGTTAGGTGATGTTAGAGAAACAATGAGTTACTTGTTTCAACATGCCAA<br>TTTAGATTCTTGCAAAAGAGTCTTGAACGTGGTGTGTAAAACTTGTGGACAACAGCAGACAACCCTTAAGGGTGTA<br>GAAGCTGTTATGTACATGGGCACACTTTCTTATGAACAATTTAAGAAAGGTGTTCAGATACCTTGTACGTGTGGTA<br>AACAAGCTACAAAATATCTAGTACAACAGGAGTCACCTTTTGTTATGATGTCAGCACCACCTGCTCAGTATGAACT<br>TAAGCATGGTACATTTACTTGTGCTAGTGAGTACACTGGTAATTACCAGTGTGGTCACTATAAACATATAACTTCTA<br>AAGAAACTTTGTATTGCATAGACGGTGCTTTACTTACAAAGTCCTCAGAATACAAAGGTCCTATTACGGATGTTTT<br>CTACAAAGAAAACAGTTACACAACAACCATAAAACCAGTTACTTATAAATTGGATGGTGTTGTTTGTACAGAAATT<br>GACCCTAAGTTGGACAATTATTATAAGAAAGACAATTCTTATTTCACAGAGCAACCAATTGATCTTGTACCAAACC<br>AACCATATCCAAACGCAAGCTTCGATAATTTTAAGTTTGTATGTGATAATATCAAATTTGCTGATGATTTAAACCA<br>GTTAACTGGTTATAAGAAACCTGCTTCAAGAGAGCTTAAAGTTACATTTTTCCCTGACTTAAATGGTGATGTGGTG<br>GCTATTGATTATAAACACTACACACCCTCTTTTAAGAAAGGAGCTAAATTGTTACATAAACCTATTGTTTGGCATGT |

-continued

| SEQUENCE LISTING |
|---|
| TAACAATGCAACTAATAAAGCCACGTATAAACCAAATACCTGGTGTATACGTTGTCTTTGGAGCACAAAACCAGTT<br>GAAACATCAAATTCGTTTGATGTACTGAAGTCAGAGGACGCGCAGGGAATGGATAATCTTGCCTGCGAAGATCTA<br>AAACCAGTCTCTGAAGAAGTAGTGGAAAATCCTACCATACAGAAAGACGTTCTTGAGTGTAATGTGAAAACTACC<br>GAAGTTGTAGGAGACATTATACTTAAACCAGCAAATAATAGTTTAAAAATTACAGAAGAGGTTGGCCACACAGAT<br>CTAATGGCTGCTTATGTAGACAATTCTAGTCTTACTATTAAGAAACCTAATGAATTATCTAGAGTATTAGGTTTGAA<br>AACCCTTGCTACTCATGGTTTAGCTGCTGTTAATAGTGTCCCTTGGGATACTATAGCTAATTATGCTAAGCCTTTTC<br>TTAACAAAGTTGTTAGTACAACTACTAACATAGTTACACGGTGTTTAAACCGTGTTTGTACTAATTATATGCCTTAT<br>TTCTTTACTTTATTGCTACAATTGTGTACTTTTACTAGAAGTACAAATTCTAGAATTAAAGCATCTATGCCGACTAC<br>TATAGCAAAGAATACTGTTAAGAGTGTCGGTAAATTTTGTCTAGAGGCTTCATTTAATTATTTGAAGTCACCTAATT<br>TTTCTAAACTGATAAATATTATAATTTGGTTTTTACTATTAAGTGTTTGCCTAGGTTCTTTAATCTACTCAACCGCTG<br>CTTTAGGTGTTTTAATGTCTAATTTAGGCATGCCTTCTTACTGTACTGGTTACAGAGAAGGCTATTTGAACTCTACT<br>AATGTCACTATTGCAACCTACTGTACTGGTTCTATACCTTGTAGTGTTTGTCTTAGTGGTTTAGATTCTTTAGACACC<br>TATCCTTCTTTAGAAACTATACAAATTACCATTTCATCTTTTAAATGGGATTTAACTGCTTTTGGCTTAGTTGCAGA<br>GTGGTTTTTGGCATATATTCTTTTCACTAGGTTTTTCTATGTACTTGGATTGGCTGCAATCATGCAATTGTTTTTCAG<br>CTATTTTGCAGTACATTTTATTAGTAATTCTTGGCTTATGTGGTTAATAATTAATCTTGTACAAATGGCCCCGATTTC<br>AGCTATGGTTAGAATGTACATCTTCTTTGCATCATTTTATTATGTATGGAAAAGTTATGTGCATGTTGTAGACGGTT<br>GTAATTCATCAACTTGTATGATGTGTTACAAACGTAATAGAGCAACAAGAGTCGAATGTACAACTATTGTTAATGG<br>TGTTAGAAGGTCCTTTTATGTCTATGCTAATGGAGGTAAAGGCTTTTGCAAACTACACAATTGGAATTGTGTTAATT<br>GTGATACATTCTGTGCTGGTAGTACATTTATTAGTGATGAAGTTGCGAGAGACTTGTCACTACAGTTTAAAAGACC<br>AATAAATCCTACTGACCAGTCTTCTTACATCGTTGATAGTGTTACAGTGAAGAATGGTTCCATCCATCTTTACTTTG<br>ATAAAGCTGGTCAAAAGACTTATGAAAGACATTCTCTCTCTCATTTTGTTAACTTAGACAACCTGAGAGCTAATAA<br>CACTAAAGGTTCATTGCCTATTAATGTTATAGTTTTTGATGGTAAATCAAAATGTGAAGAATCATCTGCAAAATCA<br>GCGTCTGTTTACTACAGTCAGCTTATGTGTCAACCTATACTGTTACTAGATCAGGCATTAGTGTCTGATGTTGGTGA<br>TAGTGCGGAAGTTGCAGTTAAAATGTTTGATGCTTACGTTAATACGTTTTCATCAACTTTTAACGTACCAATGGAAA<br>AACTCAAAACACTAGTTGCAACTGCAGAAGCTGAACTTGCAAAGAATGTGTCCTTAGACAATGTCTTATCTACTTT<br>TATTTCAGCAGCTCGGCAAGGGTTTGTTGATTCAGATGTAGAAACTAAAGATGTTGTTGAATGTCTTAAATTGTCA<br>CATCAATCTGACATAGAAGTTACTGGCGATAGTTGTAATAACTATATGCTCACCTATAACAAAGTTGAAAACATGA<br>CACCCCGTGACCTTGGTGCTTGTATTGACTGTAGTGCGCGTCATATTAATGCGCAGGTAGCAAAAAGTCACAACAT<br>TGCTTTGATATGGAACGTTAAAGATTTCATGTCATTGTCTGAACAACTACGAAAACAAATACGTAGTGCTGCTAAA<br>AAGAATAACTTACCTTTTAAGTTGACATGTGCAACTACTAGACAAGTTGTTAATGTTGTAACAACAAAGATAGCAC<br>TTAAGGGTGGTAAAATTGTTAATAATTGGTTGAAGCAGTTAATTAAAGTTACACTTGTGTTCCTTTTTGTTGCTGCT<br>ATTTTCTATTTAATAACACCTGTTCATGTCATGTCTAAACATACTGACTTTTCAAGTGAAATCATAGGATACAAGGC<br>TATTGATGGTGGTGTCACTCGTGACATAGCATCTACAGATACTTGTTTTGCTAACAAACATGCTGATTTTGACACAT<br>GGTTTAGCCAGCGTGGTGGTAGTTATACTAATGACAAAGCTTGCCCATTGATTGCTGCAGTCATAACAAGAGAAGT<br>GGGTTTTGTCGTGCCTGGTTTGCCTGGCACGATATTACGCACAACTAATGGTGACTTTTTGCATTTCTTACCTAGAG<br>TTTTTAGTGCAGTTGGTAACATCTGTTACACACCATCAAAACTTATAGAGTACACTGACTTTGCAACATCAGCTTGT<br>GTTTTGGCTGCTGAATGTACAATTTTTAAAGATGCTTCTGGTAAGCCAGTACCATATTGTTATGATACCAATGTACT<br>AGAAGGTTCTGTTGCTTATGAAAGTTTACGCCCTGACACACGTTATGTGCTCATGGATGGCTCTATTATTCAATTTC<br>CTAACACCTACCTTGAAGGTTCTGTTAGAGTGGTAACAACTTTTGATTCTGAGTACTGTAGGCACGGCACTTGTGA<br>AAGATCAGAAGCTGGTGTTTGTGTATCTACTAGTGGTAGATGGGTACTTAACAATGATTATTACAGATCTTTACCA<br>GGAGTTTTCTGTGGTGTAGATGCTGTAAATTTACTTACTAATATGTTTACACCACTAATTCAACCTATTGGTGCTTT<br>GGACATATCAGCATCTATAGTAGCTGGTGGTATTGTAGCTATCGTAGTAACATGCCTTGCCTACTATTTTATGAGGT<br>TTAGAAGAGCTTTTGGTGAATACAGTCATGTAGTTGCCTTTAATACTTTACTATTCCTTATGTCATTCACTGTACTCT<br>GTTTAACACCAGTTTACTCATTCTTACCTGGTGTTTATTCTGTTATTTACTTGTACTTGACATTTTATCTTACTAATG<br>ATGTTTCTTTTTTAGCACATATTCAGTGGATGGTTATGTTCACACCTTTAGTACCTTTCTGGATAACAATTGCTTATA<br>TCATTTGTATTTCCACAAAGCATTTCTATTGGTTCTTTAGTAATTACCTAAAGAGACGTGTAGTCTTTAATGGTGTTT<br>CCTTTAGTACTTTTGAAGAAGCTGCGCTGTGCACCTTTTTGTTAAATAAAGAAATGTATCTAAAGTTGCGTAGTGAT<br>GTGCTATTACCTCTTACGCAATATAATAGATACTTAGCTCTTTATAATAAGTACAAGTATTTTAGTGGAGCAATGGA<br>TACAACTAGCTACAGAGAAGCTGCTTGTTGTCATCTCGCAAAGGCTCTCAATGACTTCAGTAACTCAGGTTCTGAT<br>GTTCTTTACCAACCACCACAAACCTCTATCACCTCAGCTGTTTTGCAGAGTGGTTTTAGAAAAATGGCATTCCCATC<br>TGGTAAAGTTGAGGGTTGTATGGTACAAGTAACTTGTGGTACAACTACACTTAACGGTCTTTGGCTTGATGACGTA |

-continued

| SEQUENCE LISTING |
|---|
| GTTTACTGTCCAAGACATGTGATCTGCACCTCTGAAGACATGCTTAACCCTAATTATGAAGATTTACTCATTCGTAA<br>GTCTAATCATAATTTCTTGGTACAGGCTGGTAATGTTCAACTCAGGGTTATTGGACATTCTATGCAAAATTGTGTAC<br>TTAAGCTTAAGGTTGATACAGCCAATCCTAAGACACCTAAGTATAAGTTTGTTCGCATTCAACCAGGACAGACTTT<br>TTCAGTGTTAGCTTGTTACAATGGTTCACCATCTGGTGTTTACCAATGTGCTATGAGGCCCAATTTCACTATTAAGG<br>GTTCATTCCTTAATGGTTCATGTGGTAGTGTTGGTTTTAACATAGATTATGACTGTGTCTCTTTTTGTTACATGCACC<br>ATATGGAATTACCAACTGGAGTTCATGCTGGCACAGACTTAGAAGGTAACTTTTATGGACCTTTTGTTGACAGGCA<br>AACAGCACAAGCAGCTGGTACGGACACAACTATTACAGTTAATGTTTTAGCTTGGTTGTACGCTGCTGTTATAAAT<br>GGAGACAGGTGGTTTCTCAATCGATTTACCACAACTCTTAATGACTTTAACCTTGTGGCTATGAAGTACAATTATG<br>AACCTCTAACACAAGACCATGTTGACATACTAGGACCTCTTTCTGCTCAAACTGGAATTGCCGTTTTAGATATGTGT<br>GCTTCATTAAAAGAATTACTGCAAAATGGTATGAATGGACGTACCATATTGGGTAGTGCTTTATTAGAAGATGAAT<br>TTACACCTTTTGATGTTGTTAGACAATGCTCAGGTGTTACTTTCCAAAGTGCAGTGAAAAGAACAATCAAGGGTAC<br>ACACCACTGGTTGTTACTCACAATTTTGACTTCACTTTTAGTTTTAGTCCAGAGTACTCAATGGTCTTTGTTCTTTTT<br>TTTGTATGAAAATGCCTTTTTACCTTTTGCTATGGGTATTATTGCTATGTCTGCTTTTGCAATGATGTTTGTCAAACA<br>TAAGCATGCATTTCTCTGTTTGTTTTTGTTACCTTCTCTTGCCACTGTAGCTTATTTTAATATGGTCTATATGCCTGCT<br>AGTTGGGTGATGCGTATTATGACATGGTTGGATATGGTTGATACTAGTTTGTCTGGTTTTAAGCTAAAAGACTGTGT<br>TATGTATGCATCAGCTGTAGTGTTACTAATCCTTATGACAGCAAGAACTGTGTATGATGATGGTGCTAGGAGAGTG<br>TGGACACTTATGAATGTCTTGACACTCGTTTATAAAGTTTATTATGGTAATGCTTTAGATCAAGCCATTTCCATGTG<br>GGCTCTTATAATCTCTGTTACTTCTAACTACTCAGGTGTAGTTACAACTGTCATGTTTTTGGCCAGAGGTATTGTTTT<br>TATGTGTGTTGAGTATTGCCCTATTTTCTTCATAACTGGTAATACACTTCAGTGTATAATGCTAGTTTATTGTTTCTT<br>AGGCTATTTTTGTACTTGTTACTTTGGCCTCTTTTGTTTACTCAACCGCTACTTTAGACTGACTCTTGGTGTTTATGA<br>TTACTTAGTTTCTACACAGGAGTTTAGATATATGAATTCACAGGGACTACTCCCACCCAAGAATAGCATAGATGCC<br>TTCAAACTCAACATTAAATTGTTGGGTGTTGGTGGCAAACCTTGTATCAAAGTAGCCACTGTACAGTCTAAAATGT<br>CAGATGTAAAGTGCACATCAGTAGTCTTACTCTCAGTTTTGCAACAACTCAGAGTAGAATCATCATCTAAATTGTG<br>GGCTCAATGTGTCCAGTTACACAATGACATTCTCTTAGCTAAAGATACTACTGAAGCCTTTGAAAAAATGGTTTCA<br>CTACTTTCTGTTTTGCTTTCCATGCAGGGTGCTGTAGACATAAACAAGCTTTGTGAAGAAATGCTGGACAACAGGG<br>CAACCTTACAAGCTATAGCCTCAGAGTTTAGTTCCCTTCCATCATATGCAGCTTTTGCTACTGCTCAAGAAGCTTAT<br>GAGCAGGCTGTTGCTAATGGTGATTCTGAAGTTGTTCTTAAAAAGTTGAAGAAGTCTTTGAATGTGGCTAAATCTG<br>AATTTGACCGTGATGCAGCCATGCAACGTAAGTTGGAAAAGATGGCTGATCAAGCTATGACCCAAATGTATAAAC<br>AGGCTAGATCTGAGGACAAGAGGGCAAAAGTTACTAGTGCTATGCAGACAATGCTTTTCACTATGCTTAGAAAGTT<br>GGATAATGATGCACTCAACAACATTATCAACAATGCAAGAGATGGTTGTGTTCCCTTGAACATAATACCTCTTACA<br>ACAGCAGCCAAACTAATGGTTGTCATACCAGACTATAACACATATAAAAATACGTGTGATGGTACAACATTTACTT<br>ATGCATCAGCATTGTGGGAAATCCAACAGGTTGTAGATGCAGATAGTAAAATTGTTCAACTTAGTGAAATTAGTAT<br>GGACAATTCACCTAATTTAGCATGGCCTCTTATTGTAACAGCTTTAAGGGCCAATTCTGCTGTCAAATTACAGAAT<br>AATGAGCTTAGTCCTGTTGCACTACGACAGATGTCTTGTGCTGCCGGTACTACACAAACTGCTTGCACTGATGACA<br>ATGCGTTAGCTTACTACAACACAACAAAGGGAGGTAGGTTTGTACTTGCACTGTTATCCGATTTACAGGATTTGAA<br>ATGGGCTAGATTCCCTAAGAGTGATGGAACTGGTACTATCTATACAGAACTGGAACCACCTTGTAGGTTTGTTACA<br>GACACACCTAAAGGTCCTAAAGTGAAGTATTTATACTTTATTAAAGGATTAAACAACCTAAATAGAGGTATGGTAC<br>TTGGTAGTTTAGCTGCCACAGTACGTCTACAAGCTGGTAATGCAACAGAAGTGCCTGCCAATTCAACTGTATTATC<br>TTTCTGTGCTTTTGCTGTAGATGCTGCTAAAGCTTACAAAGATTATCTAGCTAGTGGGGGACAACCAATCACTAATT<br>GTGTTAAGATGTTGTGTACACACACTGGTACTGGTCAGGCAATAACAGTTACACCGGAAGCCAATATGGATCAAG<br>AATCCTTTGGTGGTGCATCGTGTTGTCTGTACTGCCGTTGCCACATAGATCATCCAAATCCTAAAGGATTTTGTGAC<br>TTAAAAGGTAAGTATGTACAAATACCTACAACTTGTGCTAATGACCCTGTGGGTTTTACACTTAAAAACACAGTCT<br>GTACCGTCTGCGGTATGTGGAAAGGTTATGGCTGTAGTTGTGATCAACTCCGCGAACCCATGCTTCAGTCAGCTGA<br>TGCACAATCGTTTTTAAACGGGTTTGCGGTGTAAGTGCAGCCCGTCTTACACCGTGCGGCACAGGCACTAGTACTG<br>ATGTCGTATACAGGGCTTTTGACATCTACAATGATAAAGTAGCTGGTTTTGCTAAATTCCTAAAAACTAATTGTTGT<br>CGCTTCCAAGAAAAGGACGAAGATGACAATTTAATTGATTCTTACTTTGTAGTTAAGAGACACACTTTCTCTAACT<br>ACCAACATGAAGAAACAATTTATAATTTACTTAAGGATTGTCCAGCTGTTGCTAAACATGACTTCTTTAAGTTTAG<br>AATAGACGGTGACATGGTACCACATATATCACGTCAACGTCTTACTAAATACACAATGGCAGACCTCGTCTATGCT<br>TTAAGGCATTTTGATGAAGGTAATTGTGACACATTAAAAGAAATACTTGTCACATACAATTGTTGTGATGATGATT<br>ATTTCAATAAAAAGGACTGGTATGATTTTGTAGAAAACCCAGATATATTACGCGTATACGCCAACTTAGGTGAACG<br>TGTACGCCAAGCTTTGTTAAAAACAGTACAATTCTGTGATGCCATGCGAAATGCTGGTATTGTTGGTGTACTGACA |

-continued

| SEQUENCE LISTING |
| --- |
| TTAGATAATCAAGATCTCAATGGTAACTGGTATGATTTCGGTGATTTCATACAAACCACGCCAGGTAGTGGAGTTC<br>CTGTTGTAGATTCTTATTATTCATTGTTAATGCCTATATTAACCTTGACCAGGGCTTTAACTGCAGAGTCACATGTT<br>GACACTGACTTAACAAAGCCTTACATTAAGTGGGATTTGTTAAAATATGACTTCACGGAAGAGAGGTTAAAACTCT<br>TTGACCGTTATTTTAAATATTGGGATCAGACATACCACCCAAATTGTGTTAACTGTTTGGATGACAGATGCATTCTG<br>CATTGTGCAAACTTTAATGTTTTATTCTCTACAGTGTTCCCACCTACAAGTTTTGGACCACTAGTGAGAAAAATATT<br>TGTTGATGGTGTTCCATTTGTAGTTTCAACTGGATACCACTTCAGAGAGCTAGGTGTTGTACATAATCAGGATGTAA<br>ACTTACATAGCTCTAGACTTAGTTTTAAGGAATTACTTGTGTATGCTGCTGACCCTGCTATGCACGCTGCTTCTGGT<br>AATCTATTACTAGATAAACGCACTACGTGCTTTTCAGTAGCTGCACTTACTAACAATGTTGCTTTTCAAACTGTCAA<br>ACCCGGTAATTTTAACAAAGACTTCTATGACTTTGCTGTGTCTAAGGGTTTCTTTAAGGAAGGAAGTTCTGTTGAAT<br>TAAAACACTTCTTCTTTGCTCAGGATGGTAATGCTGCTATCAGCGATTATGACTACTATCGTTATAATCTACCAACA<br>ATGTGTGATATCAGACAACTACTATTTGTAGTTGAAGTTGTTGATAAGTACTTTGATTGTTACGATGGTGGCTGTAT<br>TAATGCTAACCAAGTCATCGTCAACAACCTAGACAAATCAGCTGGTTTTCCATTTAATAAATGGGGTAAGGCTAGA<br>CTTTATTATGATTCAATGAGTTATGAGGATCAAGATGCACTTTTCGCATATACAAAACGTAATGTCATCCCTACTAT<br>AACTCAAATGAATCTTAAGTATGCCATTAGTGCAAAGAATAGAGCTCGCACCGTAGCTGGTGTCTCTATCTGTAGT<br>ACTATGACCAATAGACAGTTTCATCAAAAATTATTGAAATCAATAGCCGCCACTAGAGGAGCTACTGTAGTAATTG<br>GAACAAGCAAATTCTATGGTGGTTGGCACAACATGTTAAAAACTGTTTATAGTGATGTAGAAAACCCTCACCTTAT<br>GGGTTGGGATTATCCTAAATGTGATAGAGCCATGCCTAACATGCTTAGAATTATGGCCTCACTTGTTCTTGCTCGCA<br>AACATACAACGTGTTGTAGCTTGTCACACCGTTTCTATAGATTAGCTAATGAGTGTGCTCAAGTATTGAGTGAAAT<br>GGTCATGTGTGGCGGTTCACTATATGTTAAACCAGGTGGAACCTCATCAGGAGATGCCACAACTGCTTATGCTAAT<br>AGTGTTTTTAACATTTGTCAAGCTGTCACGGCCAATGTTAATGCACTTTTATCTACTGATGGTAACAAAATTGCCGA<br>TAAGTATGTCCGCAATTTACAACACAGACTTTATGAGTGTCTCTATAGAAATAGAGATGTTGACACAGACTTTGTG<br>AATGAGTTTTACGCATATTTGCGTAAACATTTCTCAATGATGATACTCTCTGACGATGCTGTTGTGTGTTTCAATAG<br>CACTTATGCATCTCAAGGTCTAGTGGCTAGCATAAAGAACTTTAAGTCAGTTCTTTATTATCAAAACAATGTTTTTA<br>TGTCTGAAGCAAAATGTTGGACTGAGACTGACCTTACTAAAGGACCTCATGAATTTTGCTCTCAACATACAATGCT<br>AGTTAAACAGGGTGATGATTATGTGTACCTTCCTTACCCAGATCCATCAAGAATCCTAGGGGCCGGCTGTTTTGTA<br>GATGATATCGTAAAAACAGATGGTACACTTATGATTGAACGGTTCGTGTCTTTAGCTATAGATGCTTACCCACTTA<br>CTAAACATCCTAATCAGGAGTATGCTGATGTCTTTCATTTGTACTTACAATACATAAGAAAGCTACATGATGAGTT<br>AACAGGACACATGTTAGACATGTATTCTGTTATGCTTACTAATGATAACACTTCAAGGTATTGGGAACCTGAGTTT<br>TATGAGGCTATGTACACACCGCATACAGTCTTACAGGCTGTTGGGGCTTGTGTTCTTTGCAATTCACAGACTTCATT<br>AAGATGTGGTGCTTGCATACGTAGACCATTCTTATGTTGTAAATGCTGTTACGACCATGTCATATCAACATCACATA<br>AATTAGTCTTGTCTGTTAATCCGTATGTTTGCAATGCTCCAGGTTGTGATGTCACAGATGTGACTCAACTTTACTTA<br>GGAGGTATGAGCTATTATTGTAAATCACATAAACCACCCATTAGTTTTCCATTGTGTGCTAATGGACAAGTTTTTGG<br>TTTATATAAAAATACATGTGTTGGTAGCGATAATGTTACTGACTTTAATGCAATTGCAACATGTGACTGGACAAAT<br>GCTGGTGATTACATTTTAGCTAACACCTGTACTGAAAGACTCAAGCTTTTTGCAGCAGAAACGCTCAAAGCTACTG<br>AGGAGACATTTAAACTGTCTTATGGTATTGCTACTGTACGTGAAGTGCTGTCTGACAGAGAATTACATCTTTCATG<br>GGAAGTTGGTAAACCTAGACCACCACTTAACCGAAATTATGTCTTTACTGGTTATCGTGTAACTAAAAACAGTAAA<br>GTACAAATAGGAGAGTACACCTTTGAAAAAGGTGACTATGGTGATGCTGTTGTTTACCGAGGTACAACAACTTACA<br>AATTAAATGTTGGTGATTATTTTGTGCTGACATCACATACAGTAATGCCATTAAGTGCACCTACACTAGTGCCACA<br>AGAGCACTATGTTAGAATTACTGGCTTATACCCAACACTCAATATCTCAGATGAGTTTTCTAGCAATGTTGCAAATT<br>ATCAAAAGGTTGGTATGCAAAAGTATTCTACACTCCAGGGACCACCTGGTACTGGTAAGAGTCATTTTGCTATTGG<br>CCTAGCTCTCTACTACCCTTCTGCTCGCATAGTGTATACAGCTTGCTCTCATGCCGCTGTTGATGCACTATGTGAGA<br>AGGCATTAAAATATTTGCCTATAGATAAATGTAGTAGAATTATACCTGCACGTGCTCGTGTAGAGTGTTTTGATAA<br>ATTCAAAGTGAATTCAACATTAGAACAGTATGTCTTTTGTACTGTAAATGCATTGCCTGAGACGACAGCAGATATA<br>GTTGTCTTTGATGAAATTTCAATGGCCACAAATTATGATTTGAGTGTTGTCAATGCCAGATTACGTGCTAAGCACTA<br>TGTGTACATTGGCGACCCTGCTCAATTACCTGCACCACGCACATTGCTAACTAAGGGCACACTAGAACCAGAATAT<br>TTCAATTCAGTGTGTAGACTTATGAAAACTATAGGTCCAGACATGTTCCTCGGAACTTGTCGGCGTTGTCCTGCTGA<br>AATTGTTGACACTGTGAGTGCTTTGGTTTATGATAATAAGCTTAAAGCACATAAAGACAAATCAGCTCAATGCTTT<br>AAAATGTTTTATAAGGGTGTTATCACGCATGATGTTTCATCTGCAATTAACAGGCCACAAATAGGCGTGGTAAGAG<br>AATTCCTTACACGTAACCCTGCTTGGAGAAAAGCTGTCTTTATTTCACCTTATAATTCACAGAATGCTGTAGCCTCA<br>AAGATTTTGGGACTACCAACTCAAACTGTTGATTCATCACAGGGCTCAGAATATGACTATGTCATATTCACTCAAA<br>CCACTGAAACAGCTCACTCTTGTAATGTAAACAGATTTAATGTTGCTATTACCAGAGCAAAAGTAGGCATACTTTG |

-continued

| SEQUENCE LISTING |
|---|
| CATAATGTCTGATAGAGACCTTTATGACAAGTTGCAATTTACAAGTCTTGAAATTCCACGTAGGAATGTGGCAACT |
| TTACAAGCTGAAAATGTAACAGGACTCTTTAAAGATTGTAGTAAGGTAATCACTGGGTTACATCCTACACAGGCAC |
| CTACACACCTCAGTGTTGACACTAAATTCAAAACTGAAGGTTTATGTGTTGACATACCTGGCATACCTAAGGACAT |
| GACCTATAGAAGACTCATCTCTATGATGGGTTTTAAAATGAATTATCAAGTTAATGGTTACCCTAACATGTTTATCA |
| CCCGCGAAGAAGCTATAAGACATGTACGTGCATGGATTGGCTTCGATGTCGAGGGGTGTCATGCTACTAGAGAAG |
| CTGTTGGTACCAATTTACCTTTACAGCTAGGTTTTTCTACAGGTGTTAACCTAGTTGCTGTACCTACAGGTTATGTT |
| GATACACCTAATAATACAGATTTTTCCAGAGTTAGTGCTAAACCACCGCCTGGAGATCAATTTAAACACCTCATAC |
| CACTTATGTACAAAGGACTTCCTTGGAATGTAGTGCGTATAAAGATTGTACAAATGTTAAGTGACACACTTAAAAA |
| TCTCTCTGACAGAGTCGTATTTGTCTTATGGGCACATGGCTTTGAGTTGACATCTATGAAGTATTTTGTGAAAATAG |
| GACCTGAGCGCACCTGTTGTCTATGTGATAGACGTGCCACATGCTTTTCCACTGCTTCAGACACTTATGCCTGTTGG |
| CATCATTCTATTGGATTTGATTACGTCTATAATCCGTTTATGATTGATGTTCAACAATGGGGTTTTACAGGTAACCT |
| ACAAAGCAACCATGATCTGTATTGTCAAGTCCATGGTAATGCACATGTAGCTAGTTGTGATGCAATCATGACTAGG |
| TGTCTAGCTGTCCACGAGTGCTTTGTTAAGCGTGTTGACTGGACTATTGAATATCCTATAATTGGTGATGAACTGAA |
| GATTAATGCGGCTTGTAGAAAGGTTCAACACATGGTTGTTAAAGCTGCATTATTAGCAGACAAATTCCCAGTTCTT |
| CACGACATTGGTAACCCTAAAGCTATTAAGTGTGTACCTCAAGCTGATGTAGAATGGAAGTTCTATGATGCACAGC |
| CTTGTAGTGACAAAGCTTATAAAATAGAAGAATTATTCTATTCTTATGCCACACATTCTGACAAATTCACAGATGG |
| TGTATGCCTATTTTGGAATTGCAATGTCGATAGATATCCTGCTAATTCCATTGTTTGTAGATTTGACACTAGAGTGC |
| TATCTAACCTTAACTTGCCTGGTTGTGATGGTGGCAGTTTGTATGTAAATAAACATGCATTCCACACACCAGCTTTT |
| GATAAAAGTGCTTTTGTTAATTTAAAACAATTACCATTTTTCTATTACTCTGACAGTCCATGTGAGTCTCATGGAAA |
| ACAAGTAGTGTCAGATATAGATTATGTACCACTAAAGTCTGCTACGTGTATAACACGTTGCAATTTAGGTGGTGCT |
| GTCTGTAGACATCATGCTAATGAGTACAGATTGTATCTCGATGCTTATAACATGATGATCTCAGCTGGCTTTAGCTT |
| GTGGGTTTACAAACAATTTGATACTTATAACCTCTGGAACACTTTTACAAGACTTCAGAGTTTAGAAAATGTGGCT |
| TTTAATGTTGTAAATAAGGGACACTTTGATGGACAACAGGGTGAAGTACCAGTTTCTATCATTAATAACACTGTTT |
| ACACAAAAGTTGATGGTGTTGATGTAGAATTGTTTGAAAATAAAACAACATTACCTGTTAATGTAGCATTTGAGCT |
| TTGGGCTAAGCGCAACATTAAACCAGTACCAGAGGTGAAAATACTCAATAATTTGGGTGTGGACATTGCTGCTAAT |
| ACTGTGATCTGGGACTACAAAAGAGATGCTCCAGCACATATATCTACTATTGGTGTTTGTTCTATGACTGACATAG |
| CCAAGAAACCAACTGAAACGATTTGTGCACCACTCACTGTCTTTTTTGATGGTAGAGTTGATGGTCAAGTAGACTT |
| ATTTAGAAATGCCCGTAATGGTGTTCTTATTACAGAAGGTAGTGTTAAAGGTTTACAACCATCTGTAGGTCCCAAA |
| CAAGCTAGTCTTAATGGAGTCACATTAATTGGAGAAGCCGTAAAAACACAGTTCAATTATTATAAGAAAGTTGATG |
| GTGTTGTCCAACAATTACCTGAAACTTACTTTACTCAGAGTAGAAATTTACAAGAATTTAAACCCAGGAGTCAAAT |
| GGAAATTGATTTCTTAGAATTAGCTATGGATGAATTCATTGAACGGTATAAATTAGAAGGCTATGCCTTCGAACAT |
| ATCGTTTATGGAGATTTTAGTCATAGTCAGTTAGGTGGTTTACATCTACTGATTGGACTAGCTAAACGTTTTAAGGA |
| ATCACCTTTTGAATTAGAAGATTTTATTCCTATGGACAGTACAGTTAAAAACTATTTCATAACAGATGCGCAAACA |
| GGTTCATCTAAGTGTGTGTGTTCTGTTATTGATTTATTACTTGATGATTTTGTTGAAATAATAAAATCCCAAGATTT |
| ATCTGTAGTTTCTAAGGTTGTCAAAGTGACTATTGACTATACAGAAATTTCATTTATGCTTTGGTGTAAAGATGGCC |
| ATGTAGAAACATTTTACCCAAAATTACAATCTAGTCAAGCGTGGCAACCGGGTGTTGCTATGCCTAATCTTTACAA |
| AATGCAAAGAATGCTATTAGAAAAGTGTGACCTTCAAAATTATGGTGATAGTGCAACATTACCTAAAGGCATAAT |
| GATGAATGTCGCAAAATATACTCAACTGTGTCAATATTTAAACACATTAACATTAGCTGTACCCTATAATATGAGA |
| GTTATACATTTTGGTGCTGGTTCTGATAAAGGAGTTGCACCAGGTACAGCTGTTTTAAGACAGTGGTTGCCTACGG |
| GTACGCTGCTTGTCGATTCAGATCTTAATGACTTTGTCTCTGATGCAGATTCAACTTTGATTGGTGATTGTGCAACT |
| GTACATACAGCTAATAAATGGGATCTCATTATTAGTGATATGTACGACCCTAAGACTAAAAATGTTACAAAAGAA |
| AATGACTCTAAAGAGGGTTTTTTCACTTACATTTGTGGGTTTATACAACAAAAGCTAGCTCTTGGAGGTTCCGTGGC |
| TATAAAGATAACAGAACATTCTTGGAATGCTGATCTTTATAAGCTCATGGGACACTTCGCATGGTGGACAGCCTTT |
| GTTACTAATGTGAATGCGTCATCATCTGAAGCATTTTTAATTGGATGTAATTATCTTGGCAAACCACGCGAACAAA |
| TAGATGGTTATGTCATGCATGCAAATTACATATTTTGGAGGAATACAAATCCAATTCAGTTGTCTTCCTATTCTTTA |
| TTTGACATGAGTAAATTTCCCCTTAAATTAAGGGGTACTGCTGTTATGTCTTTAAAAGAAGGTCAAATCAATGATA |
| TGATTTTATCTCTTCTTAGTAAAGGTAGACTTATAATTAGAGAAAACAACAGAGTTGTTATTTCTAGTGATGTTCTT |
| GTTAACAACTAAACGAACAATGTTTGTTTTTCTTGTTTTATTGCCACTAGTCTCTAGTCAGTGTGTTAATCTTACAAC |
| CAGAACTCAATTACCCCCTGCATACACTAATTCTTTCACACGTGGTGTTTATTACCCTGACAAAGTTTTCAGATCCT |
| CAGTTTTACATTCAACTCAGGACTTGTTCTTACCTTTCTTTTCCAATGTTACTTGGTTCCATGCTATACATGTCTCTG |
| GGACCAATGGTACTAAGAGGTTTGATAACCCTGTCCTACCATTTAATGATGGTGTTTATTTTGCTTCCACTGAGAAG |

-continued

| SEQUENCE LISTING |
|---|
| TCTAACATAATAAGAGGCTGGATTTTTGGTACTACTTTAGATTCGAAGACCCAGTCCCTACTTATTGTTAATAACGC<br>TACTAATGTTGTTATTAAAGTCTGTGAATTTCAATTTTGTAATGATCCATTTTTGGGTGTTTATTACCACAAAAACA<br>ACAAAAGTTGGATGGAAAGTGAGTTCAGAGTTTATTCTAGTGCGAATAATTGCACTTTTGAATATGTCTCTCAGCC<br>TTTTCTTATGGACCTTGAAGGAAAACAGGGTAATTTCAAAAATCTTAGGGAATTTGTGTTTAAGAATATTGATGGT<br>TATTTTAAAATATATTCTAAGCACACGCCTATTAATTTAGTGCGTGATCTCCCTCAGGGTTTTTCGGCTTTAGAACC<br>ATTGGTAGATTTGCCAATAGGTATTAACATCACTAGGTTTCAAACTTTACTTGCTTTACATAGAAGTTATTTGACTC<br>CTGGTGATTCTTCTTCAGGTTGGACAGCTGGTGCTGCAGCTTATTATGTGGGTTATCTTCAACCTAGGACTTTTCTA<br>TTAAAATATAATGAAAATGGAACCATTACAGATGCTGTAGACTGTGCACTTGACCCTCTCTCAGAAACAAAGTGTA<br>CGTTGAAATCCTTCACTGTAGAAAAAGGAATCTATCAAACTTCTAACTTTAGAGTCCAACCAACAGAATCTATTGT<br>TAGATTTCCTAATATTACAAACTTGTGCCCTTTTGGTGAAGTTTTTAACGCCACCAGATTTGCATCTGTTTATGCTTG<br>GAACAGGAAGAGAATCAGCAACTGTGTTGCTGATTATTCTGTCCTATATAATTCCGCATCATTTTCCACTTTTAAGT<br>GTTATGGAGTGTCTCCTACTAAATTAAATGATCTCTGCTTTACTAATGTCTATGCAGATTCATTTGTAATTAGAGGT<br>GATGAAGTCAGACAAATCGCTCCAGGGCAAACTGGAAAGATTGCTGATTATAATTATAAATTACCAGATGATTTTA<br>CAGGCTGCGTTATAGCTTGGAATTCTAACAATCTTGATTCTAAGGTTGGTGGTAATTATAATTACCTGTATAGATTG<br>TTTAGGAAGTCTAATCTCAAACCTTTTGAGAGAGATATTTCAACTGAAATCTATCAGGCCGGTAGCACACCTTGTA<br>ATGGTGTTGAAGGTTTTAATTGTTACTTTCCTTTACAATCATATGGTTTCCAACCCACTAATGGTGTTGGTTACCAA<br>CCATACAGAGTAGTAGTACTTTCTTTTGAACTTCTACATGCACCAGCAACTGTTTGTGGACCTAAAAAGTCTACTAA<br>TTTGGTTAAAAACAAATGTGTCAATTTCAACTTCAATGGTTTAACAGGCACAGGTGTTCTTACTGAGTCTAACAAA<br>AAGTTTCTGCCTTTCCAACAATTTGGCAGAGACATTGCTGACACTACTGATGCTGTCCGTGATCCACAGACACTTG<br>AGATTCTTGACATTACACCATGTTCTTTTGGTGGTGTCAGTGTTATAACACCAGGAACAAATACTTCTAACCAGGTT<br>GCTGTTCTTTATCAGGATGTTAACTGCACAGAAGTCCCTGTTGCTATTCATGCAGATCAACTTACTCCTACTTGGCG<br>TGTTTATTCTACAGGTTCTAATGTTTTTCAAACACGTGCAGGCTGTTTAATAGGGGCTGAACATGTCAACAACTCAT<br>ATGAGTGTGACATACCCATTGGTGCAGGTATATGCGCTAGTTATCAGACTCAGACTAATTCTCCTCGGCGGGCACG<br>TAGTGTAGCTAGTCAATCCATCATTGCCTACACTATGTCACTTGGTGCAGAAAATTCAGTTGCTTACTCTAATAACT<br>CTATTGCCATACCCACAAATTTTACTATTAGTGTTACCACAGAAATTCTACCAGTGTCTATGACCAAGACATCAGTA<br>GATTGTACAATGTACATTTGTGGTGATTCAACTGAATGCAGCAATCTTTTGTTGCAATATGGCAGTTTTTGTACACA<br>ATTAAACCGTGCTTTAACTGGAATAGCTGTTGAACAAGACAAAAACACCCAAGAAGTTTTTGCACAAGTCAAACA<br>AATTTACAAAACACCACCAATTAAAGATTTTGGTGGTTTTAATTTTTCACAAATATTACCAGATCCATCAAAACCA<br>AGCAAGAGGTCATTTATTGAAGATCTACTTTTCAACAAAGTGACACTTGCAGATGCTGGCTTCATCAAACAATATG<br>GTGATTGCCTTGGTGATATTGCTGCTAGAGACCTCATTTGTGCACAAAAGTTTAACGGCCTTACTGTTTTGCCACCT<br>TTGCTCACAGATGAAATGATTGCTCAATACACTTCTGCACTGTTAGCGGGTACAATCACTTCTGGTTGGACCTTTGG<br>TGCAGGTGCTGCATTACAAATACCATTTGCTATGCAAATGGCTTATAGGTTTAATGGTATTGGAGTTACACAGAAT<br>GTTCTCTATGAGAACCAAAAATTGATTGCCAACCAATTTAATAGTGCTATTGGCAAAATTCAAGACTCACTTTCTTC<br>CACAGCAAGTGCACTTGGAAAACTTCAAGATGTGGTCAACCAAAATGCACAAGCTTTAAACACGCTTGTTAAACA<br>ACTTAGCTCCAATTTTGGTGCAATTTCAAGTGTTTTAAATGATATCCTTTCACGTCTTGACAAAGTTGAGGCTGAAG<br>TGCAAATTGATAGGTTGATCACAGGCAGACTTCAAAGTTTGCAGACATATGTGACTCAACAATTAATTAGAGCTGC<br>AGAAATCAGAGCTTCTGCTAATCTTGCTGCTACTAAAATGTCAGAGTGTGTACTTGGACAATCAAAAAGAGTTGAT<br>TTTTGTGGAAAGGGCTATCATCTTATGTCCTTCCCTCAGTCAGCACCTCATGGTGTAGTCTTCTTGCATGTGACTTAT<br>GTCCCTGCACAAGAAAAGAACTTCACAACTGCTCCTGCCATTTGTCATGATGGAAAAGCACACTTTCCTCGTGAAG<br>GTGTCTTTGTTTCAAATGGCACACACTGGTTTGTAACACAAAGGAATTTTTATGAACCACAAATCATTACTACAGA<br>CAACACATTTGTGTCTGGTAACTGTGATGTTGTAATAGGAATTGTCAACAACACAGTTTATGATCCTTTGCAACCTG<br>AATTAGACTCATTCAAGGAGGAGTTAGATAAATATTTTAAGAATCATACATCACCAGATGTTGATTTAGGTGACAT<br>CTCTGGCATTAATGCTTCAGTTGTAAACATTCAAAAAGAAATTGACCGCCTCAATGAGGTTGCCAAGAATTTAAAT<br>GAATCTCTCATCGATCTCCAAGAACTTGGAAAGTATGAGCAGTATATAAAATGGCCATGGTACATTTGGCTAGGTT<br>TTATAGCTGGCTTGATTGCCATAGTAATGGTGACAATTATGCTTTGCTGTATGACCAGTTGCTGTAGTTGTCTCAAG<br>GGCTGTTGTTCTTGTGGATCCTGCTGCAAATTTGATGAAGACGACTCTGAGCCAGTGCTCAAAGGAGTCAAATTAC<br>ATTACACATAAACGAACTTATGGATTTGTTTATGAGAATCTTCACAATTGGAACTGTAACTTTGAAGCAAGGTGAA<br>ATCAAGGATGCTACTCCTTCAGATTTTGTTCGCGCTACTGCAACGATACCGATACAAGCCTCACTCCCTTTCGGATG<br>GCTTATTGTTGGCGTTGCACTTCTTGCTGTTTTTCAGAGCGCTTCCAAAATCATAACCCTCAAAAAGAGATGGCAAC<br>TAGCACTCTCCAAGGGTGTTCACTTTGTTTGCAACTTGCTGTTGTTGTTTGTAACAGTTTACTCACACCTTTTGCTCG<br>TTGCTGCTGGCCTTGAAGCCCCTTTTCTCTATCTTTATGCTTTAGTCTACTTCTTGCAGAGTATAAACTTTGTAAGAA |

-continued

SEQUENCE LISTING

TAATAATGAGGCTTTGGCTTTGCTGGAAATGCCGTTCCAAAAACCCATTACTTTATGATGCCAACTATTTTCTTTGC
TGGCATACTAATTGTTACGACTATTGTATACCTTACAATAGTGTAACTTCTTCAATTGTCATTACTTCAGGTGATGG
CACAACAAGTCCTATTTCTGAACATGACTACCAGATTGGTGGTTATACTGAAAAATGGGAATCTGGAGTAAAAGA
CTGTGTTGTATTACACAGTTACTTCACTTCAGACTATTACCAGCTGTACTCAACTCAATTGAGTACAGACACTGGTG
TTGAACATGTTACCTTCTTCATCTACAATAAAATTGTTGATGAGCCTGAAGAACATGTCCAAATTCACACAATCGA
CGGTTCATCCGGAGTTGTTAATCCAGTAATGGAACCAATTTATGATGAACCGACGACGACTACTAGCGTGCCTTTG
TAAGCACAAGCTGATGAGTACGAACTTATGTACTCATTCGTTTCGGAAGAGACAGGTACGTAAATAGTTAATAGCT
GACTTCTTTTTCTTGCTTTCGTGTGATTCTTGCTAGTTACACTAGCCATCCTTACTGCGCTTCGATTGTGTGCGTACT
GCTGCAATATTGTTAACGTGAGTCTTGTAAAACCTTCTTTTTACGTTTACTCTCGTGTTAAAAATCTGAATTCTTCTA
GAGTTCCTGATCTTCTGGTCTAAACGAACTAAATATTATATTAGTTTTTCTGTTTGGAACTTTAATTTTAGCCATGGC
AGATTCCAACGGTACTATTACCGTTGAAGAGCTTAAAAAGCTCCTTGAACAATGGAACCTAGTAATAGGTTTCCTA
TTCCTTACATGGATTTGTCTTCTACAATTTGCCTATGCCAACAGGAATAGGTTTTTGTATATAATTAAGTTAATTTTC
CTCTGGCTGTTATGGCCAGTAACTTTAGCTTGTTTTGTGCTTGCTGCTGTTTACAGAATAAATTGGATCACCGGTGG
AATTGCTATCGCAATGGCTTGTCTTGTAGGCTTGATGTGGCTCAGCTACTTCATTGCTTCTTTCAGACTGTTTGCGC
GTACGCGTTCCATGTGGTCATTCAATCCAGAAACTAACATTCTTCTCAACGTGCCACTCCATGGCACTATTCTGACC
AGACCGCTTCTAGAAAGTGAACTCGTAATCGGAGCTGTGATCCTTCGTGGACATCTTCGTATTGCTGGACACCATC
TAGGACGCTGTGACATCAAGGACCTGCCTAAAGAAATCACTGTTGCTACATCACGAACGCTTTCTTATTACAAATT
GGGAGCTTCGCAGCGTGTAGCAGGTGACTCAGGTTTTGCTGCATACAGTCGCTACAGGATTGGCAACTATAAATTA
AACACAGACCATTCCAGTAGCAGTGACAATATTGCTTTGCTTGTACAATGATAATGAAACTTGTCACGCCTAAACG
AAC atgaacaacaggtggatcctccacgctgcgttcctgctgtgcttctccaccacagccctctccatcaactataagcagctccagctccaagaaaggacgaacattcggaaatgtcagg
agctcctggagcagctgaatggaaagatcaacctcacctacagggcggacttcaagatccctatggagatgacggagaagatgcagaagagttacactgcctttgccatccaagagatgct
ccagaatgtctttcttgtcttcagaaacaatttctccagcactgggtggaatgagactattgttgtacgtctcctggatgaactccaccagcagacagtgtttctgaagacagtactagaggaaaa
gcaagaggaaagattgacgtgggagatgtcctcaactgctctccacttgaagagctattactggagggtgcaaaggtaccttaaactcatgaagtacaacagctacgcctggatggtggtcc
gagcagagatcttcaggaactttctcatcattcgaagacttaccagaaacttccaaaactgaGACGTTCGTGTTGTTTTAGATTTCATCTAAACGAACAAA
CTAAAATGTCTGATAATGGACCCCAAAATCAGCGAAATGCACCCCGCATTACGTTTGGTGGACCCTCAGATTCAAC
TGGCAGTAACCAGAATGGAGAACGCAGTGGGGCGCGATCAAAACAACGTCGGCCCCAAGGTTTACCCAATAATAC
TGCGTCTTGGTTCACCGCTCTCACTCAACATGGCAAGGAAGACCTTAAATTCCCTCGAGGACAAGGCGTTCCAATT
AACACCAATAGCAGTCCAGATGACCAAATTGGCTACTACCGAAGAGCTACCAGACGAATTCGTGGTGGTGACGGT
AAAATGAAAGATCTCAGTCCAAGATGGTATTTCTACTACCTAGGAACTGGGCCAGAAGCTGGACTTCCCTATGGTG
CTAACAAAGACGGCATCATATGGGTTGCAACTGAGGGAGCCTTGAATACACCAAAAGATCACATTGGCACCCGCA
ATCCTGCTAACAATGCTGCAATCGTGCTACAACTTCCTCAAGGAACAACATTGCCAAAAGGCTTCTACGCAGAAGG
GAGCAGAGGCGGCAGTCAAGCCTCTTCTCGTTCCTCATCACGTAGTCGCAACAGTTCAAGAAATTCAACTCCAGGC
AGCAGTAGGGGAACTTCTCCTGCTAGAATGGCTGGCAATGGCGGTGATGCTGCTCTTGCTTTGCTGCTGCTTGACA
GATTGAACCAGCTTGAGAGCAAAATGTCTGGTAAAGGCCAACAACAACAAGGCCAAACTGTCACTAAGAAATCTG
CTGCTGAGGCTTCTAAGAAGCCTCGGCAAAAACGTACTGCCACTAAAGCATACAATGTAACACAAGCTTTCGGCA
GACGTGGTCCAGAACAAACCCAAGGAAATTTTGGGGACCAGGAACTAATCAGACAAGGAACTGATTACAAACATT
GGCCGCAAATTGCACAATTTGCCCCCAGCGCTTCAGCGTTCTTCGGAATGTCGCGCATTGGCATGGAAGTCACACC
TTCGGGAACGTGGTTGACCTACACAGGTGCCATCAAATTGGATGACAAAGATCCAAATTTCAAAGATCAAGTCATT
TTGCTGAATAAGCATATTGACGCATACAAAACATTCCCACCAACAGAGCCTAAAAAGGACAAAAAGAAGAAGGCT
GATGAAACTCAAGCCTTACCGCAGAGACAGAAGAAACAGCAAACTGTGACTCTTCTTCCTGCTGCAGATTTGGATG
ATTTCTCCAAACAATTGCAACAATCCATGAGCAGTGCTGACTCAACTCAGGCCTAAACTCATGCAGACCACACAAG
GCAGATGGGCTATATAAACGTTTTCGCTTTTCCGTTTACGATATATAGTCTACTCTTGTGCAGAATGAATTCTCGTA
ACTACATAGCACAAGTAGATGTAGTTAACTTTAATCTCACATAGCAATCTTTAATCAGTGTGTAACATTAGGGAGG
ACTTGAAAGAGCCACCACATTTTCACCGAGGCCACGCGGAGTACGATCGAGTGTACAGTGAACAATGCTAGGGAG
AGCTGCCTATATGGAAGAGCCCTAATGTGTAAAATTAATTTTAGTAGTGCTATCCCCATGTGATTTTAATAGCTTCT
TAGGAGAATGACAAAAAAAAAAAAAAAAAAAAA -continued

SEQUENCE LISTING

SEQ ID NO: 10 (human IFN-beta DNA)
atgaccaacaagtgtctcctccaaattgctctcctgttgtgcttctccactacagctctttccatgagctacaacttgcttggattcctacaaagaagcagcaattttcagtgtcagaagctcctgtg
gcaattgaatgggaggcttgaatactgcctcaaggacaggatgaactttgacatccctgaggagattaagcagctgcagcagttccagaaggaggacgccgcattgaccatctatgagatgc
tccagaacatctttgctattttcagacaagattcatctagcactggctggaatgagactattgttgagaacctcctggctaatgtctatcatcagataaaccatctgaagacagtcctggaagaaaa
actggagaaagaagatttcaccaggggaaaactcatgagcagtctgcacctgaaaagatattatgggaggattctgcattacctgaaggccaaggagtacagtcactgtgcctggaccatag
tcagagtggaaatcctaaggaacttttacttcattaacagacttacaggttacctccgaaactga SEQ ID NO: 11 (mouse IFN-beta DNA)
atgaacaacaggtggatcctccacgctgcgttcctgctgtgcttctccaccacagccctctccatcaactataagcagctccagctccaagaaaggacgaacattcggaaatgtcaggagctc
ctggagcagctgaatggaaagatcaacctcacctacagggggacttcaagatccctatggagatgacggagaagatgcagaagagttacactgcctttgccatccaagagatgctccaga
atgtctttcttgtcttcagaaacaatttctccagcactgggtggaatgagactattgttgtacgtctcctggatgaactccaccagcagacagtgtttctgaagacagtactagaggaaaagcaag
aggaaagattgacgtgggagatgtcctcaactgctctccacttgaagagctattactggagggtgcaaaggtaccttaaactcatgaagtacaacagctacgcctggatggtggtccgagca
gagatcttcaggaactttctcatcattcgaagacttaccagaaacttccaaaactga SEQ ID NO: 12 (SARS-COV-2 wild-type Envelope DNA sequence)
ATGTACTCATTCGTTTCGGAAGAGACAGGTACGTTAATAGTTAATAGCGTACTTCTTTTTCTTGCTTTCGTGGTATT
CTTGCTAGTTACACTAGCCATCCTTACTGCGCTTCGATTGTGTGCGTACTGCTGCAATATTGTTAACGTGAGTCTTG
TAAAACCTTCTTTTTACGTTTACTCTCGTGTTAAAAATCTGAATTCTTCTAGAGTTCCTGATCTTCTGGTCTAA SEQ ID NO: 13 (SARS-COV-2 modified Envelope amino acid polypeptide sequence; * indicates stop codon)
MYSFVSEETGT*IVNS*LLFLAFV*FLLVTLAILTALRLCAYCCNIVNVSLVKPSFYVYSRVKNLNSSRVPDLLV*

SEQ ID NO: 14 (SARS-COV-2 modified Envelope DNA sequence; underlined sequences are inserted mutations for IBIS genome)
ATGTACTCATTCGTTTCGGAAGAGACAGGTACGTAAATAGTTAATAGCTGACTTCTTTTTCTTGCTTTCGTGTGATT
CTTGCTAGTTACACTAGCCATCCTTACTGCGCTTCGATTGTGTGCGTACTGCTGCAATATTGTTAACGTGAGTCTTG
TAAAACCTTCTTTTTACGTTTACTCTCGTGTTAAAAATCTGAATTCTTCTAGAGTTCCTGATCTTCTGGTCTAA SEQ ID NO: 15 (SARS-COV-2 engineered Envelope DNA sequence; underlined sequences are inserted mutations for host cell Vero-A9B21 transgene)
ATGTATAGCTTTGTGAGCGAGGAAACCGGCACCCTGATCGTGAACTCCGTGCTGCTGTTCCTGGCCTTTGTGTTTCT
GCTGGTGACCCTGGCTATTCTGACCGCCCTGAGACTCTGCGCCTATTGCTGTAACATCGTGAATGTCTCCCTGGTGA
AGCCCAGCTTCTATGTGTATAGCAGGGTGAACCTCAACAGCAGCAGAGTGCCCGACCTGCTGTAA SEQ ID NO: 16 (SARS-COV-2 engineered Envelope amino acid polypeptide sequence; * indicates stop codon)
MYSFVSEETGTLIVNSVLLFLAFVVFLLVTLAILTALRLCAYCCNIVNVSLVKPSFYVYSRVKNLNSSRVPDLLV*

What is claimed is:

1. A construct comprising a modified genome of a sarbecovirus, wherein the modified genome of the sarbecovirus comprises a modified envelope gene of the sarbecovirus and a nucleic acid encoding an interferon integrated into the modified genome of the sarbecovirus, wherein the modified envelope gene of the sarbecovirus comprises one or more stop codons, wherein the modified envelope gene of the sarbecovirus does not produce a functional envelope protein of the sarbecovirus, and wherein the construct is replication incompetent as a result of the modified envelope gene of the sarbecovirus not producing functional envelope protein of the sarbecovirus.

2. The construct of claim 1, wherein the nucleic acid encoding the interferon is inserted into the modified genome of the sarbecovirus.

3. The construct of claim 1, wherein the nucleic acid encoding the interferon replaces open reading frame 8 (ORF8).

4. The construct of claim 1, wherein the modified envelope gene comprises at least three stop codons.

5. The construct of claim 4, wherein at least one stop codon is present within the 5'-terminal 100 nucleotides of the modified envelope gene.

6. The construct of claim 1, wherein one or more of ORF6, ORF7a, ORF7b, and ORF8, or functional portion thereof, in the modified genome is deleted and/or inactivated by introducing a stop codon.

7. The construct of claim 1, wherein the sarbecovirus is SARS-CoV-2.

8. The construct of claim 1, wherein the modified genome comprises a wild-type spike gene.

9. The construct of claim 1, wherein the modified genome comprises a variant spike gene.

10. The construct of claim 1, wherein the interferon is type I interferon.

11. The construct of claim 10, wherein the interferon is interferon β.

12. A recombinant sarbecovirus comprising the construct of claim 1.

13. A sarbecovirus vaccine comprising the recombinant sarbecovirus of claim 12.

14. The sarbecovirus vaccine of claim 13, wherein the sarbecovirus vaccine is formulated for mucosal administration, nasal spray, or parenteral administration.

15. An isolated host cell comprising the construct of claim 1.

16. The isolated host cell of claim 15, wherein the isolated host cell is defective in interferon signaling.

17. The isolated host cell of claim 15, wherein the isolated host cell further comprises a heterologous nucleic acid encoding a functional envelope protein of the sarbecovirus.

18. A method of making a recombinant sarbecovirus, comprising culturing the isolated host cell of claim 15, and isolating the recombinant sarbecovirus.

19. A method of vaccinating an individual against sarbecovirus, comprising administering the sarbecovirus vaccine of claim 13 to the individual.

20. The method of claim 19, wherein the sarbecovirus vaccine is administered intranasally.

* * * * *